United States Patent
Kugler et al.

(10) Patent No.: US 11,547,835 B2
(45) Date of Patent: Jan. 10, 2023

(54) SYSTEMS, METHODS AND APPARATUS FOR GUIDING AND SUPPORTING CATHETERS AND METHODS OF MANUFACTURE

(71) Applicant: Seigla Medical, Inc., Buffalo, MN (US)

(72) Inventors: Chad J. Kugler, Buffalo, MN (US); Ross A. Olson, Anoka, MN (US)

(73) Assignee: Seigla Medical, Inc., Buffalo, MN (US)

( * ) Notice: Subject to any disclaimer, the term of this patent is extended or adjusted under 35 U.S.C. 154(b) by 0 days.

(21) Appl. No.: 17/508,459

(22) Filed: Oct. 22, 2021

(65) Prior Publication Data

US 2022/0080156 A1   Mar. 17, 2022

Related U.S. Application Data

(63) Continuation-in-part of application No. 16/572,330, filed on Sep. 16, 2019, and a continuation-in-part of application No. 16/572,307, filed on Sep. 16, 2019.
(Continued)

(51) Int. Cl.
*A61M 25/00* (2006.01)
*A61M 25/02* (2006.01)

(52) U.S. Cl.
CPC .......... *A61M 25/02* (2013.01); *A61M 25/005* (2013.01); *A61M 25/0045* (2013.01); *A61M 25/0012* (2013.01); *A61M 2025/0293* (2013.01)

(58) Field of Classification Search
CPC .......... A61M 25/0012; A61M 25/0052; A51M 25/005
See application file for complete search history.

(56) References Cited

U.S. PATENT DOCUMENTS 4,478,898 A   10/1984   Kato
4,547,193 A   10/1985   Rydell
(Continued)

FOREIGN PATENT DOCUMENTS

WO   WO2001010492 A1   2/2001
WO   WO2005004969 A1   1/2005
(Continued)

OTHER PUBLICATIONS

Midgley, Measurements of the X-ray linear attenuation coefficient for low atomic number materials at energies 32-66 and 140keV, Mar. 2005, Radiation Physics and Chemistry, vol. 72, Iss. 11, pp. 525-535 (Year: 2004).
(Continued)

*Primary Examiner* — William R Carpenter
(74) *Attorney, Agent, or Firm* — Christensen, Fonder, Dardi & Herbert PLLC

(57) ABSTRACT

A device for guiding and supporting a stent delivery catheter and other catheters is disclosed. The device may comprise a tubular guiding member and an elongated positioning member extending in a proximal direction beyond the tubular guiding member for advancing and retracting the tubular guiding member in distal and proximal directions. A distal portion of the elongate positioning member may be coupled to the proximal portion of the tubular guide. In embodiments, the device includes a ribbon having a distal portion and a proximal portion. In embodiments, the distal portion of the ribbon extends distally into the tubular guiding member and the proximal portion of the ribbon overlays an inner surface of the elongate positioning member. Methods for making medical devices and portions of medical devices (e.g., intravascular catheters, catheter shafts, and tubular guiding members) are also provided. Example methods may include providing a first ribbon comprising one or more
(Continued)

thermoplastic materials and a piece of shrink tubing defining a shrink tube lumen and forming a first assembly by positioning the first ribbon inside the shrink tube lumen and urging the first ribbon to assume a tubular shape in which the first ribbon defines a ribbon lumen. A second assembly may be formed by loading an inner tubular member over a mandrel and forming or placing a support structure over an outer surface of the inner tubular member. A third assembly may be formed by inserting the second assembly into the ribbon lumen defined by the first ribbon of the first assembly. The third assembly may be heated to a process temperature.

13 Claims, 95 Drawing Sheets

Related U.S. Application Data

(60) Provisional application No. 62/900,645, filed on Sep. 15, 2019, provisional application No. 62/999,929, filed on Sep. 13, 2019, provisional application No. 62/732,282, filed on Sep. 17, 2018.

(56) References Cited

U.S. PATENT DOCUMENTS

| | | |
|---|---|---|
| 4,636,346 A | 1/1987 | Gold et al. |
| 5,047,045 A | 9/1991 | Arney et al. |
| 5,120,323 A | 6/1992 | Shockey et al. |
| 5,217,440 A | 6/1993 | Frassica |
| 5,400,785 A | 3/1995 | Crowley |
| 5,439,445 A | 8/1995 | Kontos |
| 5,540,707 A | 7/1996 | Ressemann et al. |
| 5,569,221 A | 10/1996 | Houser et al. |
| 5,628,787 A | 5/1997 | Mayer |
| 5,667,499 A | 9/1997 | Welch et al. |
| 5,695,468 A | 12/1997 | Lafontaine et al. |
| 5,785,685 A | 7/1998 | Kugler et al. |
| 5,836,868 A | 11/1998 | Ressemann et al. |
| 5,897,567 A | 4/1999 | Ressemann et al. |
| 5,911,715 A | 6/1999 | Berg et al. |
| 5,980,486 A | 11/1999 | Enger |
| 6,092,526 A | 7/2000 | LaFontaine et al. |
| 6,129,756 A | 10/2000 | Kugler et al. |
| 6,183,443 B1 | 2/2001 | Kratoska et al. |
| 6,217,566 B1 | 4/2001 | Ju et al. |
| 6,273,909 B1 | 8/2001 | Kugler et al. |
| 6,280,466 B1 | 8/2001 | Kugler et al. |
| 6,443,158 B1 | 9/2002 | LaFontaine et al. |
| 6,508,806 B1 | 1/2003 | Hoste |
| 6,517,572 B2 | 2/2003 | Kugler et al. |
| 6,652,572 B2 | 11/2003 | Kugler et al. |
| 6,790,222 B2 | 9/2004 | Kugler et al. |
| 6,884,260 B2 | 4/2005 | Kugler et al. |
| 6,939,371 B2 | 9/2005 | Kugler et al. |
| 6,991,617 B2 | 1/2006 | Hektner et al. |
| 7,112,217 B1 | 9/2006 | Kugler et al. |
| 7,306,585 B2 | 12/2007 | Ross |
| 7,316,678 B2 | 1/2008 | Nash et al. |
| 7,445,010 B2 | 11/2008 | Kugler et al. |
| 7,497,822 B1 | 3/2009 | Kugler et al. |
| 7,553,387 B2* | 6/2009 | Leeflang .......... B32B 1/08 156/218 |
| 7,604,612 B2 | 10/2009 | Ressemann et al. |
| 7,644,714 B2 | 1/2010 | Atkinson et al. |
| 7,695,427 B2 | 4/2010 | Kugler et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 7,896,825 B2 | 3/2011 | Atkinson et al. |
| 7,918,870 B2 | 4/2011 | Kugler et al. |
| 7,938,819 B2 | 5/2011 | Kugler et al. |
| 8,025,655 B2 | 9/2011 | Kugler et al. |
| 8,048,032 B2 | 11/2011 | Root et al. |
| 8,083,727 B2 | 12/2011 | Kugler et al. |
| 8,142,413 B2 | 3/2012 | Root et al. |
| 8,172,863 B2 | 5/2012 | Robinson et al. |
| 8,187,164 B2 | 5/2012 | Kugler et al. |
| 8,202,246 B2 | 6/2012 | Kugler et al. |
| 8,292,850 B2 | 10/2012 | Root et al. |
| 8,323,261 B2 | 12/2012 | Kugler et al. |
| 8,337,425 B2 | 12/2012 | Olson et al. |
| 8,496,679 B2 | 7/2013 | Robinson et al. |
| 8,512,310 B2 | 8/2013 | Kugler et al. |
| 8,632,556 B2 | 1/2014 | Jacobs et al. |
| 8,636,712 B2 | 1/2014 | Kugler et al. |
| 8,709,028 B2 | 4/2014 | Robinson et al. |
| 8,753,312 B2 | 6/2014 | Bowe et al. |
| RE45,380 E | 2/2015 | Root et al. |
| 8,961,494 B2 | 2/2015 | Kugler et al. |
| 8,996,095 B2 | 3/2015 | Anderson et al. |
| 9,005,225 B2 | 4/2015 | Robinson et al. |
| 9,060,802 B2 | 6/2015 | Kugler et al. |
| RE45,760 E | 10/2015 | Root et al. |
| RE45,776 E | 10/2015 | Root et al. |
| 9,237,897 B2 | 1/2016 | Kugler et al. |
| 9,308,019 B2 | 4/2016 | Kugler et al. |
| 9,351,747 B2 | 5/2016 | Kugler et al. |
| 9,352,123 B2 | 5/2016 | Zhou et al. |
| RE46,116 E | 8/2016 | Root et al. |
| 9,486,611 B2 | 11/2016 | Petersen et al. |
| 9,717,889 B2 | 8/2017 | Kugler et al. |
| 9,764,118 B2 | 9/2017 | Anderson et al. |
| 9,782,561 B2 | 10/2017 | Kugler et al. |
| 9,788,855 B2 | 10/2017 | Kugler et al. |
| 9,872,685 B2 | 1/2018 | Kugler et al. |
| 9,878,128 B2 | 1/2018 | Kugler et al. |
| 9,943,314 B2 | 4/2018 | Kugler et al. |
| 9,968,763 B2 | 5/2018 | Root et al. |
| 9,993,613 B2 | 6/2018 | Wang et al. |
| 10,016,188 B2 | 7/2018 | Jacobs et al. |
| 10,124,147 B2* | 11/2018 | Anderson ......... A61M 25/0905 |
| 10,124,148 B2 | 11/2018 | Falk et al. |
| 10,143,487 B2 | 12/2018 | Kugler et al. |
| 10,159,821 B2 | 12/2018 | Root et al. |
| 10,166,035 B2 | 1/2019 | Kugler et al. |
| 10,173,052 B2 | 1/2019 | Daniels et al. |
| 10,245,050 B2 | 4/2019 | Kugler |
| RE47,379 E | 5/2019 | Root et al. |
| 10,315,010 B2 | 6/2019 | Kugler et al. |
| 10,342,569 B2 | 7/2019 | Kugler et al. |
| 10,390,849 B2 | 8/2019 | Kugler et al. |
| 10,391,305 B2 | 8/2019 | Asleson et al. |
| 10,398,440 B2 | 9/2019 | Kugler et al. |
| 10,448,940 B2 | 10/2019 | Jacobs et al. |
| 2001/0016702 A1 | 8/2001 | Benjamin |
| 2001/0053931 A1 | 12/2001 | Hess et al. |
| 2002/0143360 A1 | 10/2002 | Douk et al. |
| 2003/0125709 A1 | 7/2003 | Eidenschink |
| 2004/0010280 A1 | 1/2004 | Adams et al. |
| 2004/0116832 A1 | 6/2004 | Friedrich et al. |
| 2004/0122360 A1 | 6/2004 | Waldhauser et al. |
| 2005/0015073 A1 | 1/2005 | Kataishi et al. |
| 2005/0119616 A1 | 6/2005 | Goodin et al. |
| 2007/0260219 A1 | 11/2007 | Root et al. |
| 2008/0125752 A1 | 5/2008 | Gunderson et al. |
| 2009/0024110 A1 | 1/2009 | Heideman et al. |
| 2009/0196178 A1 | 8/2009 | Stewart et al. |
| 2009/0198178 A1 | 8/2009 | Gurm |
| 2009/0240235 A1 | 9/2009 | Murata |
| 2010/0324567 A1 | 12/2010 | Root et al. |
| 2011/0208164 A1 | 8/2011 | Pal |
| 2012/0165756 A1 | 6/2012 | Root et al. |
| 2014/0012281 A1* | 1/2014 | Wang ............... A61M 25/0023 606/108 |
| 2014/0039461 A1 | 2/2014 | Anderson et al. |
| 2014/0052097 A1 | 2/2014 | Petersen et al. |
| 2014/0081243 A1* | 3/2014 | Zhou ............... A61M 25/0069 604/524 |
| 2015/0151090 A1 | 6/2015 | Sutton et al. |
| 2015/0246209 A1 | 9/2015 | Holzer |
| 2015/0320971 A1 | 11/2015 | Ng et al. |
| 2016/0101261 A1 | 4/2016 | Kugler et al. |

(56) References Cited

U.S. PATENT DOCUMENTS

| | | |
|---|---|---|
| 2016/0114126 A1 | 4/2016 | Heideman et al. |
| 2016/0121080 A1* | 5/2016 | Cottone ............ A61M 25/0023 604/528 |
| 2016/0346502 A1* | 12/2016 | Fuller .................. A61M 25/04 |
| 2016/0346515 A1 | 12/2016 | Buller et al. |
| 2017/0028170 A1 | 2/2017 | Ho |
| 2017/0087339 A1 | 3/2017 | Taber |
| 2017/0252043 A1 | 9/2017 | Fuller et al. |
| 2017/0296783 A1 | 10/2017 | Connolly et al. |
| 2017/0354800 A1 | 12/2017 | O'Donovan |
| 2018/0028177 A1 | 2/2018 | Van Oepen et al. |
| 2018/0104445 A1 | 4/2018 | Fuller et al. |
| 2018/0161547 A1 | 6/2018 | Brenizer et al. |
| 2019/0030283 A2 | 1/2019 | Cottone |
| 2019/0117938 A1 | 4/2019 | Norman et al. |
| 2019/0151607 A9 | 5/2019 | O'Connell et al. |
| 2019/0160259 A1* | 5/2019 | Cottone ............. A61M 25/0113 |
| 2019/0247619 A1 | 8/2019 | Brenizer et al. |
| 2019/0255297 A1 | 8/2019 | Fischell et al. |
| 2019/0255299 A1 | 8/2019 | Fischell et al. |
| 2020/0155732 A1 | 5/2020 | Rangwala et al. |

FOREIGN PATENT DOCUMENTS

| | | |
|---|---|---|
| WO | WO2006020044 A1 | 2/2006 |
| WO | WO2006039392 A2 | 4/2006 |
| WO | WO2009085486 A1 | 7/2009 |
| WO | WO2013070758 | 5/2013 |
| WO | WO2013185148 | 12/2013 |
| WO | WO2014043694 | 3/2014 |
| WO | WO 2020/061076 A1 | 3/2020 |
| WO | WO 2020/061088 A1 | 3/2020 |

OTHER PUBLICATIONS

Saeko Takahashi, et al., New Method to Increase a Backup Support of a 6 French Guiding Coronary Catheter, Catheterization and Cardiovascular Interventions 63:452-456 (2004).

International Search Report for Application No. PCT/US2019/51554, dated Dec. 4, 2019, 2 pages.

International Search Report for Application No. PCT/US2019/051569, dated Nov. 20, 2019, 2 pages.

* cited by examiner

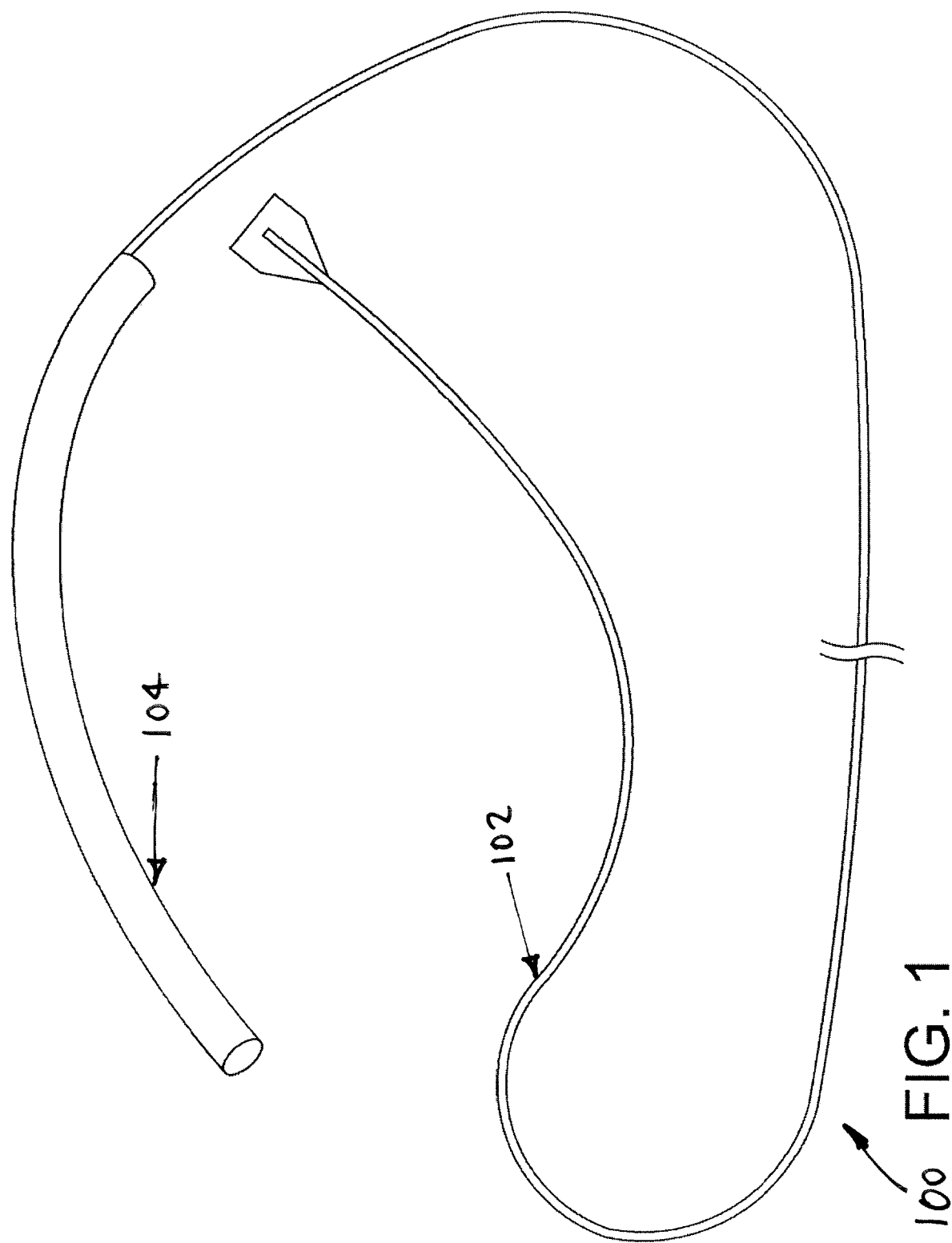

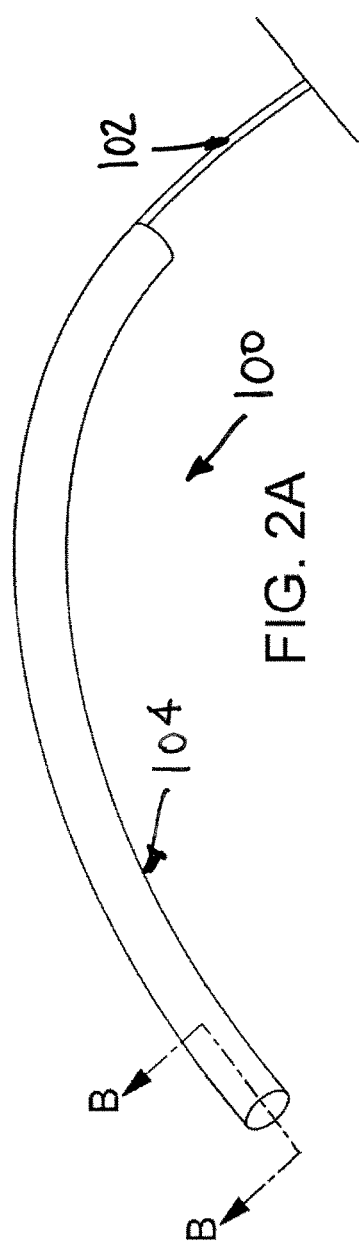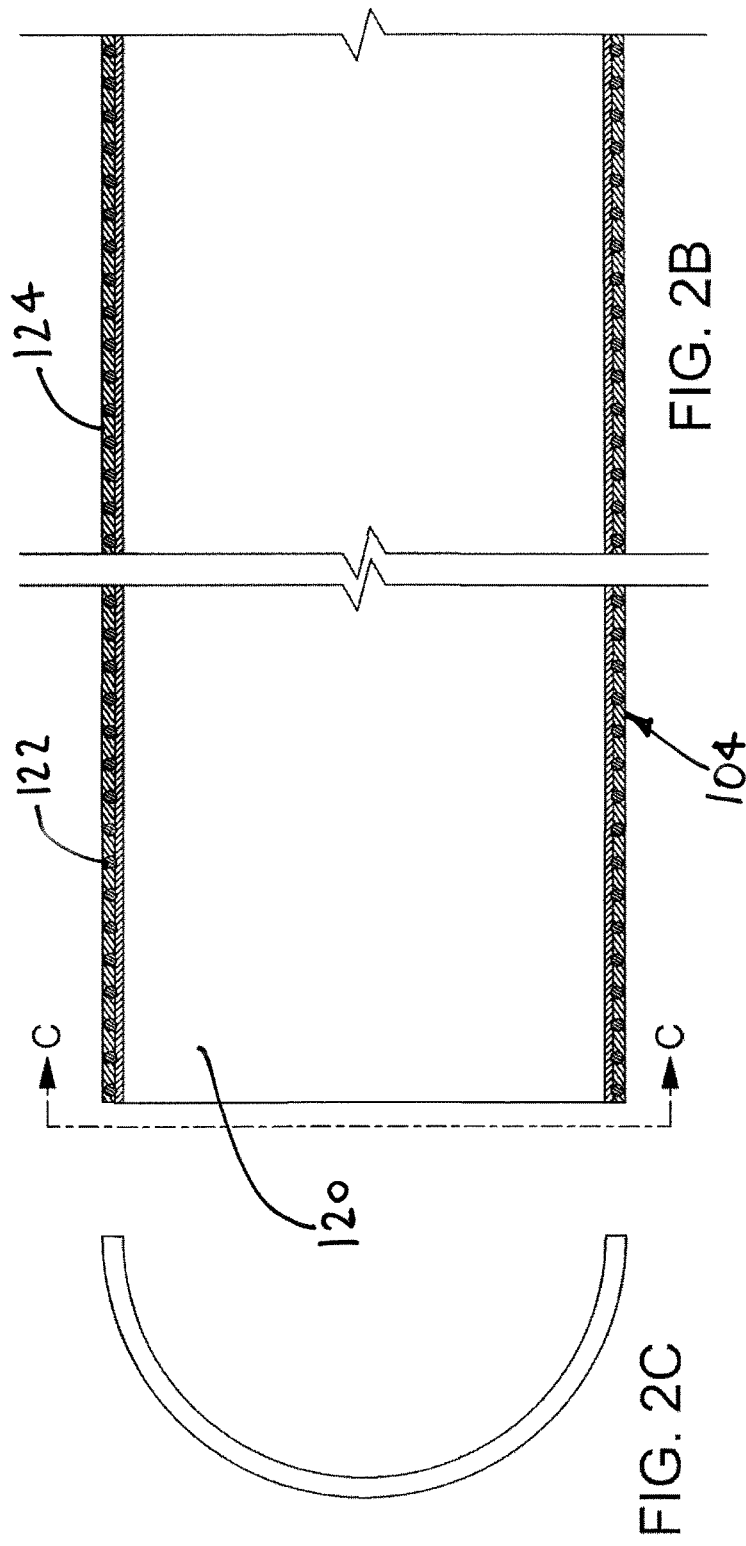

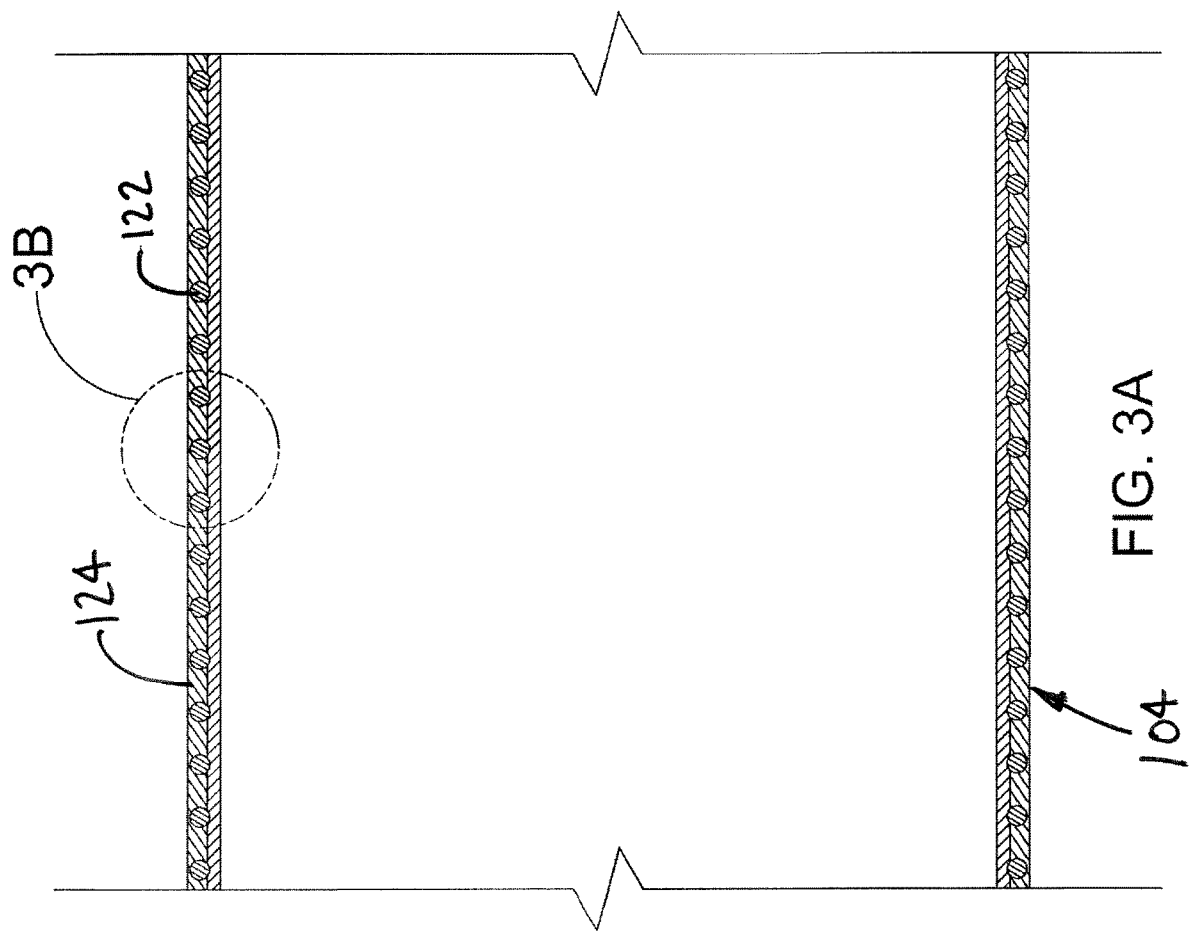

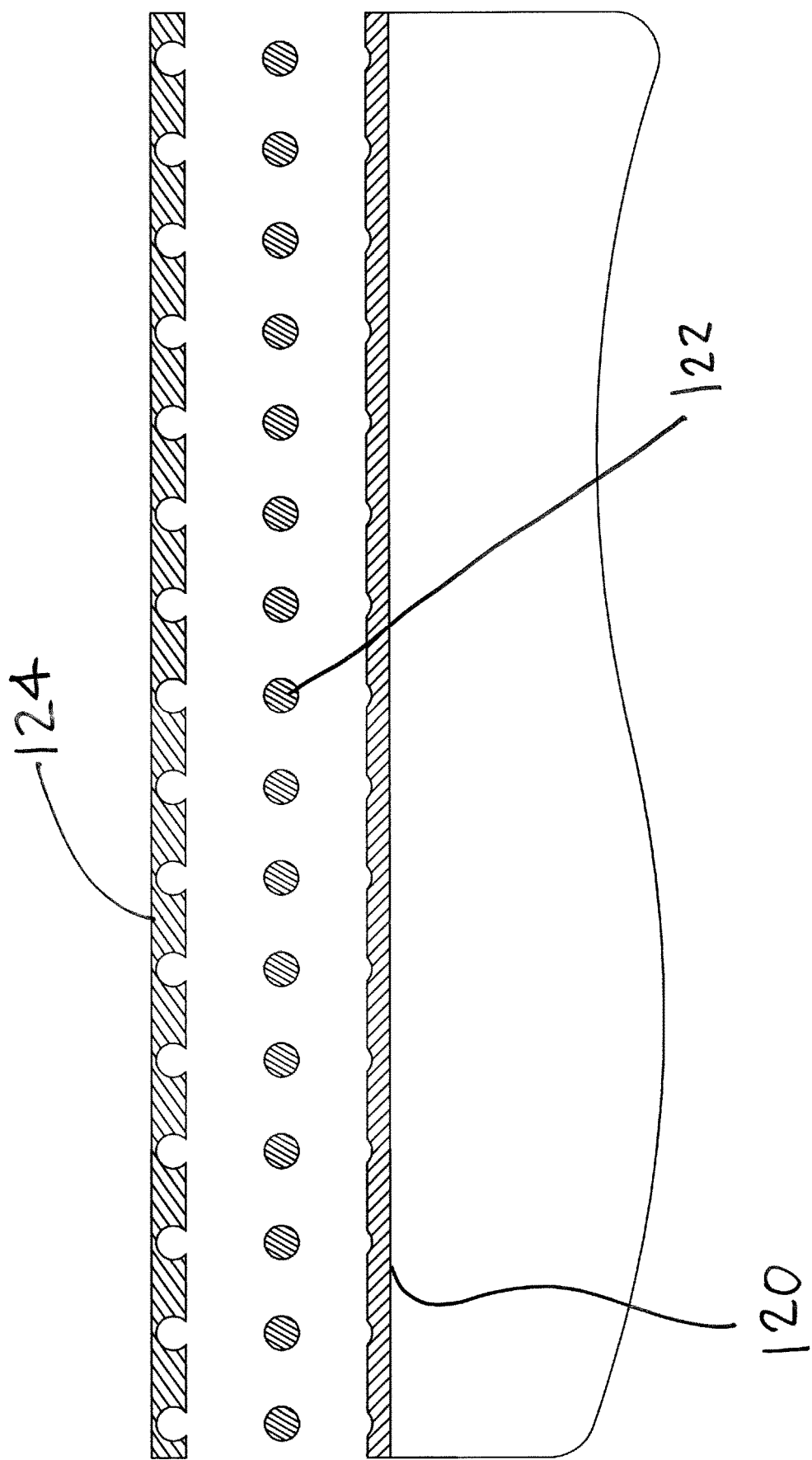

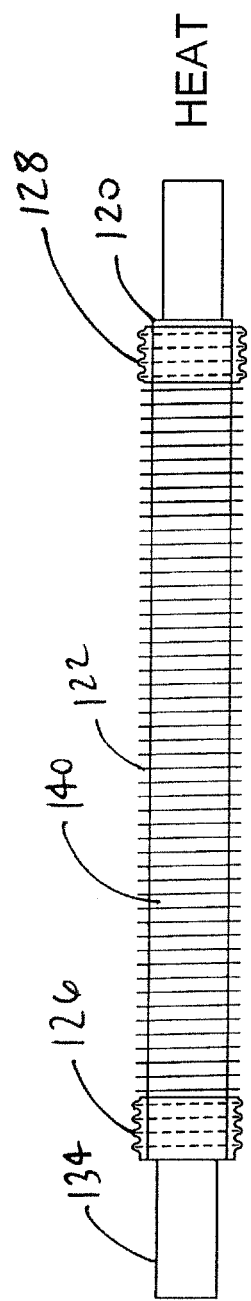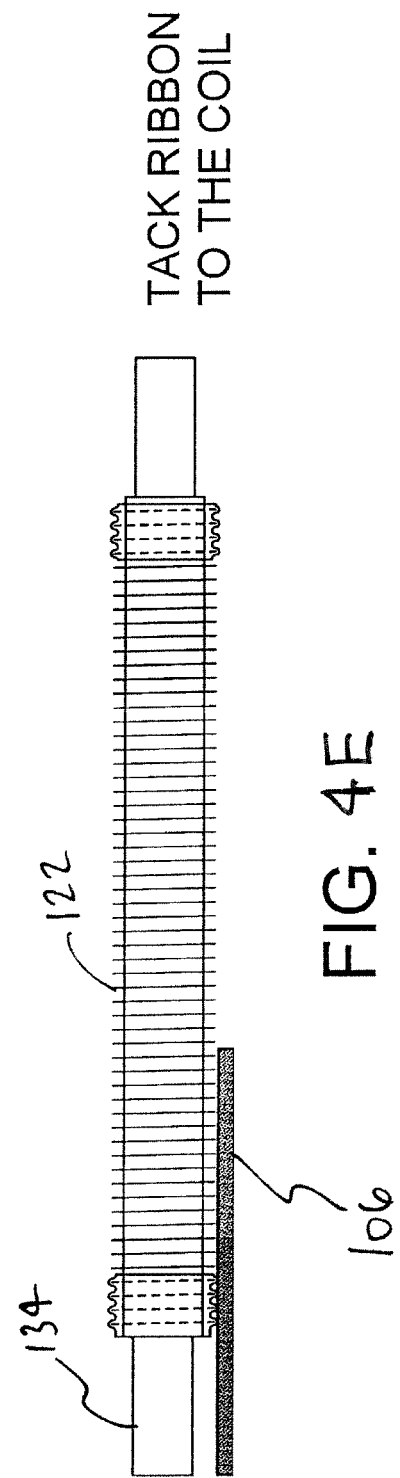
FIG. 4D
FIG. 4E

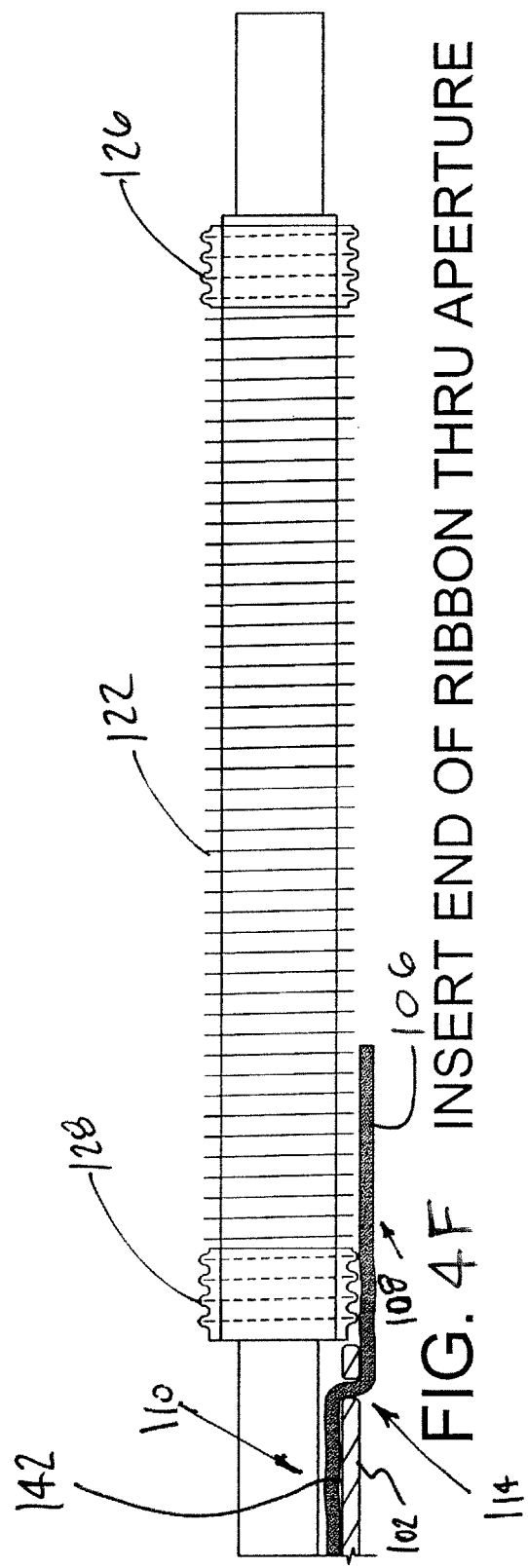
FIG. 4F INSERT END OF RIBBON THRU APERTURE
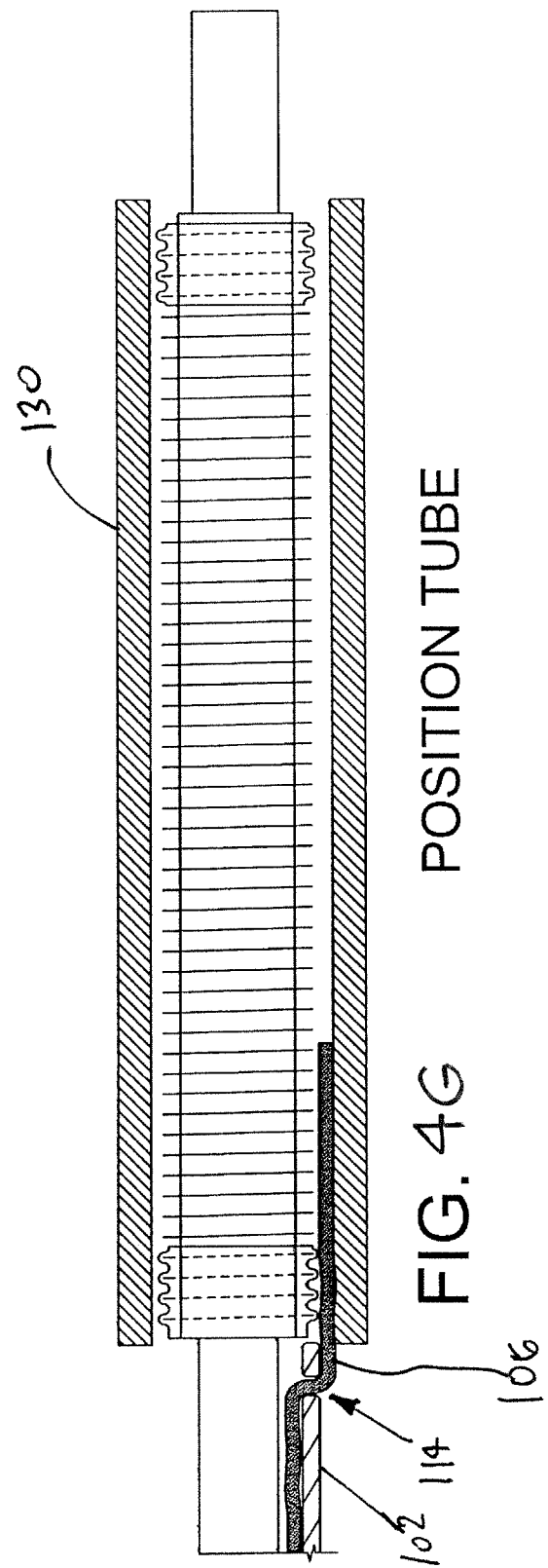
FIG. 4G POSITION TUBE

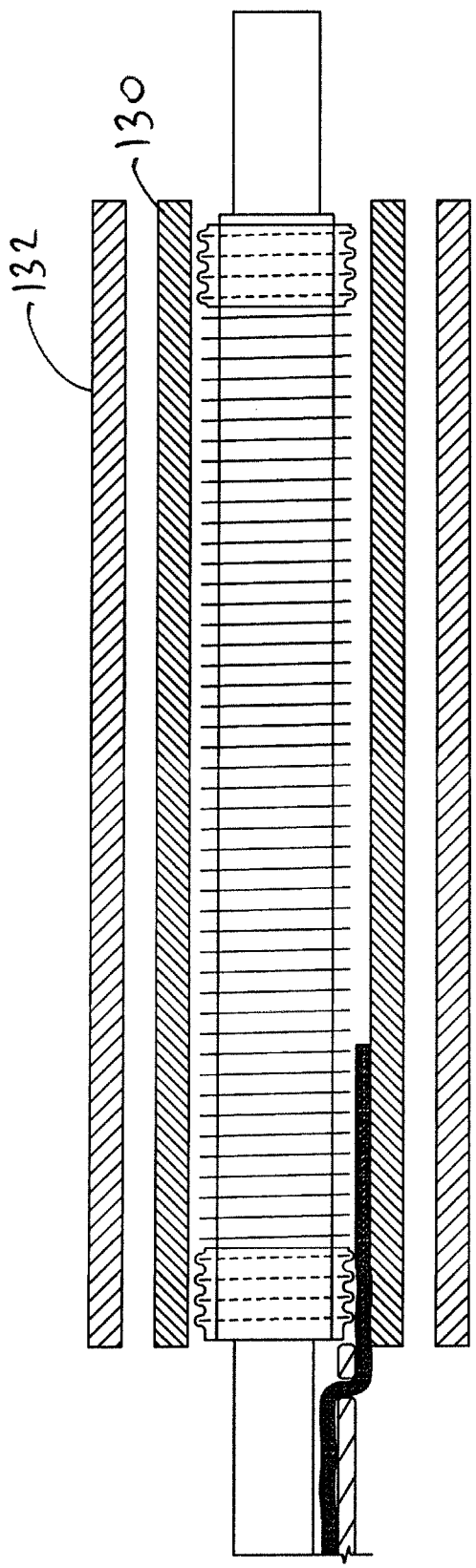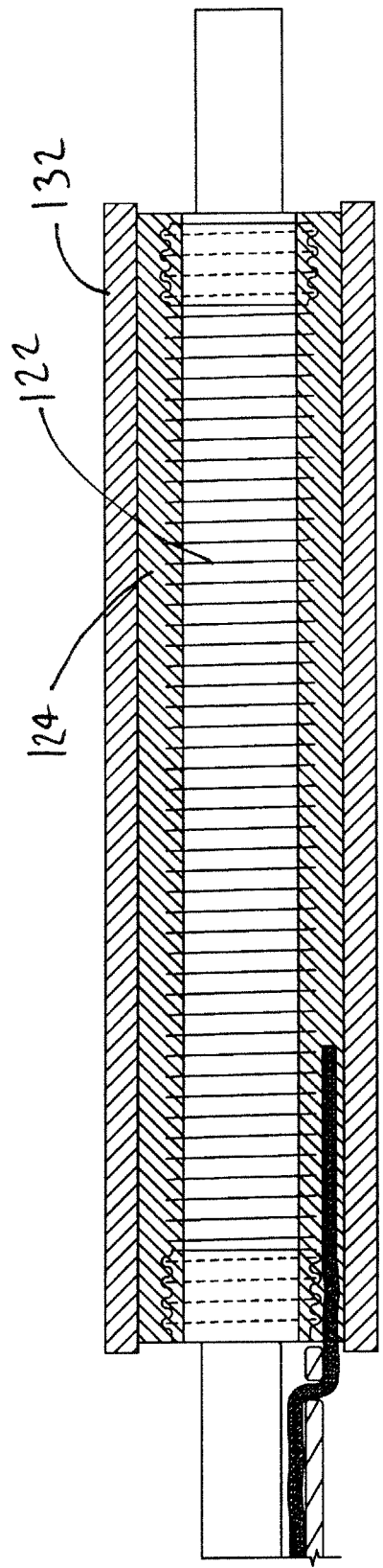
FIG. 4H POSITION SHRINK TUBING
FIG. 4I HEAT

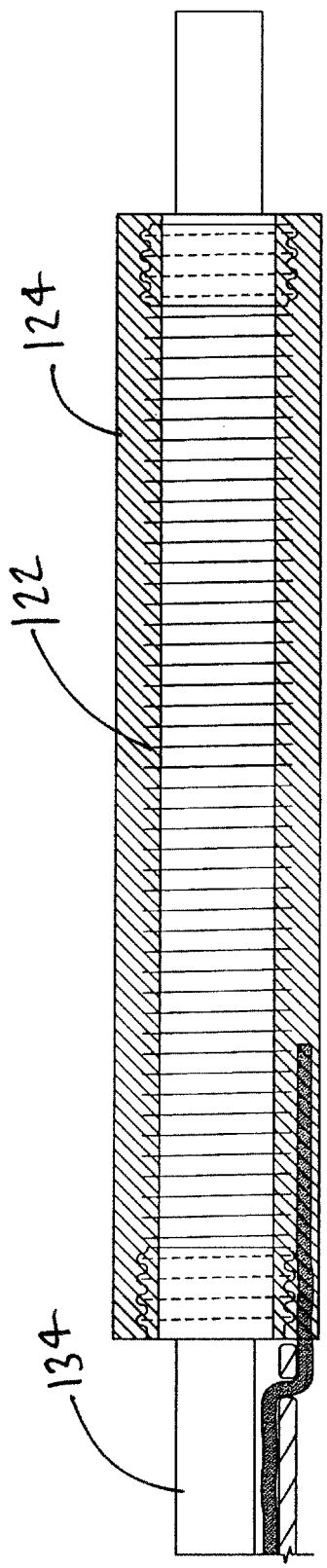
FIG. 4J  REMOVE SHRINK TUBING
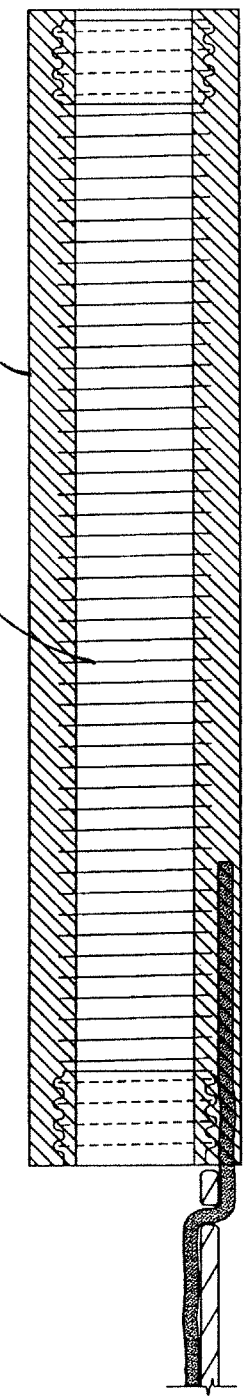
FIG. 4K  REMOVE MANDREL

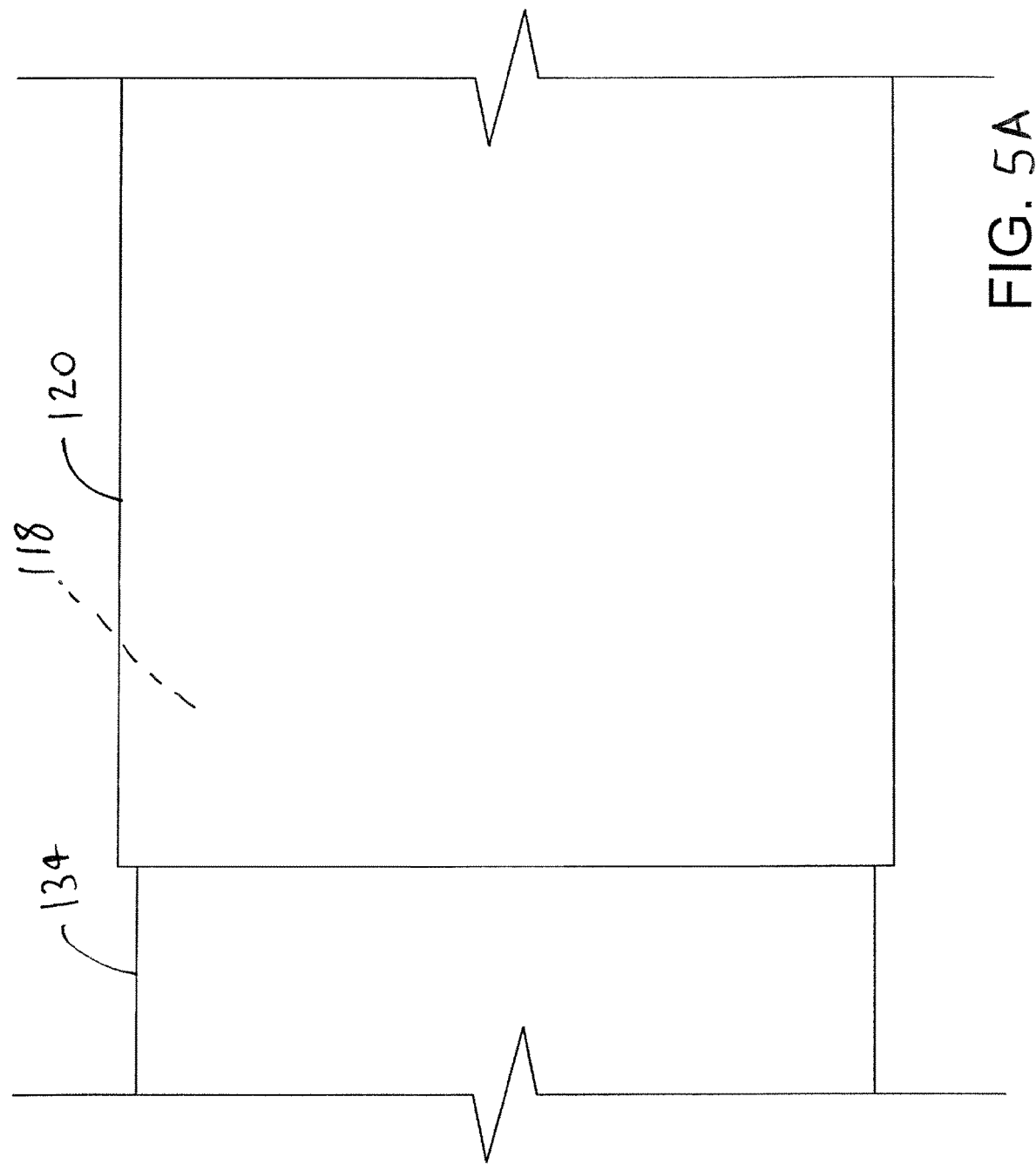

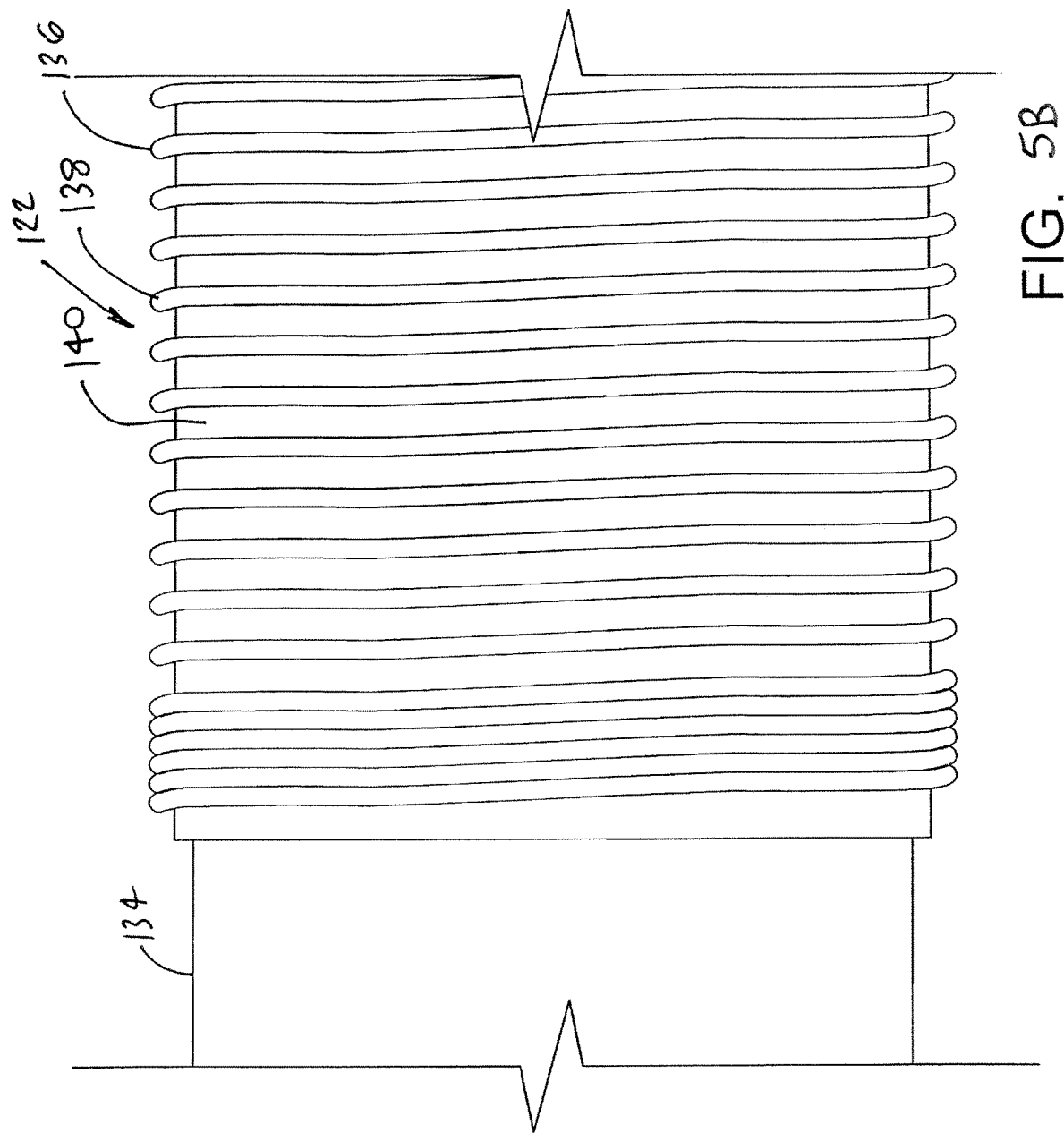

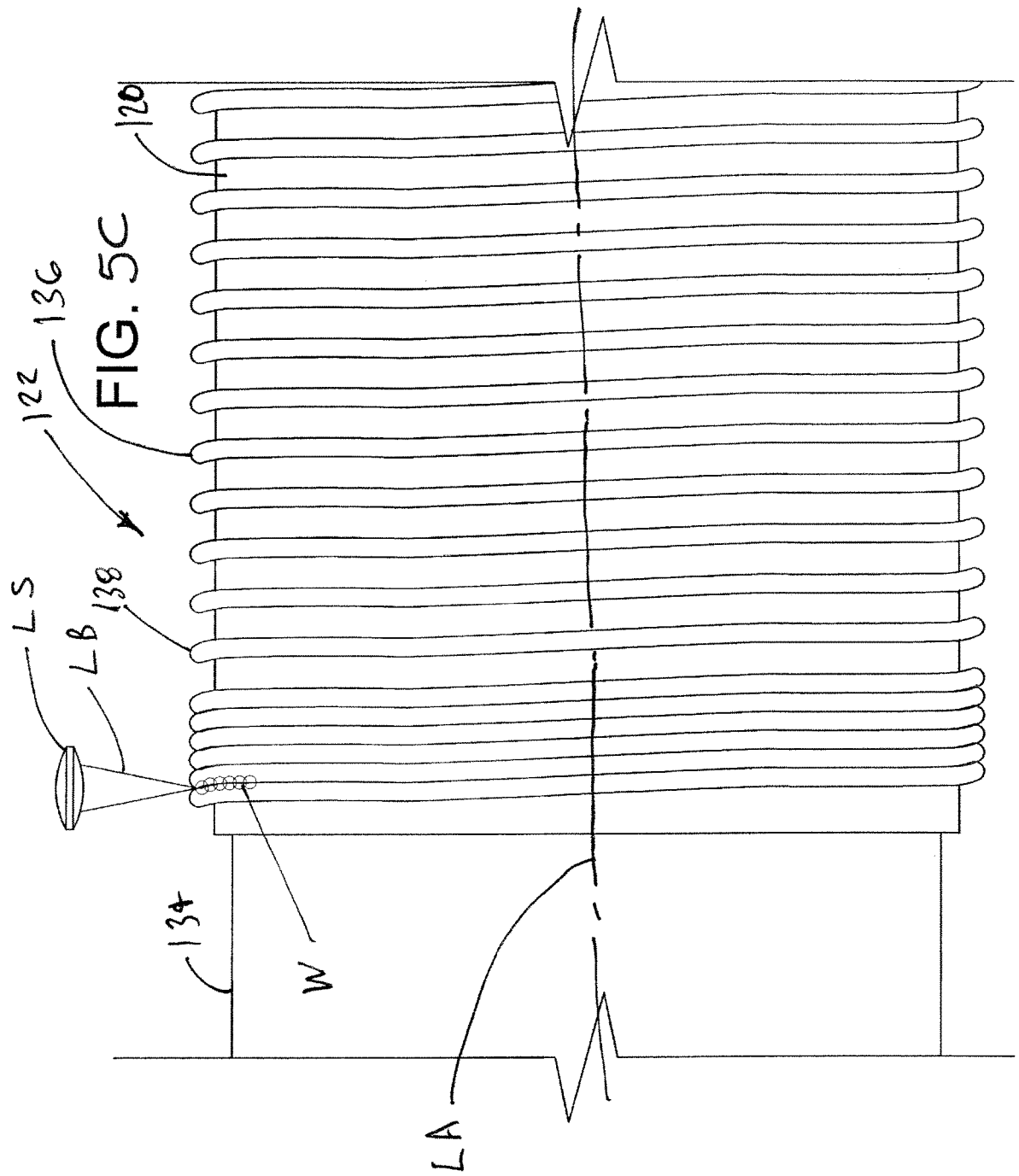

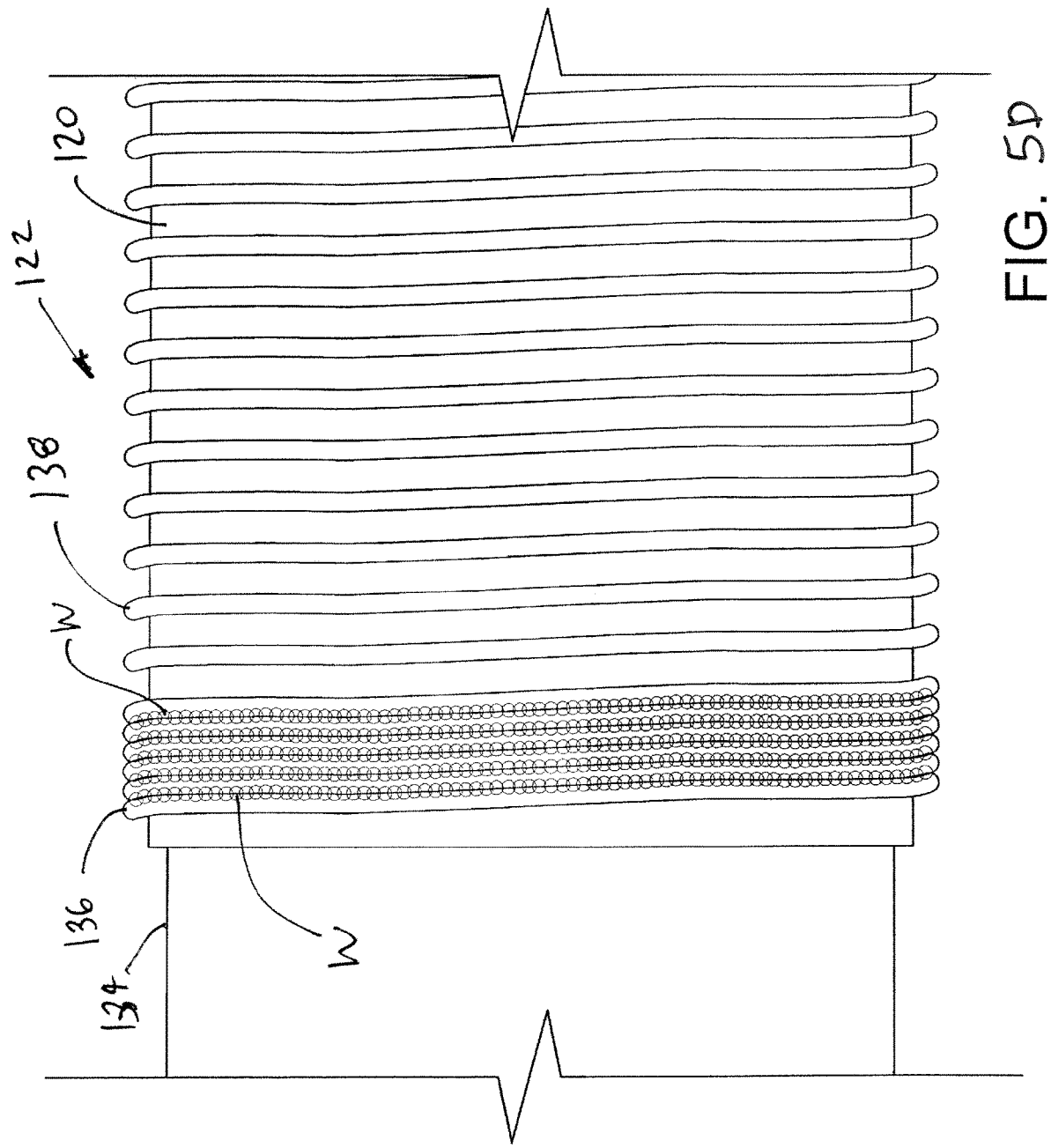

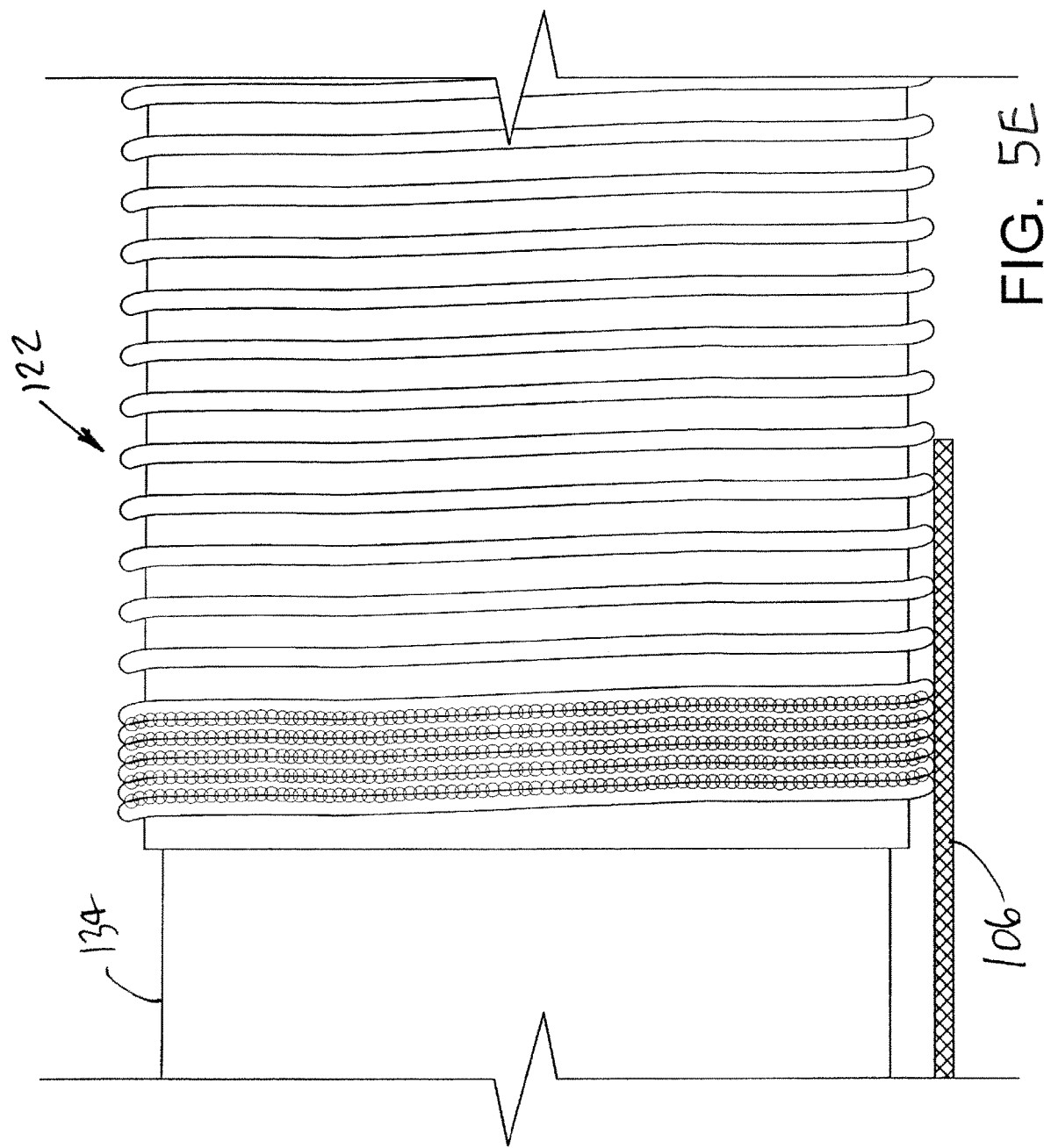

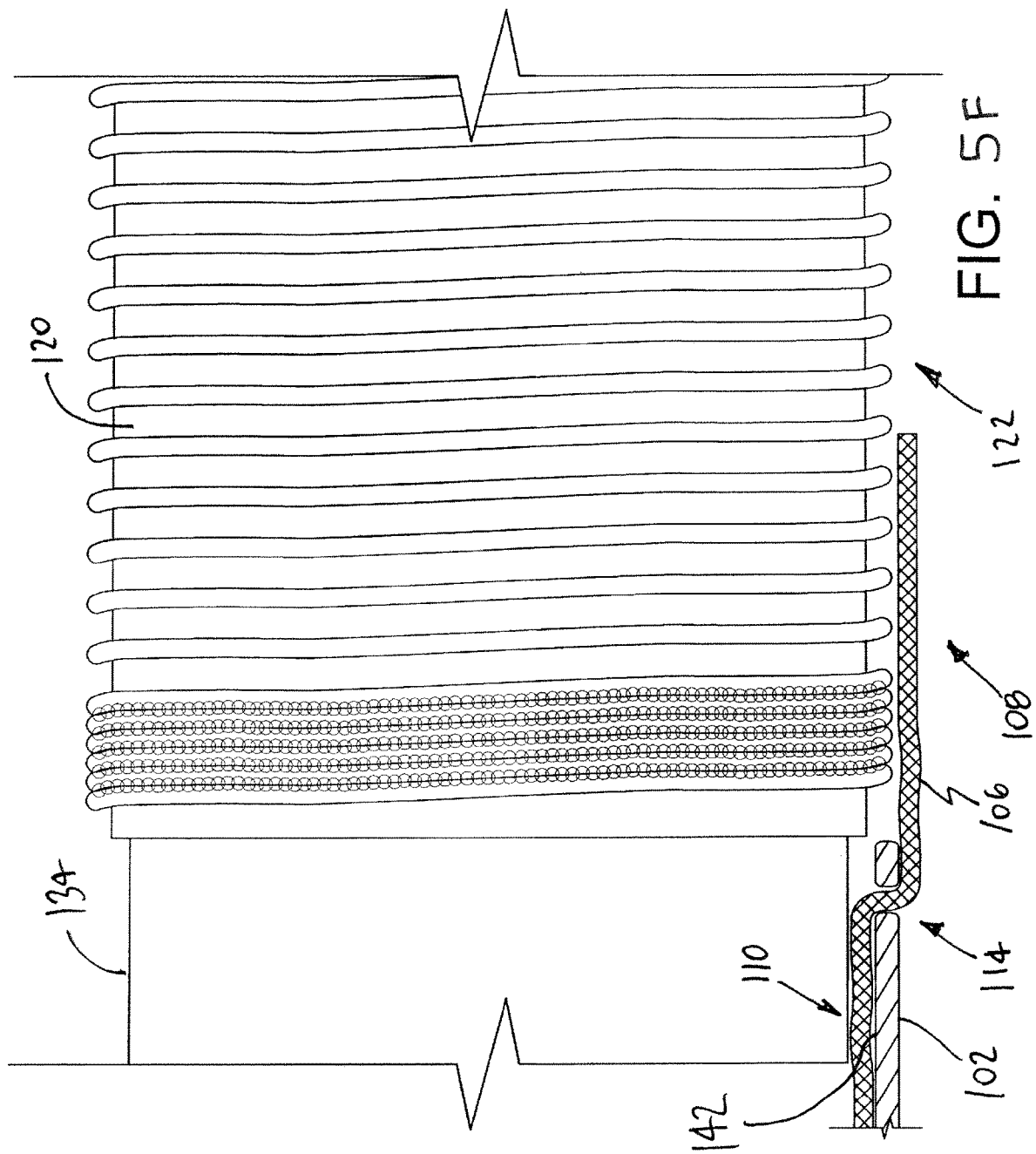

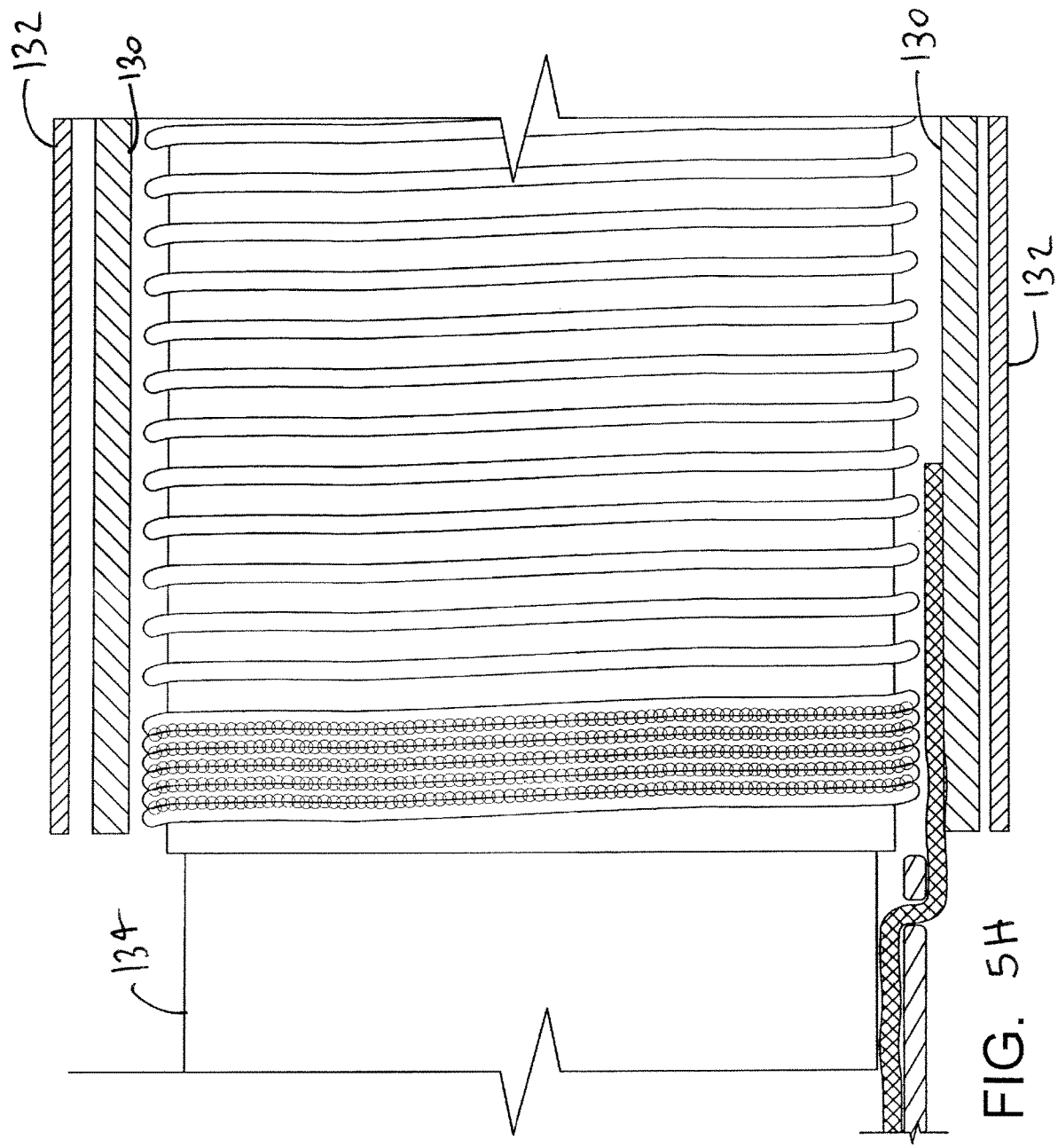

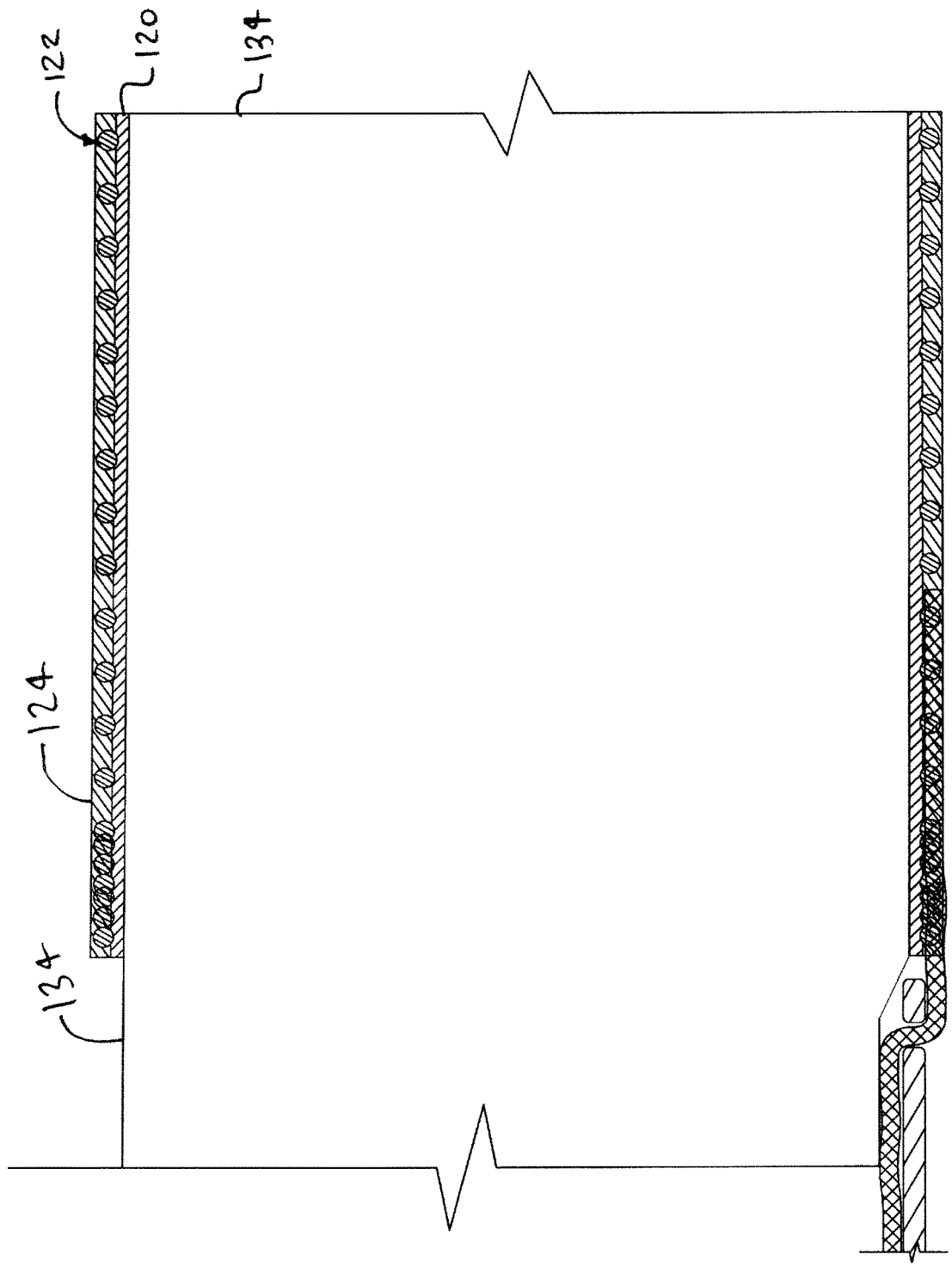

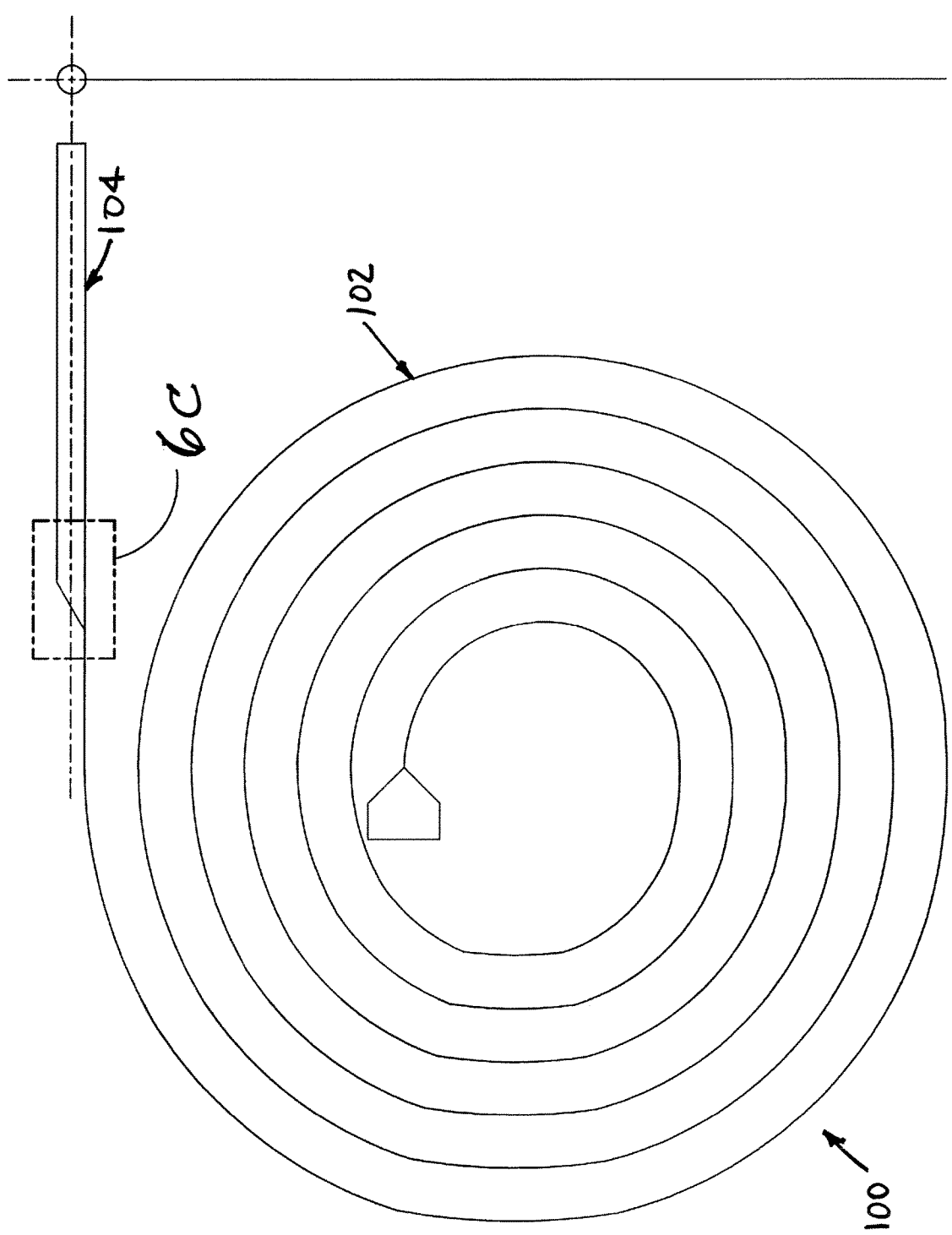

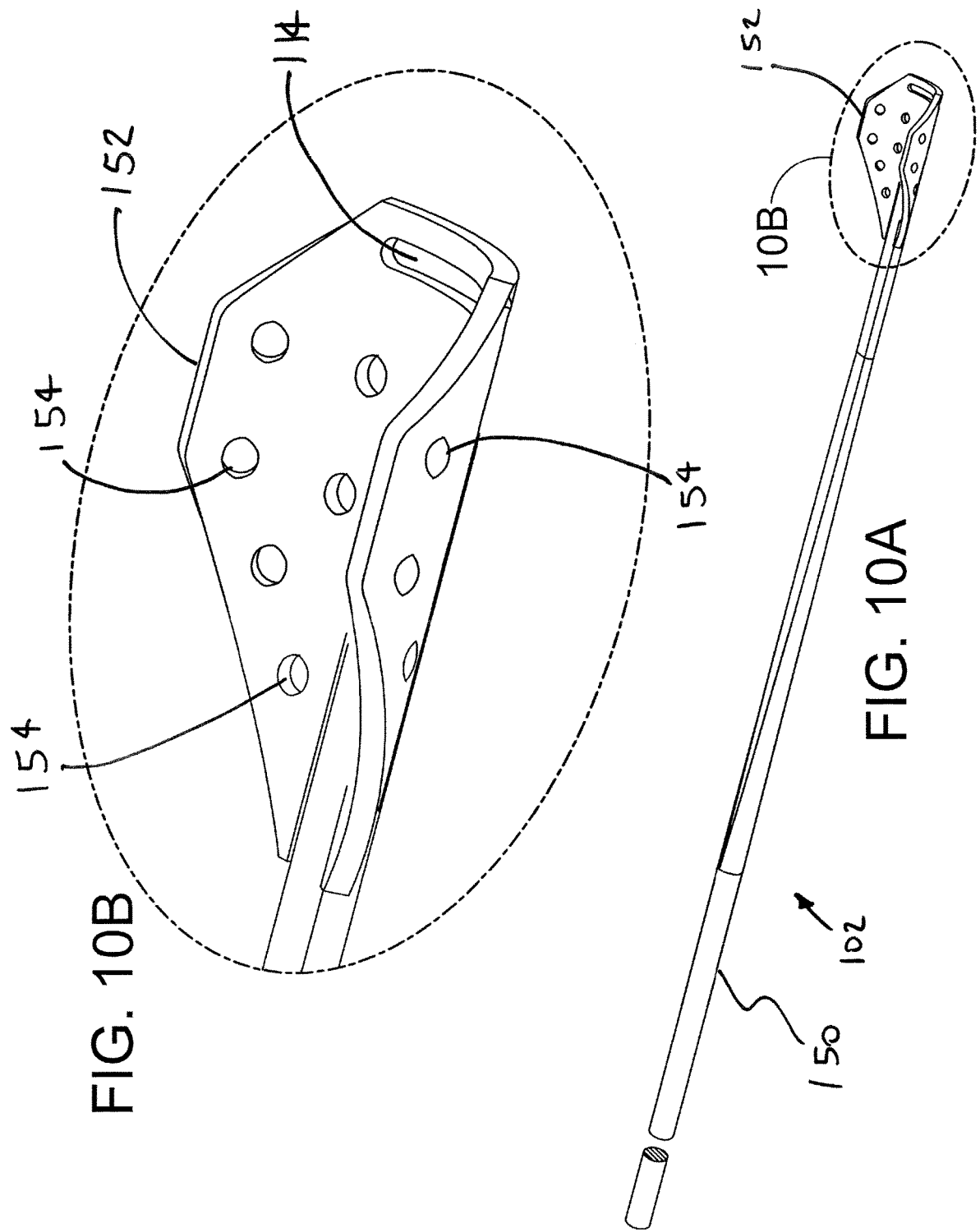

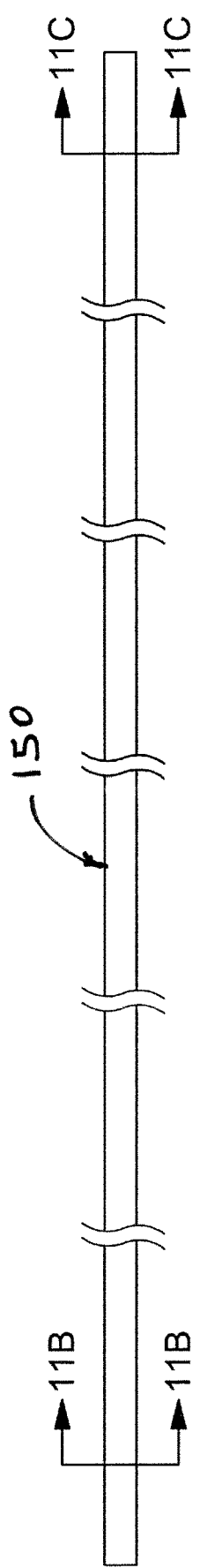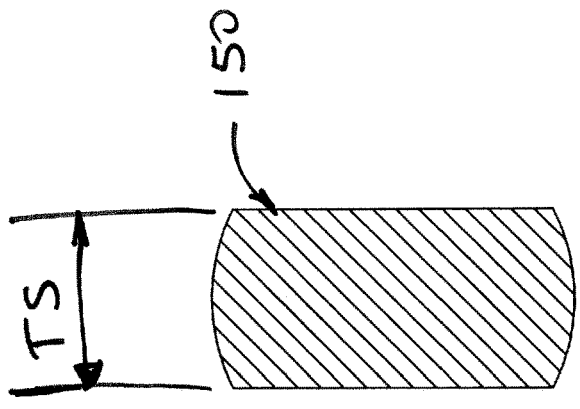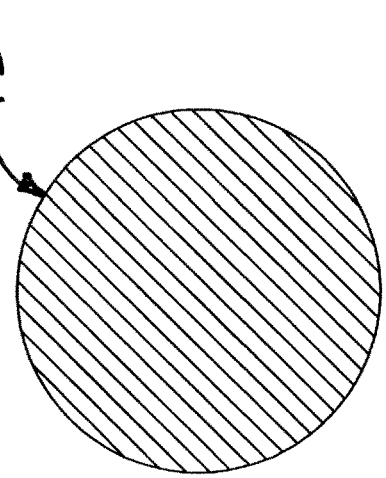

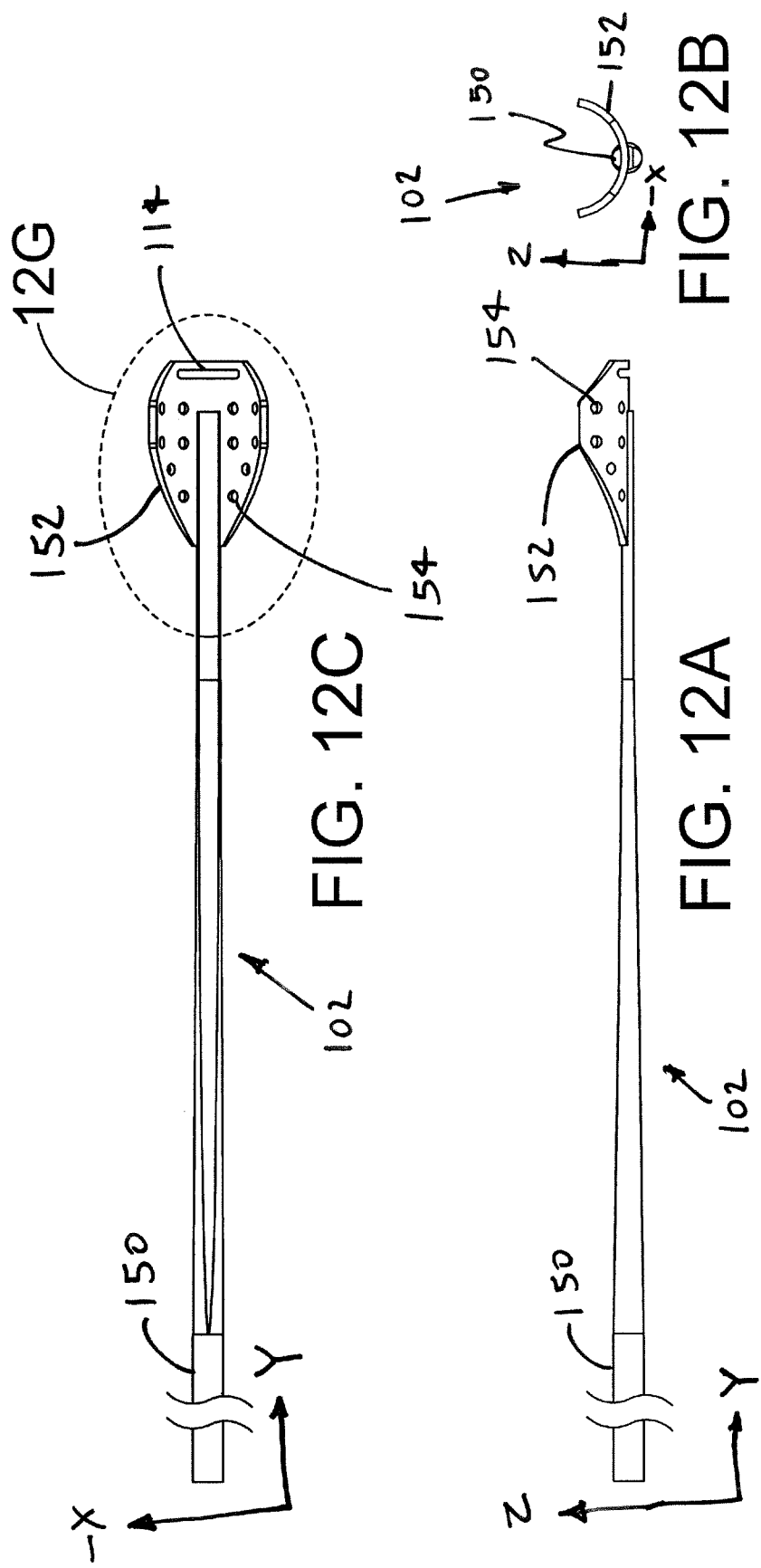

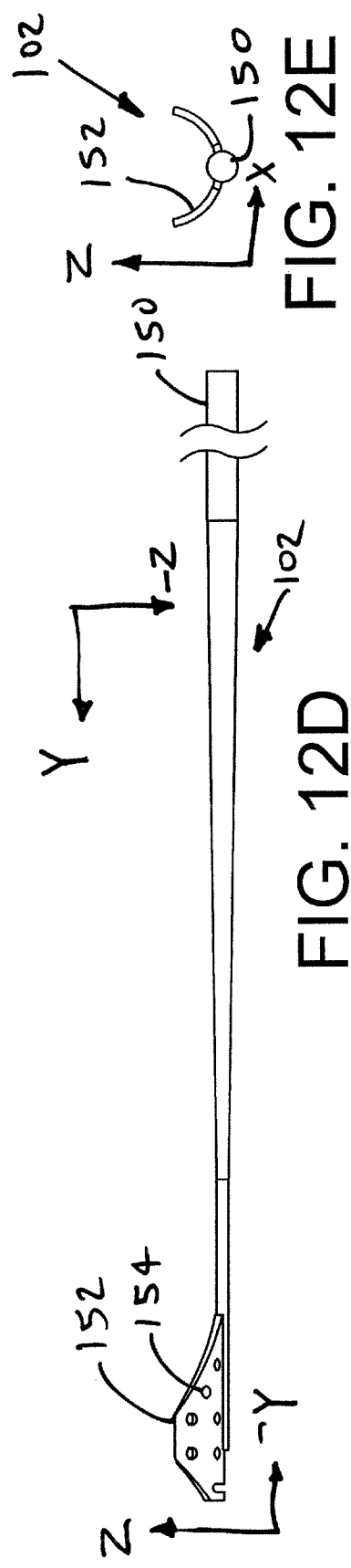
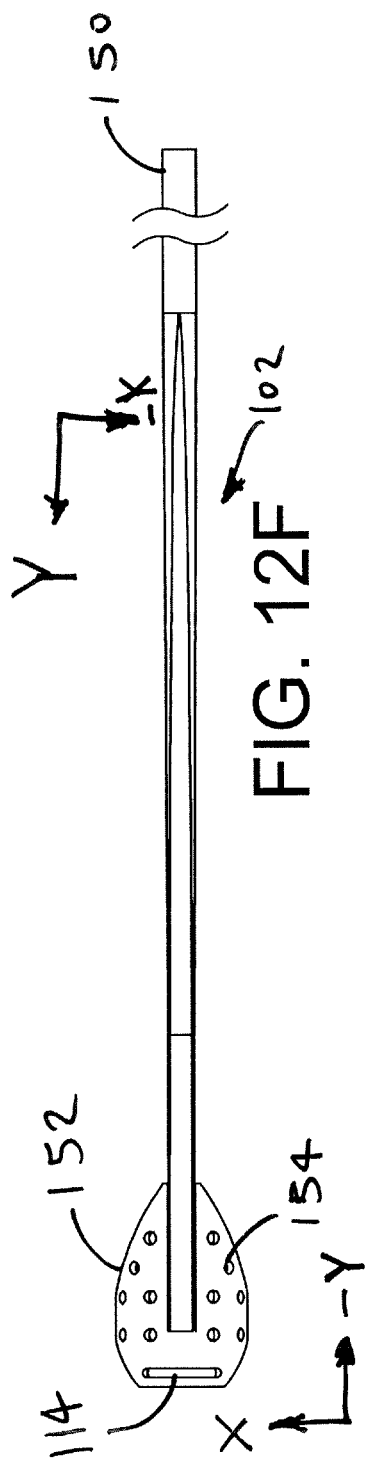
FIG. 12D
FIG. 12E
FIG. 12F

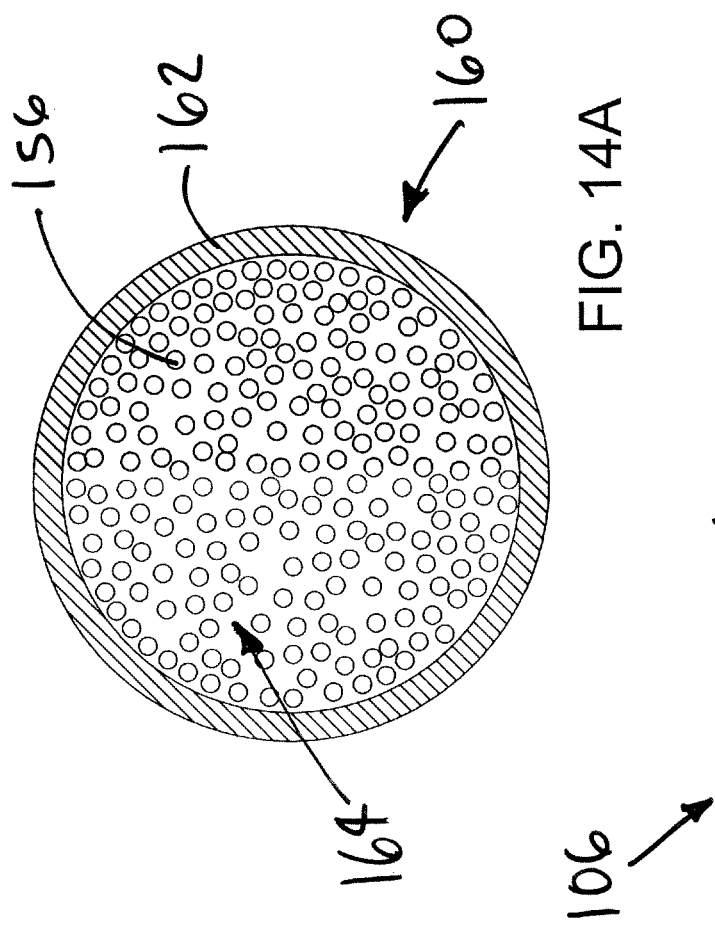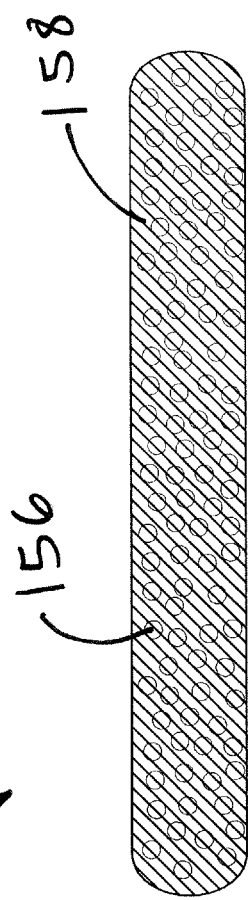
FIG. 14A
FIG. 14B

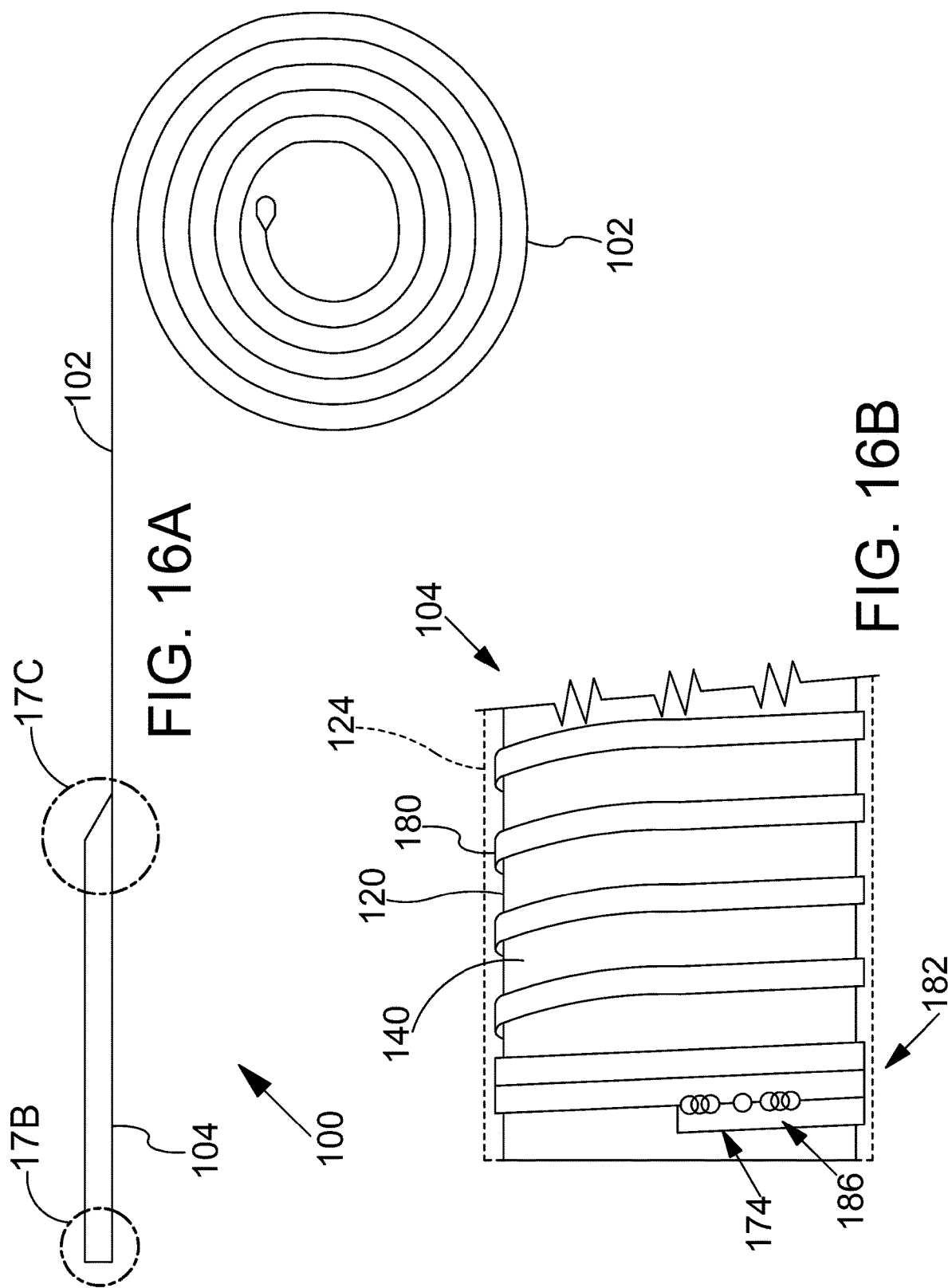

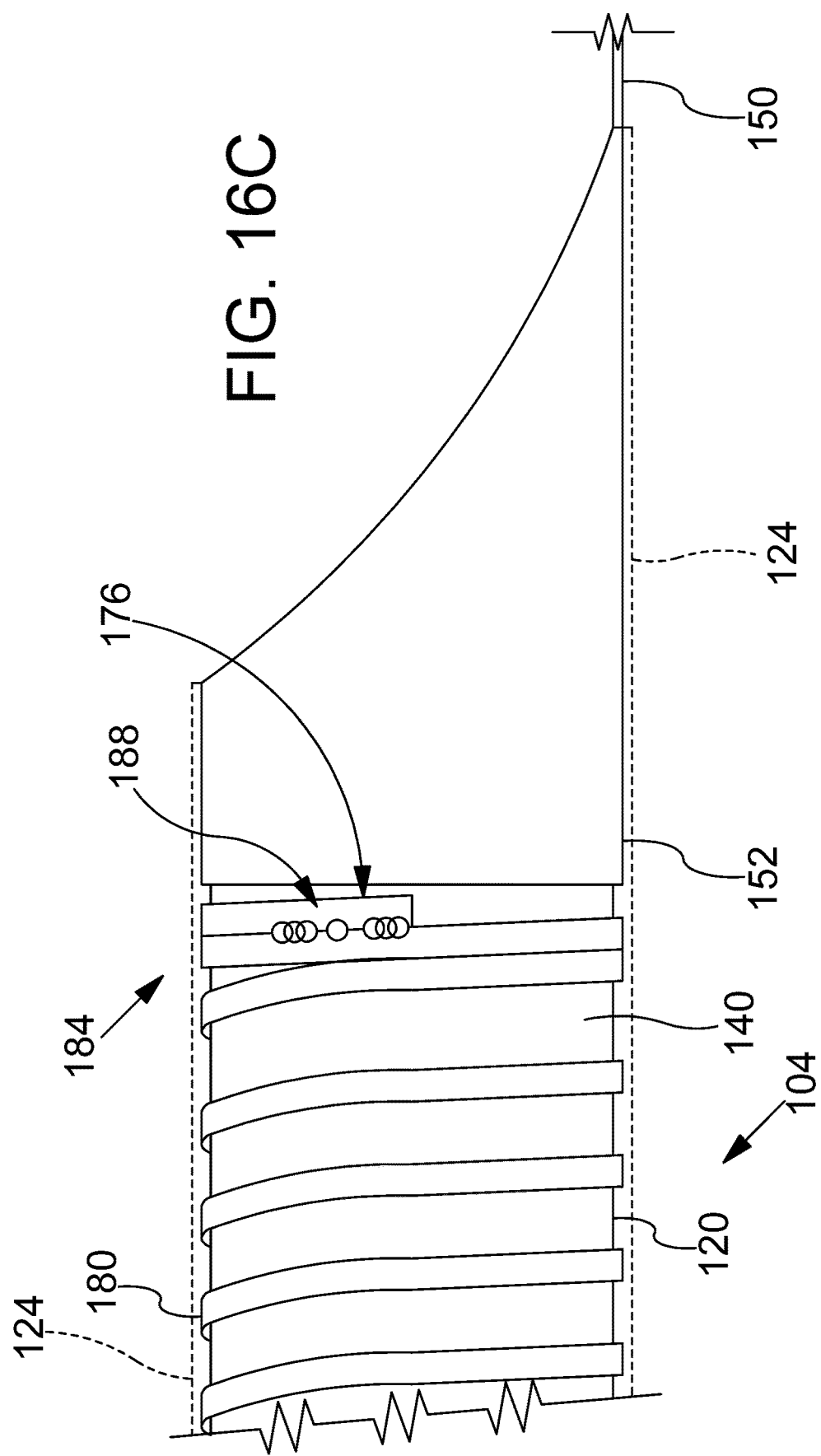

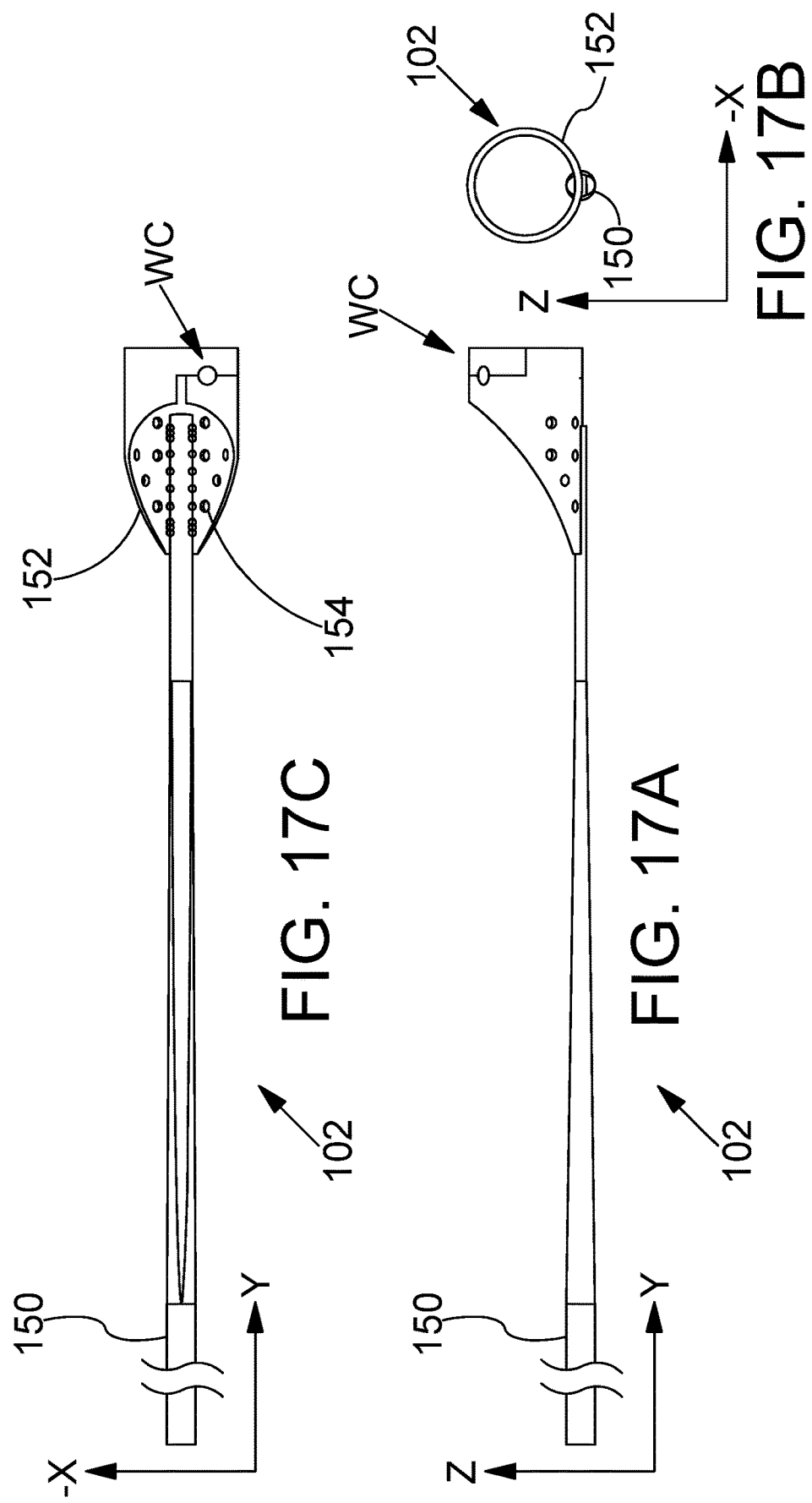

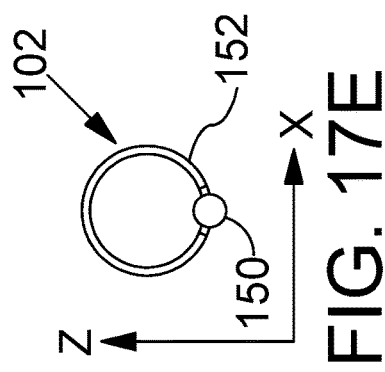
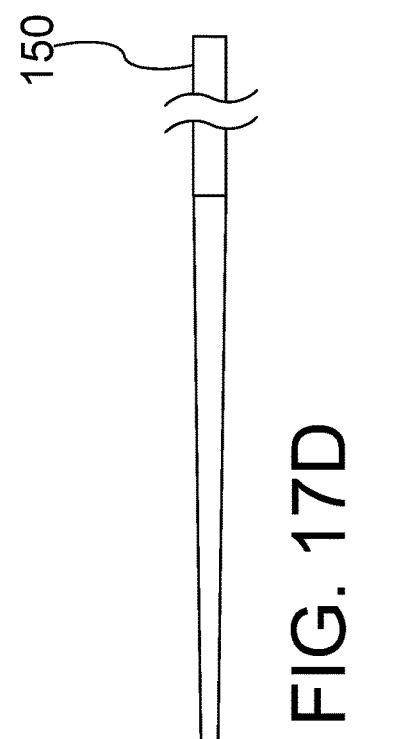
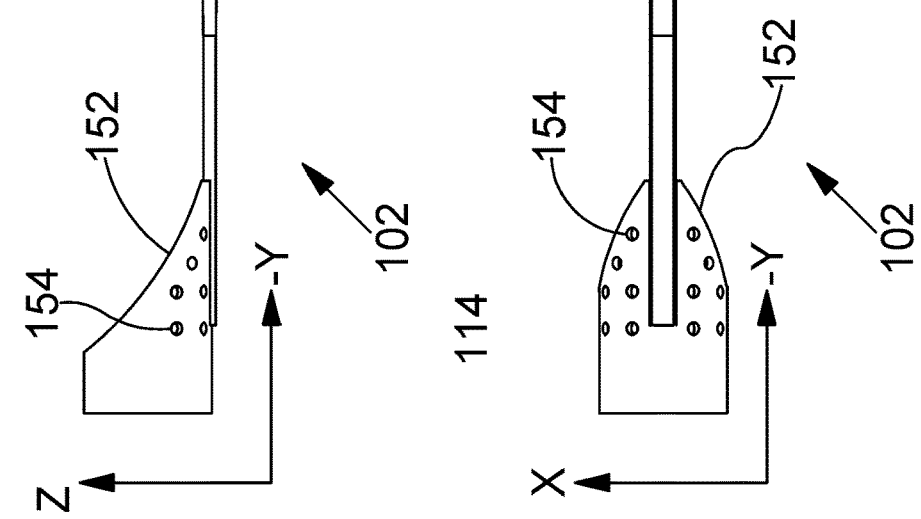

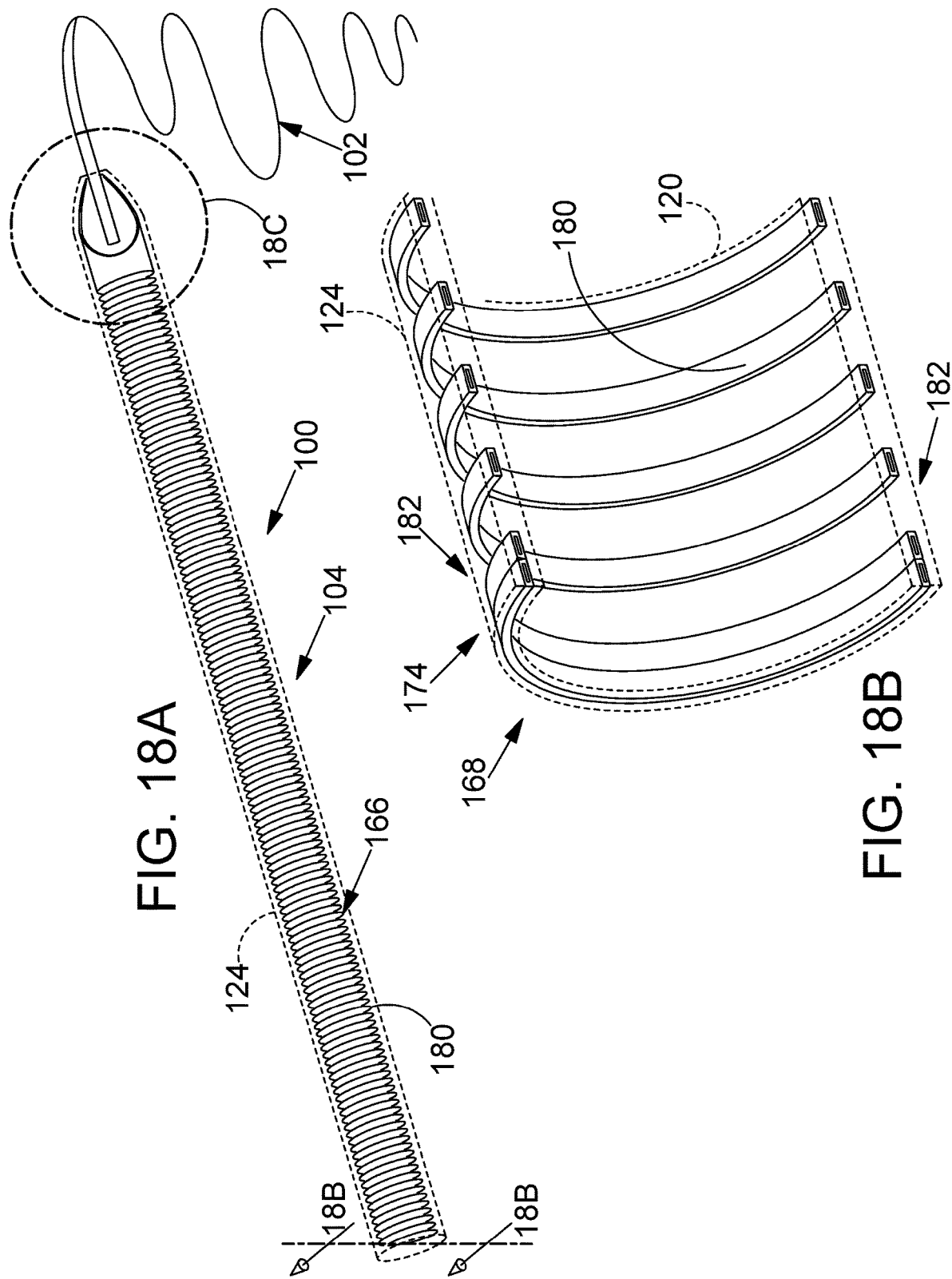

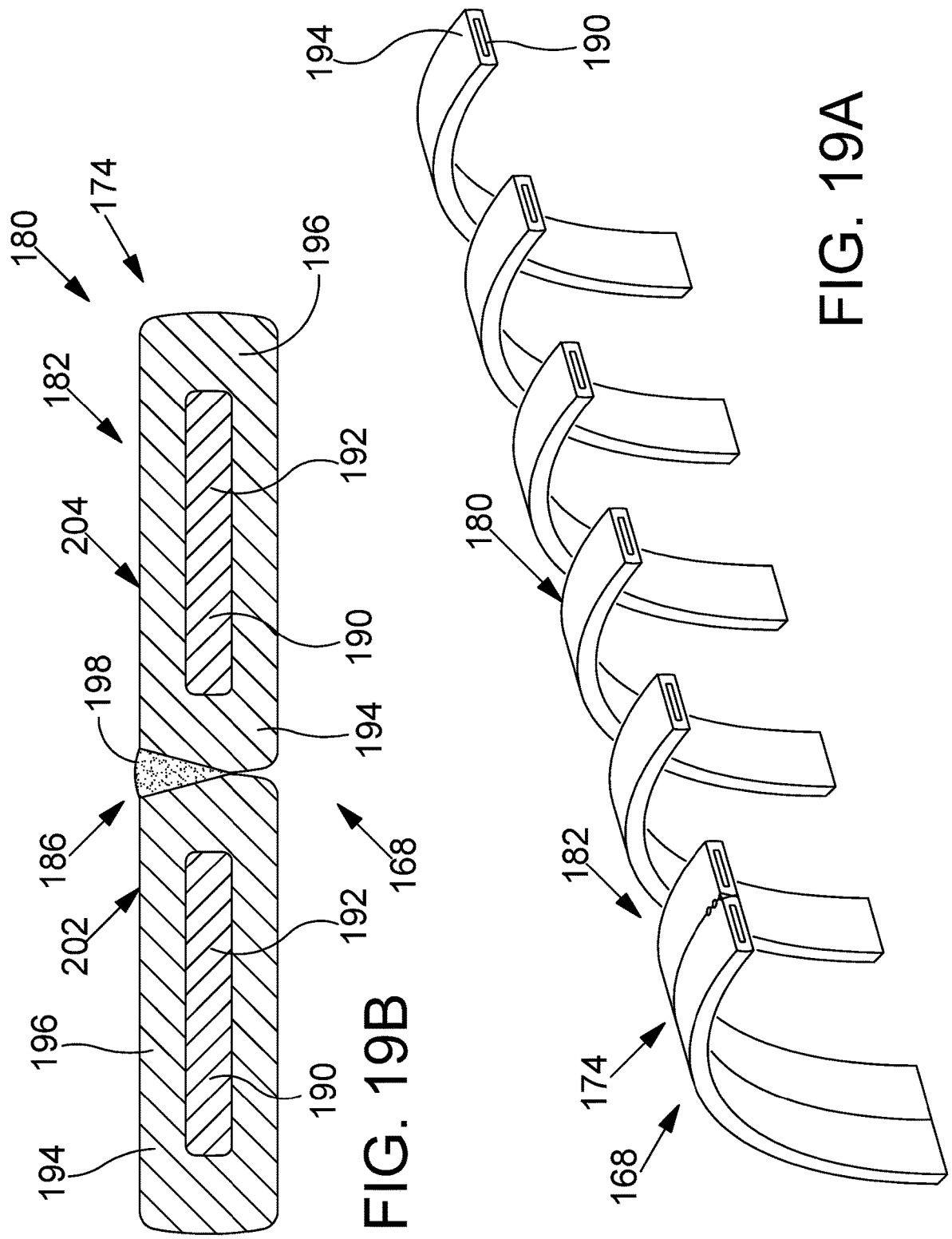

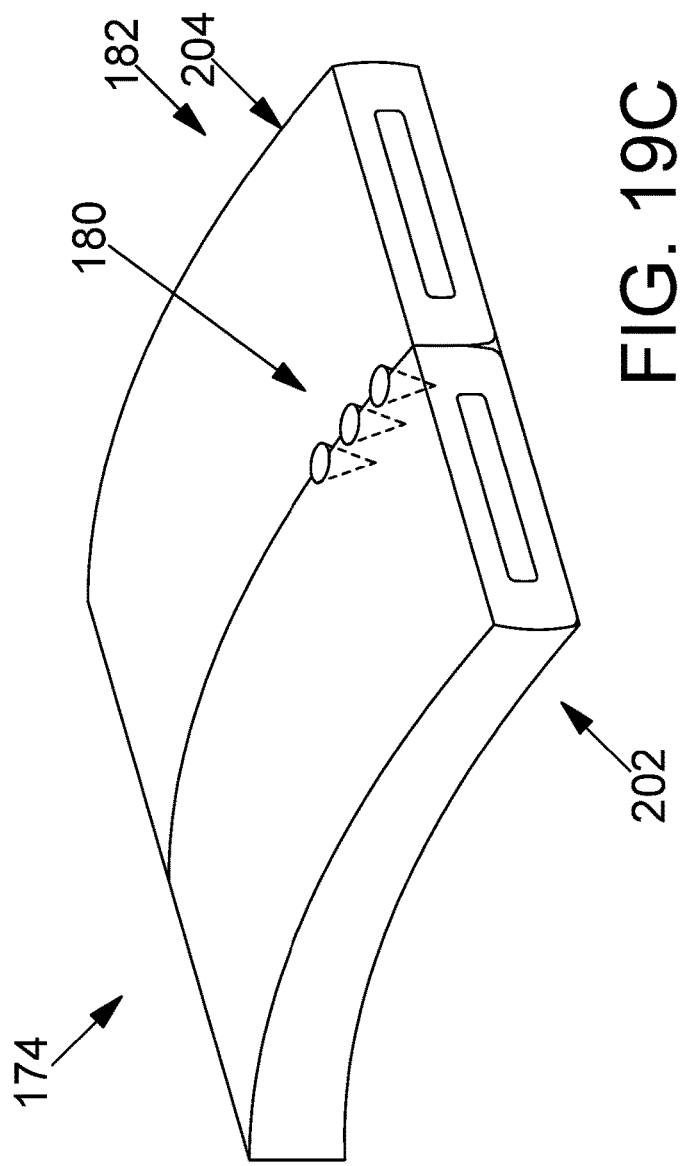
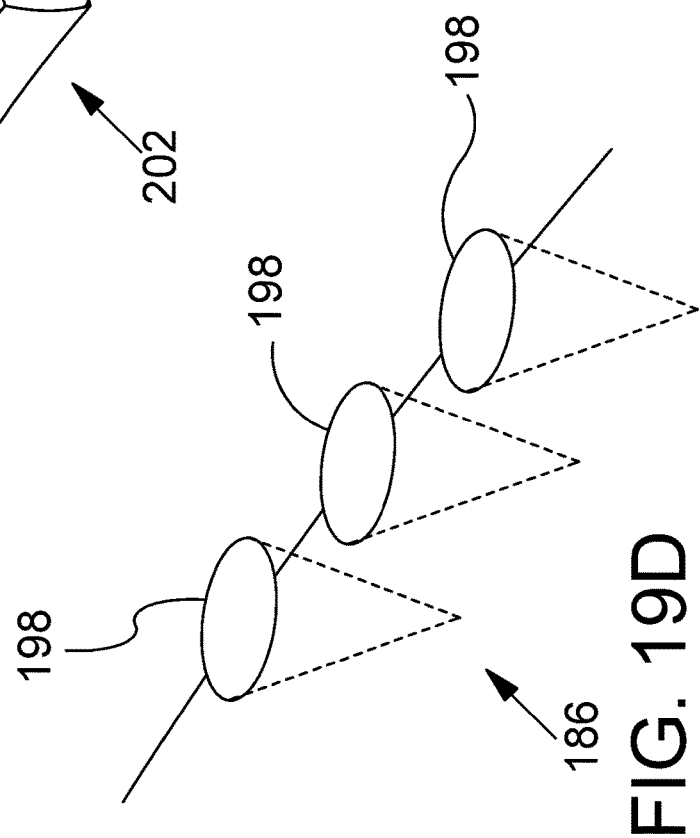
FIG. 19C
FIG. 19D

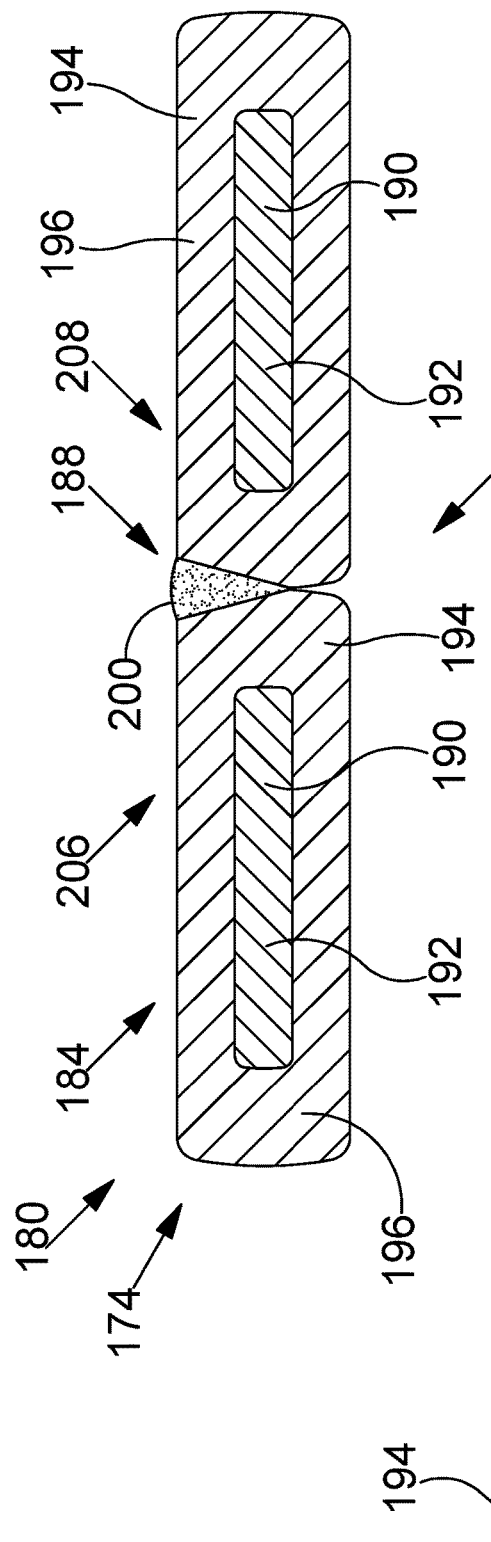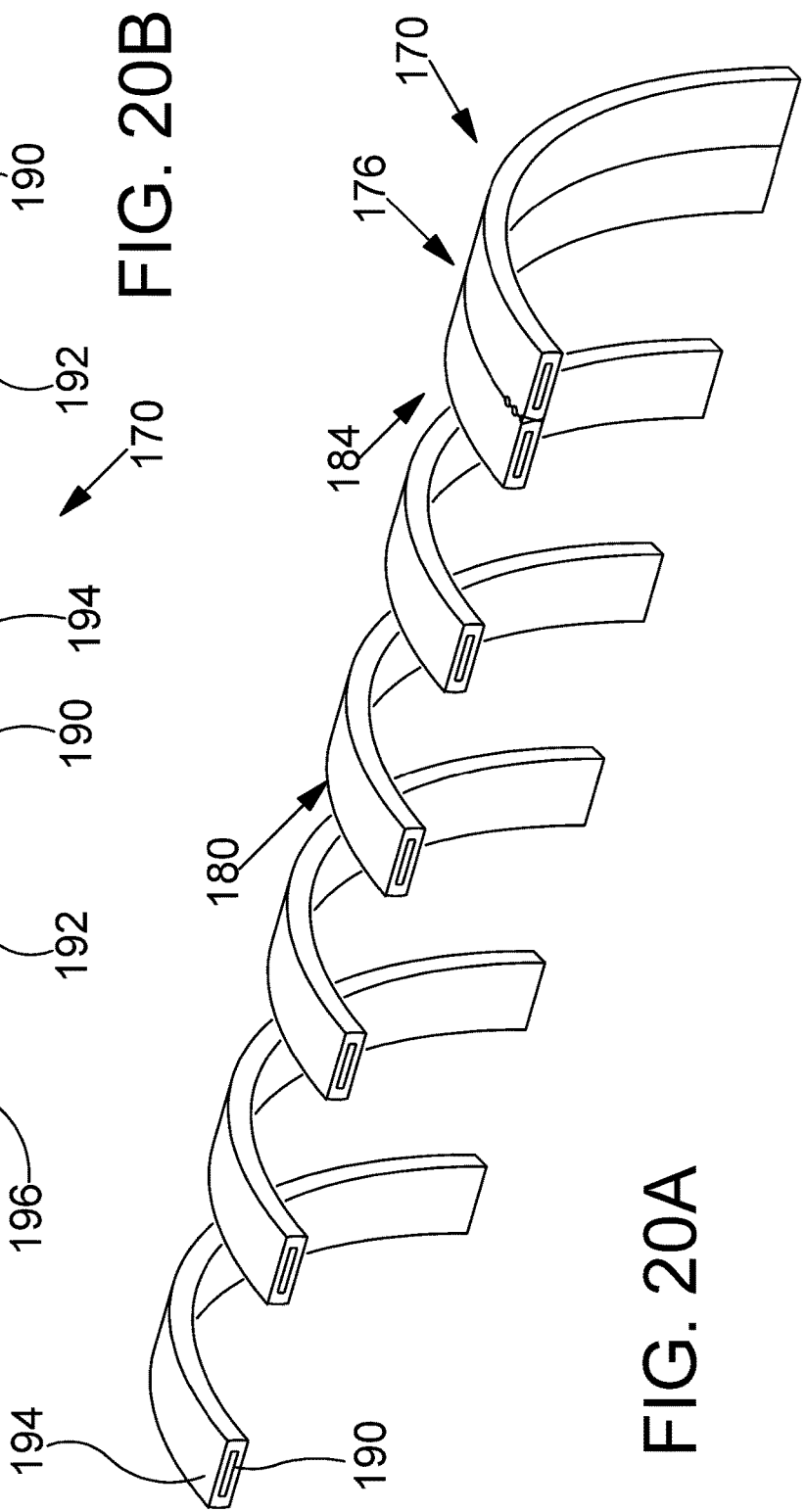

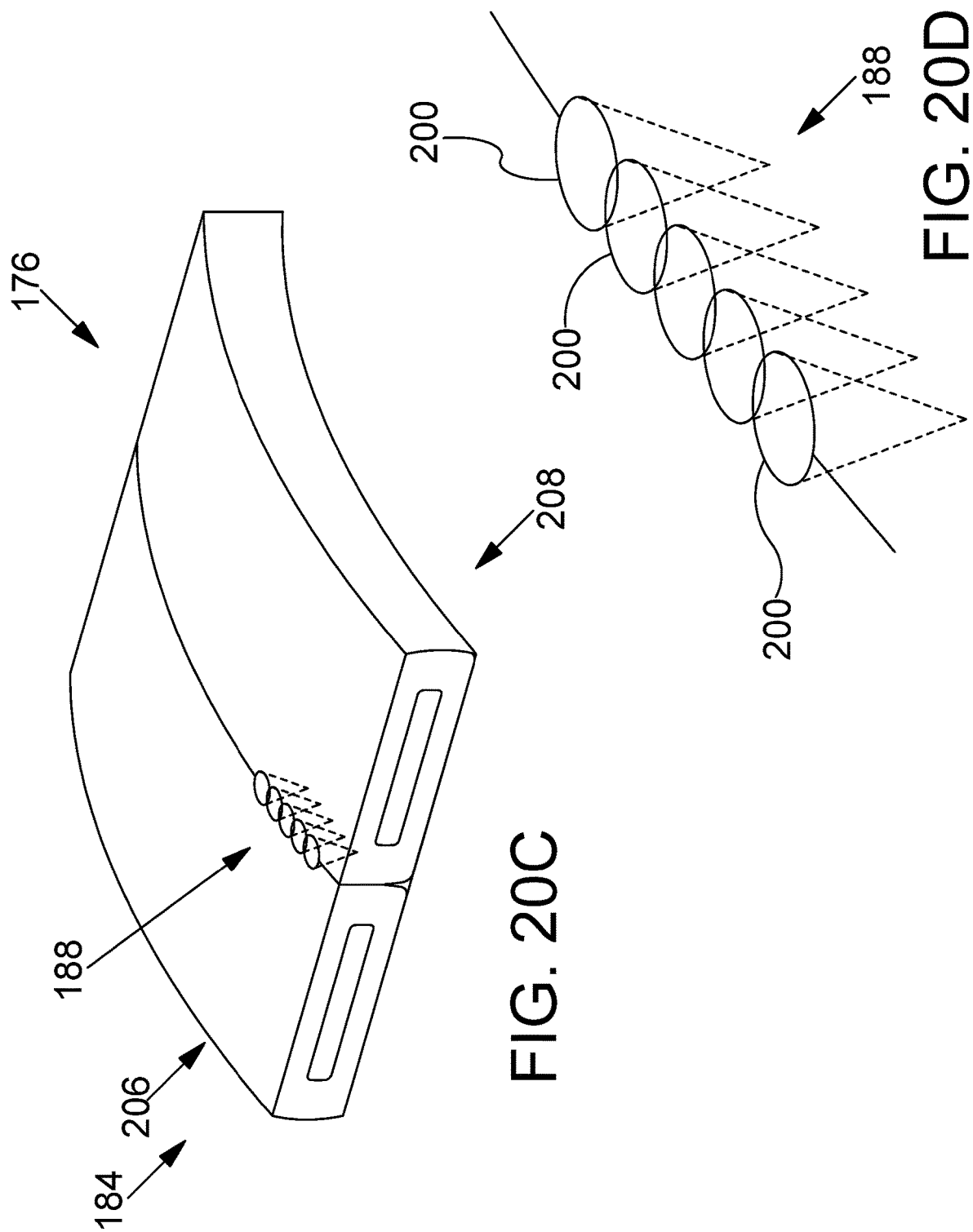

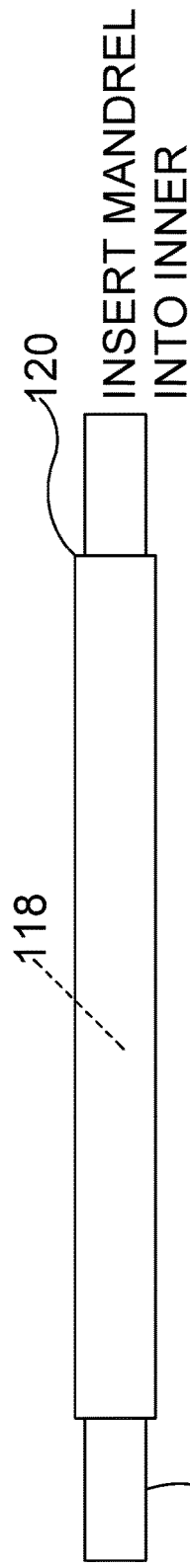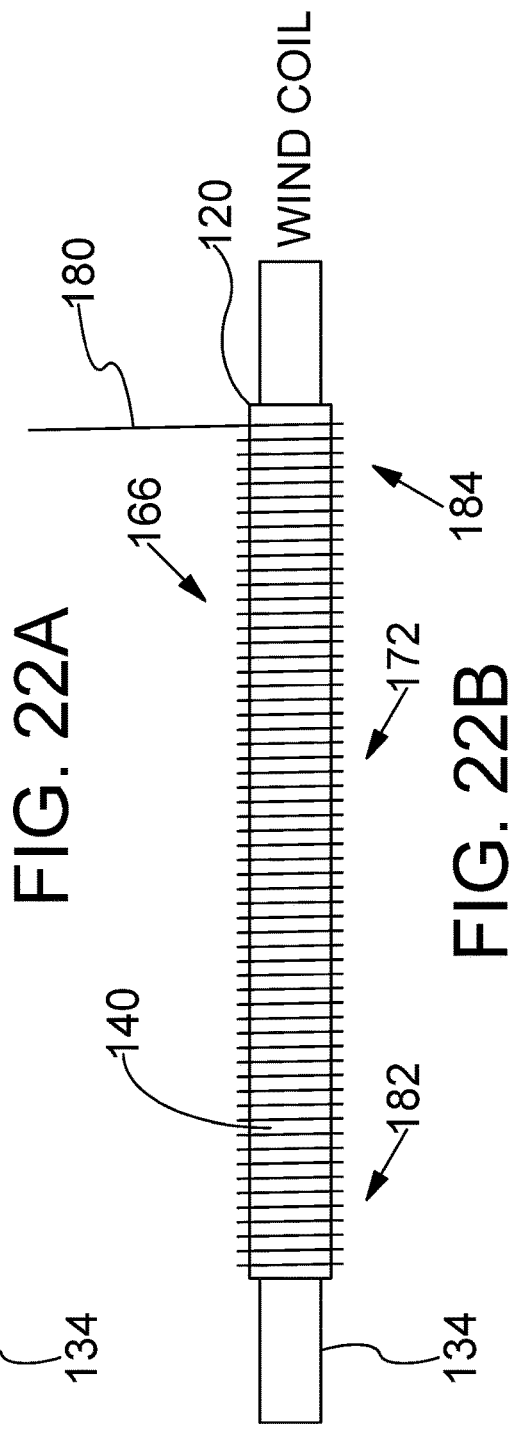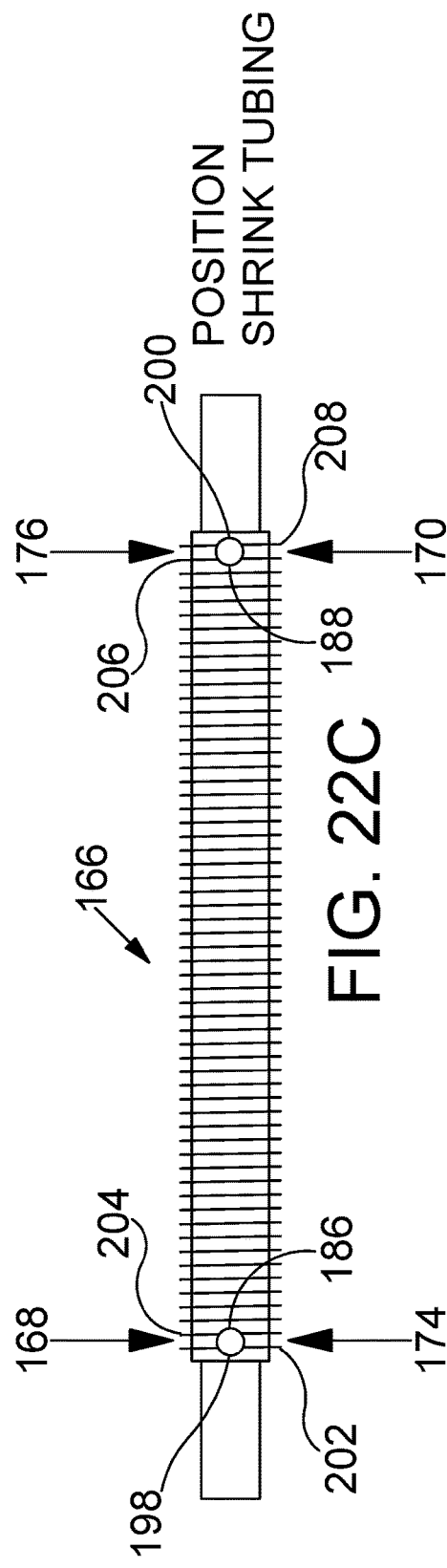

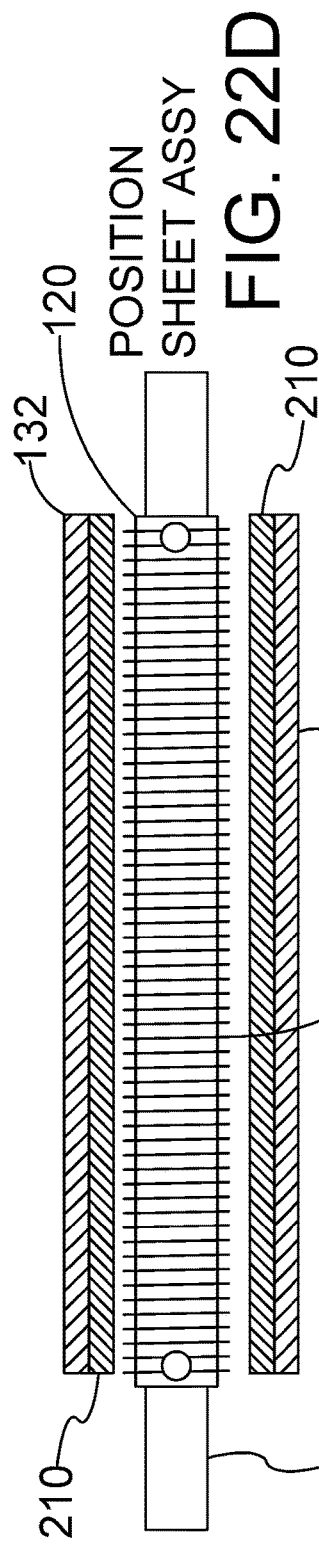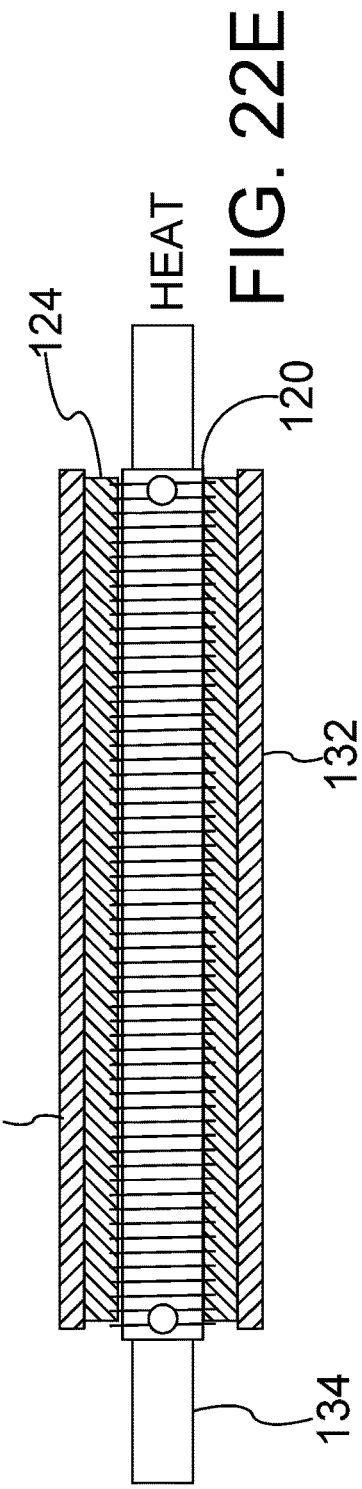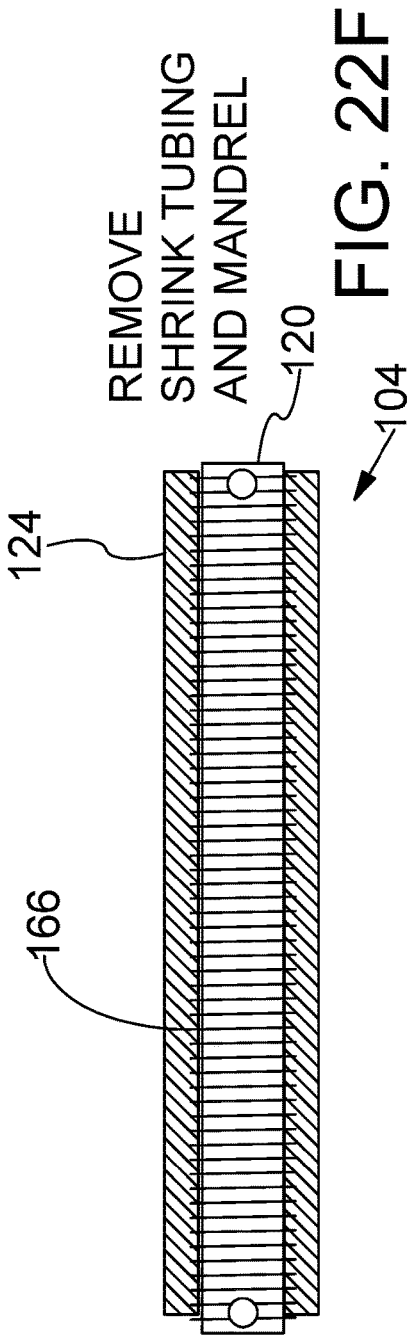

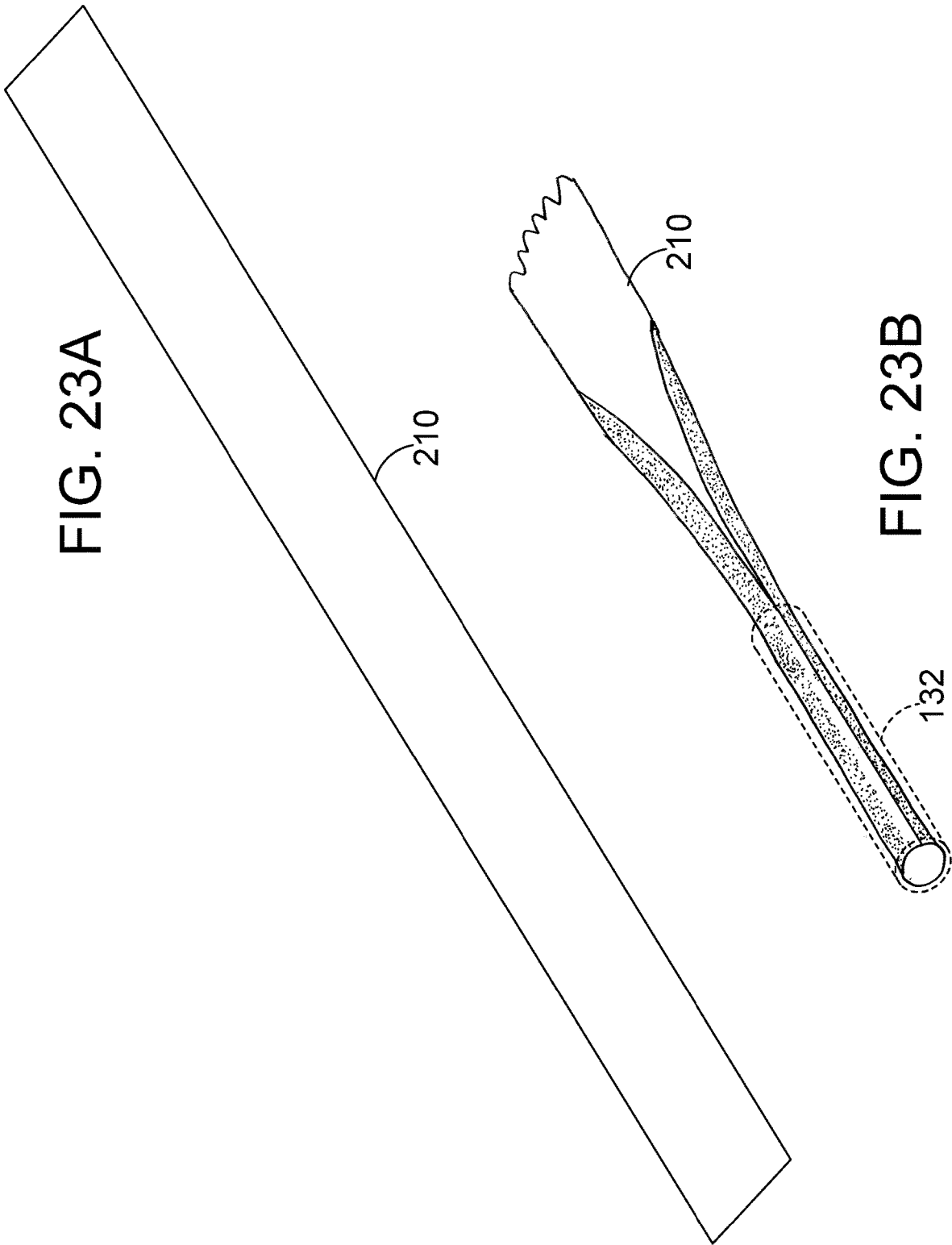

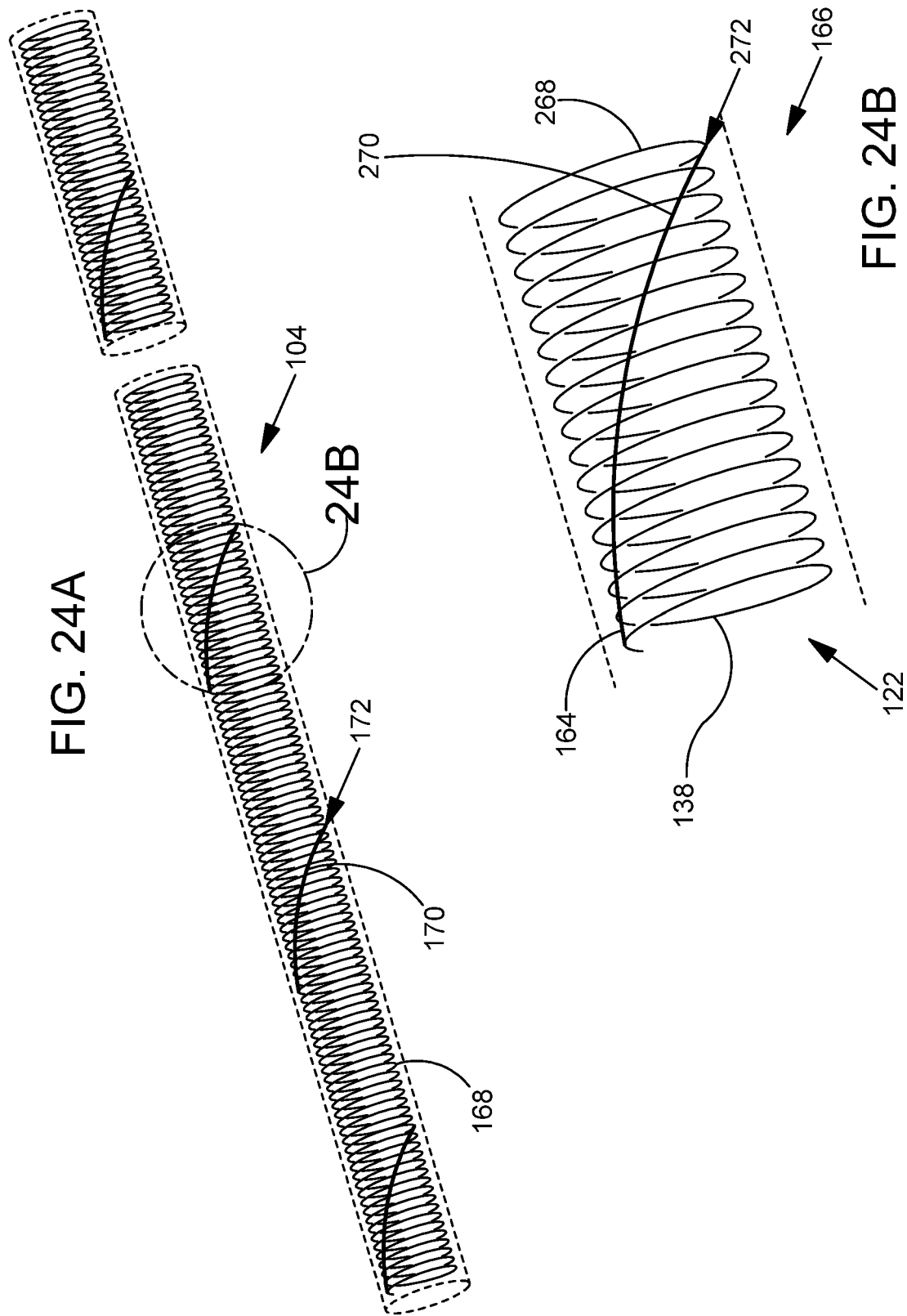

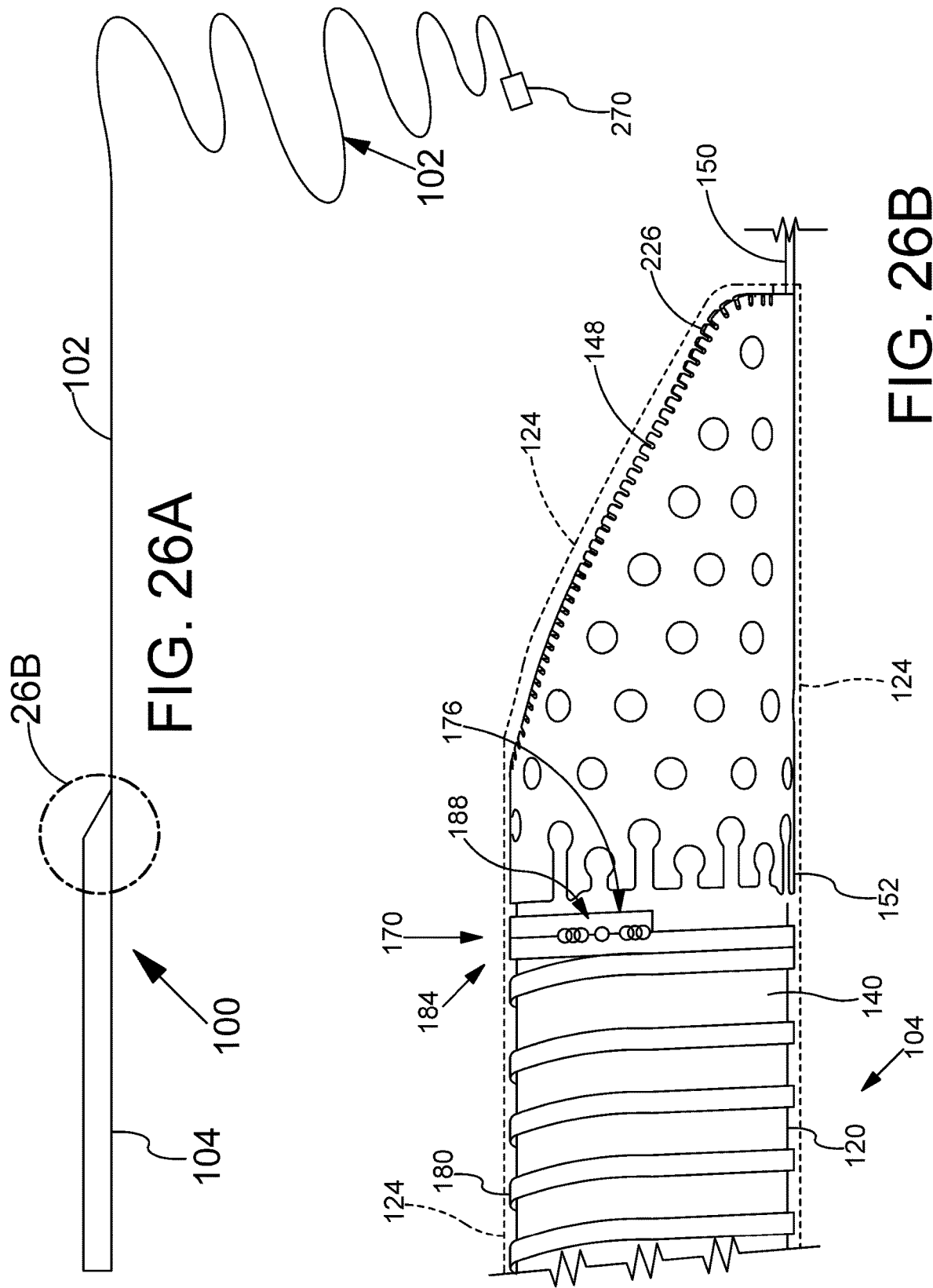

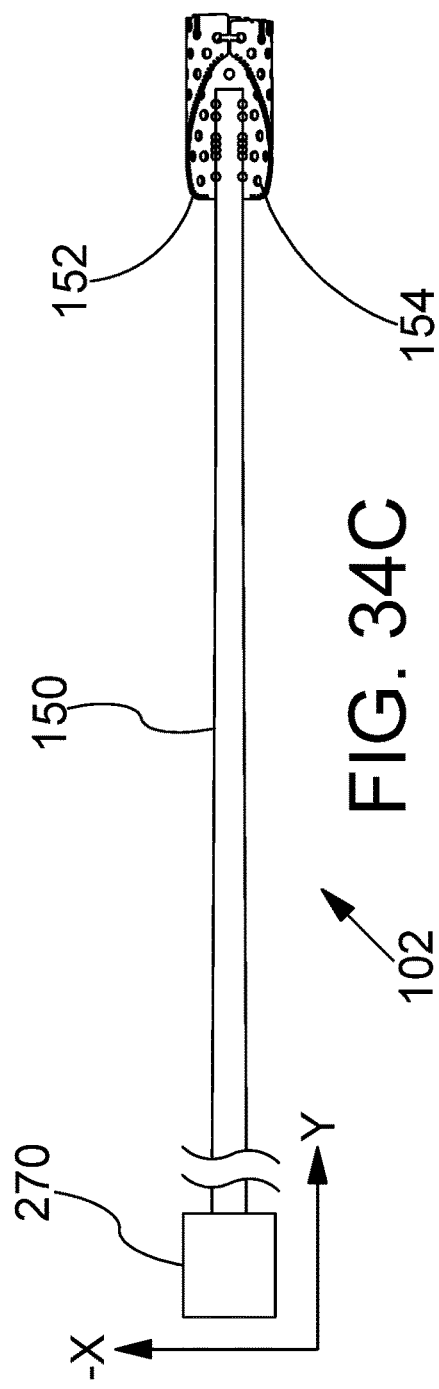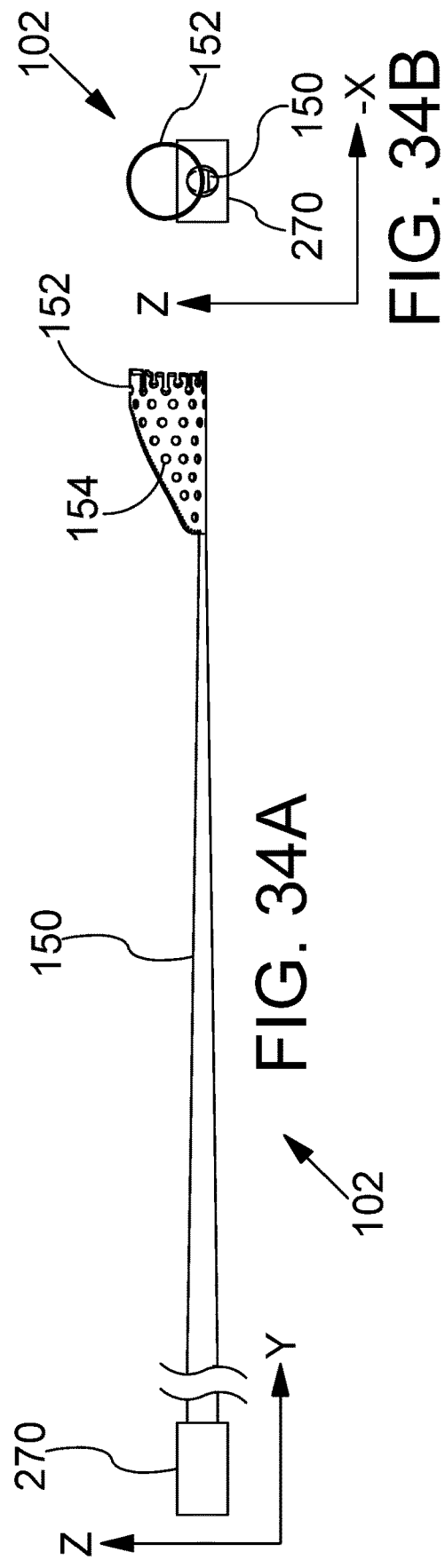

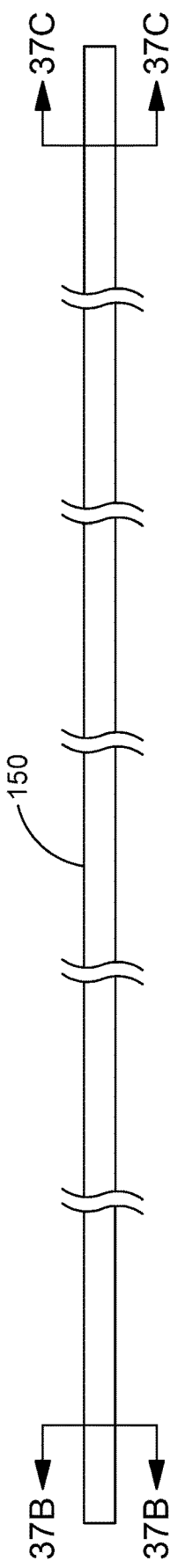
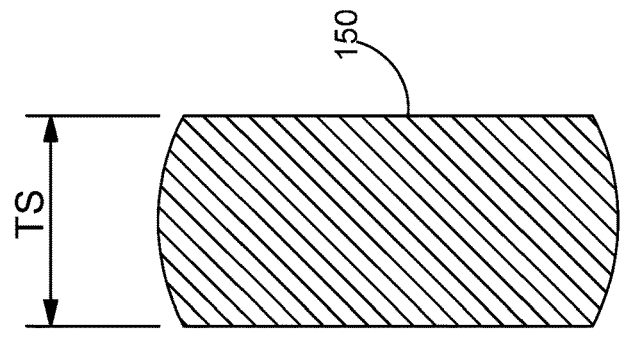
FIG 37A
FIG. 37C
FIG. 37B

SYSTEMS, METHODS AND APPARATUS FOR GUIDING AND SUPPORTING CATHETERS AND METHODS OF MANUFACTURE

CROSS-REFERENCE TO RELATED APPLICATIONS

This application is a continuation-in-part of U.S. patent application Ser. No. 16/572,307 filed Sep. 16, 2019 and U.S. patent application Ser. No. 16/572,330 filed Sep. 16, 2019; which claim the benefit of U.S. Provisional Application No. 62/900,645, filed Sep. 15, 2019, U.S. Provisional Application No. 62/899,929, filed Sep. 13, 2019, and U.S. Provisional Application No. 62/732,282, filed Sep. 17, 2018, the entire disclosures of which are incorporated herein by reference.

FIELD OF THE INVENTION

This disclosure relates to medical catheters and assemblies comprising a catheter in combination with a guide tube, sheath or sleeve.

BACKGROUND OF THE DISCLOSURE

The blood pumping action of the heart muscle is critical to sustaining the life of a patient. In order for the heart to function properly the tissues of the heart muscle must be continuously supplied and re-supplied with oxygen. To receive an adequate supply of oxygen, the heart muscle must be well perfused with blood. In a healthy heart, blood perfusion is accomplished with a system of arteries and capillaries. In some cases, however a build-up of plaque may occur inside an artery. These plaque deposits limit blood flow to the portions of the heart that are supplied by the artery. When these deposits build up in the arteries of the heart, this condition is sometimes referred to as coronary artery disease (CAD). CAD may be treated using relatively non-invasive techniques such as percutaneous transluminal angioplasty (PTA) and percutaneous transluminal coronary angioplasty (PTCA). These therapeutic techniques typically involve the use of guidewires, balloon catheters, and stents. In these procedures, the balloon catheter is advanced over the guidewire such that the balloon is positioned within a restriction in a diseased vessel. The balloon is then inflated and the restriction in the vessel is opened. To prevent subsequent closure of the vessel or restenosis, a physician may implant a stent. The stent is implanted through the use of a stent delivery system including a stent delivery catheter and a stent.

SUMMARY

A device for guiding and supporting a stent delivery catheter and other catheters is disclosed. In embodiments, the device comprises a tubular guiding member and an elongated positioning member extending in a proximal direction beyond the tubular guiding member for advancing and retracting the tubular guiding member in distal and proximal directions. In embodiments, the tubular guiding member comprises an inner tubular member having an outer surface, an elongate support member disposed along a helical path around the outer surface and an encapsulation layer overlaying the outer surface and the elongate support member. In embodiments, the encapsulation layer is mechanically interlocked with and adhered to the elongate support member. In embodiments, the encapsulation layer comprises thermoplastic material from a sheet, the thermoplastic material having melted, mixed and solidified during a reflow process.

A feature and benefit of embodiments is a tubular guiding member that is configured and dimensioned to make new treatment options available to physicians. A feature and benefit of embodiments is a device having a tubular guiding member with a thin wall and a high inner diameter to wall thickness ratio to enable medical procedures using combinations of catheters such as a guide catheter, an extension catheter and a therapy catheter (e.g., a stent delivery catheter). In some example embodiments, the tubular guiding member is dimensioned and configured to be received in a six French guide catheter along with a stent delivery catheter. In some example embodiments, the tubular guiding member can be received in the lumen of a six French guide catheter and the lumen of the tubular guide member can receive a stent delivery catheter configured for use with a six French guide catheter. The term of art "French" may be defined as three times the diameter of a device as measured in millimeters. For example, a nine French catheter has a three millimeter diameter. In some example embodiments, the tubular guiding member can be received in the lumen of a selected French size guide catheter and the lumen of the tubular guide member can receive a stent delivery catheter configured for use with the same French size guide catheter. In some example embodiments the tubular guiding member has an inner diameter to wall thickness ratio equal to or greater than 24:1. In some example embodiments the tubular guiding member has an inner diameter to wall thickness ratio equal to or greater than 22:1. In some example embodiments the tubular guiding member has an inner diameter to wall thickness ratio equal to or greater than 18:1.

In some embodiments, devices are provided with thin walled structures and arrangements having no dedicated marker band. In some example embodiments, the device includes an elongate support member comprising a core portion comprising a core material and a jacket portion disposed about the core portion. In some embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

In some example embodiments, the jacket material of the elongate support member has a first radiopacity, the core material of the elongate support member has a second radiopacity, and the second radiopacity is greater than the first radiopacity. In embodiments, the jacket material has an X-ray attenuation coefficient less than 50 l/cm and the core material has an X-ray attenuation coefficient greater than the 50 l/cm. In some example embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

In some example embodiments, the jacket material comprises stainless steel or nitinol. In some example embodiments, the core material comprises tantalum. In some example embodiments, the elongate support member has a rectangular cross-sectional shape and the rectangular cross-sectional shape has a width dimension and a thickness dimension, the width dimension being greater than the thickness dimension. In some embodiments, a ratio of the width dimension to the thickness dimension is greater than four.

A feature and benefit of some embodiments is a device having a high pull strength. In some embodiments, the device includes an encapsulation layer that is mechanically interlocked with and adhered to a saddle member.

A feature and benefit of some embodiments is a device including a guiding member having an overhanging lip of polymer material located at a proximal lumen entrance. In some embodiments, this arrangement prevents a guidewire from scraping on a metal edge. In some embodiments, this arrangement reduces the likelihood that a polymer coating of the guidewire will be scraped off of a metal wire of the guidewire.

In embodiments a device for guiding and supporting a stent delivery catheter and/or other catheters, the device includes a tubular guiding member comprising and inner tubular member, a support structure, and an encapsulation layer overlaying the inner tubular member and the support structure. In embodiment, the inner tubular member has a proximal end, a distal end and an inner surface, the inner surface defining a lumen extending between the proximal end and the distal end. In embodiments, the support structure is disposed about an outer surface of the inner tubular member. In embodiments, the support structure includes a distal collar portion, a proximal collar portion, and an intermediate portion extending between the distal collar portion and the proximal collar portion. In embodiments, the portions of the support structure are formed by an elongate support member, the elongate support member being disposed along a helical path around the outer surface of the inner tubular member. In embodiments, the elongate support member forms a plurality of turns and the turns are arranged in a single layer.

In some example embodiments, the distal collar portion of the support structure includes a distal closed loop, the distal closed loop comprising a distal weld and a distal portion of the elongate support member, the distal portion extending around the outer surface of the inner tubular member. In these example embodiments, the proximal collar portion of the support structure including a proximal closed loop, the proximal closed loop may comprise a proximal weld and a proximal portion of the elongate support member, the proximal portion extending around the outer surface of the inner tubular member. In some example embodiment, the elongate support member comprises a core portion core material and a jacket portion disposed about the core portion. In embodiments, core portion comprises a core material and the jacket portion comprises a jacket material that is different material than the core material. In some useful embodiment, the core material comprises a radiopaque material and the core portion of the elongate support member serves as a sole radiographic marker of the device, the device having no radiopaque marker separate from the elongate support member.

In some example embodiments, the distal collar portion of the support structure includes a distal closed loop includes a distal weld and the distal weld comprises a distal weld body, the distal weld body comprising jacket material from a first forward part of the elongate support member and jacket material from a second forward part of the elongate support member, the materials having melted, mixed and solidified during a welding process. In embodiments, the distal weld body has V-shape in cross-section, the V-shape having an included angle less than 45 degrees. In embodiments, the distal weld body has conical shape, the conical shape having a cone angle less than 45 degrees. In some example embodiments, the distal weld has a distal weld depth that is less than 90% of a thickness of the elongate support member. In some embodiments, depth of the distal weld is less than 75% the thickness of the elongate support member. In embodiments, the distal weld depth is less than 60% the thickness of the elongate support member.

In some example embodiments, the proximal collar portion of the support structure includes a proximal closed loop includes a proximal weld and the proximal weld comprises a proximal weld body, the proximal weld body comprising jacket material from a first forward part of the elongate support member and jacket material from a second forward part of the elongate support member, the materials having melted, mixed and solidified during a welding process. In some embodiments, the proximal weld body has V-shape in cross-section, the V-shape having an included angle less than 45 degrees. In some embodiments, the proximal weld body has conical shape, the conical shape having a cone angle less than 45 degrees. In some example embodiments, the proximal weld has a proximal weld depth that is less than 90% of a thickness of the elongate support member. In some embodiments, the depth of the proximal weld is less than 75% the thickness of the elongate support member. In embodiments, the depth of the proximal weld is less than 60% the thickness of the elongate support member.

In some example embodiments, tubular guiding member comprises a saddle member and the elongate positioning member comprises an elongate shaft fixed to the saddle member fixed to a distal end of the elongate shaft. In some example embodiments, the elongate positioning member comprises an elongate shaft and a saddle member fixed to a distal end of the elongate shaft. In some embodiments, the elongate shaft comprises a distal portion, the distal portion being tapered so that a thickness of the distal portion decreases as the distal portion extends distally. In some embodiments, the elongate shaft comprises a proximal portion, the proximal portion having a circular shape in lateral cross-section. In some embodiments, the elongate shaft has a solid lateral cross-sectional shape throughout its length. In some embodiments, the elongate shaft comprises stainless steel.

In some example embodiments, the inner tubular member of the tubular guiding member comprise a polymer material having a first melt temperature, the encapsulation layer of the tubular guiding member comprises a polymer material having a second melt temperature different from first melt temperature. In some embodiments, the first melt temperature is higher than the second melt temperature. In some embodiments, the elongate support member comprises a metallic core material and a metallic jacket material disposed about the metallic core material. In some example embodiments, the jacket material comprises stainless steel or nitinol. In some example embodiments, the core material comprises tantalum.

Methods for making medical devices and portions of medical devices are also provided. The medical devices may include, for example, intravascular catheters, catheter shafts, and tubular guiding members. Example methods may include providing a first ribbon comprising one or more thermoplastic materials and a piece of shrink tubing defining a shrink tube lumen and forming a first assembly by positioning the first ribbon inside the shrink tube lumen and urging the first ribbon to assume a tubular shape in which the first ribbon defines a ribbon lumen. Some example methods may also include forming a second assembly by loading an inner tubular member over a mandrel and forming or placing a support structure over an outer surface of the inner tubular member. A third assembly may be formed by inserting the second assembly into the ribbon lumen defined by the first ribbon of the first assembly in some embodiments. Some methods may include heating the third assembly to a process temperature, the process temperature being selected such that the one or more thermoplastic materials of the first ribbon reflow to form an encapsulation layer overlaying the support structure and the inner tubular member, the encapsulation layer being mechanically interlocked with and adhered to the support structure.

Example methods may further include allowing the third assembly to cool, removing the heat shrink tubing from around the encapsulation layer, and withdrawing the mandrel from the lumen defined by the inner tubular member. In some embodiments, one of the one or more the thermoplastic materials of the first ribbon has a first glass transition temperature, the liner material has a second glass transition temperature, and the second glass transition temperature is greater than the first glass transition temperature. In some embodiments, the process temperature is less than the second glass transition temperature and greater than the first glass transition temperature.

In some example methods, providing the first ribbon comprises providing a first ribbon having more than one layer and, upon heating the third assembly to the process temperature, the first ribbon reflows to form an encapsulation layer. In some embodiments, the first ribbon comprises five or more layers. In some embodiments, the first ribbon comprises ten or more layers. In some embodiments, the first ribbon comprises twenty or more layers.

Example methods may further include providing a second ribbon comprising one or more thermoplastic materials and a second piece of shrink tubing defining a second shrink tube lumen and forming a fourth assembly by positioning the second ribbon inside the second shrink tube lumen and urging the second ribbon to assume a tubular shape in which the second ribbon defines a ribbon lumen. Some methods include forming a fifth assembly by inserting the third assembly into the ribbon lumen defined by the second ribbon of the fifth assembly and heating the fifth assembly to a process temperature, the process temperature being selected such that the one or more thermoplastic materials of the second ribbon reflow and form part of an encapsulation layer overlaying the support structure and the inner tubular member, the encapsulation layer being mechanically interlocked with and adhered to the support structure.

Some example methods may further include positioning a ring member about the shrink tubing and moving the ring member in a proximal direction and/or a distal direction along the shrink tubing. In some embodiments, the ring member comprises an elastomeric O-ring. Some example methods include comprising positioning a ring member about the shrink tubing and moving the ring member in a proximal direction along the shrink tubing while the thermoplastic material of the encapsulation layer is molten and creating proximally directed flow in the molten thermoplastic material. Some example methods include positioning a ring member about the shrink tubing and moving the ring member in a proximal direction along the shrink tubing while the thermoplastic material of the encapsulation layer is molten and extruding a portion of the molten thermoplastic material out of a lumen defined by the shrink tubing. Some example methods may further include positioning a structural member over the inner tubular member and positioning a second ring member around the shrink tubing at a location generally aligned with the structural member while the thermoplastic material of the encapsulation layer is molten, and allowing the thermoplastic material of the encapsulation layer to cool while elastic clamping forces produced by the second ring member are applied to the structural member.

In some example methods, forming or placing the support structure over the inner tubular member comprises winding an elongate support member around the outer surface of the inner tubular member to form a coil. In other example methods, forming or placing the support structure over the inner tubular member comprises braiding one or more elongate support members to form a tubular braid. In other example methods, forming or placing the support structure over the inner tubular member comprises knitting one or more elongate support members to form a tubular knit structure. In some example methods, forming or placing the support structure over the inner tubular member comprises winding an elongate support member around the outer surface of the inner tubular member to form a coil, fixing a distal end of the elongate support member at a distal weld joint, and fixing a proximal end of the elongate support member at a proximal weld joint.

Some example methods further include placing a therapy device inside the lumen defined by the inner tubular member. In some example methods, placing a therapy device inside the lumen defined by the inner tubular member comprises placing a stent inside the lumen defined by the inner tubular member. In some example methods, placing a therapy device inside the lumen defined by the inner tubular member comprises placing an occlusion device inside the lumen defined by the inner tubular member. Some example methods further include attaching a therapy device to a catheter shaft formed by the inner tubular member, the support structure and the encapsulation layer. In some example methods, attaching a therapy device to the catheter shaft comprises attaching a balloon to the outside of the catheter shaft. Some example methods further include attaching a connector to the catheter shaft formed by the inner tubular member, the support structure and the encapsulation layer for delivering fluids to locations inside the body of a patient. Some example methods further include attaching a connector to the catheter shaft formed by the inner tubular member, the support structure and the encapsulation layer for applying vacuum or low pressure to locations inside the body of a patient for removing materials from the body. Some example methods further include attaching a hub to the catheter shaft formed by the inner tubular member, the support structure and the encapsulation layer. In some example methods, the hub is attached using an adhesive bonding process. Some example methods further include forming a hub on the catheter shaft formed by the inner tubular member, the support structure and the encapsulation layer. In some example methods, the hub formed using a thermoplastic injection molding process.

In some example methods, urging the first ribbon to assume the tubular shape comprises urging the first ribbon to assume the tubular shape having an angular span of less than 360 degrees so that the first ribbon defines a longitudinal gap located between a first longitudinal edge of the first ribbon and a second longitudinal edge of the first ribbon. In some example methods urging the first ribbon to assume the tubular shape comprises urging the first ribbon to assume the tubular shape having an angular span of less than 345 degrees. In some example methods, urging the first ribbon to assume the tubular shape comprises pulling the first ribbon into the shrink tube lumen. In some example methods, pulling the first ribbon into the shrink tube lumen comprises inserting an end of a pulling tool through the lumen of the shrink tube, coupling the end of the pulling tool to a distal portion of the first ribbon, and applying a pulling force to the pull tool to pull the first ribbon into the lumen of the shrink tube. In some embodiments, the pulling tool has a hook shaped distal portion and coupling the end of the pulling tool to a distal portion of the first ribbon comprises inserting a distal end of the hook shaped distal portion through a hole defined by the first ribbon. In some example methods, urging the first ribbon to assume the tubular shape comprises pushing the first ribbon into the shrink tube lumen. In some example methods pushing the first ribbon into the shrink tube lumen comprises coupling the distal portion of a pushing tool to a distal portion of the first ribbon, and applying a pushing force to the pull tool to push the first ribbon into the lumen of the shrink tube. In some embodiments, the pushing tool has a fork shaped distal portion and coupling the end of the pushing tool to a distal portion of the first ribbon comprises inserting a distal end of the hook shaped distal portion through a hole defined by the first ribbon.

A feature and benefit of some embodiments is a catheter shaft and/or tubular guiding member that is configured and dimensioned to make new treatment options available to physicians. A feature and benefit of embodiments is a device having a catheter shaft and/or tubular guiding member with a thin wall and a high inner diameter to wall thickness ratio to enable medical procedures using combinations of catheters such as a guide catheter, an extension catheter and a therapy catheter (e.g., a stent delivery catheter). In some example embodiments, the tubular guiding member is dimensioned and configured to be received in a six French guide catheter along with a stent delivery catheter. In some example embodiments, the tubular guiding member can be received in the lumen of a six French guide catheter and the lumen of the tubular guide member can receive a stent delivery catheter configured for use with a six French guide catheter. The term of art "French" may be defined as three times the diameter of a device as measured in millimeters. For example, a nine French catheter has a three millimeter diameter. In some example embodiments, the tubular guiding member can be received in the lumen of a selected French size guide catheter and the lumen of the tubular guide member can receive a stent delivery catheter configured for use with the same French size guide catheter. In some example embodiments the tubular guiding member has an inner diameter to wall thickness ratio equal to or greater than 24:1. In some example embodiments the tubular guiding member has an inner diameter to wall thickness ratio equal to or greater than 22:1. In some example embodiments the tubular guiding member has an inner diameter to wall thickness ratio equal to or greater than 18:1.

In some embodiments, devices are provided with thin walled structures and arrangements having no dedicated marker band. In some example embodiments, the device includes an elongate support member comprising a core portion comprising a core material and a jacket portion disposed about the core portion. In some embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

In some example embodiments, the jacket material of the elongate support member has a first radiopacity, the core material of the elongate support member has a second radiopacity, and the second radiopacity is greater than the first radiopacity. In embodiments, the jacket material has an X-ray attenuation coefficient less than 50 l/cm and the core material has an X-ray attenuation coefficient greater than the 50 l/cm. In some example embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

In some example embodiments, the jacket material comprises stainless steel or nitinol. In some example embodiments, the core material comprises tantalum. In some example embodiments, the elongate support member has a rectangular cross-sectional shape and the rectangular cross-sectional shape has a width dimension and a thickness dimension, the width dimension being greater than the thickness dimension. In some embodiments, a ratio of the width dimension to the thickness dimension is greater than four.

A feature and benefit of some embodiments is a device having a high pull strength. In some embodiments, the device includes an encapsulation layer that is mechanically interlocked with and adhered to a saddle member or other structural member.

The above summary is not intended to describe each illustrated embodiment or every implementation of the present disclosure.

BRIEF DESCRIPTION OF THE FIGURES

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 1 is a perspective view showing a device for guiding and supporting catheters such as, for example, stent delivery catheters.

FIG. 2A is a perspective view showing a portion of the device shown in FIG. 1.

FIG. 2B is a cross-sectional view of the device shown in FIG. 2A. In the embodiment of FIG. 2B, the device has been sectioned along section line 2B-2B shown in FIG. 2A.

FIG. 2C is an end view of the device shown in FIG. 2B.

FIG. 3A is an enlarged cross-sectional view showing a portion of the device shown in FIG. 2B.

FIG. 3C is an exploded view further illustrating a portion of the device shown in FIGS. 3A and 3B.

FIG. 4A-FIG. 4K are a series of stylized partial cross-section views illustrating example methods in accordance with the detailed description.

FIG. 5A-FIG. 5K are a series of stylized side views illustrating example methods in accordance with the detailed description.

FIG. 6A is a plan view showing a device for guiding and supporting catheters such as, for example, stent delivery catheters.

FIG. 6B is a side view of the device shown in FIG. 6A.

FIG. 10A is a perspective view of an elongate positioning member in accordance with the detailed description.

FIG. 10B is an enlarged perspective view further illustrating a portion of the elongate positioning member shown in FIG. 10A.

FIG. 11A is a top view of a shaft member in accordance with the detailed description.

FIG. 11B is a cross-sectional view of the device shown in FIG. 11A. In the embodiment of FIG. 11B, the device has been sectioned along section line 11B-11B shown in FIG. 11A.

FIG. 11C is a cross-sectional view of the device shown in FIG. 11A. In the embodiment of FIG. 11C, the device has been sectioned along section line 11C-11C shown in FIG. 11A.

FIG. 12A is a left side view of an elongate guiding member in accordance with the detailed description.

FIG. 12B is a front view of the elongate guiding member shown in FIG. 12A.

FIG. 12C is a top view of the elongate guiding member shown in FIG. 12A.

FIG. 12D is a right side view of the elongate guiding member shown in FIG. 12A.

FIG. 12E is a rear view of the elongate guiding member shown in FIG. 12A.

FIG. 12F is a bottom view of the elongate guiding member shown in FIG. 12A.

FIG. 14A is a cross-sectional view of an assembly for forming a ribbon.

FIG. 14B is a cross-sectional view of a ribbon formed from the assembly shown in FIG. 14A.

FIG. 16A is a side view showing a device for guiding and supporting catheters such as, for example, stent delivery catheters.

FIG. 16B is an enlarged detail view showing a distal end portion of the device shown in FIG. 16A.

FIG. 16C is an enlarged detail view showing an intermediate portion of the device shown in FIG. 16A.

FIG. 17A is a left side view of an elongate guiding member in accordance with the detailed description.

FIG. 17B is a front view of the elongate guiding member shown in FIG. 17A.

FIG. 17C is a top view of the elongate guiding member shown in FIG. 17A.

FIG. 17D is a right side view of the elongate guiding member shown in FIG. 17A.

FIG. 17E is a rear view of the elongate guiding member shown in FIG. 17A.

FIG. 17F is a bottom view of the elongate guiding member shown in FIG. 17A.

FIG. 18A is a perspective view showing a device for guiding and supporting catheters such as, for example, stent delivery catheters.

FIG. 18B is a cross-sectional view of the device shown in FIG. 18A. In the embodiment of FIG. 18B, the device has been sectioned along section line 18B-18B shown in FIG. 18A.

FIG. 19A is a partial perspective view showing a distal portion of a support structure in accordance with the detailed description.

FIG. 19B is an enlarged cross-sectional view further illustrating a portion of the support structure shown in FIG. 19A.

FIG. 19C is an enlarged perspective view further illustrating a portion of the support structure shown in FIG. 19A.

FIG. 19D is an enlarged perspective view further illustrating weld structure shown in FIG. 19C.

FIG. 20A is a partial perspective view showing a proximal portion of a support structure in accordance with the detailed description.

FIG. 20B is an enlarged cross-sectional view further illustrating a portion of the support structure shown in FIG. 20A.

FIG. 20C is an enlarged perspective view further illustrating a portion of the support structure shown in FIG. 20A.

FIG. 20D is an enlarged perspective view further illustrating weld structure shown in FIG. 20C.

FIG. 22A through FIG. 22F are a series of stylized partial cross-sectional views illustrating example methods in accordance with this detailed description.

The FIGS. 23H through 23O are a series of stylized perspective views illustrating example methods in accordance with this detailed description.

Figure 23C:
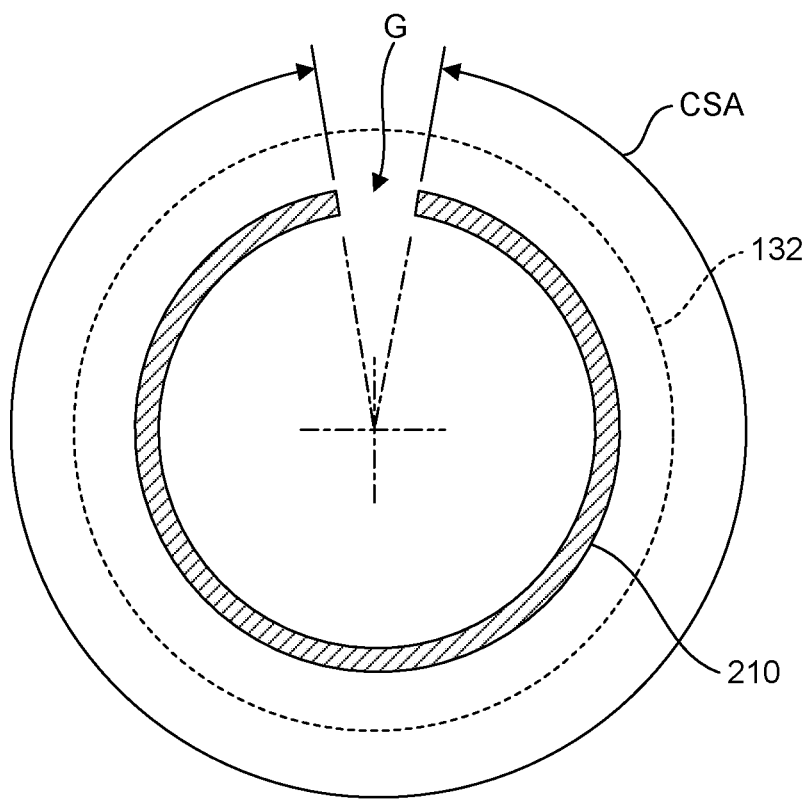
FIG. 23C is a cross-sectional view further illustrating the sheet and the shrink tubing of the assembly shown in FIG. 23B.
Figure 23D:
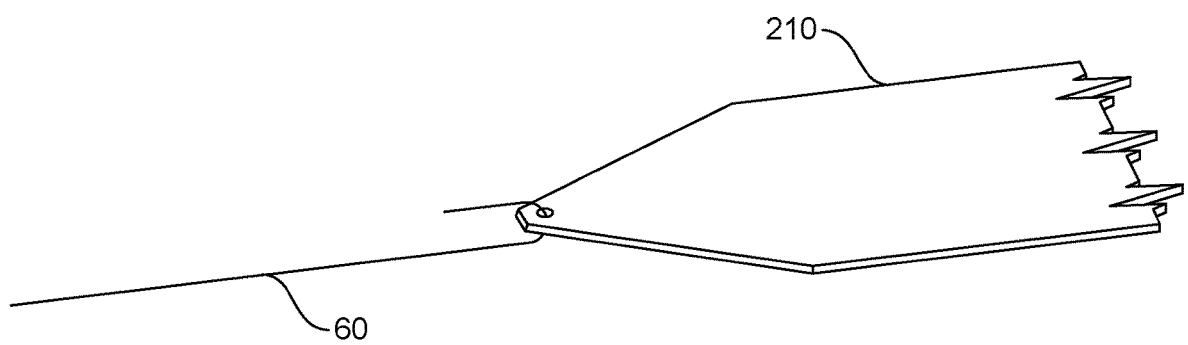
FIG. 23D is a perspective view showing a sheet defining a hole and a pulling tool having a hook shaped portion engaging the hole defined by the sheet.
Figure 23E:
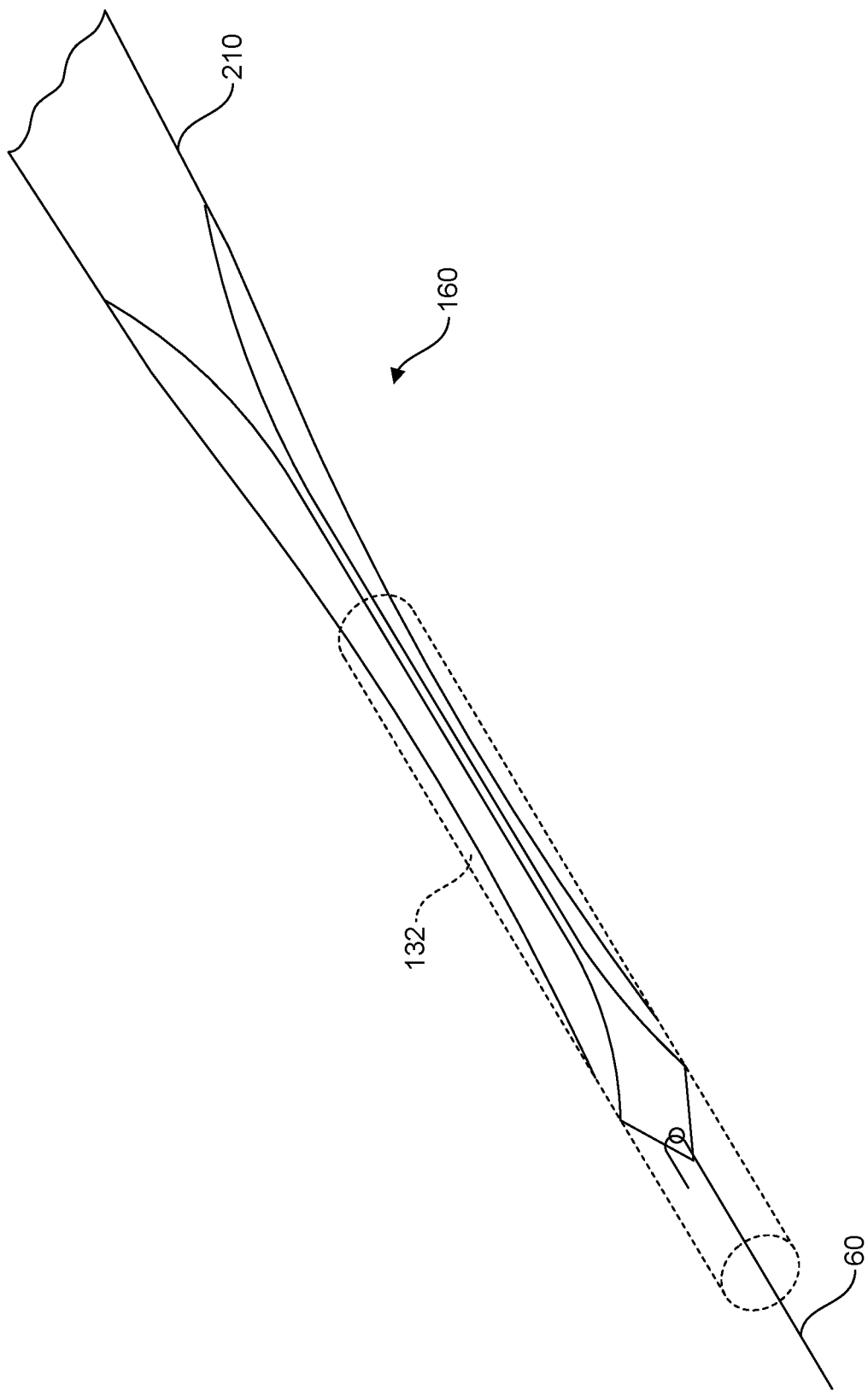
FIG. 23E is a perspective view showing the sheet of FIG. 23D as it is pulled into a lumen defined by a length of shrink tubing.
Figure 23F:
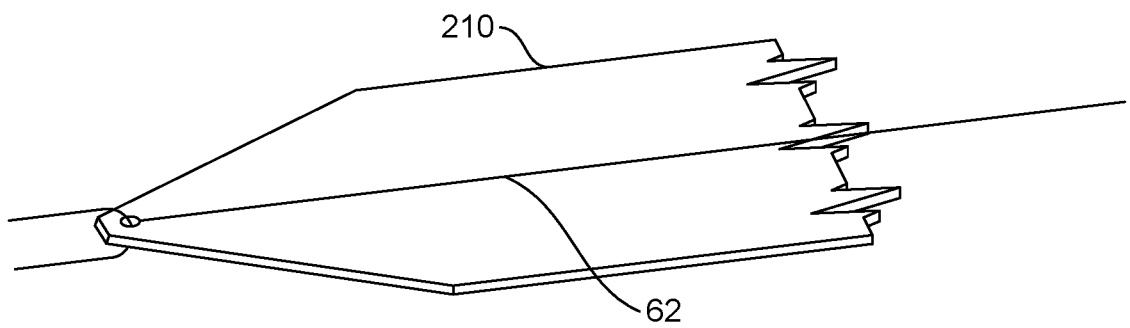
FIG. 23F is a perspective view showing a sheet defining a hole and a pushing tool having a fork shaped portion engaging the hole defined by the sheet.
Figure 23G:
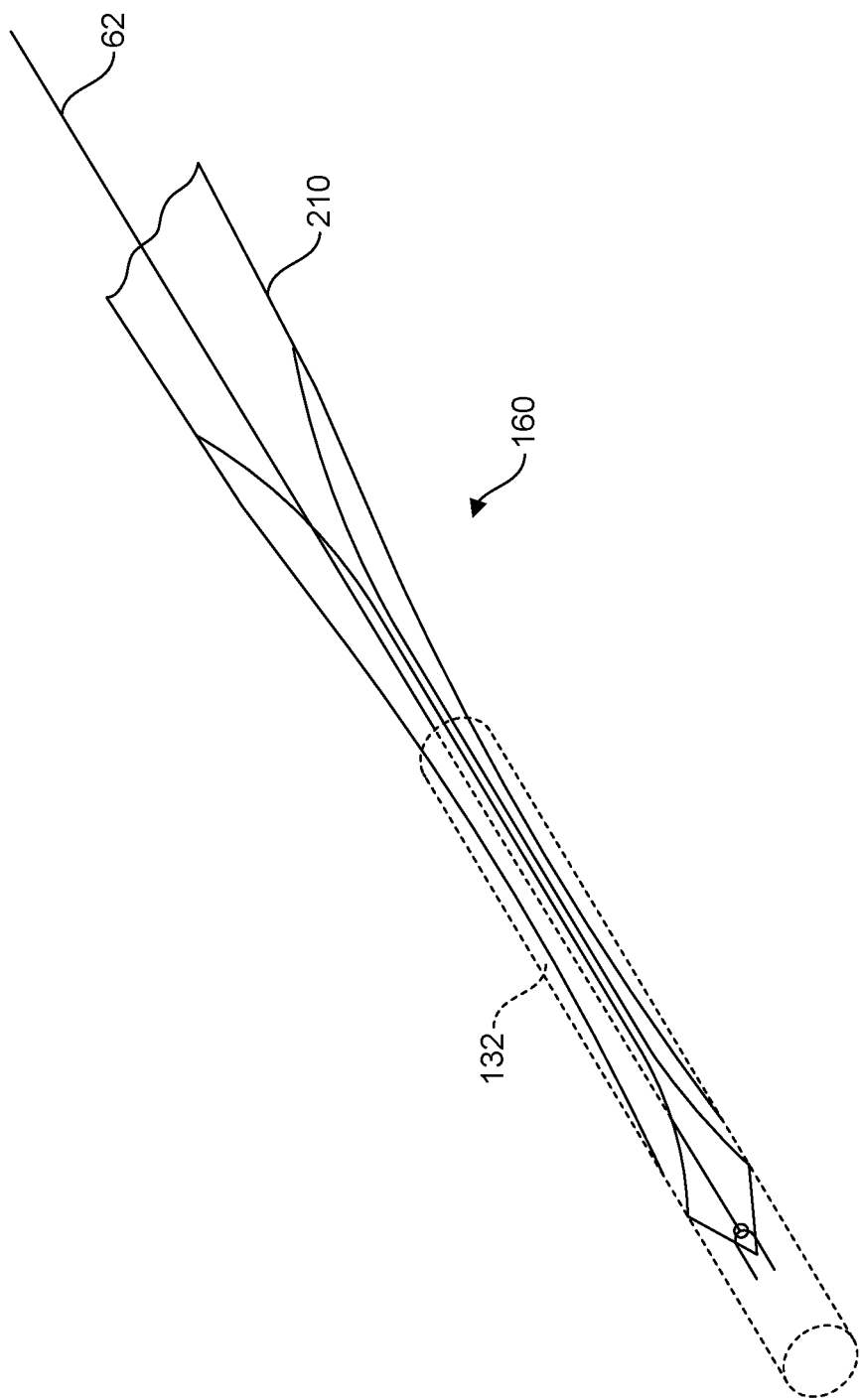
FIG. 23G is a perspective view showing the sheet of FIG. 23F as it is pushed into a lumen defined by a length of shrink tubing.
Figure 23H:
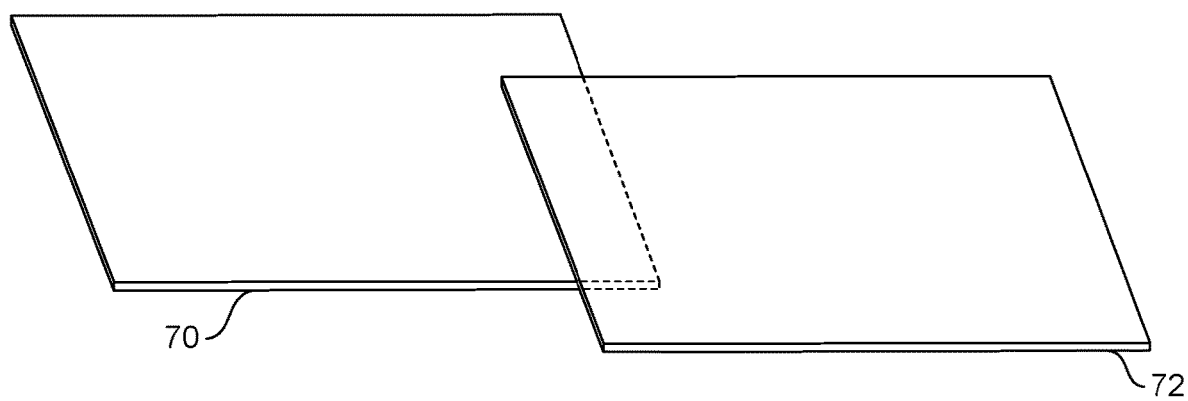
FIG. 23A is a perspective view showing a sheet and FIG. 23B is a perspective view showing the sheet as it is inserted and/or drawn into a lumen defined by a length of shrink tubing.
Figure 23I:
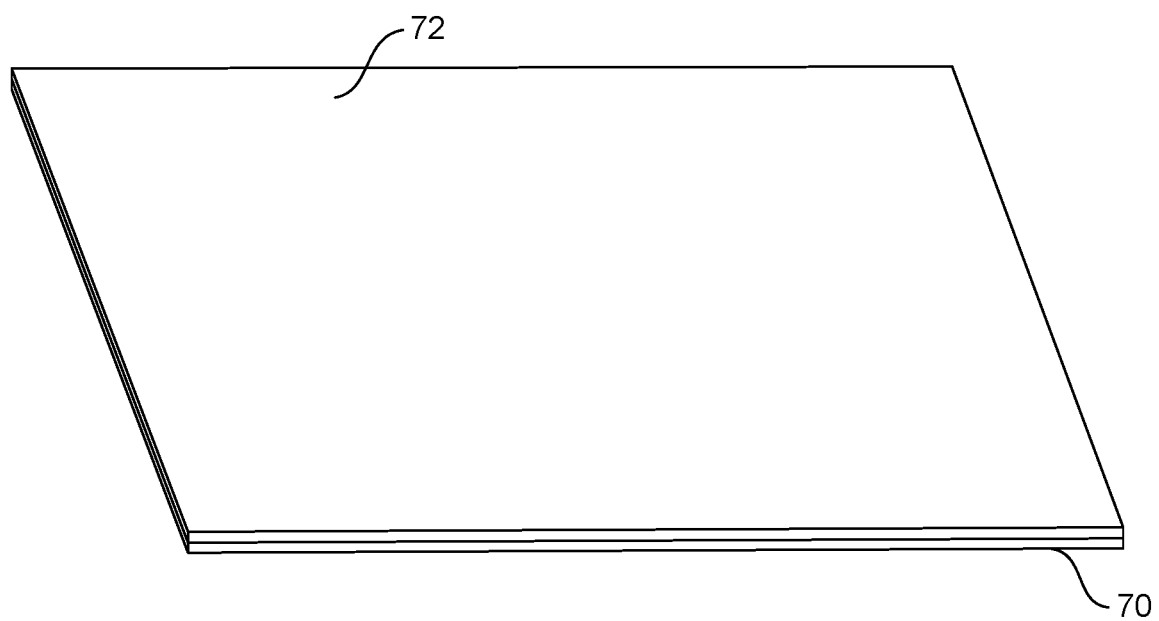
Figure 23J:
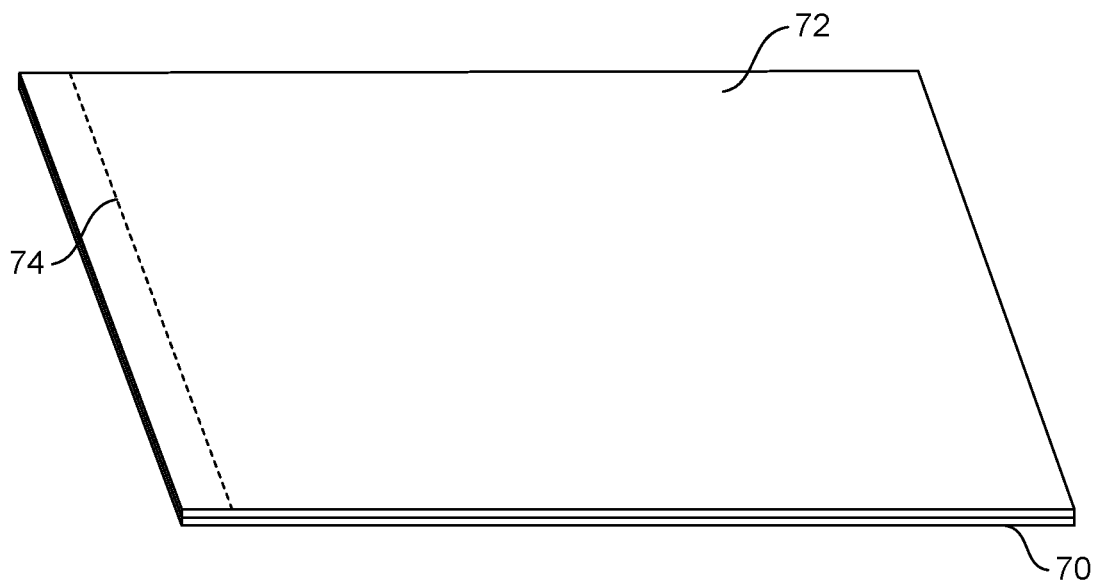
Figure 23K:
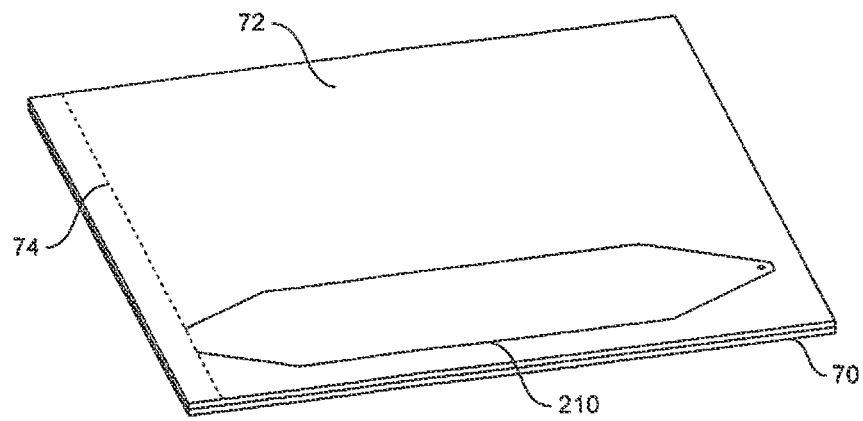
Figure 23L:
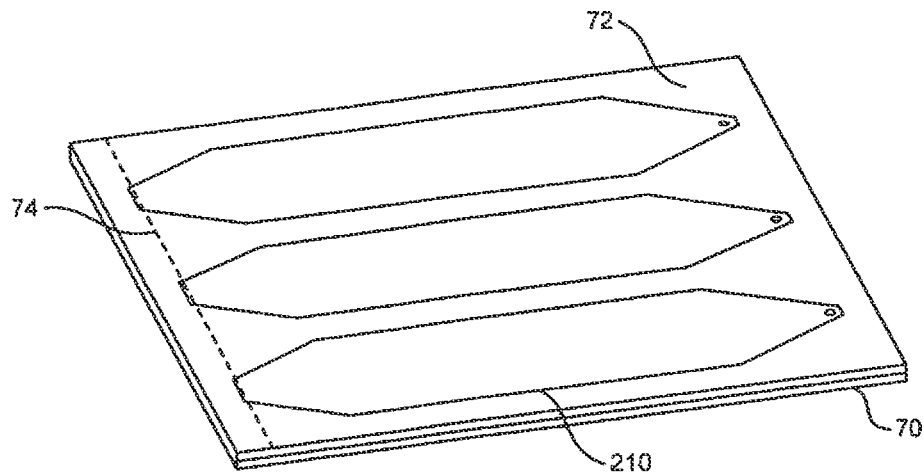
Figure 23M:
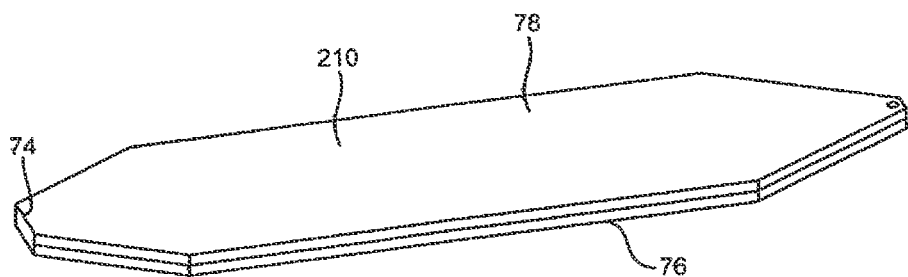
Figure 23N:
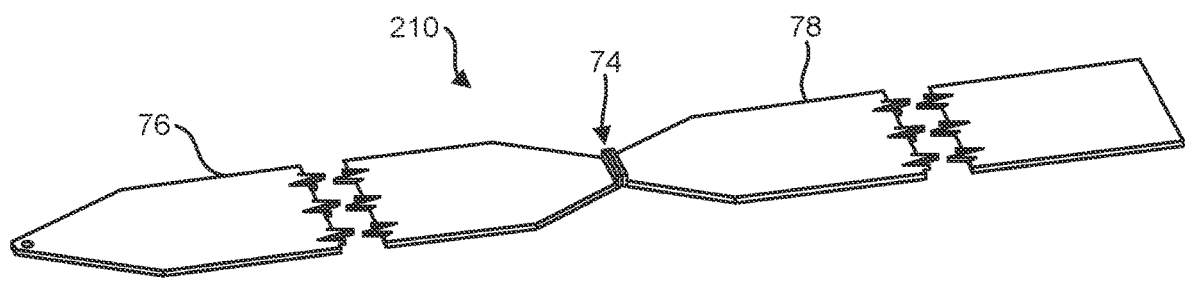
Figure 23O:
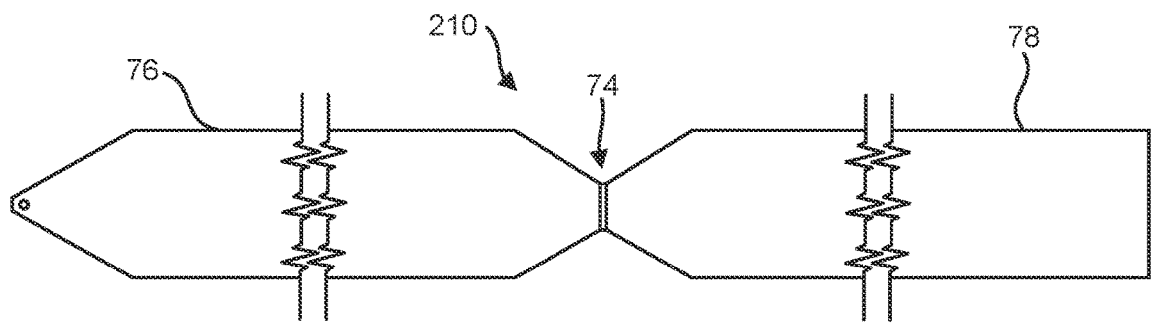
Figure 23P:
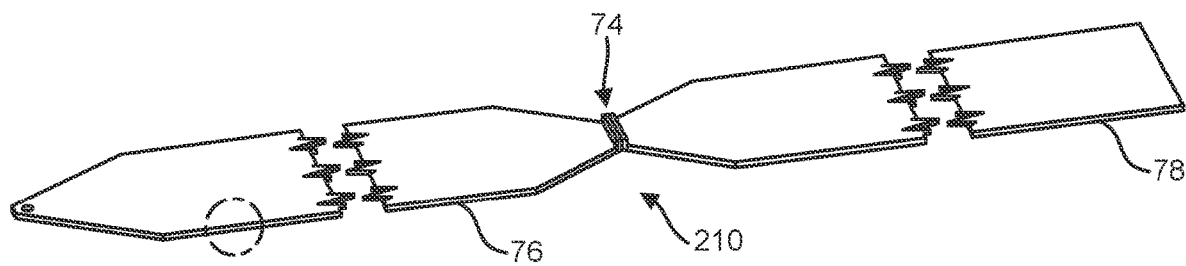

FIG. 23P is a perspective view showing an example ribbon in accordance with this detailed description.

Figures 23Q, 23R:
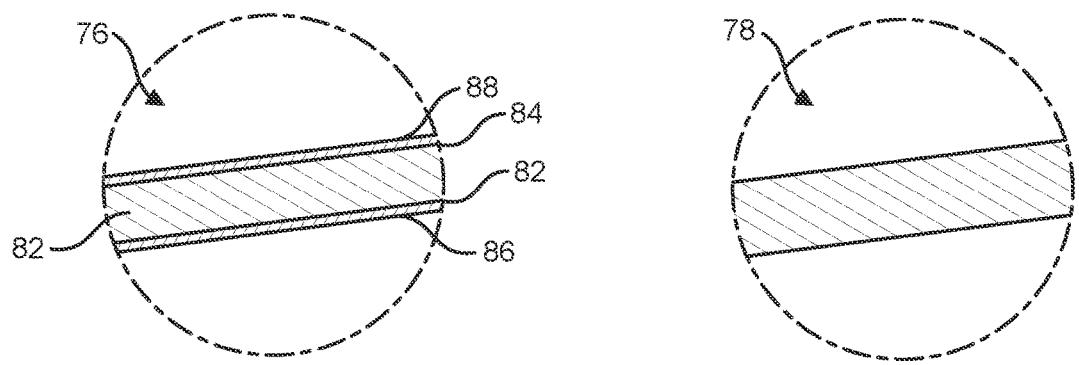

FIG. 23Q is a partial cross-sectional view illustrating the structure of a distal strip of the ribbon shown in FIG. 23P.

FIG. 23R is a partial cross-sectional view illustrating the structure of a proximal strip of the ribbon shown in FIG. 23P.

Figure 23S:
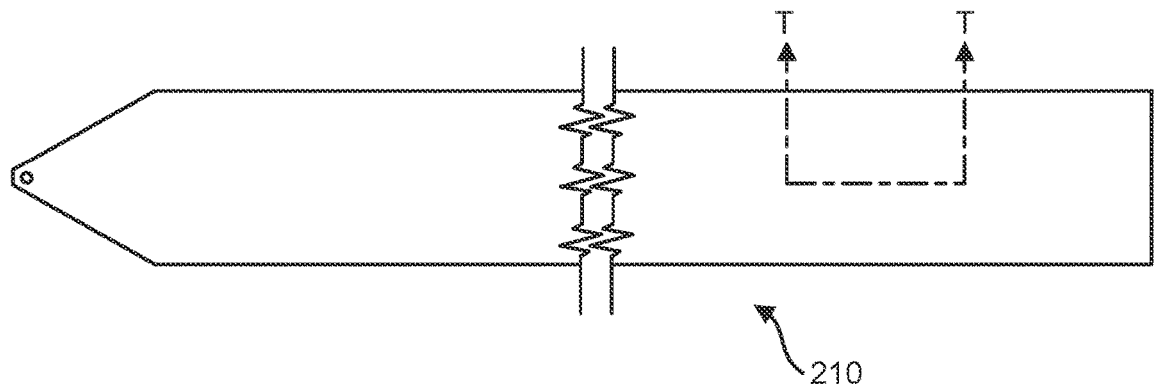

FIG. 23S is a top plan view of a ribbon in accordance with an example embodiment.

Figure 23T:
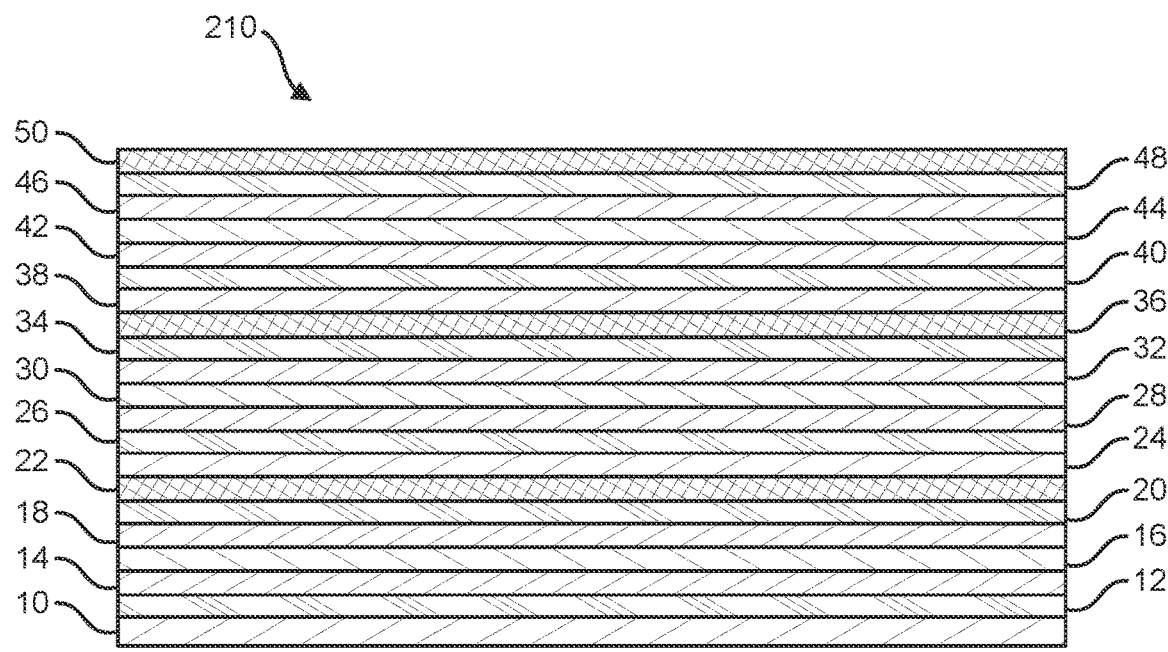

FIG. 23T is a partial cross-sectional view of the ribbon shown in FIG. 23S. In the embodiment of FIG. 23T, the ribbon has been sectioned along section line T-T shown in FIG. 23S.

FIG. 24A is a perspective view showing an example tubular guiding member in accordance with the detailed description.

FIG. 24B is an enlarged perspective view showing a portion of the example tubular guiding member shown in FIG. 24A.

Figure 25:
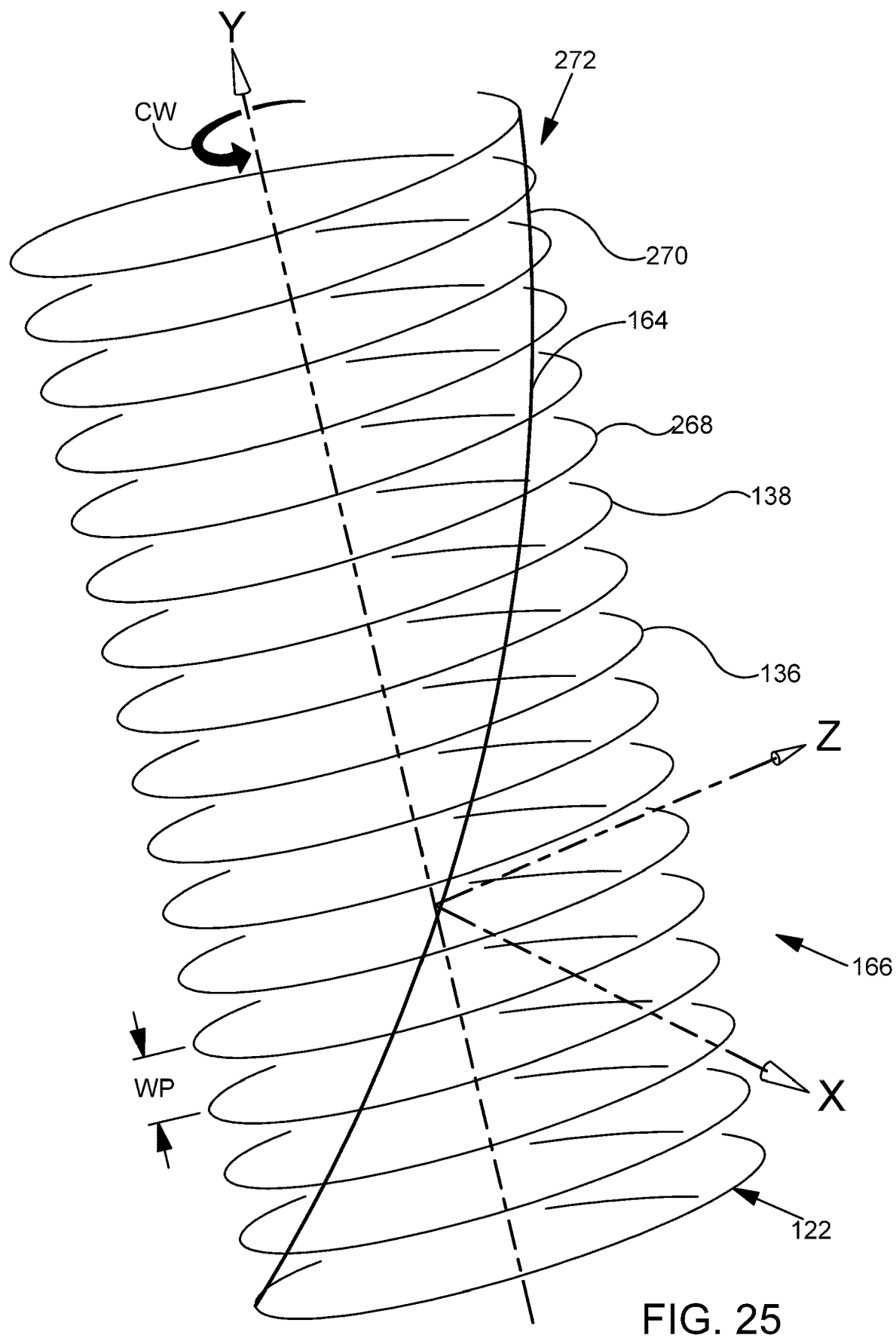

FIG. 25 is a perspective view showing an example support structure including a first support member and a second support member.

FIG. 26A is a side view showing a device for guiding and supporting catheters such as, for example, stent delivery catheters.

FIG. 26B is an enlarged detail view further illustrating a portion of the device shown in FIG. 26A.

Figure 26C:
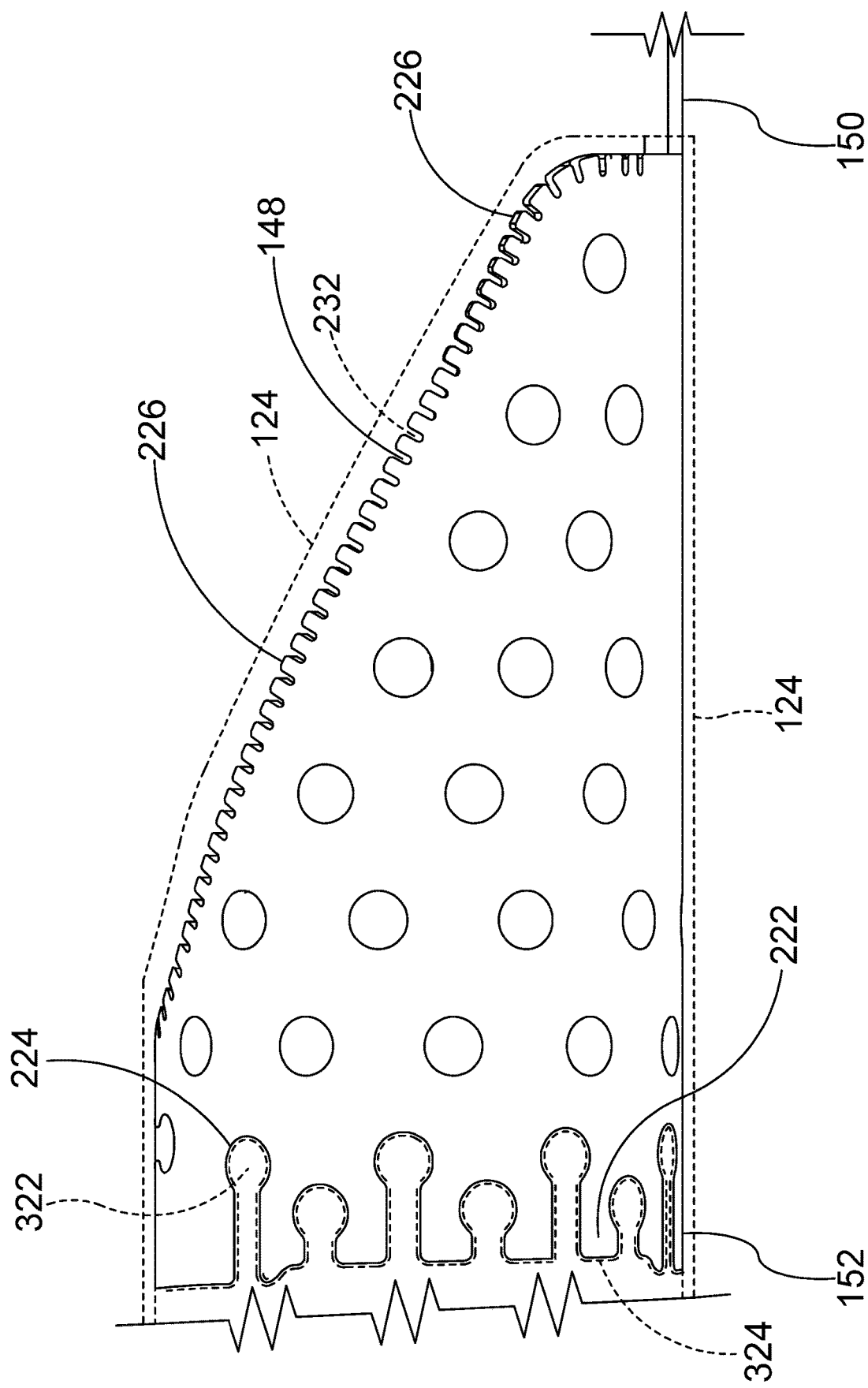

FIG. 26C is an enlarged side view further illustrating the apparatus shown in FIG. 26B.

FIG. 26D through FIG. 26M are a series of stylized partial cross-sectional views illustrating example methods in accordance with this detailed description.

Figure 27:
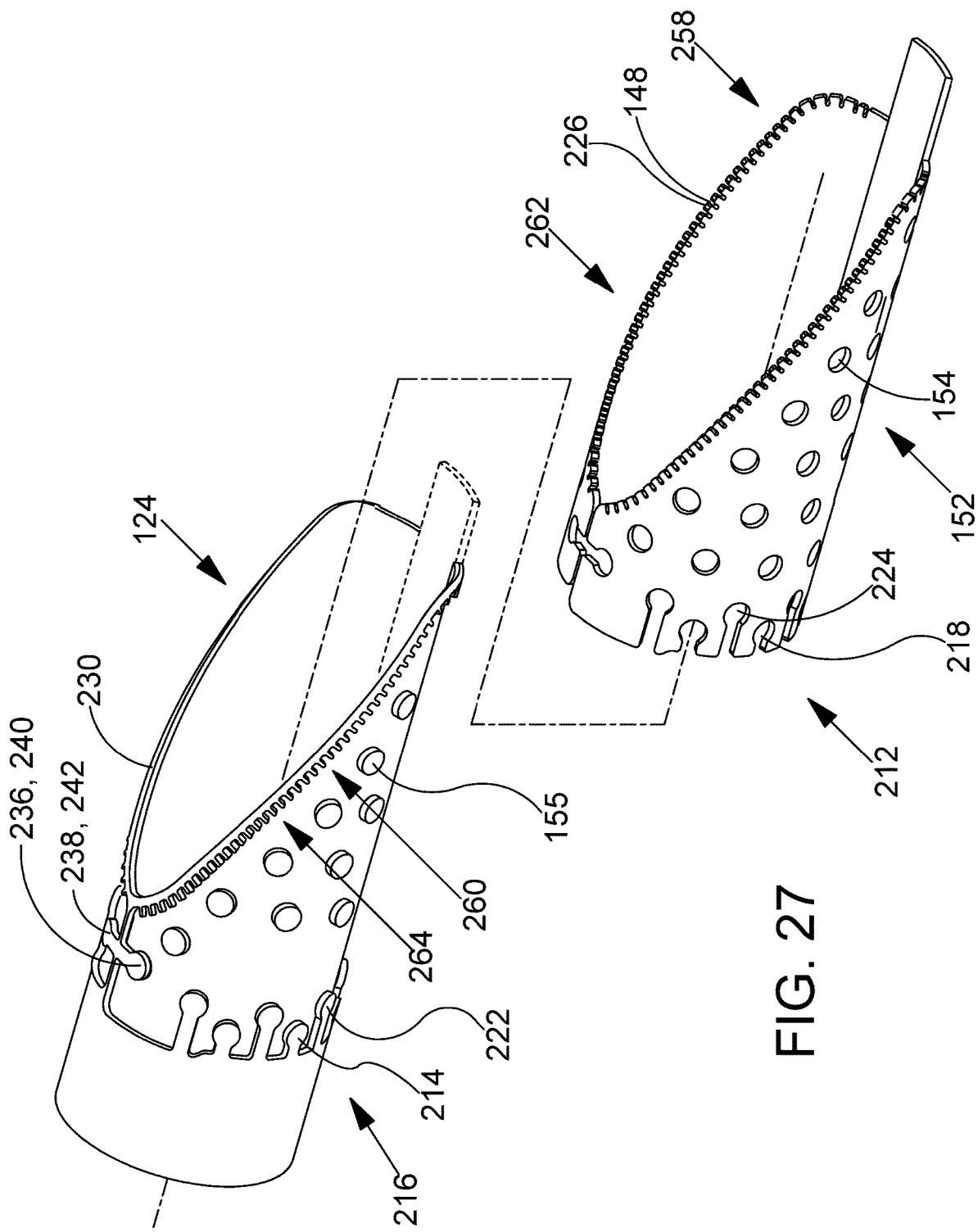

FIG. 27 is a stylized exploded view illustrating the saddle interlocking portion of the saddle member and the complementary interlocking portion of the encapsulation layer.

Figure 28:
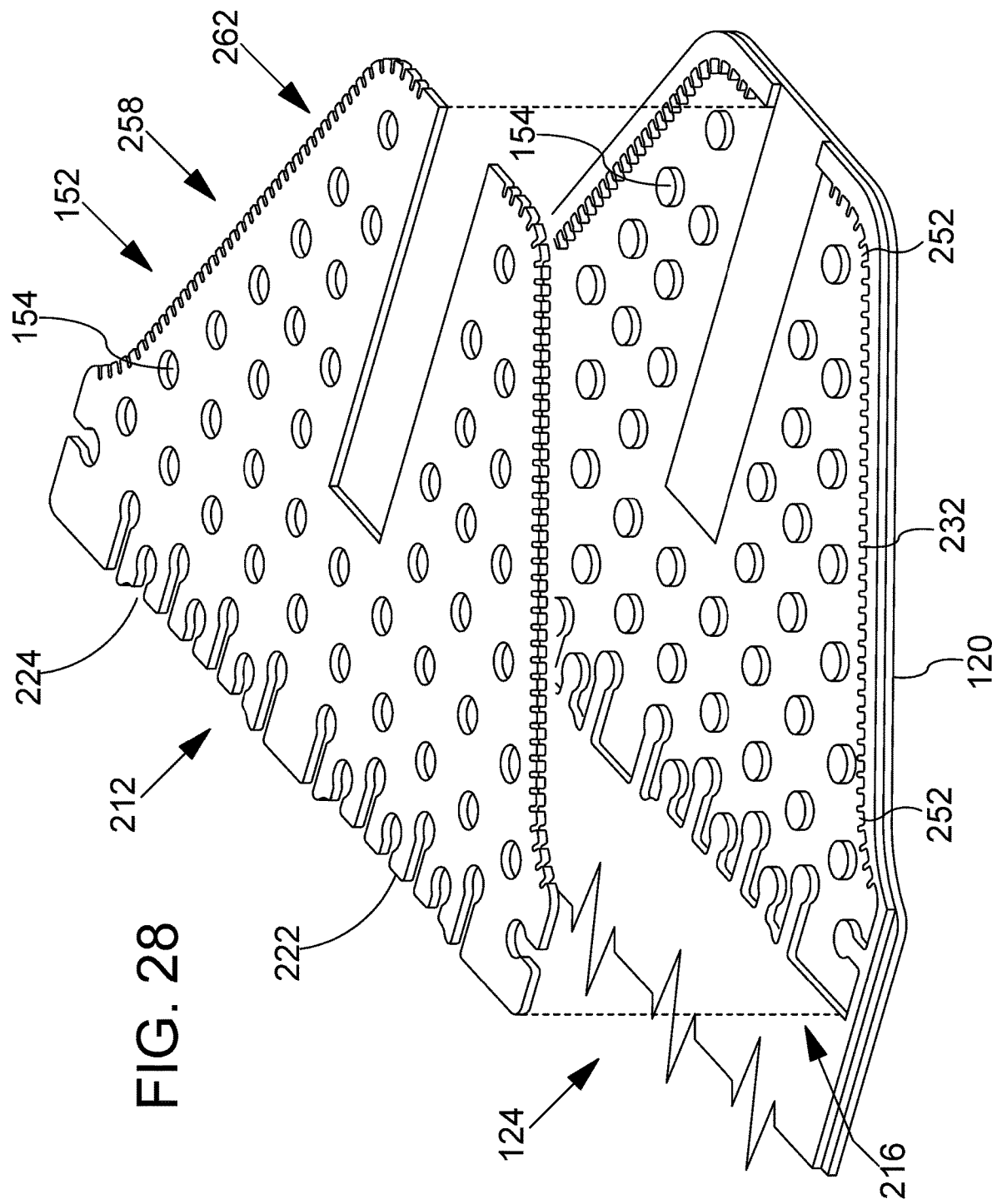

FIG. 28 is an additional stylized exploded view further illustrating the saddle interlocking portion of the saddle member and the complementary interlocking portion of the encapsulation layer.

Figure 29:
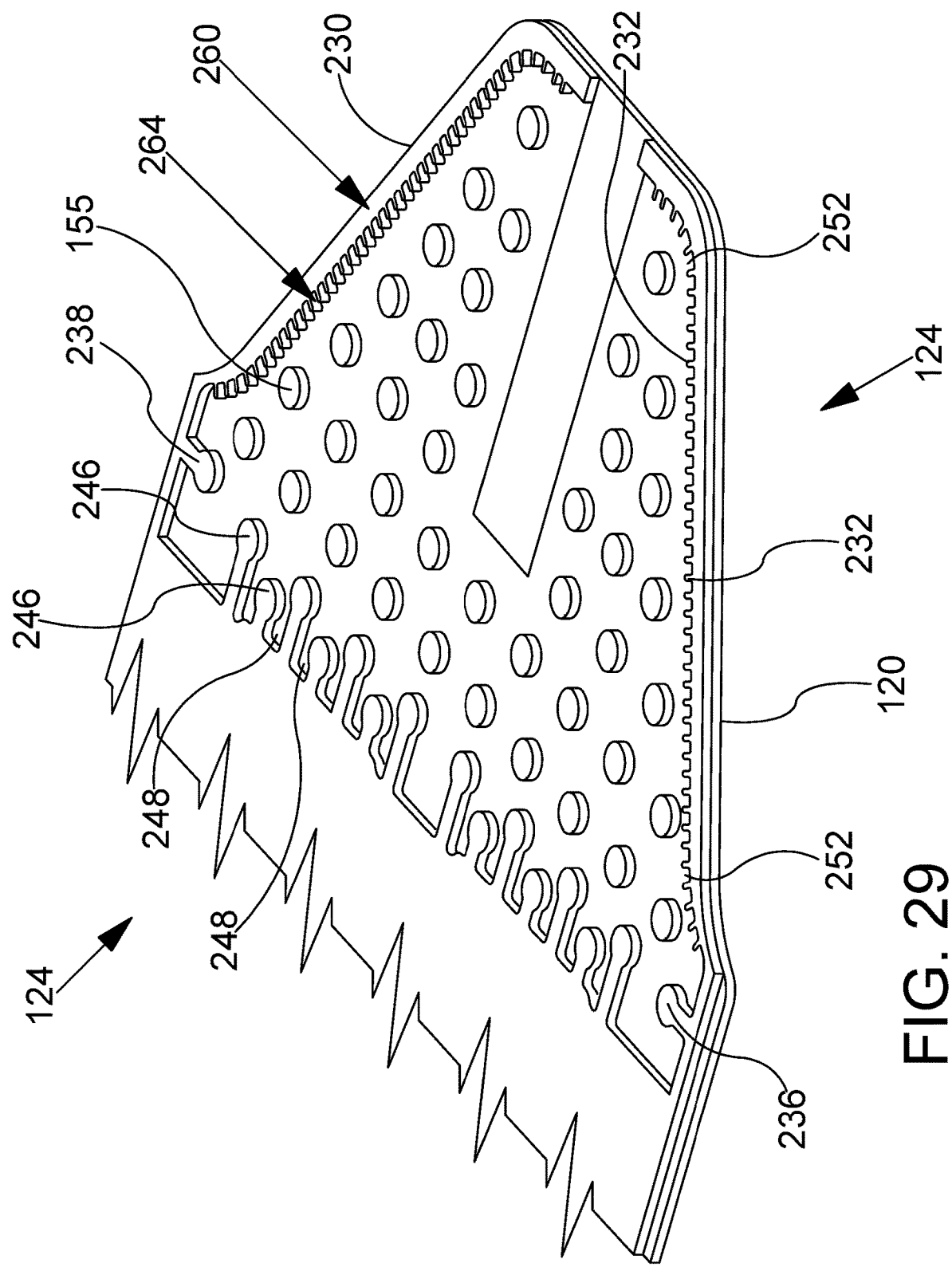

FIG. 29 is an enlarged perspective view showing the encapsulation layer shown in the previous figure.

Figure 30:
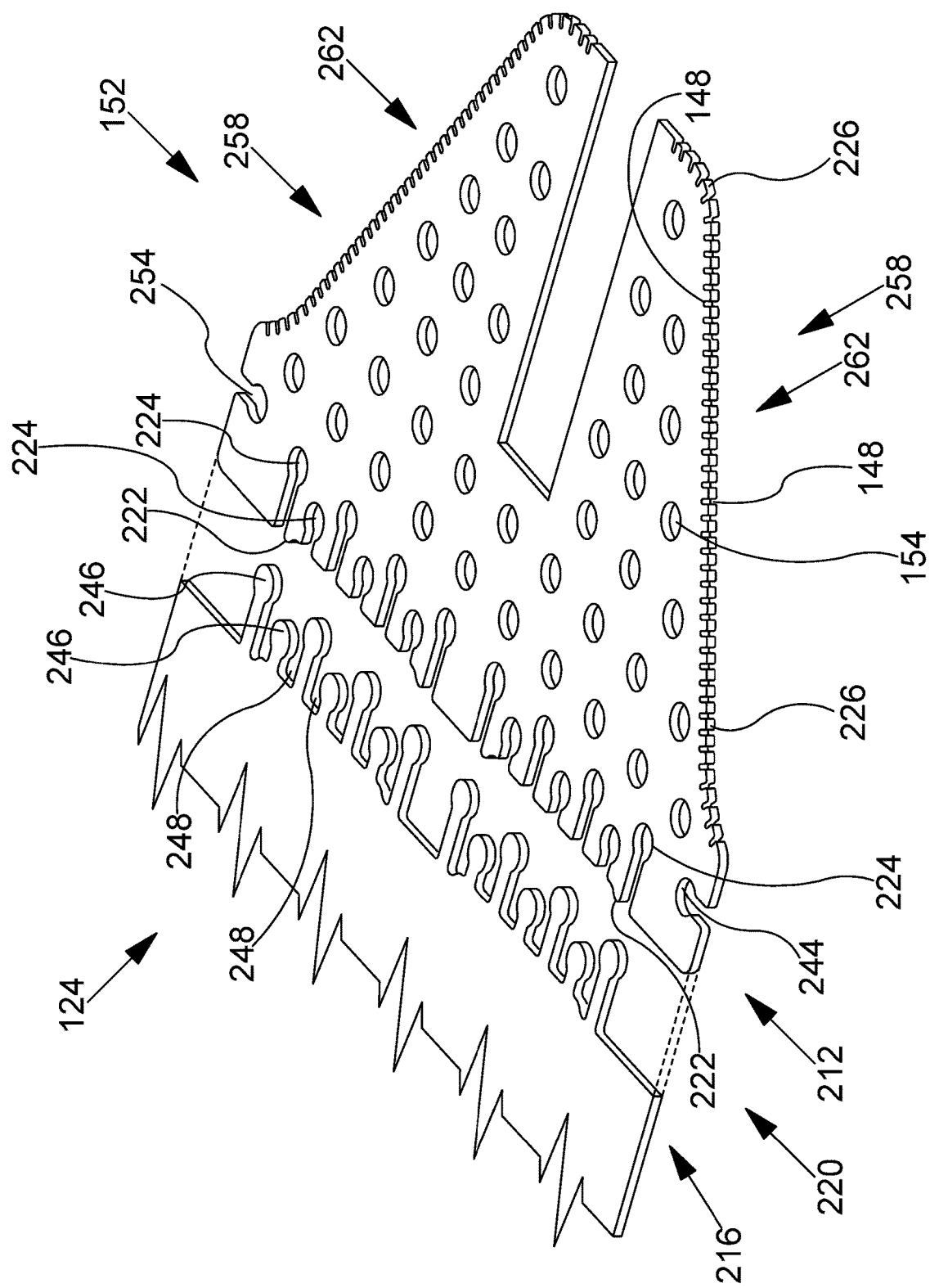

FIG. 30 is a stylized exploded view illustrating the saddle interlocking portion of the saddle member and the complementary interlocking portion of the encapsulation layer.

Figure 31:
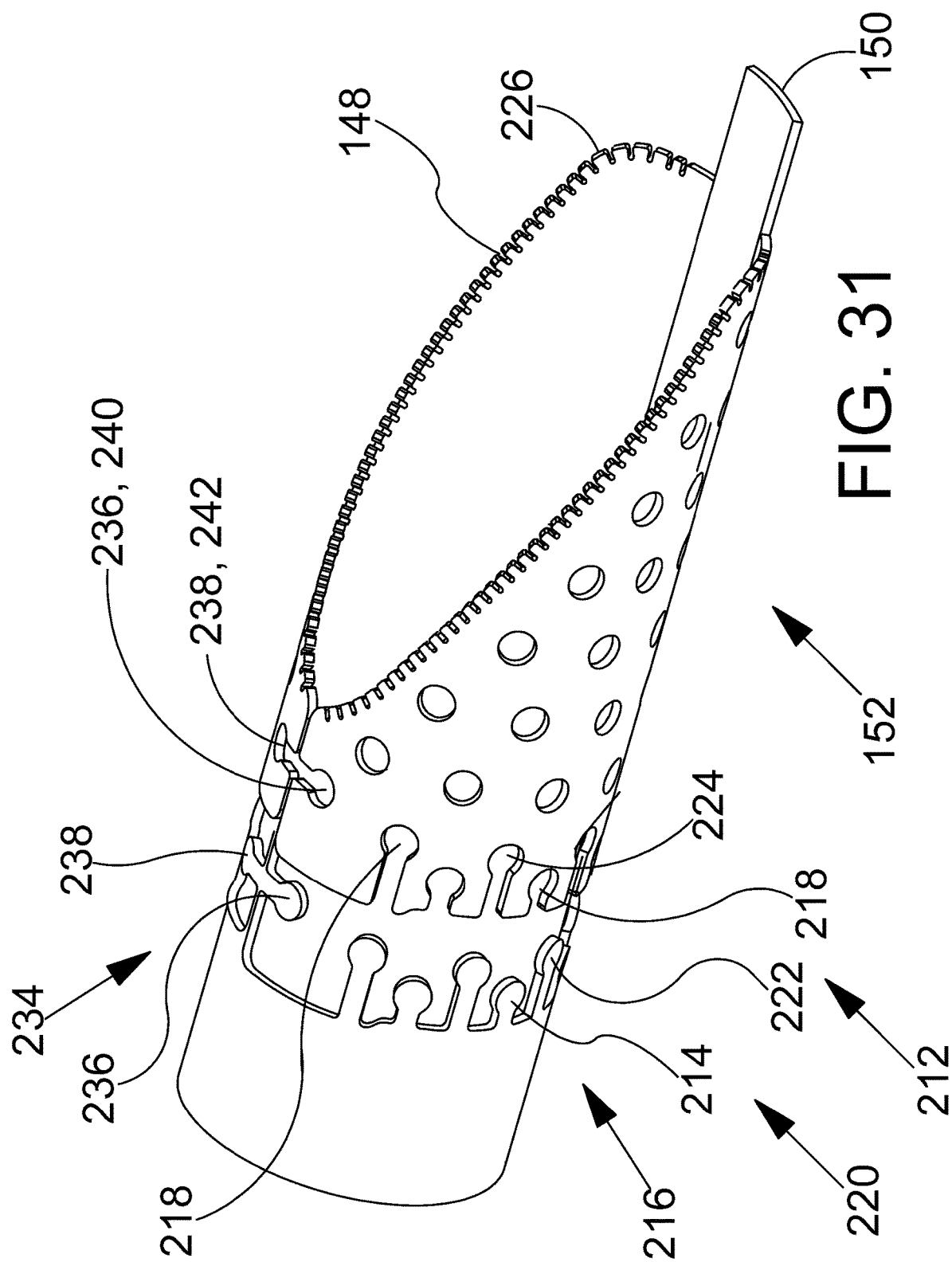

FIG. 31 is a stylized exploded view illustrating the saddle interlocking portion of the saddle member and the complementary interlocking portion of the encapsulation layer.

Figure 32:
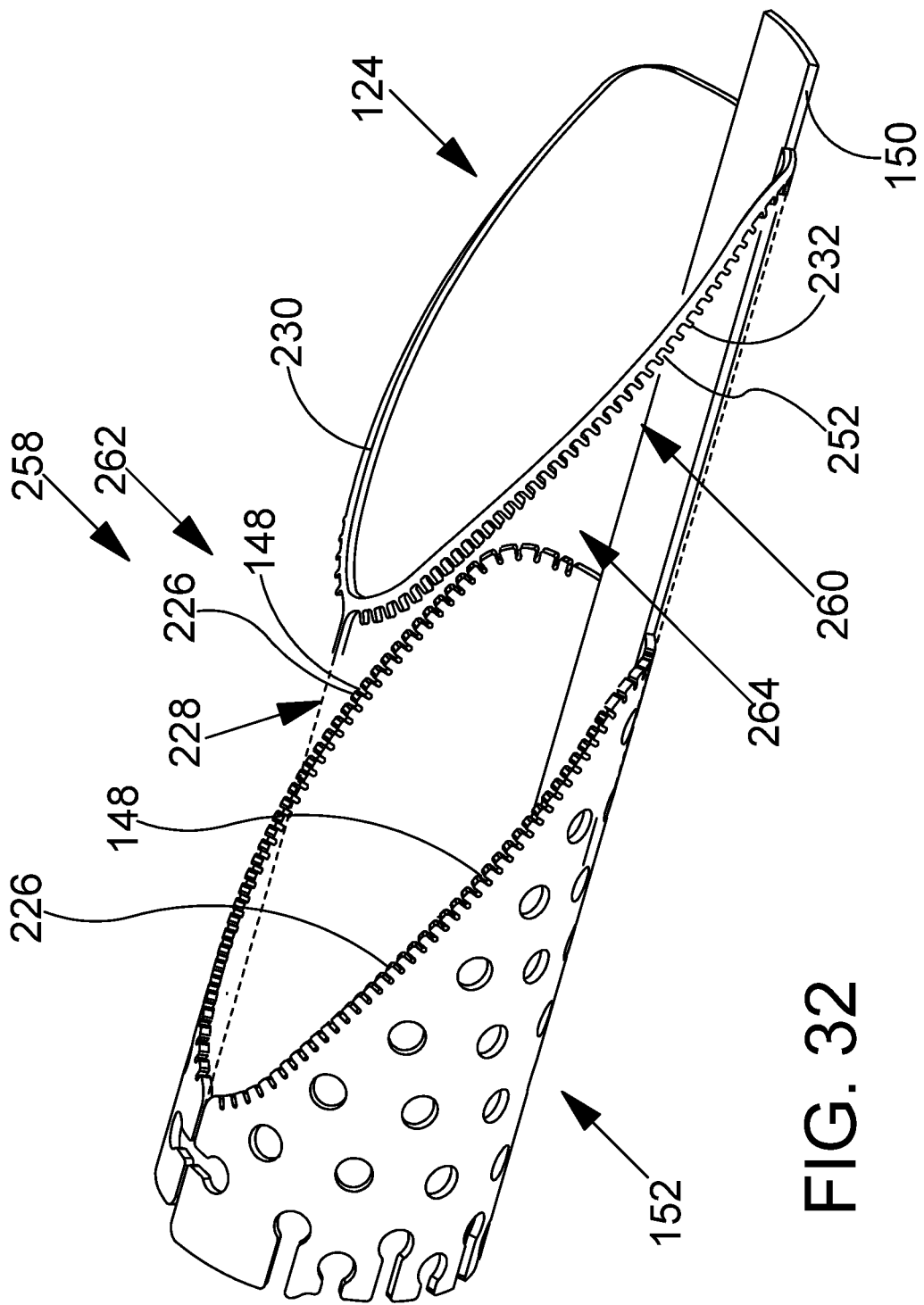

FIG. 32 is an additional stylized exploded view further illustrating the serrated edge of the saddle member and the overhanging lip portion of the encapsulation layer.

Figure 33:
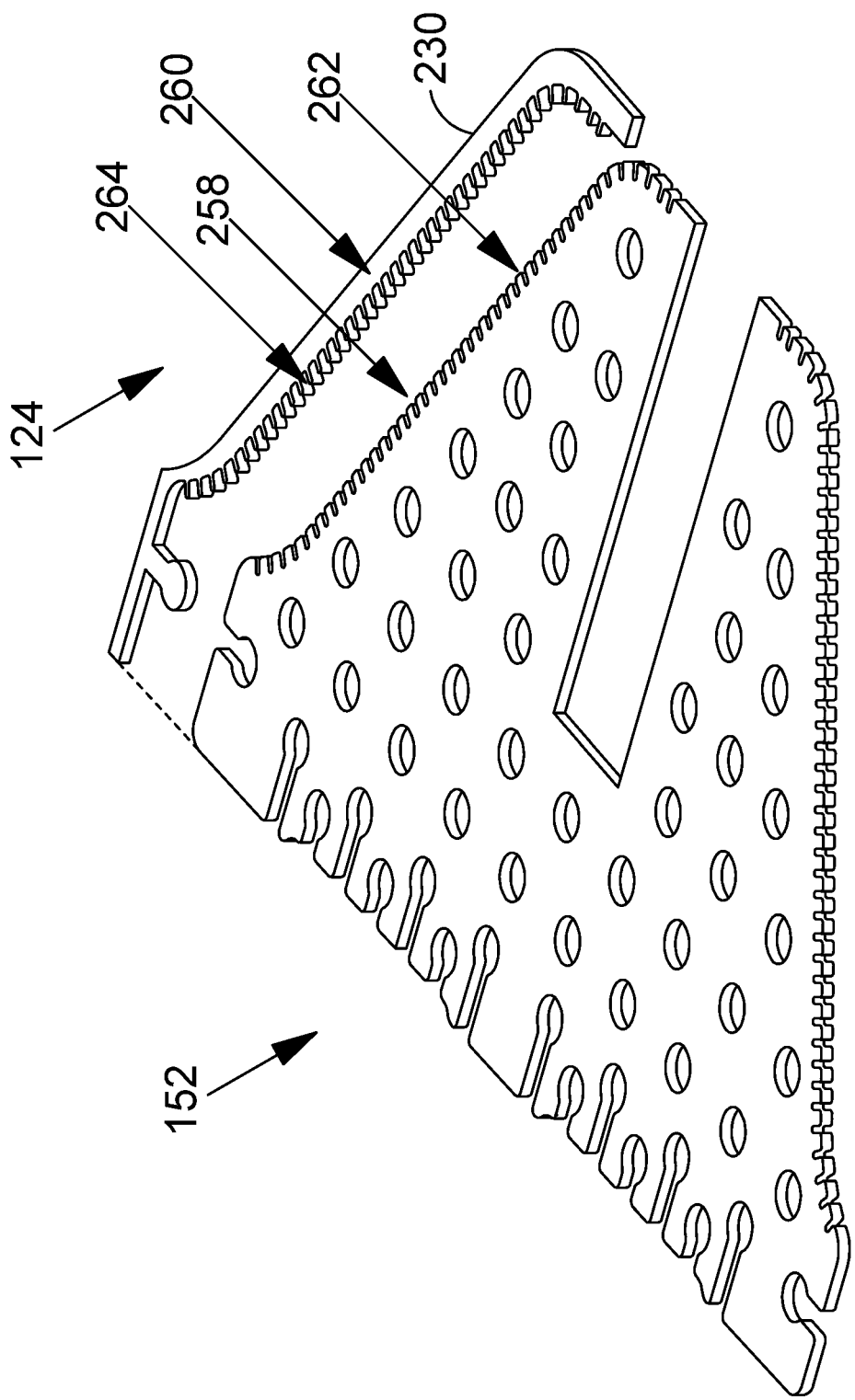

FIG. 33 is an additional stylized exploded view further illustrating the serrated edge of the saddle member and the overhanging lip portion of the encapsulation layer.

FIG. 34A through FIG. 34F are elevation and plan views showing six sides of an elongate positioning member.

Figure 34E:
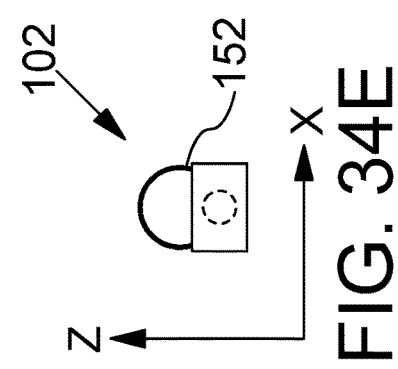
Figure 34D:
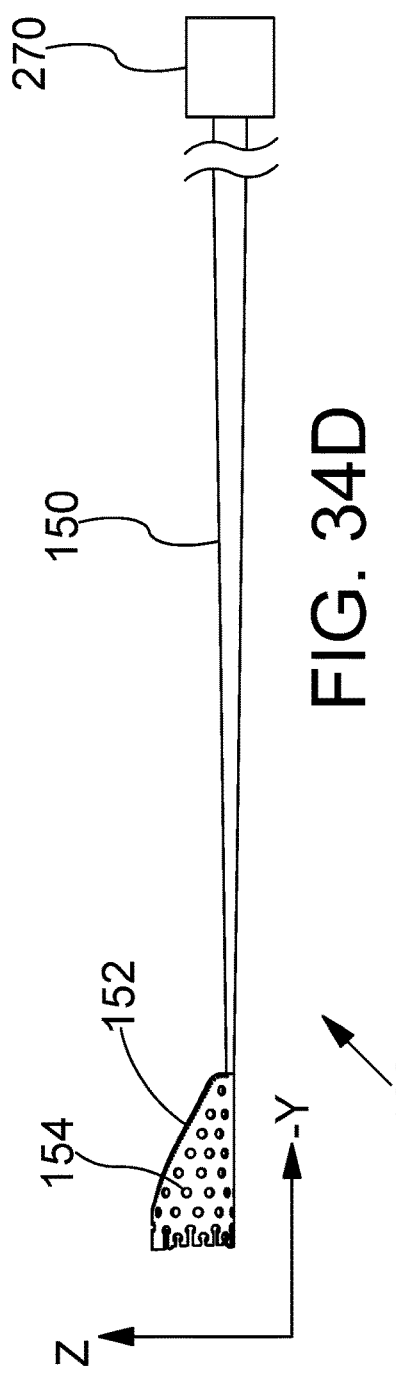
Figure 34F:
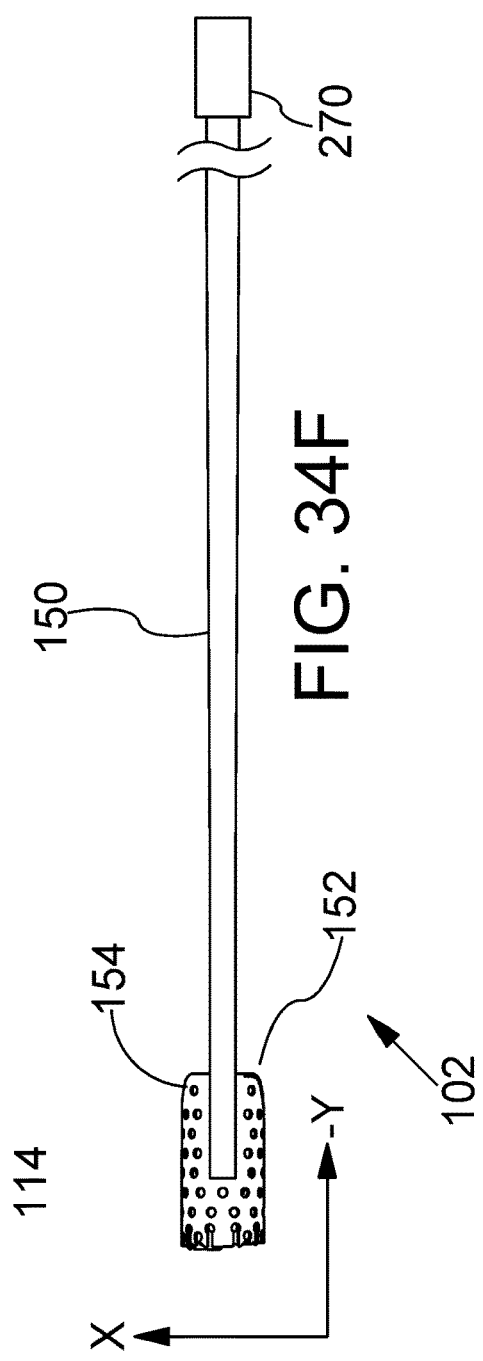
Figure 35:
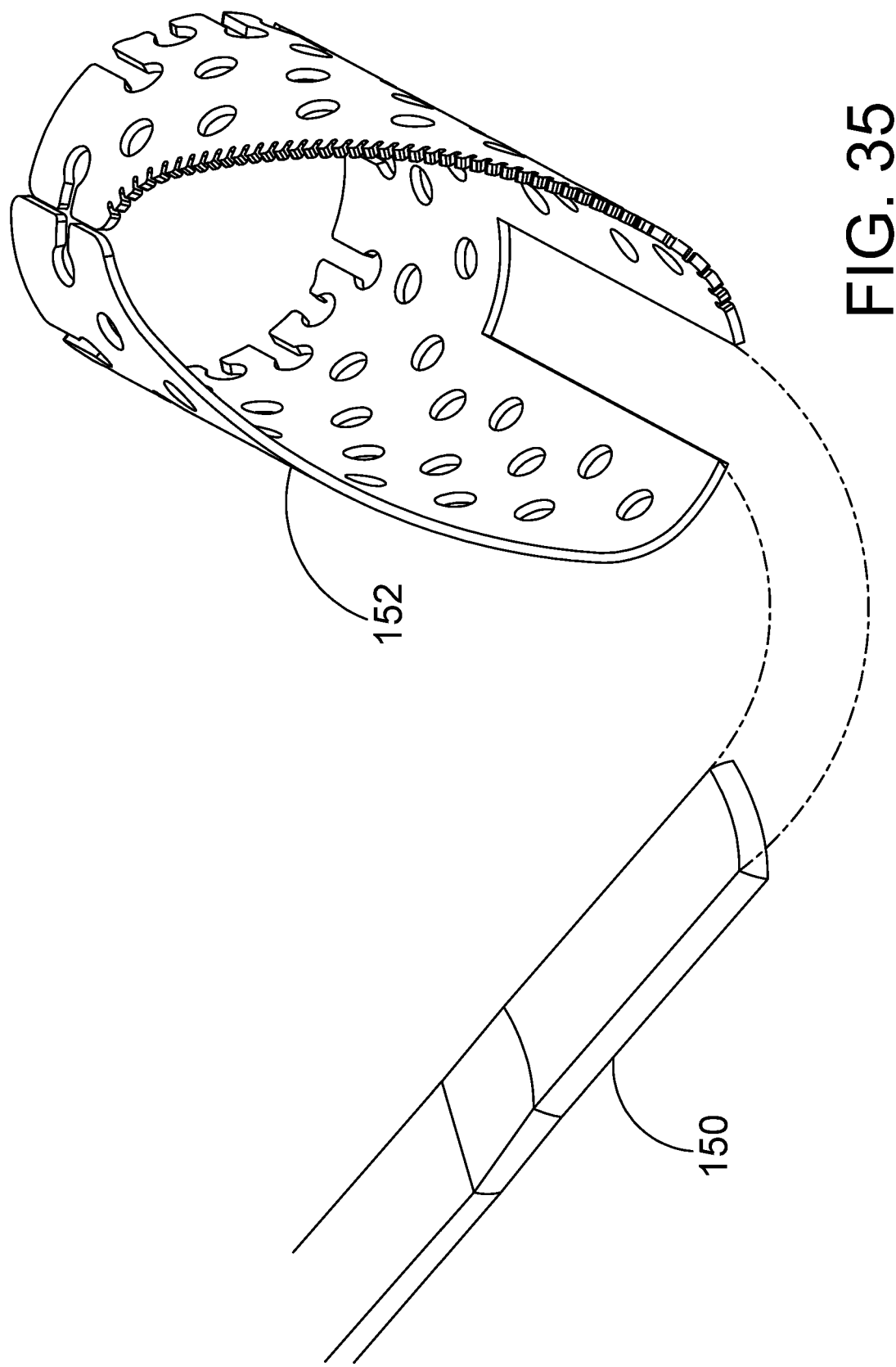

FIG. 35 is an exploded perspective view showing a distal portion of the elongate positioning member shown in FIG. 34.

Figure 36:
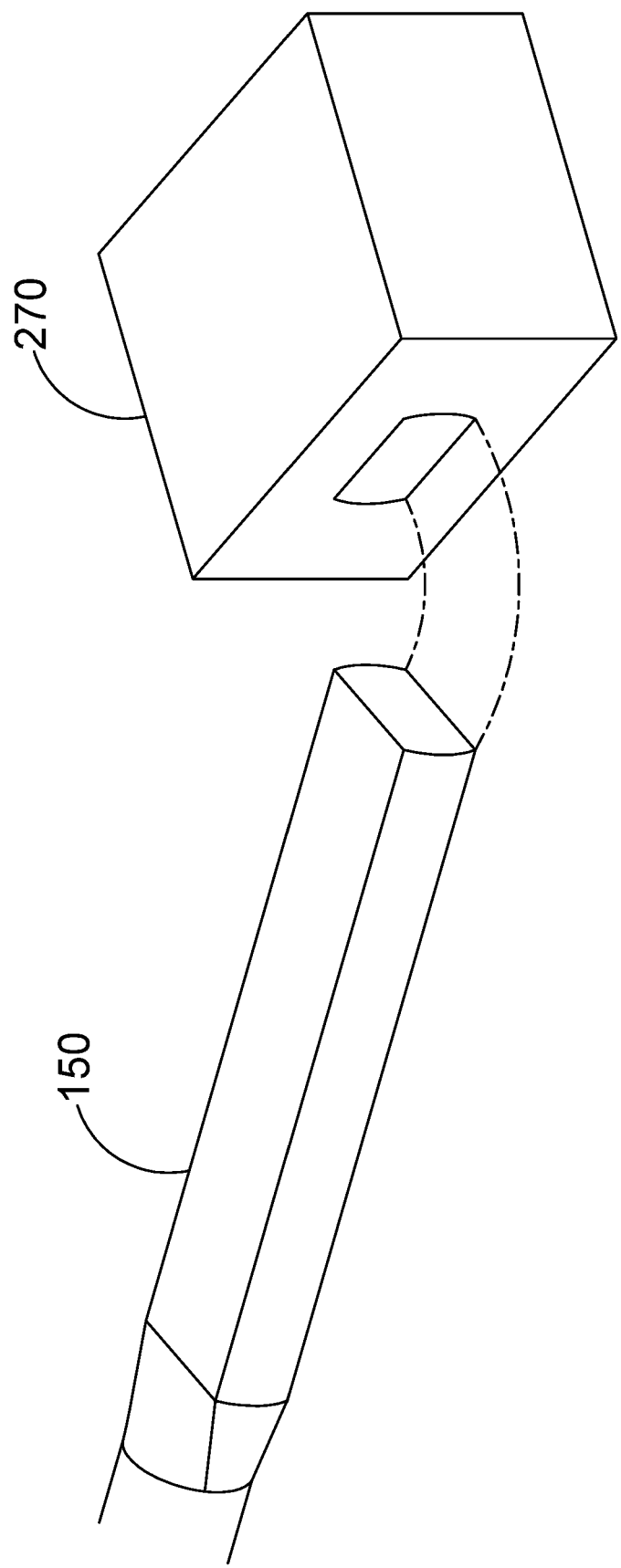

FIG. 36 is an exploded perspective view showing a proximal portion of the elongate positioning member shown in FIG. 34.

FIG. 37A is a top view of a shaft member for an elongate positioning member in accordance with this detailed description. FIG. 37B and FIG. 37C are cross-sectional views of the shaft member shown in FIG. 37A.

FIG. 38A through FIG. 38F are elevation and plan views showing six sides of a saddle member.

Figure 39A:
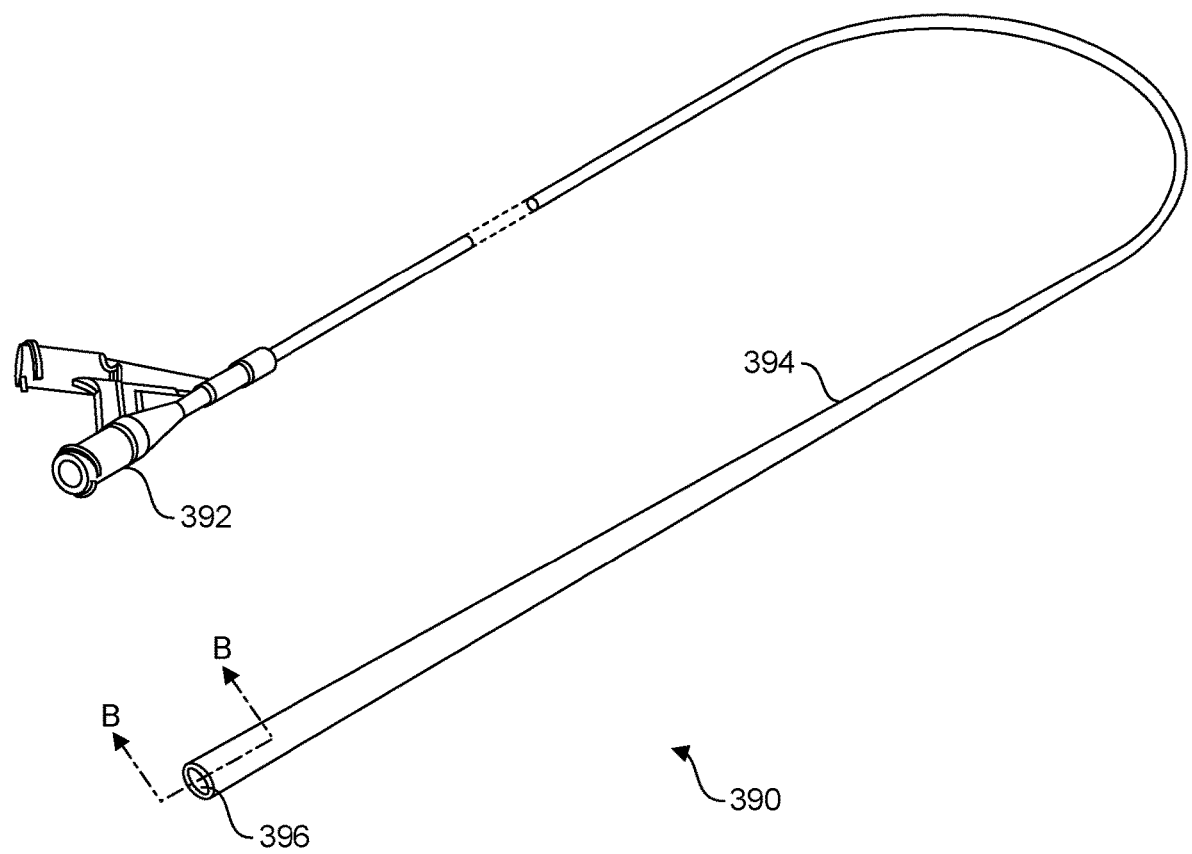

FIG. 39A is a perspective view showing a catheter.

Figure 39B:
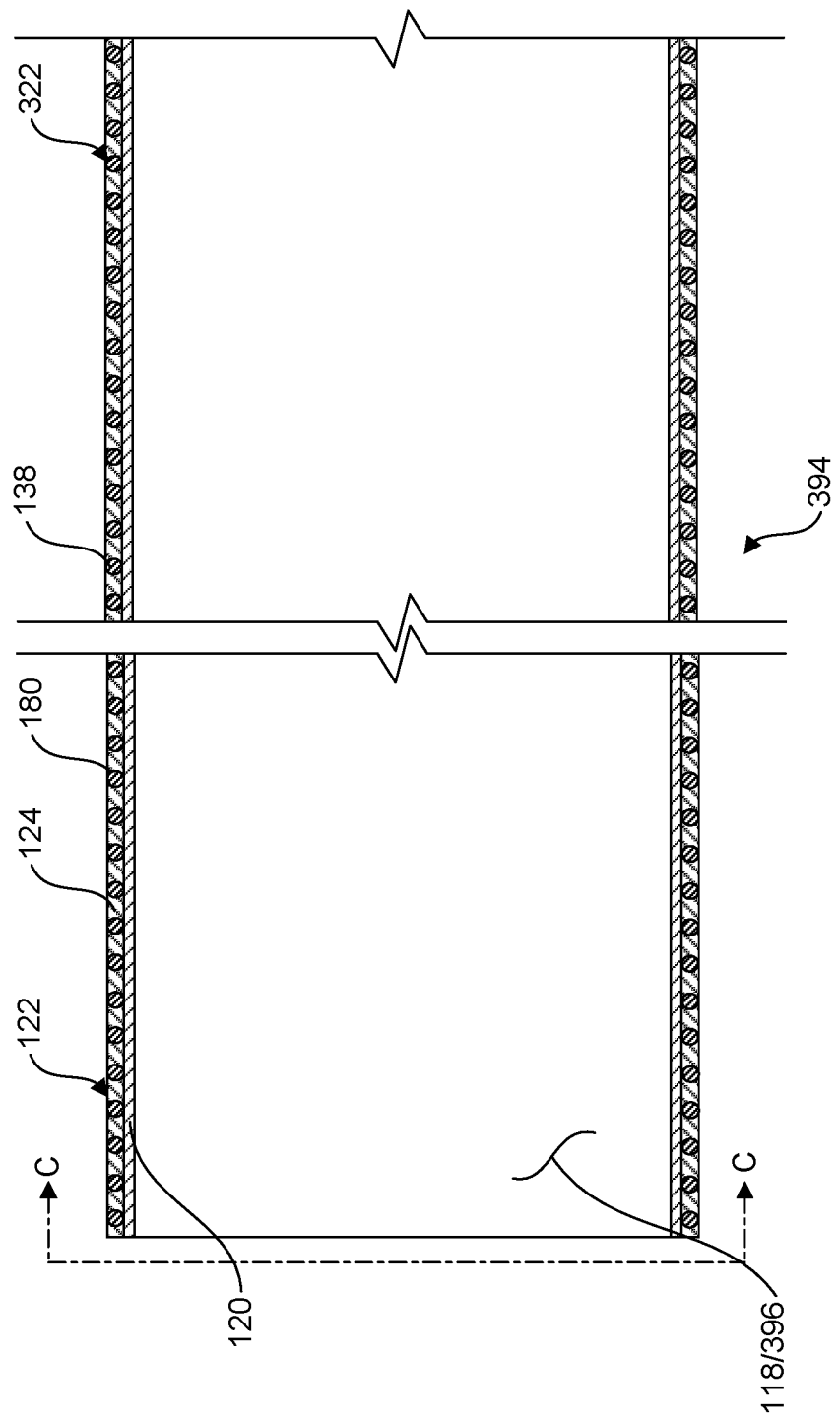

FIG. 39B is a partial cross-sectional view of the catheter shown in FIG. 39A. In the embodiment of FIG. 39B, the catheter has been sectioned along section line B-B shown in FIG. 39A.

Figure 39C:
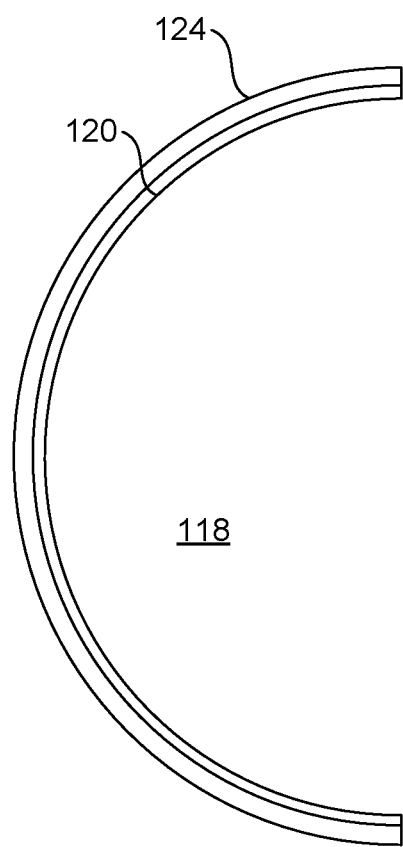

FIG. 39C is an end view of the catheter section shown in FIG. 39B.

Figure 40A:
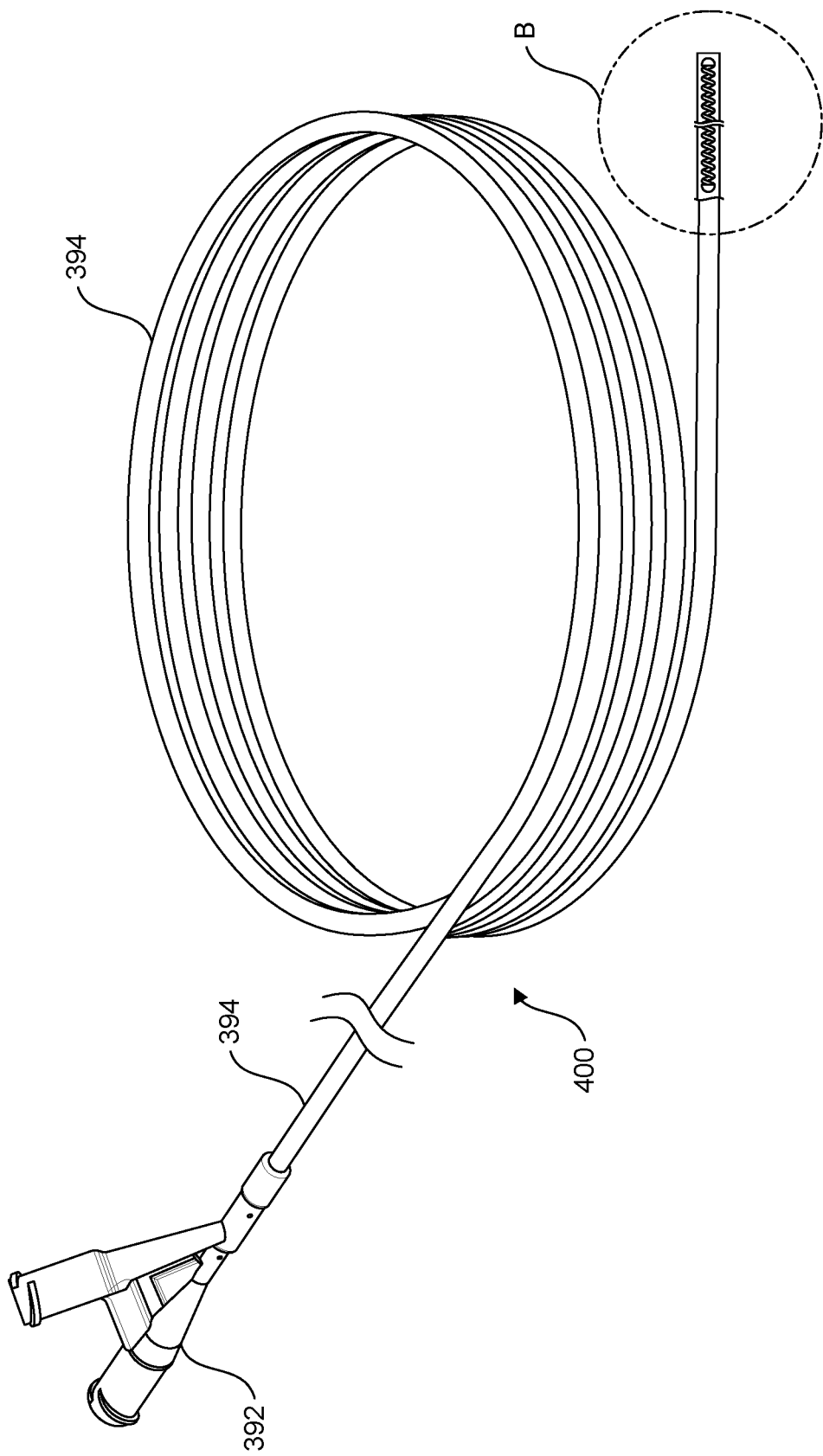

FIG. 40A is a perspective view showing a catheter for delivering an embolic coil.

Figure 40B:
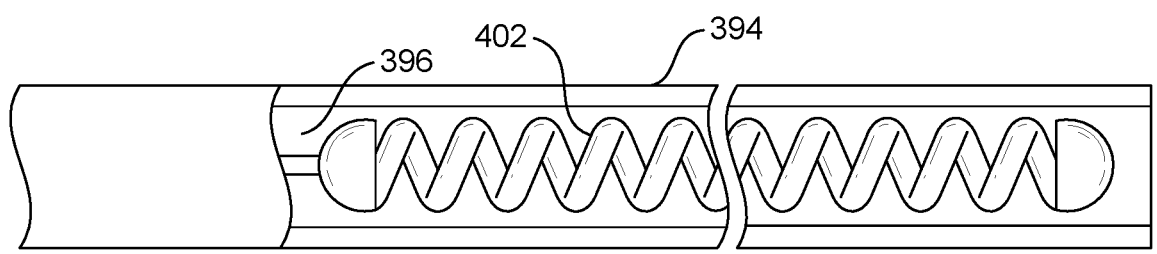

FIG. 40B is an enlarged detail view showing a portion of the catheter shown in FIG. 40A.

Figure 41A:
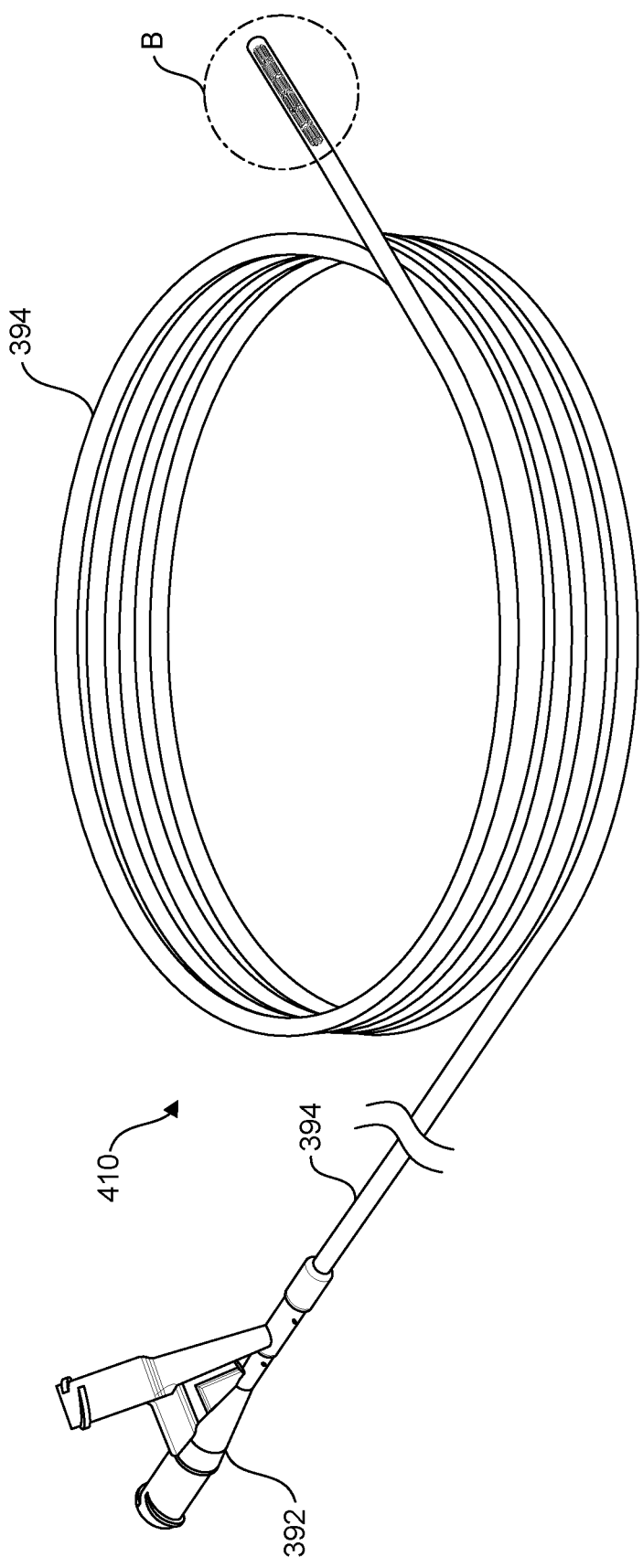

FIG. 41A is a perspective view showing a stent delivery catheter.

Figure 41B:
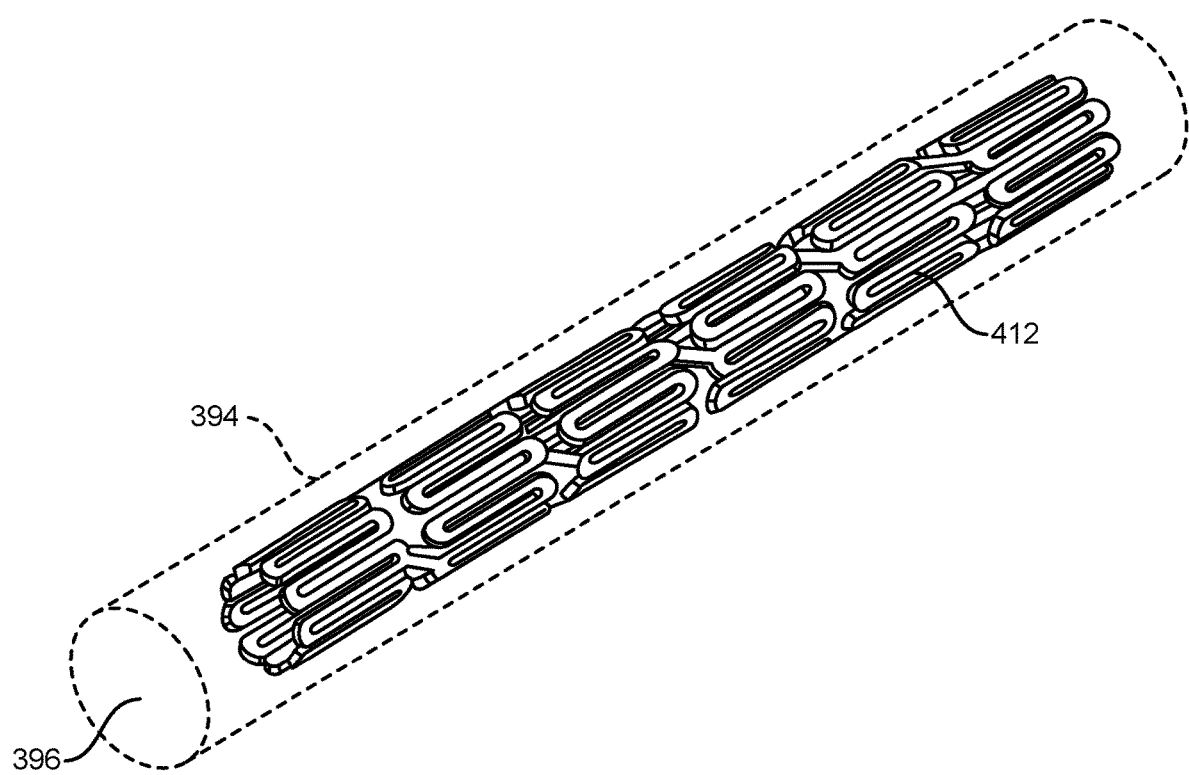

FIG. 41B is an enlarged detail view showing a portion of the catheter shown in FIG. 41A.

Figure 42:
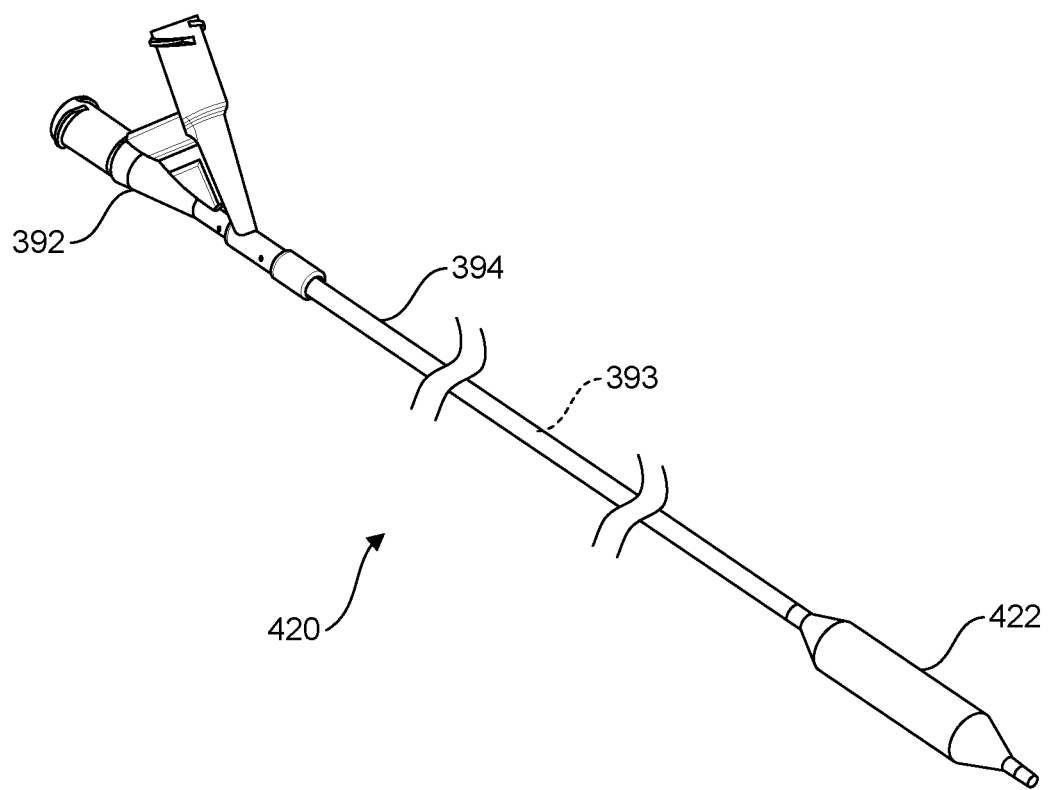

FIG. 42 is a perspective view showing a balloon catheter.

Figure 43A:
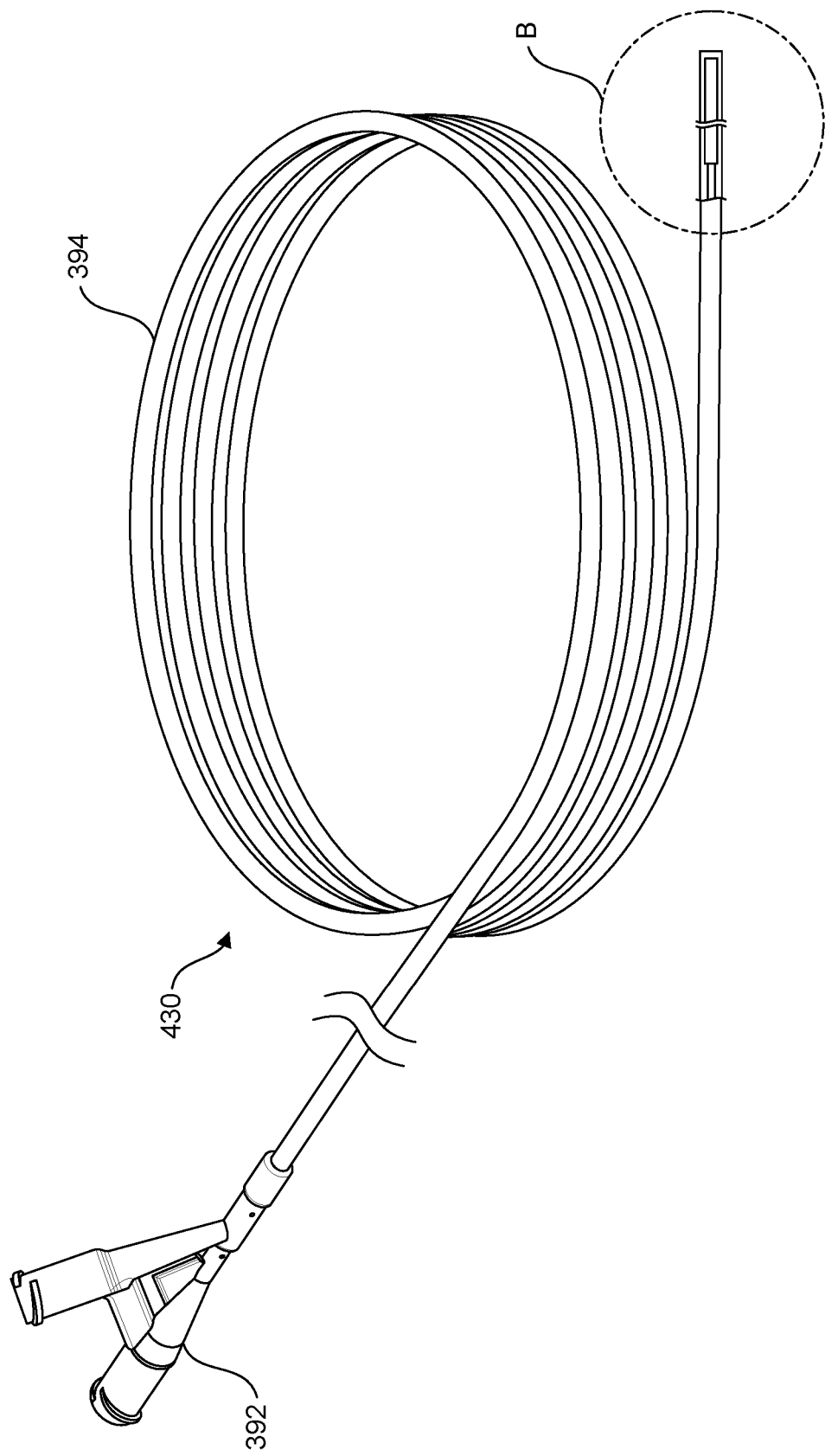

FIG. 43A is a perspective view showing an ultrasound catheter.

Figure 43B:
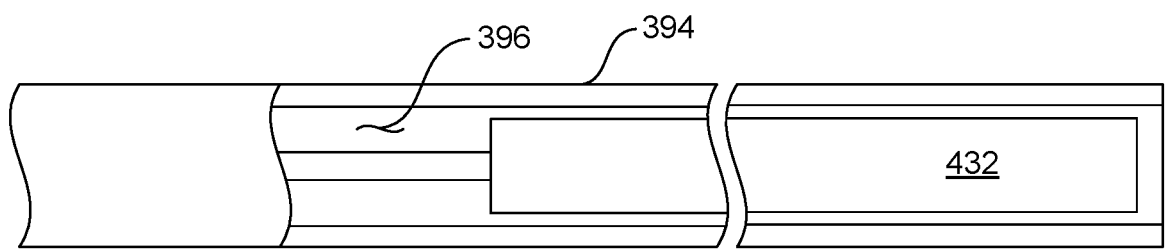

FIG. 43B is an enlarged detail view showing a portion of the catheter shown in FIG. 43A.

While embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

FIG. 1 is a perspective view showing a device 100 for guiding and supporting catheters such as, for example, stent delivery catheters. In the embodiment of FIG. 1, the device 100 comprises a tubular guiding member 104 and an elongate positioning member 102 extending in a proximal direction beyond the tubular guiding member 104 for advancing and retracting the tubular guiding member 104 in distal and proximal directions. In embodiments, a distal portion of the elongate positioning member 102 is coupled to a proximal portion of the tubular guiding member 104 at a joint region. In embodiments, a ribbon comprising a plurality of fibers extends through the joint region.

FIG. 2A is a perspective view showing a portion of the device 100 shown in FIG. 1. FIG. 2B is a cross-sectional view of the device 100 shown in FIG. 2A. In the embodiment of FIG. 2B, the device 100 has been sectioned along section line 2B-2B shown in FIG. 2A. FIG. 2C is an end view of the device shown in FIG. 2B. FIG. 2A-FIG. 2B may be collectively referred to as FIG. 2. In the embodiment of FIG. 2, the device 100 comprises a tubular guiding member 104 and an elongate positioning member 102 extending in a proximal direction beyond the tubular guiding member 104 for advancing and retracting the tubular guiding member 104 in distal and proximal directions.

With reference to FIG. 2B, it will be appreciated that the tubular guiding member 104 comprises an inner tubular member 120, a coil 122 disposed about the inner tubular member 120, and an encapsulation layer 124 overlaying the coil 122 and the inner tubular member 120. In some useful embodiments, the coil 122 is made of a radiopaque material that serves as a radiographic marker. In some useful embodiments, the coil 122 comprises tungsten wire. With reference to FIG. 2, it will be appreciated that the inner tubular member 120 defines a lumen 118 extending between a proximal end of the tubular guiding member 104 and a distal end of the tubular guiding member 104. In the example embodiment of FIG. 2, the coil 122 forms a plurality of turns with each turn encircling the inner tubular member 120.

Figure 3B:
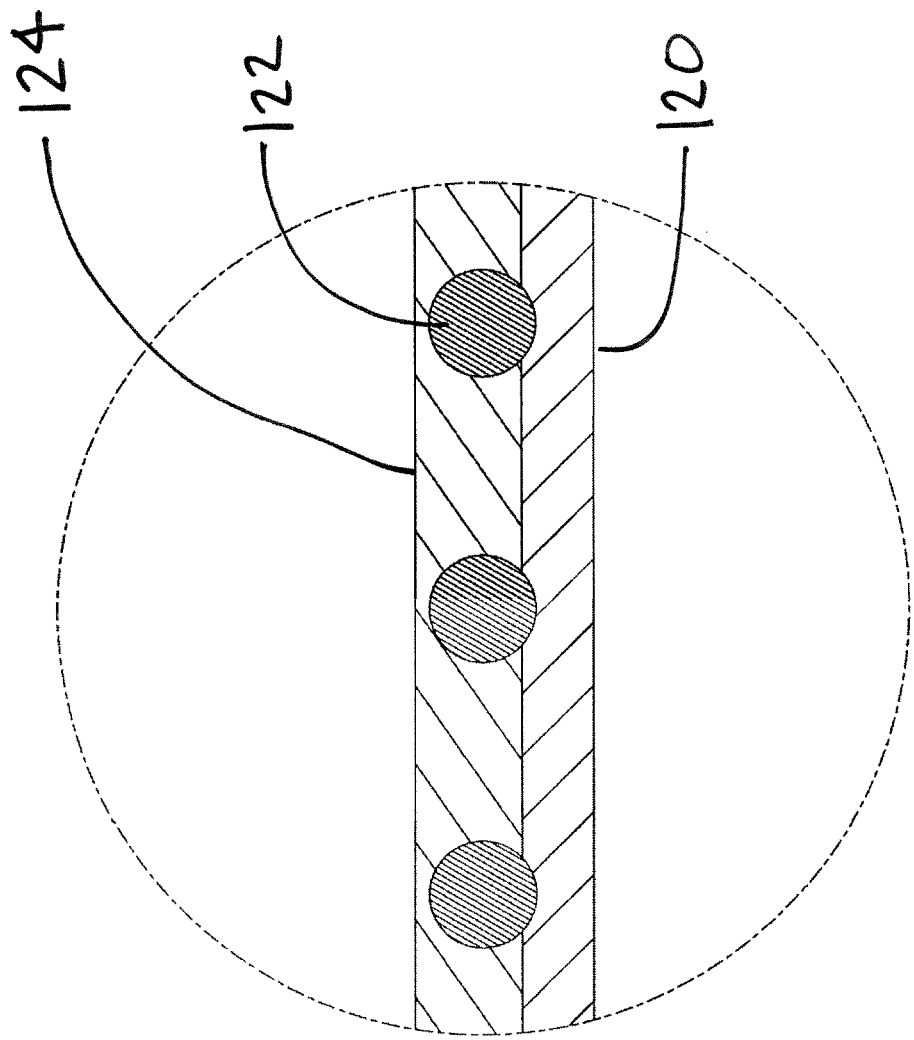
FIG. 3B is an enlarged detail view showing a portion of the device shown in FIG. 3A.

FIG. 3A is an enlarged cross-sectional view showing a portion of the device shown in FIG. 2B. FIG. 3B is an enlarged detail view showing a portion of the device shown in FIG. 3A. In FIG. 3B, the material of the encapsulation layer 124 can be seen conforming to the turns of the coil 122. Also in FIG. 3B, the material of the encapsulation layer 124 can be seen overlaying the outer surface of the inner tubular member 120. In some useful embodiments, the encapsulation layer 124 encapsulates and is bonded to the coil 122 and the inner tubular member 120. In some useful embodiments, the encapsulation layer is mechanically interlocked with the coil 122. FIG. 3C is an exploded view further illustrating a portion of the device shown in FIGS. 3A and 3B.

FIG. 4A-FIG. 4K are a series of stylized partial cross-section views illustrating example methods in accordance with this detailed description. At FIG. 4A, an inner tubular member 120 is provided and a mandrel 134 is inserted into a lumen 118 defined by the inner tubular member 120. In some useful embodiments, the inner tubular member comprises a lubricious polymer such as polyethylene and/or a fluoropolymer such as PTFE (e.g., Teflon™).

Figure 4A:
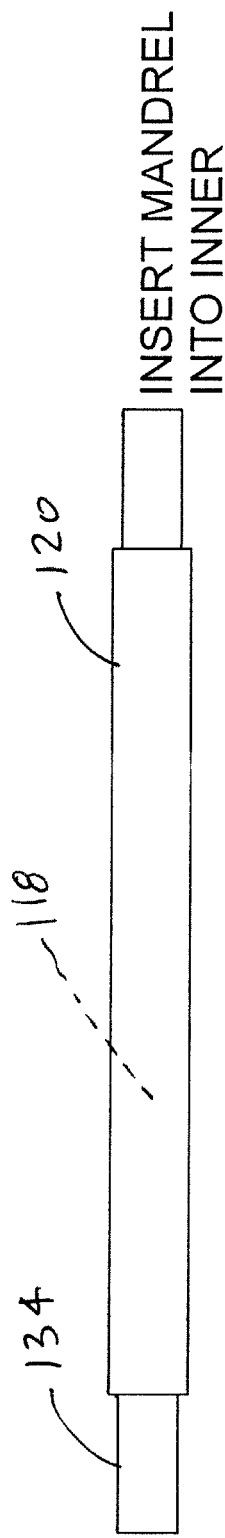
Figure 4B:
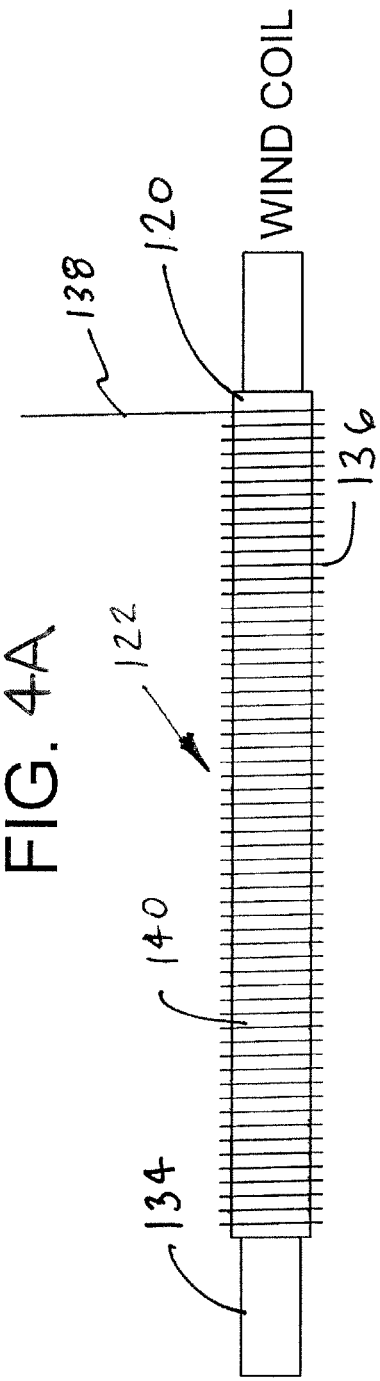

At FIG. 4B, wire 138 is wound around the outer surface 140 of the inner tubular member 120 to form a coil 122 having a plurality of turns 136. In some useful methods, the wire 138 is held under tension as the coil 122 is formed. In some useful methods, the tension on the wire 138 is sufficient to form a groove in the wall of a tubular guiding member of the inner tubular member 120. The groove may extend inwardly beyond the outer surface 140 of the wall of a tubular guiding member. In some useful embodiments, the creation of the groove facilitates the fabrication of a tubular guiding member having a wall thickness that is thinner than would be possible without the groove.

In some useful embodiments, the wire 138 comprises a material with a relatively high modulus of elasticity. The use of a wire material with a higher modulus of elasticity may allow the use of a wire 138 with a diameter that is smaller than would be possible if the wire material had a lower modulus of elasticity. The use of smaller diameter wire may, in turn, allow the wall of a tubular guiding member to have a wall thickness that is thinner than would be possible if larger diameter wire was used. In some useful embodiments, the wire 138 comprises tungsten. In some useful embodiments, the wire 138 comprises a material with a modulus of elasticity greater than 390 GPA and the wire 138 has a diameter smaller than 0.0015 inch. In some useful embodiments, the wire 138 comprises a material with a modulus of elasticity greater than 300 GPA and the wire 138 has a diameter smaller than 0.0020 inch. In some useful embodiments, the wire 138 comprises a material with a modulus of elasticity greater than 250 GPA and the wire 138 has a diameter smaller than 0.0025 inch. In some useful embodiments, the wire 138 comprises a material with a modulus of elasticity greater than 190 GPA and the wire 138 has a diameter smaller than 0.0030 inch.

In the embodiment of FIG. 4B, the coil 122 has a pitch that may be defined as the distance between the centers of adjacent turns 136. In the example embodiment of FIG. 4B, the pitch of the coil 122 is constant along the length of the coil 122. In some useful embodiments, the pitch of the coil varies along the length of the coil 122. In some useful embodiments, the radiopacity of the coil 122 varies as the pitch of the coil 122 varies.

Figure 4C:
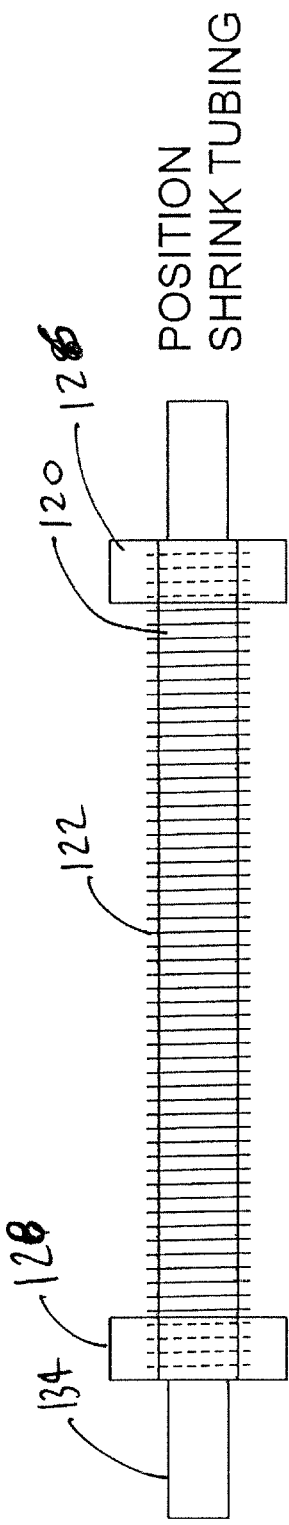

At FIG. 4C and FIG. 4D, the distal and proximal ends of the coil 122 relative to the inner tubular member 120. In some useful embodiments, the distal end and the proximal end of the coil 122 are fixed using a distal collar and a proximal collar, respectively. In some useful embodiments, each collar comprises a polyethylene teraphthalate (PET) material. In other useful embodiments, each collar is formed of an adhesive material applied to portions of the coil.

In the example embodiment of FIG. 4C, two collars are positioned for fixing the distal and proximal ends of the coil 122 relative to the inner tubular member 120. In the example method of FIG. 4C, a distal collar 126 is positioned to be disposed about a distal portion of the coil 122 and a proximal collar 128 is positioned to be disposed about a proximal portion of the coil 122. In the example method of FIG. 4C, the distal collar 126 and the proximal collar 128 each comprise a material that shrinks when heated.

In the example embodiment of FIG. 4D, heat is applied to the distal collar 126 and the proximal collar 128. In some useful embodiments, the application of heat causes the distal collar 126 to conform to the coil 122 and the outer surface 140 of the inner tubular member 120. The application of heat may also cause the proximal collar 128 to conform to the coil 122 and the outer surface 140 of the inner tubular member 120. The distal and proximal ends of the coil 122 are fixed to the inner tubular member 120 by the collars in the example embodiment of FIG. 4D.

At FIG. 4E, a ribbon 106 is tacked to the coil 122.

At FIG. 4F, a distal end of the ribbon 106 is inserted through an aperture 114 defined by an elongate positioning member 102. In the embodiment of FIG. 4F, the ribbon 106 has a distal region 108 and a proximal region 110. In FIG. 4F, the distal region 108 of the ribbon 106 is shown extending distally to overlay the coil 122 and the inner tubular member 120. The proximal region 110 of the ribbon 106 is shown overlaying an inner face 142 of the elongate positioning member 102 in FIG. 4F. An intermediate portion of the ribbon 106 can be seen extending through the aperture 114 defined by the elongate positioning member 102 in FIG. 4F.

At FIG. 4G, the coil 122 and the inner tubular member 120 are inserted into a lumen defined by a tubular body 130. In some embodiments, the tubular body 130 comprises a thermoplastic material. The thermoplastic material may comprise, by way of example and not limitation, a polyamide material such as nylon (e.g., nylon-12) and/or polyether-block-amide (e.g., Pebax™).

At FIG. 4H, a length of shrink tubing 132 is advanced over the assembly shown in FIG. 4G. In some useful embodiments, the shrink tubing 132 comprises a fluoropolymer such as FEP (e.g., Teflon™).

At FIG. 4I, the assembly shown in FIG. 4H is heated. In some useful embodiments, upon heating, the shrink tubing 132 shrinks and the material of the tubular body 130 flows to form an encapsulation layer 124 that encapsulates the coil 122.

At FIG. 4J, the shrink tubing 132 is removed.

At FIG. 4K, the mandrel 134 is removed.

FIG. 5A-FIG. 5K are a series of stylized partial cross-section views illustrating example methods in accordance with this detailed description. At FIG. 5A, an inner tubular member 120 is provided and a mandrel 134 is inserted into a lumen 118 defined by the inner tubular member 120. In some useful embodiments, the inner tubular member comprises a lubricious polymer such as polyethylene and/or a fluoropolymer such as PTFE (e.g., Teflon™).

At FIG. 5B, wire 138 is wound around the outer surface 140 of the inner tubular member 120 to form a coil 122 having a plurality of turns 136. In some useful methods, the wire 138 is held under tension as the coil 122 is formed. In some useful methods, the tension on the wire 138 is sufficient to form a groove in the wall of a tubular guiding member of the inner tubular member 120. The groove may extend inwardly beyond the outer surface 140 of the wall of a tubular guiding member. In some useful embodiments, the creation of the groove facilitates the fabrication of a tubular guiding member having a wall thickness that is thinner than would be possible without the groove.

In the embodiment of FIG. 5B, the coil 122 has a pitch that may be defined as the distance between the centers of adjacent turns 136. In the example embodiment of FIG. 5B, the pitch of the coil 122 varies along the length of the coil 122. As shown in FIG. 5B, a plurality of turns 136 are positioned immediately adjacent to one another in a proximal region of the coil 122. In some useful embodiments, a plurality of turns 136 are also positioned immediately adjacent to one another in a distal region of the coil 122.

At FIG. 5C and FIG. 5D, a plurality of turns 136 are fixed to one another in a proximal region of the coil 122. In some useful embodiments, a plurality of turns 136 are also fixed to one another in a distal region of the coil 122. Various joining processes may be used to fix adjacent turns to one another without deviating from the spirit and scope of this detailed description. Examples of joining processes that may be suitable in some applications include welding, brazing, soldering, and adhesive bonding.

In the example embodiment of FIG. 5C, a laser welding process is used to fix adjacent turns to one another. At FIG. 5C, the assembly of FIG. 5B is placed in a welding station including a laser source LS that produces a laser beam LB. In some useful embodiments, the assembly is rotated about a longitudinal axis LA and the laser beam LB forms a weld W between turns 136 that are positioned immediately adjacent to one another in a proximal region of the coil 122. The laser beam LB may also be used to form a weld between turns 136 that are positioned immediately adjacent to one another in a distal region of the coil 122.

FIG. 5D shows the assembly of FIG. 5C after the welding process. In the example embodiment of FIG. 5C, the laser beam LB has been used to form a weld W between turns 136 of the coil 122 that are positioned immediately adjacent to one another in the proximal region of the coil 122. In the example embodiment of FIG. 5C, the laser beam LB has also been used to form a weld W between turns 136 of the coil 122 that are positioned immediately adjacent to one another in a distal region of the coil 122 (not shown in FIG. 5D).

At FIG. 5E, a ribbon 106 is tacked to the coil 122.

At FIG. 5F, a distal end of the ribbon 106 is inserted through an aperture 114 defined by an elongate positioning member 102. In the embodiment of FIG. 5F, the ribbon 106 has a distal region 108 and a proximal region 110. In FIG. 5F, the distal region 108 of the ribbon 106 is shown extending distally to overlay the coil 122 and the inner tubular member 120. The proximal region 110 of the ribbon 106 is shown overlaying an inner face 142 of the elongate positioning member 102 in FIG. 5F. An intermediate portion of the ribbon 106 can be seen extending through the aperture 114 defined by the elongate positioning member 102 in FIG. 5F.

Figure 5G:
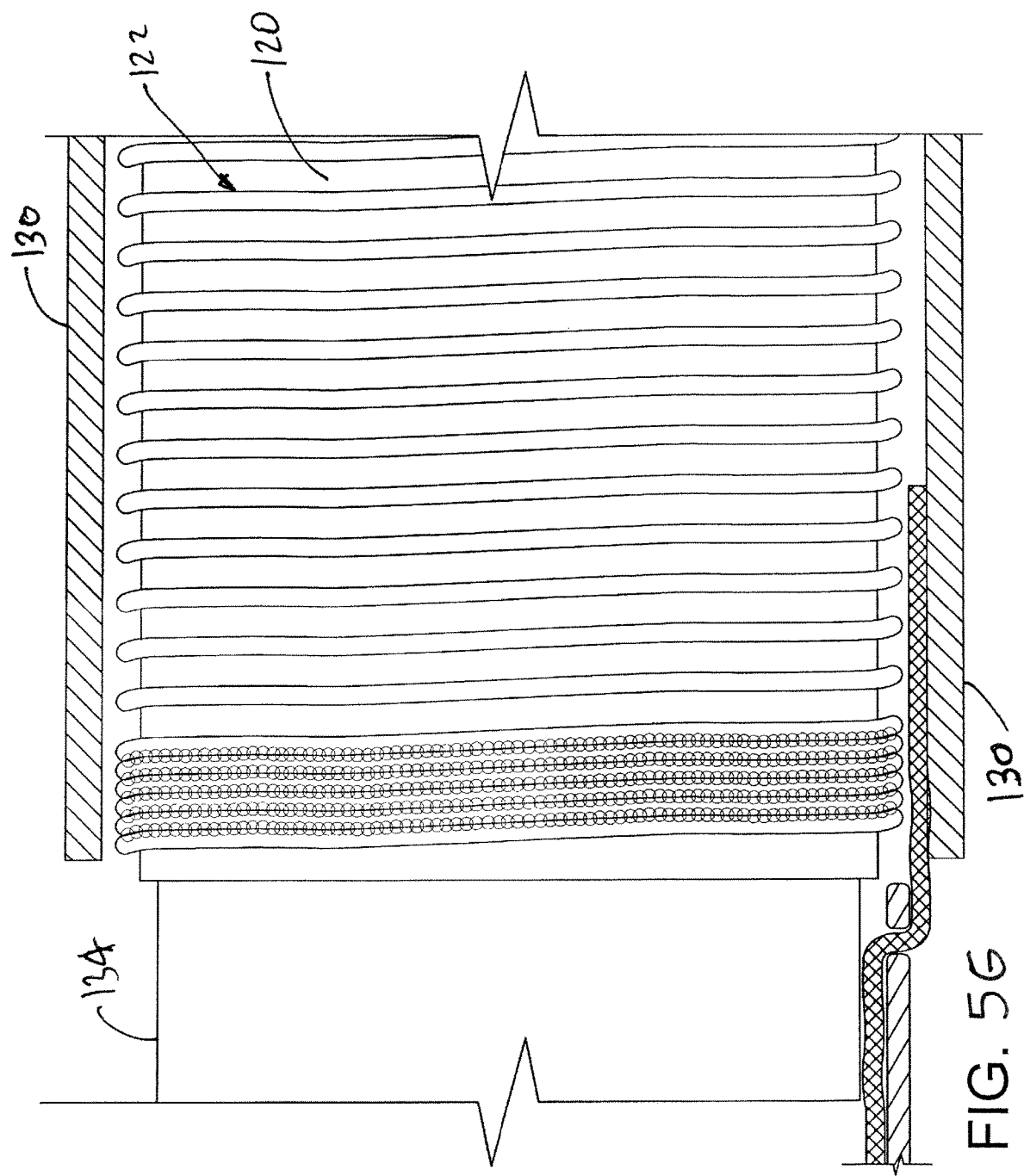

At FIG. 5G, the coil 122 and the inner tubular member 120 are inserted into a lumen defined by a tubular body 130. In some embodiments, the tubular body 130 comprises a thermoplastic material. The thermoplastic material may comprise, by way of example and not limitation, a polyamide material such as nylon (e.g., nylon-12) and/or polyether-block-amide (e.g., Pebax™).

At FIG. 5H, a length of shrink tubing 132 is advanced over the assembly shown in FIG. 5G. In some useful embodiments, the shrink tubing 132 comprises a fluoropolymer such as FEP (e.g., Teflon™).

Figure 5I:
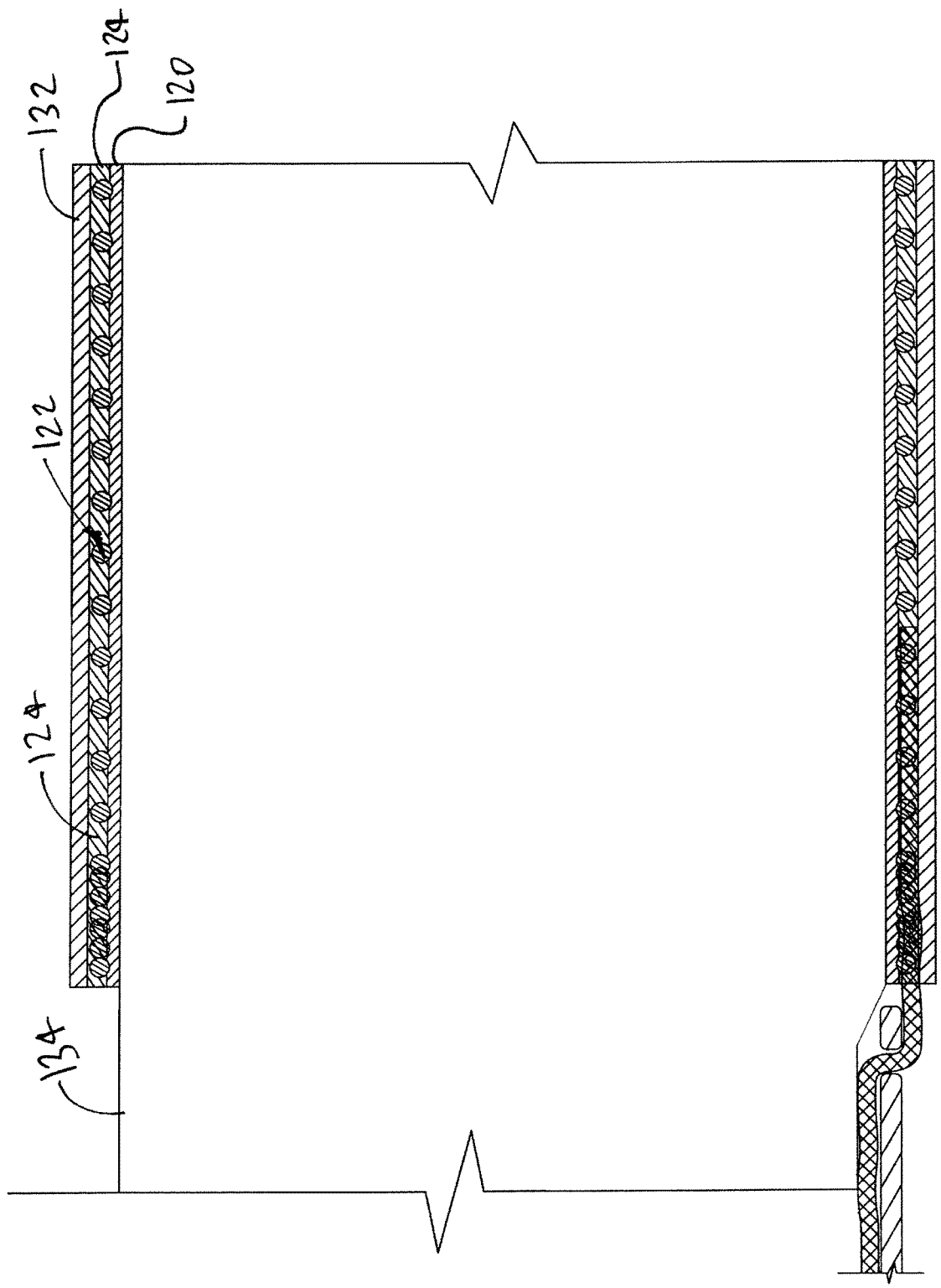

At FIG. 5I, the assembly shown in FIG. 5H is heated. In some useful embodiments, upon heating, the shrink tubing 132 shrinks and the material of the tubular body 130 flows to form an encapsulation layer 124 that encapsulates the coil 122.

At FIG. 5J, the shrink tubing 132 is removed.

Figure 5K:
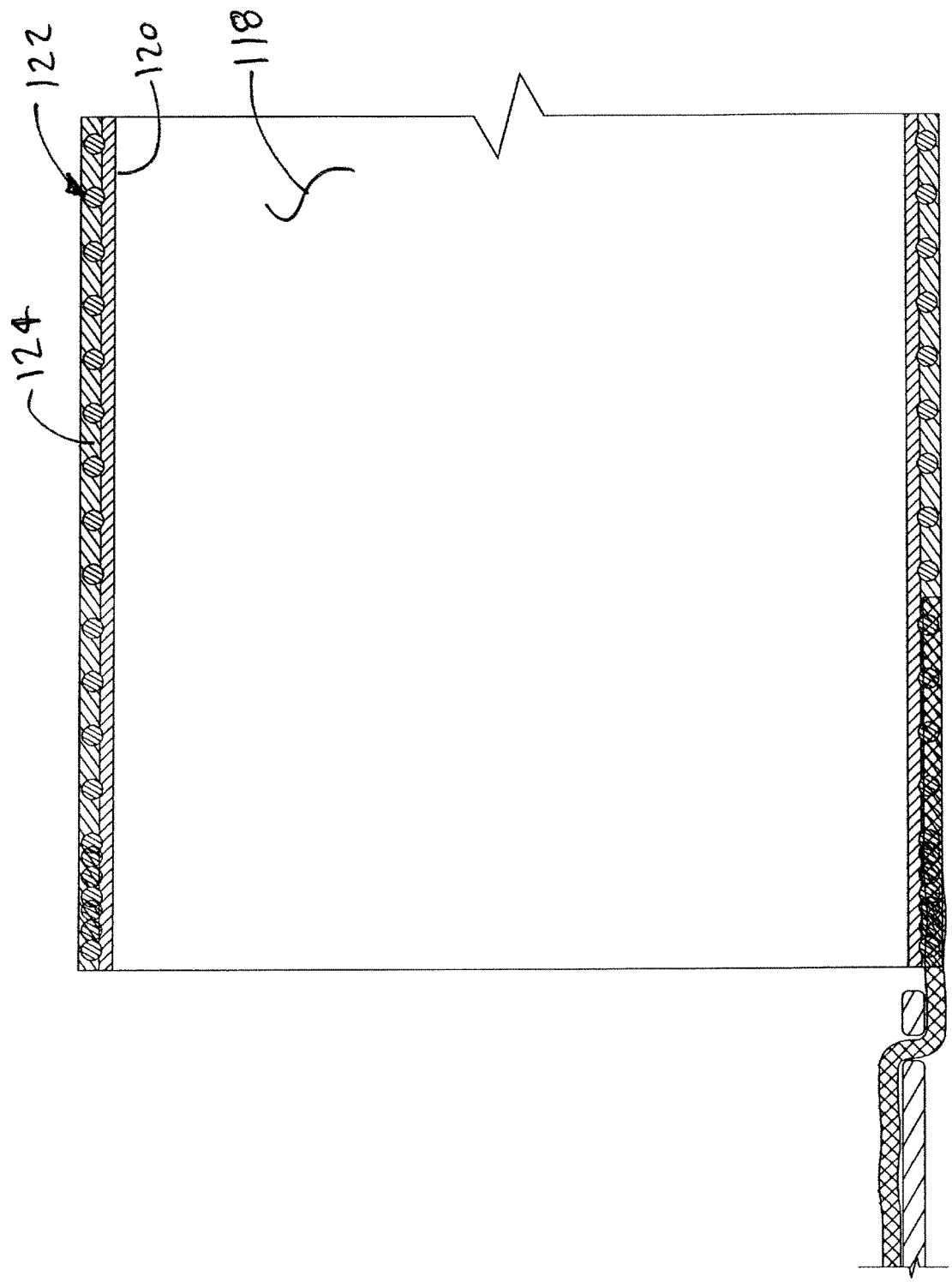

At FIG. 5K, the mandrel 134 is removed. With reference to FIG. 5K, some example methods include forming a tubular guiding member comprising an inner tubular member, a support structure disposed about the inner tubular member and an encapsulation layer overlaying the support structure and the inner tubular member, the encapsulation layer being mechanically interlocked with and adhered to the elongate support member and the saddle member. In some embodiments, the tubular guiding member has an inner diameter to wall thickness ratio equal to or greater than 18:1. In some embodiments, the tubular guiding member has an inner diameter to wall thickness ratio equal to or greater than 22:1. In some embodiments, the tubular guiding member has an inner diameter to wall thickness ratio equal to or greater than 24:1. In some embodiments, the inner tubular member having a wall thickness less than 0.0015 inch, the encapsulation layer having a layer thickness less than 0.0020 inch, and the tubular guiding member having a total wall thickness less than 0.0030 inch. In some embodiments, inner tubular member has a wall thickness less than 0.0010 inch, the encapsulation layer has a layer thickness less than 0.0017 inch, and the tubular guiding member has a total wall thickness less than 0.0027 inch. In some embodiments, the inner tubular member has a wall thickness less than 0.0010 inch, the encapsulation layer has a layer thickness less than 0.0014 inch, and the tubular guiding member has a total wall thickness less than 0.0024 inch.

Figure 6C:
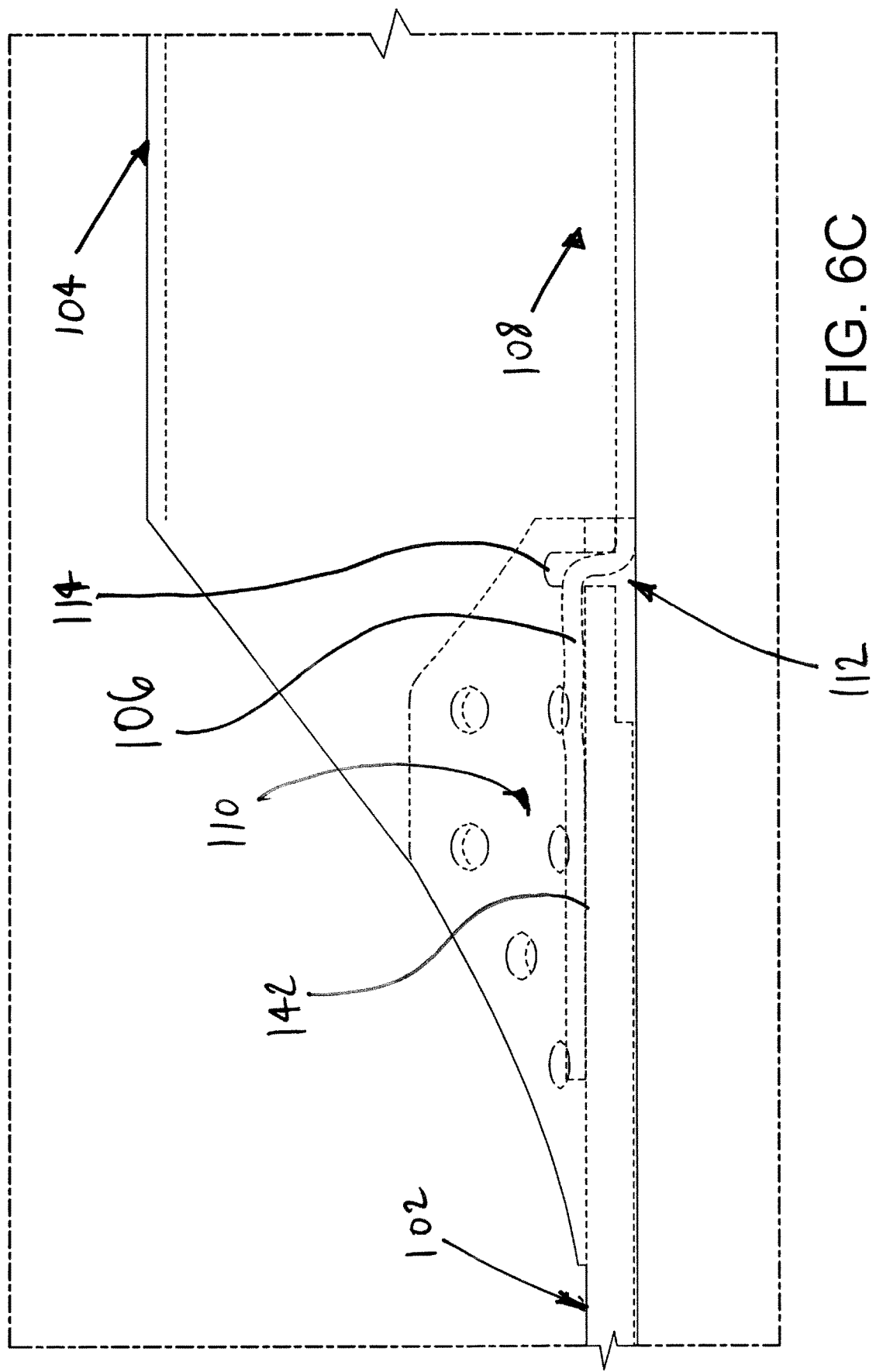
FIG. 6C is an enlarged side view further illustrating a portion of the device shown in FIG. 6A.

FIG. 6A is a plan view showing a device 100 for guiding and supporting catheters such as, for example, stent delivery catheters. FIG. 6B is a side view of the device shown in FIG. 6A. FIG. 6C is an enlarged plan view further illustrating a portion of the device shown in FIG. 6A. FIG. 6A through FIG. 6C may be collectively referred to as FIG. 6. In the embodiment of FIG. 6, the device 100 comprises a tubular guiding member 104 and an elongate positioning member 102 extending in a proximal direction beyond the tubular guiding member 104 for advancing and retracting the tubular guiding member 104 in distal and proximal directions. With reference to FIG. 6C, it will be appreciated that the tubular guiding member 104 defines a lumen 118 extending between a proximal end of the tubular guiding member 104 and a distal end of the tubular guiding member 104.

In the embodiment of FIG. 6, a distal portion of the elongate positioning member 102 is coupled to a proximal portion of the tubular guiding member 104 at a joint region. With reference to FIG. 6C, it will be appreciated that a ribbon 106 extends through the joint region. In some useful embodiments, the ribbon 106 comprises a plurality of fibers. In the embodiment of FIG. 6, the ribbon 106 has a distal region 108, a proximal region 110, and an intermediate region 112 disposed between the proximal region 110 and the distal region 108. In FIG. 6C, the distal region 108 of the ribbon 106 is shown extending distally into a wall of the tubular guiding member 104. The proximal region 110 of the ribbon 106 is shown overlaying an inner face 142 of the elongate positioning member 102 in FIG. 6. An intermediate portion of the ribbon 106 can be seen extending through an aperture 114 defined by the elongate positioning member 102 in FIG. 6.

Figure 7:
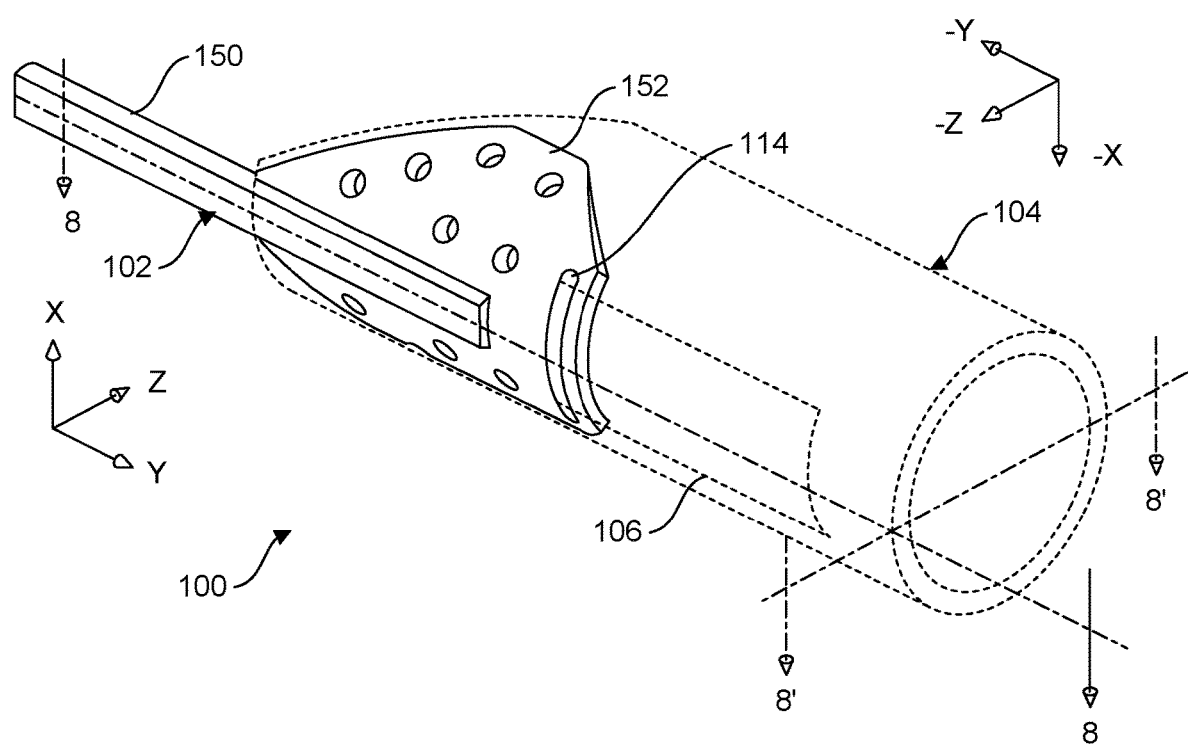
FIG. 7 is a stylized perspective view of further illustrating the device shown in FIG. 6C.

FIG. 7 is a stylized perspective view of further illustrating the device 100 shown in FIG. 6. The tubular guiding member 104 and the ribbon 106 of the device 100 are shown with dashed lines in the example embodiment of FIG. 7. The position of the elongate positioning member 102 relative to the tubular guiding member 104 and the ribbon 106 will be appreciated with reference to FIG. 7. In the embodiment of FIG. 7, the elongate positioning member 102 comprises a shaft member 150 and a saddle member 152 that is fixed to a distal portion of the shaft member 150. With reference to FIG. 7, it will be appreciated that the saddle member 152 of the elongate positioning member 102 defines an aperture 114.

Figure 8:
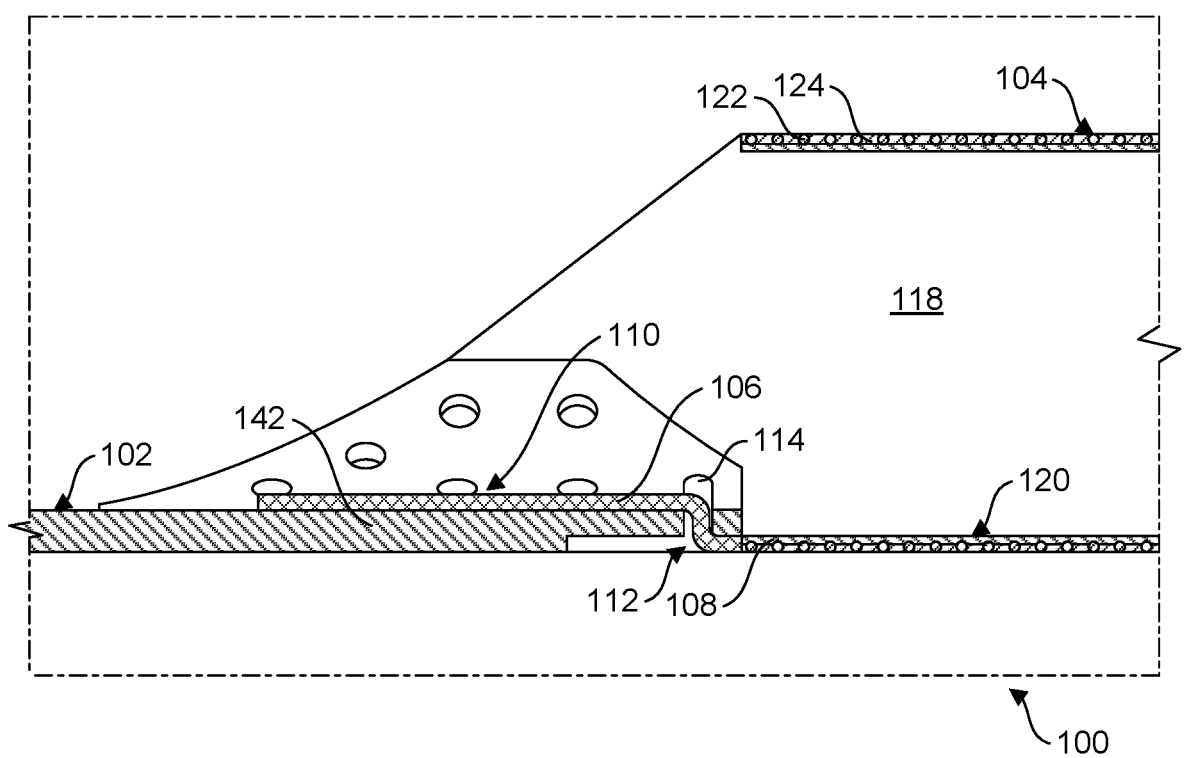
FIG. 8 is a cross-sectional view further illustrating the portion of the device shown in FIG. 7. In the embodiment of FIG. 8, the device has been sectioned along a section plane defined by section lines 8-8 and 8'-8' shown in FIG. 7.

FIG. 8 is a cross-sectional view further illustrating the portion of the device 100 shown in FIG. 7. In the embodiment of FIG. 8, the device 100 has been sectioned along a section plane defined by section lines 8-8 and 8'-8' shown in FIG. 7. In the example embodiment of FIG. 8, the device 100 comprises a tubular guiding member 104 and an elongate positioning member 102 extending in a proximal direction beyond the tubular guiding member 104 for advancing and retracting the tubular guiding member 104 in distal and proximal directions. With reference to FIG. 8, it will be appreciated that the tubular guiding member 104 comprises an inner tubular member 120, a coil 122 disposed about the inner tubular member 120, and an encapsulation layer 124 overlaying the coil 122 and the inner tubular member 120. With continuing reference to FIG. 8, it will be appreciated that the inner tubular member 120 defines a lumen 118 extending between a proximal end of the tubular guiding member 104 and a distal end of the tubular guiding member 104. In the example embodiment of FIG. 8, the coil 122 forms a plurality of turns with each turn encircling the inner tubular member 120.

In the embodiment of FIG. 8, a distal portion of the elongate positioning member 102 is coupled to a proximal portion of the tubular guiding member 104 at a joint region. With reference to FIG. 8, it will be appreciated that a ribbon 106 extends through the joint region. In some useful embodiments, the ribbon 106 comprises a plurality of fibers. In the embodiment of FIG. 8, the ribbon 106 has a distal region 108, a proximal region 110, and an intermediate region 112 disposed between the proximal region 110 and the distal region 108. In FIG. 8, the distal region 108 of the ribbon 106 is shown extending distally into the wall of the tubular guiding member 104. The proximal region 110 of the ribbon 106 is shown overlaying an inner face 142 of the elongate positioning member 102 in FIG. 8. An intermediate portion of the ribbon 106 can be seen extending through the aperture 114 defined by the elongate positioning member 102 in FIG. 8.

Figure 9:
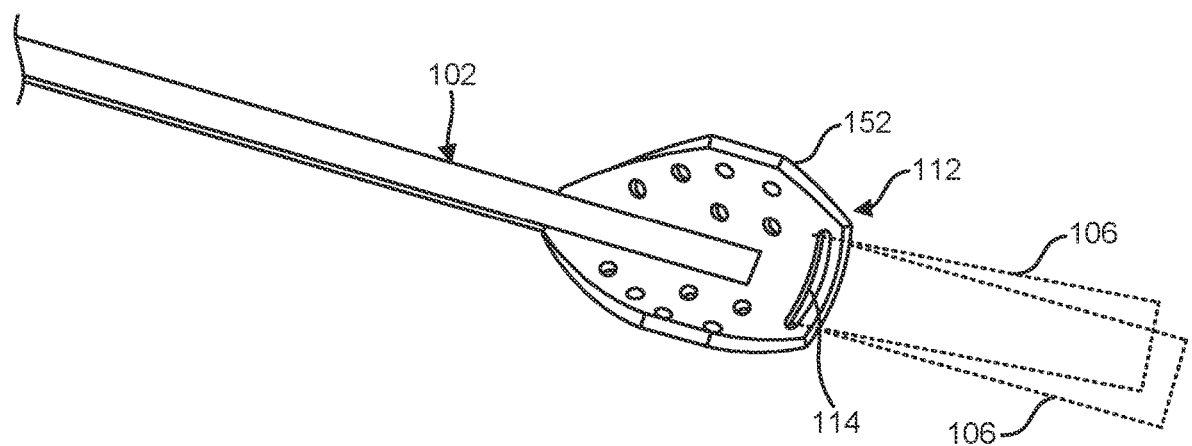
FIG. 9 is a perspective view showing elongate positioning member and a ribbon. In the embodiment of FIG. 9, the ribbon is extending through an aperture defined by the elongate positioning member.

FIG. 9 is a perspective view showing elongate positioning member 102 and a ribbon 106. In FIG. 9, the ribbon 106 is shown extending through an aperture 114 defined by a saddle member 152 of the elongate positioning member 102. In the embodiment of FIG. 9, the ribbon 106 has a first portion, a second portion, and an intermediate region 112 disposed between the second portion and the first portion in the embodiment of FIG. 9. Also, in the embodiment of FIG. 9, the first portion and the second portion both extend in a distal direction after the ribbon 106 passes through the aperture 114. In some example embodiments, the ribbon 106 may form a hinge joint. In some example embodiments, a device for guiding and supporting a stent delivery catheter and/or other catheters may comprise an elongate positioning member 102, a tubular guiding member, and a hinge joint coupling a proximal portion of the tubular guiding member to a distal portion of the elongate positioning member 102. In some embodiments, the hinge joint comprises a ribbon 106 having a first end portion, a second end portion, each end portion of the ribbon being fixed to a proximal portion of the tubular guiding member. An intermediate portion of the ribbon 106 may extend through an aperture 114 defined by a saddle member 152 of the elongate positioning member 102.

FIG. 10A is a perspective view of an elongate positioning member 102 in accordance with this detailed description. FIG. 10B is an enlarged perspective view further illustrating a portion of the elongate positioning member 102 shown in FIG. 10A. FIG. 10A and FIG. 10B may be collectively referred to as FIG. 10. In the example embodiment of FIG. 10, the elongate positioning member 102 comprises a shaft member 150 and a saddle member 152 that is fixed to a distal portion of the shaft member 150. With reference to FIG. 10, it will be appreciated that the saddle member 152 of the elongate positioning member 102 defines an aperture 114. In some useful embodiments, the aperture 114 is adapted and dimensioned to receive a ribbon. The saddle member 152 of the elongate positioning member 102 also defines a plurality of holes 154 in the embodiment of FIG. 10. In some useful embodiments, a device including the saddle member 152 may also include thermoplastic material extending through the holes 154 in the saddle member 152. With reference to FIG. 10, it will be appreciated that the saddle member 152 is C-shaped when viewed from the distal end. In the embodiment of FIG. 10, a proximal portion of the shaft member 150 has a cylindrical shape and a distal portion of the shaft member 150 tapers to smaller cross-sectional shapes as the shaft member 150 extends distally.

FIG. 11A is a top view of a shaft member 150 for an elongate positioning member in accordance with this detailed description. FIG. 11B and FIG. 11C are cross-sectional views of the shaft member 150 shown in FIG. 11A. FIGS. 11A-11C may be collectively referred to as FIG. 11. In some useful embodiments, the shaft member 150 includes a proximal portion having a cylindrical shape and a distal portion that tapers to smaller cross-sectional shapes as the shaft member 150 extends distally. In the embodiment of FIG. 11B, the shaft member 150 has been sectioned along section line 11B-11B shown in FIG. 11A. With reference to FIG. 11B, it will be appreciated that the proximal portion of the shaft member 150 has a lateral cross sectional shape that generally corresponds to a circle shape. Also with reference to FIG. 11B, it will be appreciated that the shaft member 150 has a solid lateral cross sectional shape at section line 11B-11B. In some embodiments, the shaft member 150 has a solid lateral cross-sectional shape throughout its length. In the embodiment of FIG. 11C, the shaft member 150 has been sectioned along section line 11C-11C shown in FIG. 11A. With reference to FIG. 11C, it will be appreciated that the distal portion of the shaft member 150 has a lateral cross sectional shape that includes two planar sides. A Thickness TS of the shaft member 150 is illustrated using dimension lines in FIG. 11C. In some useful embodiments, the Thickness TS of the shaft member 150 becomes smaller as the shaft member 150 extends distally.

FIG. 12A through FIG. 12F are elevation and plan views showing six sides of an elongate positioning member 102. Engineer graphics textbooks generally refer to the process used to create views showing six sides of a three dimensional object as multiview projection or orthographic projection. It is customary to refer to multiview projections using terms such as front view, right side view, top view, rear view, left side view, and bottom view. In accordance with this convention, FIG. 12A may be referred to as a left side view of the elongate positioning member 102, FIG. 12B may be referred to as a front side view of the elongate positioning member 102, and FIG. 12C may be referred to as a top view of the elongate positioning member 102. FIG. 12A through FIG. 12F may be referred to collectively as FIG. 12. Terms such as front view and right side view are used herein as a convenient method for differentiating between the views shown in FIG. 12. It will be appreciated that the elements shown in FIG. 12 may assume various orientations without deviating from the spirit and scope of this detailed description. Accordingly, the terms front view, right side view, top view, rear view, left side view, bottom view, and the like should not be interpreted to limit the scope of the invention recited in the attached claims. FIG. 12D may be referred to as a right side view of the elongate positioning member 102, FIG. 12E may be referred to as a rear view of the elongate positioning member 102, and FIG. 12F may be referred to as a bottom view of the elongate positioning member 102.

In the example embodiment of FIG. 12, the elongate positioning member 102 comprises a shaft member 150 and a saddle member 152 that is fixed to a distal portion of the shaft member 150. In some useful embodiments, the shaft member 150 and a saddle member 152 each comprise stainless steel. With reference to FIG. 12E, it will be appreciated that a proximal portion of the shaft member 150 of the elongate positioning member 102 has a cylindrical shape. With reference to FIG. 12B and FIG. 12E, it will be appreciated that the saddle member 152 of the elongate positioning member 102 is C-shaped when viewed from the distal end. With reference to FIG. 12C and FIG. 12F, it will be appreciated that the saddle member 152 of the elongate positioning member 102 defines an aperture 114. In some useful embodiments, the aperture 114 is adapted and dimensioned to receive a ribbon. With reference to FIGS. 12A, 12C, 12D and 12F, it will be appreciated that the saddle member 152 of the elongate positioning member 102 also defines a plurality of holes 154 in the embodiment of FIG. 12. In some useful embodiments, a device including the saddle member 152 may also include thermoplastic material extending through the holes 154 in the saddle member 152.

Figure 12G:
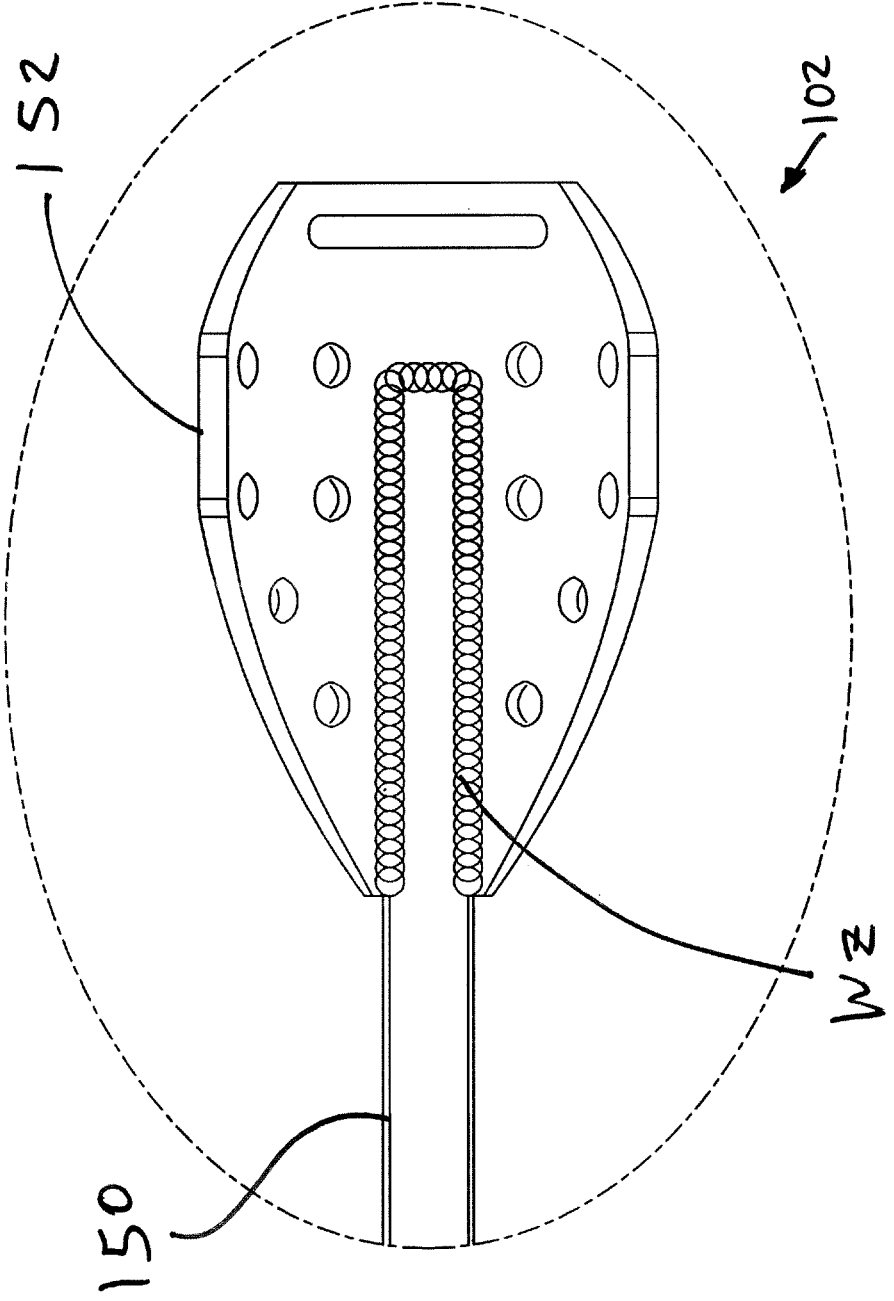
FIG. 12G is an enlarged top view further illustrating the elongate guiding member shown in FIG. 12C.

FIG. 12G is an enlarged top view further illustrating the elongate positioning member 102 in FIG. 12C. In the example embodiment of FIG. 12G, the saddle member 152 of the elongate positioning member 102 is fixed to a distal portion of the shaft member 150 at a weld WZ. In one example embodiment, weld WZ is created using a laser welding process. It should be noted, however, that various joining processes may be used to fix the saddle member 152 to the shaft member 150 without deviating from the spirit and scope of this detailed description. Examples of joining processes that may be suitable in some applications include welding, brazing, soldering, and adhesive bonding.

Referring, for example, to FIGS. 7 and 12A-12G an upward direction Z and a downward or lower direction −Z are illustrated using arrows labeled "Z" and "−Z," respectively. A forward direction Y and a rearward direction −Y are illustrated using arrows labeled "Y" and "−Y," respectively. A starboard direction X and a port direction −X are illustrated using arrows labeled "X" and "−X," respectively. The directions illustrated using these arrows are applicable to the apparatus shown and discussed throughout this application. The port direction may also be referred to as the portward direction. In one or more embodiments, the upward direction is generally opposite the downward direction. In one or more embodiments, the upward direction and the downward direction are both generally orthogonal to an XY plane defined by the forward direction and the starboard direction. In one or more embodiments, the forward direction is generally opposite the rearward direction. In one or more embodiments, the forward direction and the rearward direction are both generally orthogonal to a ZY plane defined by the upward direction and the starboard direction. In one or more embodiments, the starboard direction is generally opposite the port direction. In one or more embodiments, starboard direction and the port direction are both generally orthogonal to a ZX plane defined by the upward direction and the forward direction. Various direction-indicating terms are used herein as a convenient way to discuss the objects shown in the figures. It will be appreciated that many direction indicating terms are related to the instant orientation of the object being described. It will also be appreciated that the objects described herein may assume various orientations without deviating from the spirit and scope of this detailed description. Accordingly, direction-indicating terms such as "upwardly," "downwardly," "forwardly," "backwardly," "portwardly," and "starboardly," should not be interpreted to limit the scope of the invention recited in the attached claims.

Figure 13A:
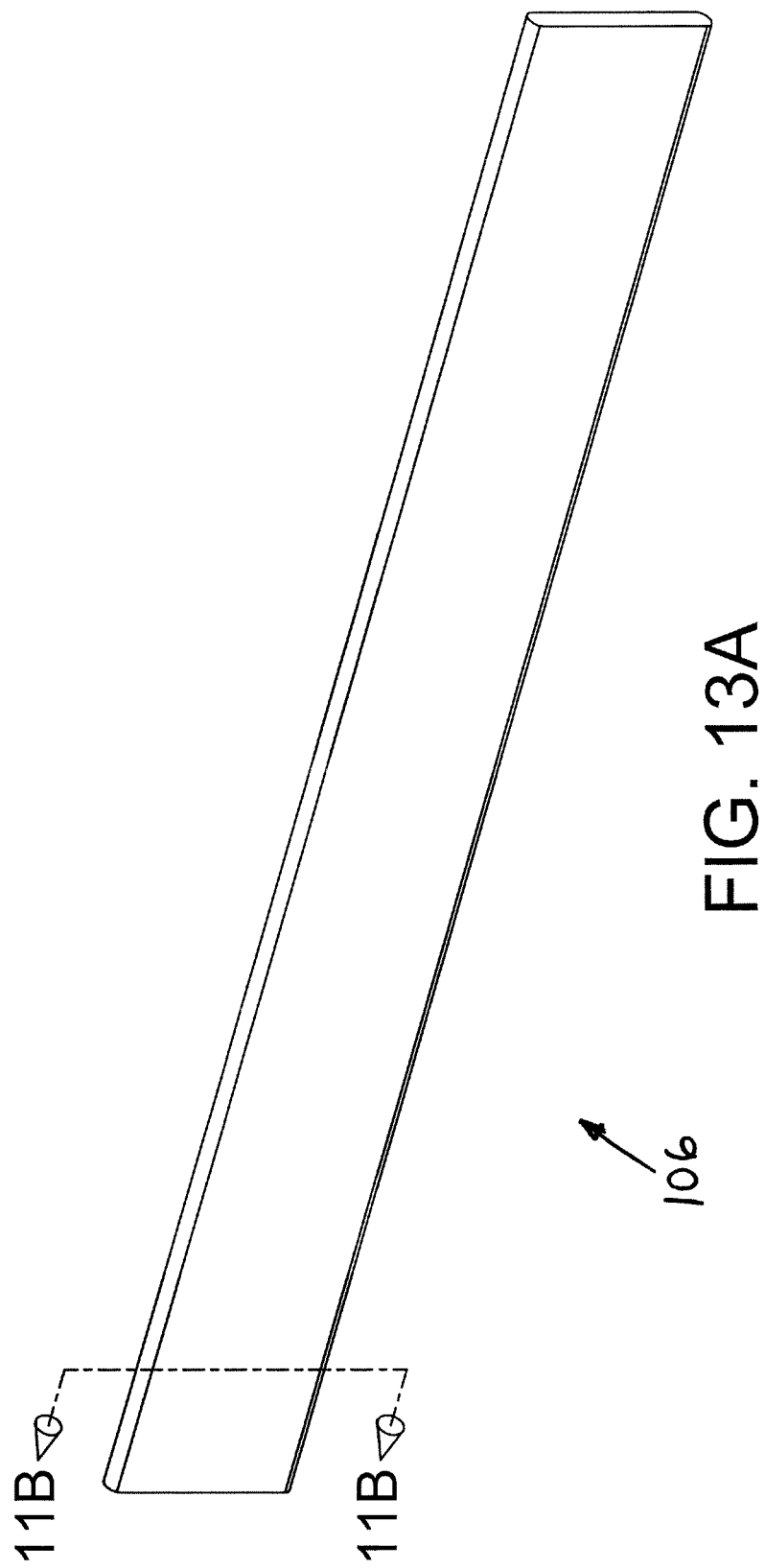
FIG. 13A is a perspective view showing a ribbon in accordance with the detailed description.
Figure 13B:
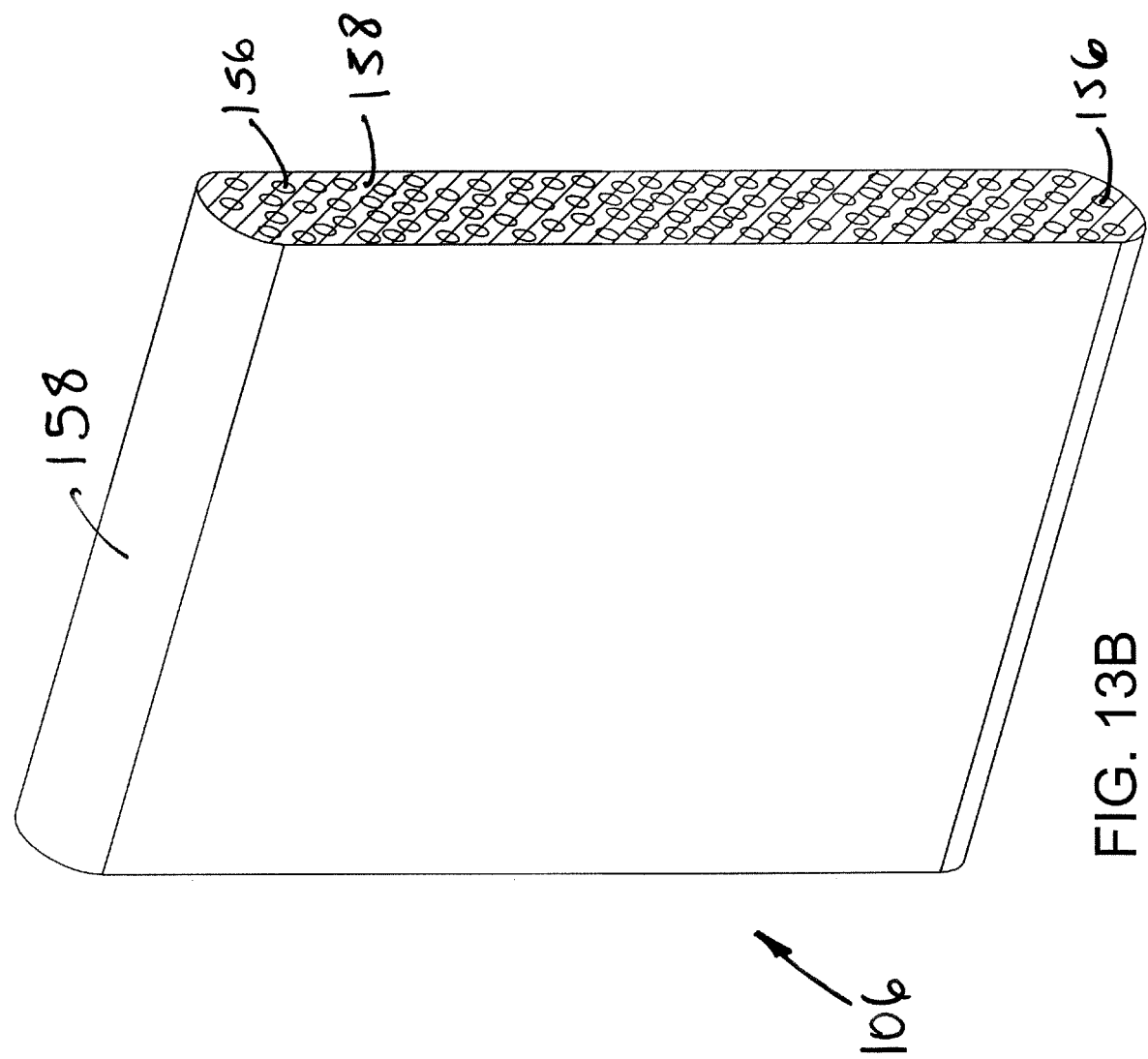
FIG. 13B is a cross-sectional view of the ribbon shown in FIG. 13A. In the embodiment of FIG. 13B, the ribbon has been sectioned along section line 13B-13B shown in FIG. 13A.

FIG. 13A is a perspective view showing a ribbon 106 in accordance with this detailed description. FIG. 13B is a cross-sectional view of the ribbon 106 shown in FIG. 13A. In the embodiment of FIG. 13B, the ribbon 106 has been sectioned along section line 13B-13B shown in FIG. 13A. FIG. 13A and FIG. 13B may be collectively referred to as FIG. 13. In some useful embodiments, the ribbon 106 comprises a plurality of fibers 156 and a polymer material 158 that holds the fibers 156 in the shape shown in FIG. 13. In some useful embodiments, the polymer material 158 binds the fibers 156 to one another. In some useful embodiments, the polymer material 158 fills interstitial spaces between the fibers 156. In some useful embodiments, the fibers 156 comprise an aramid material. In some useful embodiments, the polymer material 158 comprises a polyamide material such as nylon (e.g., nylon-12) and/or polyether-block-amide (e.g., Pebax™).

FIG. 14A is a cross-sectional view of an assembly 160 for forming a ribbon 106. FIG. 14B is a cross-sectional view of a ribbon 106 formed from the assembly 160 shown in FIG. 14A. The assembly 160 of FIG. 14A includes a preformed tube 162 and a yarn 164 that is disposed inside a lumen defined by the preformed tube 162. In the embodiment of FIGS. 14A and 14B, the yarn 164 comprises a plurality of fibers 156. A method of forming the ribbon 106 shown in FIG. 14B may include threading the yarn into the preformed tube 162 to form the assembly 160 shown in FIG. 14A. In some useful embodiments, the preformed tube 162 comprises a polyamide material such as nylon (e.g., nylon-12) and/or polyether-block-amide (e.g., Pebax™). Also in some useful embodiments, the fibers 156 of the yarn 164 comprise an aramid material. In one example method, the assembly 160 is heated and pressed between two plates, forming the ribbon 106 and infusing the fibers with polymer material from the preformed tube 162. In another example method, the yarn 164 is encapsulated in polymer material during an extrusion process to form a composite thread. The composite thread may be heated and pressed between two plates to form a ribbon 106 as shown in FIG. 14B.

Figure 15A:
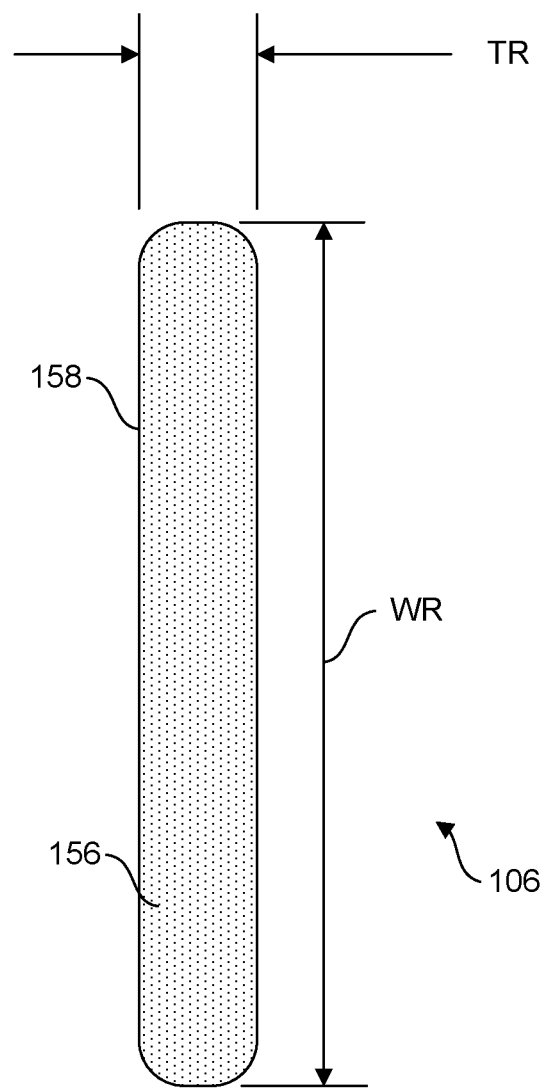
FIG. 15A is an end view of a ribbon in accordance with the detailed description.
Figure 15B:
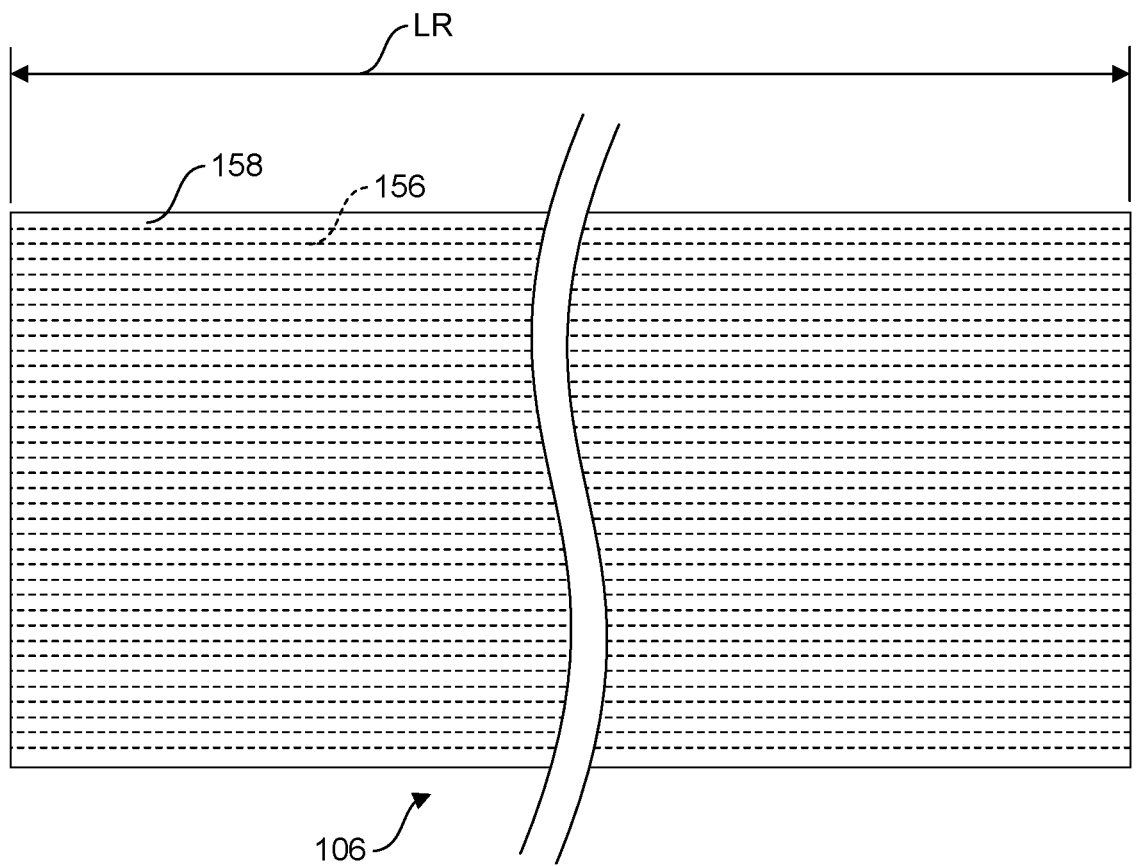
FIG. 15B is a top view of the ribbon shown in FIG. 15A.
Figure 15C:
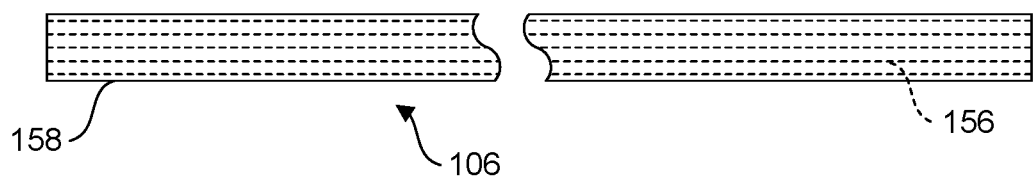
FIG. 15C is a side view of the ribbon shown in FIG. 15B.

FIG. 15A is an end view of a ribbon 160 in accordance with this detailed description. FIG. 15B is a top view of the ribbon 160 shown in FIG. 15A. FIG. 15C is a side view of the ribbon 160 shown in FIG. 15B. FIGS. 15A-15C may be collectively referred to as FIG. 15. In the example embodiment of FIG. 15, the ribbon 106 comprises a plurality of fibers 156 and a polymer material 158 that binds the fibers 156 to one another. A width WR and a thickness TR of the ribbon 106 are illustrated using dimension lines in FIG. 15A. In some embodiments, the ribbon 106 has a ratio of the width dimension to the thickness dimension greater than 4. In some embodiments, the ribbon 106 has a ratio of the width dimension to the thickness dimension greater than 8. In some embodiments, the ribbon 106 has a ratio of the width dimension to the thickness dimension greater than 12. A length LR of the ribbon 106 is illustrated using dimension lines in FIG. 15B. In some embodiments, the ribbon 106 has a ratio of the length dimension to the width dimension greater than 4. In some embodiments, the ribbon 106 has a ratio of the length dimension to the width dimension greater than 8. In some embodiments, the ribbon 106 has a ratio of the length dimension to the width dimension greater than 12. In some useful embodiments, the polymer material 158 fills interstitial spaces between the fibers 156. In some useful embodiments, the fibers 156 comprise an aramid material. In some useful embodiments, the polymer material 158 comprises a polyamide material such as nylon (e.g., nylon-12) and/or polyether-block-amide (e.g., Pebax™).

Referring to FIGS. 1-3 and 6-8, in embodiments, a device 100 for guiding and supporting a stent delivery catheter and other catheters comprises a tubular guiding member 104 and an elongate positioning member 102 extending in a proximal direction beyond the tubular guiding member 104 for advancing and retracting the tubular guiding member 104 in distal and proximal directions. A distal portion of the elongate positioning member 102 may be coupled to a proximal portion of the tubular guiding member 104. In embodiments, the device 100 includes a ribbon 106 having a distal region 108 and a proximal region 110. In embodiments, the distal region 108 of the ribbon 106 extends distally into the tubular guiding member 104 and the proximal region 110 of the ribbon 106 overlays an inner face 142 of the elongate positioning member 102.

FIG. 16A is a side view showing a device 100 for guiding and supporting catheters such as, for example, stent delivery catheters. FIG. 16B is an enlarged detail view further illustrating a distal end portion of the device 100 shown in FIG. 16A. FIGS. 16A through 16C may be collectively referred to as FIG. 16. In the embodiment of FIG. 16, the device 100 comprises a tubular guiding member 104 and an elongate positioning member 102. As shown in FIG. 16, in some example embodiments, the elongate positioning member 102 extends in a proximal direction beyond the tubular guiding member 104 for advancing and retracting the tubular guiding member 104 in distal and proximal directions. In some example embodiments, a distal portion of the elongate positioning member 102 is coupled to a proximal portion of the tubular guiding member 104. FIG. 16C is an enlarged detail view showing a portion of the device 100 where the distal portion of the elongate positioning member 102 meets the proximal portion of the tubular guiding member 104.

With reference to FIG. 16, it will be appreciated that the tubular guiding member 104 comprises an inner tubular member 120 having a proximal end, a distal end, an outer surface. In the embodiment of FIG. 16, the inner tubular member 120 has an inner surface 116, the inner surface 116 defining a lumen 118 extending between the proximal end and the distal end of the inner tubular member 120. In the embodiment of FIG. 16, the tubular guiding member 104 includes a support structure 166 disposed about the outer surface 140 of the inner tubular member 120. The support structure 166 of FIG. 16 includes a distal collar portion 168, a proximal collar portion 170, and an intermediate portion 172 extending between the distal collar portion 168 and the proximal collar portion 170. In embodiments, the portions of the support structure 166 are formed by an elongate support member 180. In embodiments, the elongate support member 180 is disposed along a helical path around the outer surface 140 of the inner tubular member 120.

In the example embodiment of FIG. 16, the tubular guiding member 104 includes an encapsulation layer 124 overlaying the inner tubular member 120 and the support structure 166. In some useful embodiments, the encapsulation layer 124 is mechanically interlocked with and adhered to the support structure 166. In some example embodiments, the encapsulation layer 124 has a layer thickness less than 0.0016 inch. In some example embodiments, the inner tubular member 120 has a wall thickness less than 0.0010 inch, the encapsulation layer 124 has a layer thickness less than 0.0016 inch and the tubular guiding member 104 has a total wall thickness less than 0.0026 inch.

A feature and benefit of embodiments is a tubular guiding member that is configured and dimensioned to make new treatment options available to physicians. A feature and benefit of embodiments is a device having a tubular guiding member with a thin wall and a high inner diameter to wall thickness ratio to enable medical procedures using combinations of catheters such as a guide catheter, an extension catheter and a therapy catheter (e.g., a stent delivery catheter). In some example embodiments, the tubular guiding member is dimensioned and configured to be received in a six French guide catheter along with a stent delivery catheter. In some example embodiments, the tubular guiding member can be received in the lumen of a six French guide catheter and the lumen of the tubular guide member can receive a stent delivery catheter configured for use with a six French guide catheter. The term of art "French" may be defined as three times the diameter of a device as measured in millimeters. For example, a nine French catheter has a three millimeter diameter. In some example embodiments, the tubular guiding member can be received in the lumen of a selected French size guide catheter and the lumen of the tubular guide member can receive a stent delivery catheter configured for use with the same French size guide catheter. In some example embodiments the tubular guiding member has an inner diameter to wall thickness ratio equal to or greater than 24:1. In some example embodiments the tubular guiding member has an inner diameter to wall thickness ratio equal to or greater than 22:1. In some example embodiments the tubular guiding member has an inner diameter to wall thickness ratio equal to or greater than 18:1. In some example embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

FIG. 16B is an enlarged detail view further illustrating a distal end portion of the device 100 shown in FIG. 16A. With reference to FIG. 16B, it will be appreciated that the distal collar portion 168 of the support structure 166 includes a distal closed loop 174 in the example embodiment shown. In the example embodiment of FIG. 16, the distal closed loop 174 comprises a distal weld 186 and a distal portion 182 of the elongate support member 180. The distal portion 182 extends around the outer surface 140 of the inner tubular member 120 in the example embodiment of FIG. 16.

Referring to FIG. 16C, a portion of the device 100 (shown in FIG. 18A) where a distal portion of the elongate positioning member 102 meets a proximal portion of the tubular guiding member 104. As shown in FIG. 16C, the proximal collar portion 170 of the support structure 166 may include a proximal closed loop 176. In the embodiment of FIG. 16, the proximal closed loop 176 may comprise a proximal weld 188 and a proximal portion 184 of the elongate support member 180 that extends around the outer surface 140 of the inner tubular member 120. In some example embodiments, the proximal weld 188 comprises a proximal weld body, the proximal weld body comprising jacket material from a first forward part of the elongate support member 180 and jacket material from a second forward part of the elongate support member 180, the materials having melted, mixed and solidified during a welding process.

FIG. 17A through FIG. 17F are elevation and plan views showing six sides of an elongate positioning member 102. Engineer graphics textbooks generally refer to the process used to create views showing six sides of a three dimensional object as multiview projection or orthographic projection. It is customary to refer to multiview projections using terms such as front view, right side view, top view, rear view, left side view, and bottom view. In accordance with this convention, FIG. 17A may be referred to as a left side view of the elongate positioning member 102, FIG. 17B may be referred to as a front side view of the elongate positioning member 102, and FIG. 17C may be referred to as a top view of the elongate positioning member 102. FIG. 17A through FIG. 17F may be referred to collectively as FIG. 17. Terms such as front view and right side view are used herein as a convenient method for differentiating between the views shown in FIG. 17. It will be appreciated that the elements shown in FIG. 17 may assume various orientations without deviating from the spirit and scope of this detailed description. Accordingly, the terms front view, right side view, top view, rear view, left side view, bottom view, and the like should not be interpreted to limit the scope of the invention recited in the attached claims. FIG. 17D may be referred to as a right side view of the elongate positioning member 102, FIG. 17E may be referred to as a rear view of the elongate positioning member 102, and FIG. 17F may be referred to as a bottom view of the elongate positioning member 102.

In the example embodiment of FIG. 17, the elongate positioning member 102 comprises a shaft member 150 and a saddle member 152 that is fixed to a distal portion of the shaft member 150. In some useful embodiments, the shaft member 150 and a saddle member 152 each comprise stainless steel. With reference to FIG. 17E, it will be appreciated that a proximal portion of the shaft member 150 of the elongate positioning member 102 has a cylindrical shape. With reference to FIG. 17B and FIG. 17E, it will be appreciated that the saddle member 152 of the elongate positioning member 102 has a circular shape when viewed from the distal end and/or the proximal end. With reference to FIG. 17C, it will be appreciated that the saddle member 152 of the elongate positioning member 102 includes a weld joint WC. In some example methods, saddle member 152 is positioned over an inner tubular member and clamping force is applied to the saddle member 152 so that the saddle member 152 tightly encircles the inner tubular member. In some example methods, a weld is formed at weld joint WC while the saddle member 152 is tightly encircling the inner tubular member.

With reference to FIGS. 17A, 17C, 17D and 17F, it will be appreciated that the saddle member 152 of the elongate positioning member 102 also defines a plurality of holes 154 in the embodiment of FIG. 17. In some useful embodiments, a device including the saddle member 152 may also include thermoplastic material extending through the holes 154 in the saddle member 152.

Figure 18C:
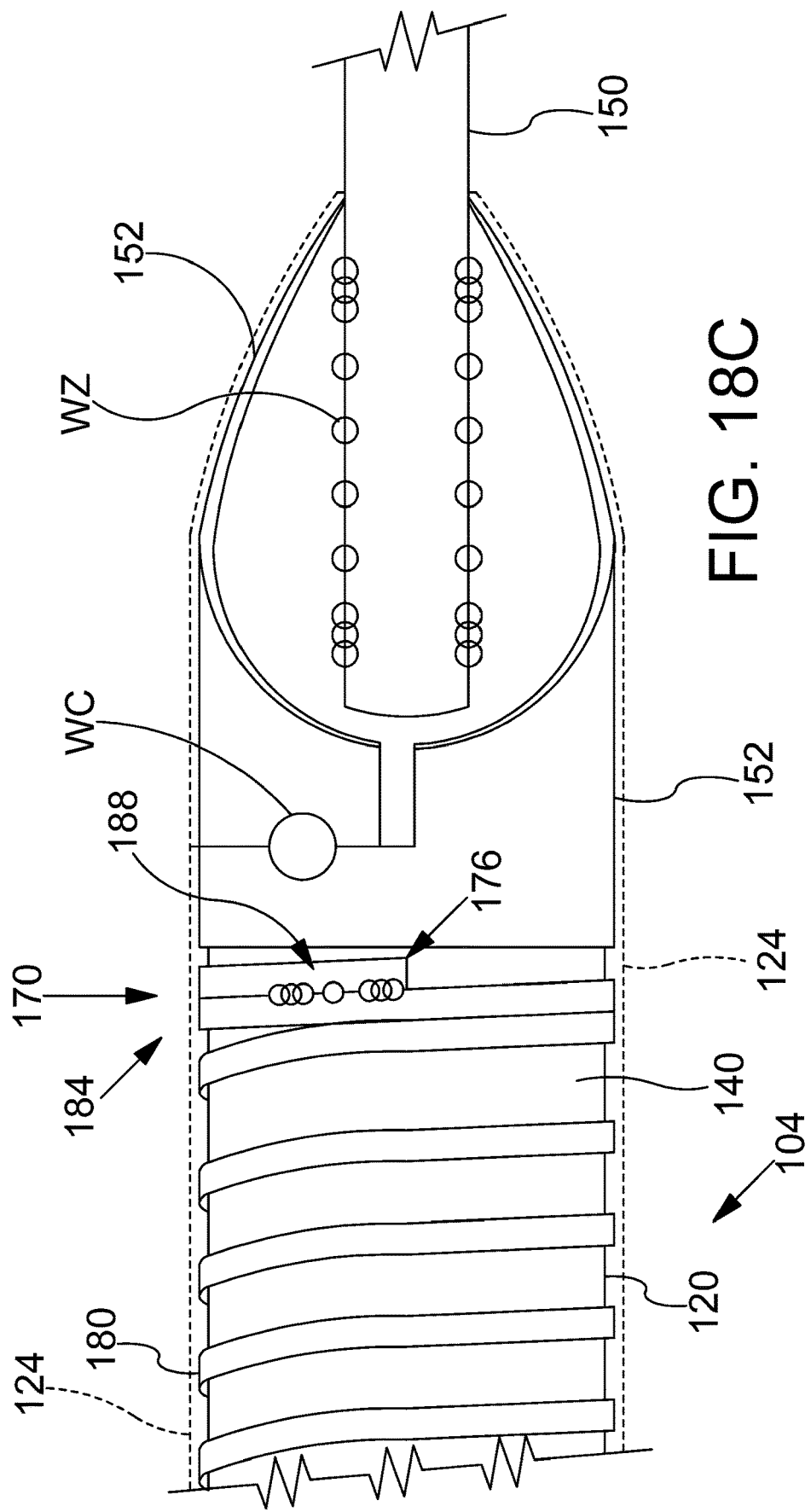
FIG. 18C is an enlarged top view showing an intermediate portion of the device shown in FIG. 18A.

FIG. 18A is a perspective view showing a device 100 for guiding and supporting catheters such as, for example, stent delivery catheters. FIG. 18B is an enlarged cross-sectional view of the device shown in FIG. 18A. In the embodiment of FIG. 18B, the device has been sectioned along section line 18B-18B shown in FIG. 18A. FIG. 18C is a partial top view showing a portion of the device 100 shown in FIG. 18A. FIGS. 18A through 18C may be collectively referred to as FIG. 18. In the embodiment of FIG. 18, the device 100 comprises a tubular guiding member 104 and an elongate positioning member 102 extending in a proximal direction beyond the tubular guiding member 104 for advancing and retracting the tubular guiding member 104 in distal and proximal directions.

With reference to FIG. 18, it will be appreciated that the tubular guiding member 104 comprises an inner tubular member 120 and a support structure 166 that is disposed about an outer surface 140 of the inner tubular member 120. As shown in FIG. 18, in some embodiments, the support structure 166 includes a distal collar portion 168, a proximal collar portion 170, and an intermediate portion 172 extending between the distal collar portion 168 and the proximal collar portion 170. The portions of the support structure 166 may be formed by an elongate support member 180. In FIG. 18, the elongate support member 180 can be seen extending along helical path around the outer surface 140 of the inner tubular member 120. In some embodiments, the elongate support member 180 forms a plurality of turns. With reference to FIG. 18B, it will be appreciated that the distal collar portion 168 of the support structure 166 may include a distal closed loop 174. In the embodiment of FIG. 18, the distal closed loop 174 comprises a distal weld 186 and a distal portion 182 of the elongate support member 180. The distal portion 182 extends around the outer surface 140 of the inner tubular member 120 in the embodiment of FIG. 18. As shown in FIG. 18C, the proximal collar portion 170 of the support structure 166 may include a proximal closed loop 176. In the embodiment of FIG. 18, the proximal closed loop 176 may comprise a proximal weld 188 and a proximal portion 184 of the elongate support member 180 that extends around the outer surface 140 of the inner tubular member 120.

Referring to FIG. 18C, a portion of the device 100 (shown in FIG. 18A) where the distal portion of the elongate positioning member 102 meets the proximal portion of the tubular guiding member 104. In the example embodiment of FIG. 18C, the saddle member 152 of the elongate positioning member 102 is fixed to a distal portion of the shaft member 150 at a weld WZ. In one example embodiment, weld WZ is created using a laser welding process. It should be noted, however, that various joining processes may be used to fix the saddle member 152 to the shaft member 150 without deviating from the spirit and scope of this detailed description. Examples of joining processes that may be suitable in some applications include TIG welding, plasma welding, laser welding, brazing, soldering, and adhesive bonding. With reference to FIG. 18C, it will be appreciated that the saddle member 152 of the elongate positioning member 102 includes a weld joint WC. In some example methods, saddle member 152 is positioned over an inner tubular member and clamping force is applied to the saddle member 152 so that the saddle member 152 tightly encircles the inner tubular member. In some example methods, a weld is formed at weld joint WC while the saddle member 152 is tightly encircling the inner tubular member.

FIG. 19A is a partial perspective view showing a distal portion 182 of a support structure 166 in accordance with this detailed description. FIG. 19B is an enlarged cross-sectional view further illustrating a portion of the support structure shown in FIG. 19A. FIG. 19C is an enlarged perspective view further illustrating a portion of the support structure shown in FIG. 19A. FIG. 19D is an enlarged perspective view further illustrating weld structure shown in FIG. 19C. FIG. 19A through 19D may be collectively referred to as FIG. 19. In some example embodiments, the distal collar portion 168 of the support structure 166 includes a distal closed loop 174. In the example embodiment of FIG. 19, the distal closed loop 174 comprises a distal weld 186 and a distal portion 182 of the elongate support member 180. The distal portion 182 may extend around the outer surface of an inner tubular member of a tubular guiding member is some example embodiments. In some example embodiments, the distal weld 186 comprises a plurality of distal weld bodies, each distal weld body 198 comprising jacket material 196 from a first forward part 202 of the elongate support member 180 and jacket material 196 from a second forward part 204 of the elongate support member 180, the materials having melted, mixed and solidified during a welding process. With reference to FIG. 19D, it will be appreciated that each distal weld body 198 has a shape that generally corresponds to the shape of a cone is some example embodiments. In the example embodiment illustrated in FIG. 19D, adjacent pairs of weld bodies are separated by spaces. With reference to the example embodiment shown in FIG. 19B, it will be appreciated that the elongate support member 180 comprises a core portion 190 comprising a core material 192 and a jacket portion 194 disposed about the core portion 190. In some example embodiments, the core material 192 comprises a radiopaque material and the core portion 190 of the elongate support member 180 serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

FIG. 20A is a partial perspective view showing a proximal portion of a support structure in accordance with the detailed description. FIG. 20B is an enlarged cross-sectional view further illustrating a portion of the support structure shown in FIG. 20A. FIG. 20C is an enlarged perspective view further illustrating a portion of the support structure shown in FIG. 20A. FIG. 20D is an enlarged perspective view further illustrating weld structure shown in FIG. 20C. FIGS. 20A through 20D may be collectively referred to as FIG. 20. In some example embodiments, the proximal collar portion 170 of the support structure 166 includes a proximal closed loop 176. In some example embodiments, the proximal closed loop 176 comprises a proximal weld 188 and a proximal portion 184 of the elongate support member 180 that extends around the outer surface of and inner tubular member of a tubular guiding member. In some example embodiments, the proximal weld 188 comprises a proximal weld body 200, the proximal weld body 200 comprising jacket material 196 from a first rearward part 206 of the elongate support member 180 and jacket material 196 from a second rearward part 208 of the elongate support member 180, the materials having melted, mixed and solidified during a welding process. With reference to FIG. 20D, it will be appreciated that each proximal weld body 200 has a shape that generally corresponds to the shape of a cone is some example embodiments. In the example embodiment illustrated in FIG. 20D, adjacent pairs of weld bodies overlap one another. With reference to the example embodiment shown in FIG. 20B, it will be appreciated that the elongate support member 180 comprises a core portion 190 comprising a core material 192 and a jacket portion 194 disposed about the core portion 190. In some example embodiments, the core material 192 comprises a radiopaque material and the core portion 190 of the elongate support member 180 serves as a sole radiographic marker of the device, the device having no radiopaque marker separate from the elongate support member. In some example embodiments, structures and arrangements with no dedicated marker band help to provide a thin walled tubular guiding member that is dimensioned and configured dimensioned to make new treatment options available to physicians.

Figure 21:
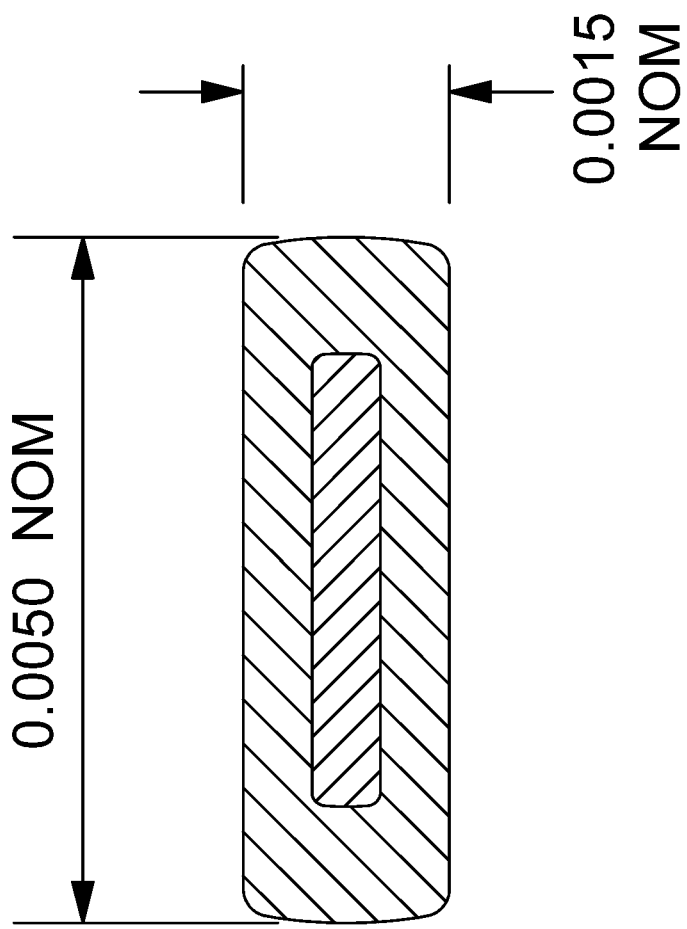
FIG. 21 is an enlarged cross-sectional view further illustrating an elongate support member.

FIG. 21 is an enlarged cross-sectional view further illustrating the elongate support member. In some example embodiments, the elongate support member has a rectangular cross-sectional shape and the rectangular cross-sectional shape has a width dimension and a thickness dimension, the width dimension being greater than the thickness dimension. In some embodiments, a ratio of the width dimension to the thickness dimension is greater than four. In the example embodiment of FIG. 21, the elongate support member has a nominal width of 0.0050 inch and a nominal thickness of 0.0015 inch.

FIG. 22A through FIG. 22F are a series of stylized partial cross-sectional views illustrating example methods in accordance with this detailed description. At FIG. 22A, an inner tubular member 120 is provided and a mandrel 134 is inserted into a lumen 118 defined by the inner tubular member 120. Some example methods include stretching the inner tubular member 120 while it is on the mandrel 134. In some example methods, tension is applied to the two ends of the inner tubular member 120. In some example methods, tension applied to the two end of the inner tubular member causes the wall of the inner tubular member 120 to become thinner. In some embodiments, the wall of the inner tubular member has a thickness of less than 0.0010 inches. In some useful embodiments, the inner tubular member comprises a lubricious polymer such as polyethylene and/or a fluoropolymer such as PTFE (e.g., Teflon™).

At FIG. 22B, an elongate support member 180 is wound around the outer surface 140 of the inner tubular member 120 to form a support structure 166. In some example embodiments, the support structure 166 has a distal portion 182, a proximal portion 184 and an intermediate portion 172 extending between the distal portion 182 and the proximal portion 184. In some useful methods, the elongate support member 180 is held under tension as the support structure 166 is formed. In the embodiment of FIG. 22B, the support structure 166 has a pitch that may be defined as the distance between the centers of adjacent turns. In some example embodiments, the pitch varies along the length of the intermediate portion 172 of the support structure 166.

In some useful embodiments, the radiopacity of the support structure 166 varies as the pitch of the support structure 166 varies. In some example embodiments, the elongate support member comprises a core portion comprising a core material and a jacket portion disposed about the core portion. In some example embodiments, the core material comprises a radiopaque material and the core portion of the elongate support member serves as a sole radiographic marker of the device, the device having no radiopaque marker separate from the elongate support member. In some example embodiments, structures and arrangements with no dedicated marker band help to provide a thin walled tubular guiding member that is dimensioned and configured to make new treatment options available to physicians.

At FIG. 22C, a distal collar portion 168 and a proximal collar portion 170 are formed. In some example embodiments, the distal collar portion 168 of the support structure 166 includes a distal closed loop 174. In some example embodiments, the distal closed loop 174 comprises a distal weld 186 and a portion of the elongate support member 180 that extends around the outer surface 140 of the inner tubular member 120. In some example embodiments, the distal weld 186 comprises a distal weld body 198, the distal weld body 198 comprising jacket material from a first forward part 202 of the elongate support member 180 and jacket material from a second forward part 204 of the elongate support member 180, the materials having melted, mixed and solidified during a welding process. In some example embodiments, the proximal collar portion 170 of the support structure 166 includes a proximal closed loop 176. In some example embodiments, the proximal closed loop 176 comprises a proximal weld 188 and a proximal portion of the elongate support member 180 that extends around the outer surface 140 of the inner tubular member 120. In some example embodiments, the proximal weld 188 comprises a proximal weld body 200, the proximal weld body 200 comprising jacket material from a first rearward part 206 of the elongate support member 180 and jacket material from a second rearward part 208 of the elongate support member 180, the materials having melted, mixed and solidified during a welding process.

At FIG. 22D, the support structure 166 and the inner tubular member 120 are inserted into a lumen defined by a sheet 210 that is part of a sheet assembly 160. In the example embodiment of the FIG. 22D, the sheet assembly 160 comprises the sheet 210 and a piece of shrink tubing 132 (as shown in FIG. 23). In some example embodiments, the shrink tubing 132 comprises a fluoropolymer such as FEP (e.g., Teflon™). In example embodiments, the sheet 210 comprises a thermoplastic material. The thermoplastic material may comprise, by way of example and not limitation, a polyamide material such as nylon (e.g., nylon-12) and/or polyether-block-amide (e.g., Pebax™). In some example methods, the thermoplastic material of the sheet 210 is melted, mixed and solidified to form an encapsulation layer of a tubular guiding member. In some example embodiments, the sheet 210 is disposed inside a lumen defined by the shrink tubing 132 with the sheet 210 assuming a tubular shape. In some example embodiments, the sheet 210 is urged to assume a tubular shape as the sheet is drawn into the lumen defined by the shrink tubing 132.

At FIG. 22E, the assembly shown in FIG. 22D is heated. In some example embodiments, upon heating, the shrink tubing 132 shrinks and the material of the sheet 210 melts and/or reflows to form an encapsulation layer 124. In some example embodiments, the encapsulation layer 124 comprises thermoplastic material of the sheet 210, the thermoplastic material having melted, mixed and solidified during a reflow process.

At FIG. 22F, the mandrel 134 is removed from the lumen defined by the inner tubular member 120 and the heat shrink tubing 132 is removed from around the encapsulation layer 124 of the tubular guiding member 104.

FIG. 23A is a perspective view showing a sheet 210 and FIG. 23B is a perspective view showing the sheet 210 as it is inserted and/or drawn into a lumen defined by a length of shrink tubing 132. As shown in FIG. 23B, in some example embodiments, the sheet 210 is urged to assume a tubular shape as the sheet is drawn into the lumen defined by the shrink tubing 132. In some example embodiments, the encapsulation layer of a tubular guiding member comprises thermoplastic material of the sheet 210 that has been melted, mixed and solidified during a reflow process.

FIG. 23C is a cross-sectional view further illustrating sheet 210 and shrink tubing 132 of assembly 160. With reference to FIG. 23C, it will be appreciated that sheet 210 is assuming a tubular shape having a circumferential span angle CSA of less than 360 degrees so that the sheet 210 defines a longitudinal gap G located between a first longitudinal edge of the sheet 210 and a second longitudinal edge of the sheet 210. Some example methods in accordance with this detailed description include urging a ribbon or sheet to assume the tubular shape having a circumferential span angle of less than 360 degrees so that the ribbon or sheet defines a longitudinal gap located between a first longitudinal edge of the ribbon or sheet and a second longitudinal edge of the ribbon or sheet. Some example methods in accordance with this detailed description include urging a ribbon or sheet to assume the tubular shape having a circumferential span angle of less than 345 degrees.

FIG. 23D is a perspective view showing a sheet 210 defining a hole and a pulling tool 60 having a hook shaped portion extending through the hole defined by the sheet 201. FIG. 23E is a perspective view showing the sheet 210 as it is pulled into a lumen defined by a length of shrink tubing 132.

FIG. 23F is a perspective view showing a sheet 210 defining a hole and a pushing tool 62 having a fork shaped portion extending through the hole defined by the sheet 201. FIG. 23G is a perspective view showing the sheet 210 as it is pushed into a lumen defined by a length of shrink tubing 132.

The FIGS. 23H through 23O are a series of stylized perspective views illustrating example methods in accordance with this detailed description.

At FIG. 23H, a first sheet 70 and a second sheet 72 are provided.

At FIG. 23I, the first sheet 70 and the second sheet 72 are positioned so that the sheets overlap one another.

At FIG. 23J, a seam weld 74 is formed between the first sheet 70 and the second sheet 72. In some example methods, a laser welding process is used to form the seam weld 74.

At FIG. 23K, a plurality of cuts are created through the first sheet 70 and the second sheet 72 to define a ribbon 210. In some example methods, a laser cutting process is used to form cuts through the first sheet 70 and the second sheet 72.

At FIG. 23L, additional cuts are created through the first sheet 70 and the second sheet 72 to define additional ribbons.

At FIG. 23M, the ribbon 210 is separated from the first sheet 70 and the second sheet 72

At FIG. 23N, the ribbon 210 has transitioned from a first, shorter state to a second, longer state. With reference to FIG. 23N, it will be appreciated that the ribbon 210 has a distal strip 76 cut from the first sheet 70 and a proximal strip 78 cut from the second sheet 72. In the embodiment of FIG. 23N, a proximal portion of the distal strip and a distal portion of the proximal strip are connected at the seam weld 74.

FIG. 23N is a perspective view showing the ribbon 210 and FIG. 23O is top plan view showing the ribbon 210. With reference, to FIG. 23N and FIG. 23O, the ribbon comprises a distal strip 76 and a proximal strip 78. A distal portion of the proximal strip 78 is attached to a proximal portion of the distal strip 76 at the seam weld 74 in the embodiment of FIG. 23N and FIG. 23O. In some embodiments, the distal strip has a first durometer and the second strip has a second durometer different from the first durometer. In some embodiments, the proximal strip has a durometer greater than 60 shore D and distal strip has a first durometer less than 60 shore D. In some embodiments, the proximal strip has a durometer between 62 and 82 shore D and the distal strip has a durometer between 35 and 55 shore D.

FIG. 23P is a perspective view showing a ribbon 210 in accordance with this detailed description. The ribbon 210 of FIG. 23P comprises a distal strip 76 and a proximal strip 78. FIG. 23Q is a partial cross-sectional view illustrating the structure of the distal strip 76. FIG. 23R is a partial cross-sectional view illustrating the structure of the proximal strip 78. FIG. 23P through FIG. 23R may be collectively referred to as FIGS. 23P-R. In the embodiment of FIGS. 23P-R, a distal portion of the proximal strip 78 is attached to a proximal portion of the distal strip 76 at a seam weld 74.

With reference to FIG. 23Q, it will be appreciated that the distal strip comprises a central layer 80 having a first planar surface 82 and a second planar surface 84. In the embodiment of FIG. 23Q, a first skin layer 86 overlays a first planar surface 82 of the central layer 80 and a second skin layer 88 overlays the second planar surface 84 of the central layer 80. In some embodiments, the first skin layer 86 a first durometer and the central layer 80 has a second durometer different from the first durometer. In some embodiments, the durometer of each skin layer is greater than the durometer of the central layer. In some embodiments, the durometer of each skin layer is greater than 60 shore D and the durometer of the central layer is less than 60 shore D. In some embodiments, the durometer of each skin layer is between 62 and 82 shore D durometer and the first durometer is between 35 and 55 shore D durometer. In some embodiments, the second skin layer of the first sheet has third durometer, the third durometer having a value within 20% of the first durometer value.

Referring to FIG. 23N and FIG. 23O, in some example methods, providing a first ribbon 210 comprises attaching a proximal end of a distal strip 76 to a distal portion of a proximal strip 78 at a seam weld 74. In some methods example methods, the distal strip 76 comprises a first material having a first durometer and the proximal strip 76 comprises a second material having a second durometer. In some embodiments, the second durometer is different from the first durometer. In some example methods, the second durometer is greater than the first durometer. In some example methods, the second durometer is greater than 60 shore D durometer and the first durometer is less than 60 shore D durometer. In some example methods, the second durometer is between 62 and 82 shore D durometer and the first durometer is between 35 and 55 shore D durometer.

Referring to FIG. 23H through FIG. 23O, in some example methods providing a ribbon comprises providing a material sheet and creating one or more cuts through the material sheet to define a ribbon. In other example methods providing a ribbon comprises providing a first sheet 70 and a second sheet 72, positioning the first sheet 70 and the second sheet 72 so that the sheets overlap one another, and forming a seam weld 74 between the first sheet 70 and the second sheet 72. Some example methods further include creating one or more cuts through the first sheet 70 and the second sheet 72 to define a ribbon having a distal strip 76 cut from the first sheet 70 and a proximal strip 78 cut from the second sheet 72 with the seam weld 74 forming a connection between a proximal portion of the distal strip 76 and a distal portion of the proximal strip 78.

In some example methods, providing a first sheet 70 and a second sheet 72 comprises providing a first sheet 70 having a first durometer and a second sheet 72 having a second durometer so that the distal strip 76 has the first durometer and the proximal strip 78 has the second durometer. In some example methods, the second durometer is different from the first durometer. In some example methods, the second durometer is greater than the first durometer. In some example methods, the second durometer is greater than 60 shore D durometer and the first durometer is less than 60 shore D durometer. In some example methods, the second durometer is between 62 and 82 shore D durometer and the first durometer is between 35 and 55 shore D durometer.

Referring to FIGS. 23P and 23Q, some example methods include providing a ribbon 210 having a central layer 80 with a first planar surface 82 and a second planar surface 84. In some embodiments, the ribbon 210 includes a first skin layer 86 overlaying the first planar surface 82 of the central layer 80 and a second skin layer 88 overlaying the second planar surface 84 of the central layer 80. In some embodiments, the first skin layer 86 has a first durometer and the central layer 80 has a second durometer different from the first durometer. In some embodiments, the durometer of each skin layer is greater than the durometer of the central layer. In some embodiments, the durometer of each skin layer is greater than 60 shore D durometer and the durometer of the central layer is less than 60 shore D durometer. In some embodiments, the durometer of each skin layer is between 62 and 82 shore D durometer and the durometer of the central layer is between 35 and 55 shore D durometer. In some embodiments, the durometer of second skin layer has third durometer, the third durometer has a value within 20% of a value the first durometer of the first skin layer.

Referring, for example, to FIGS. 23D, 23F and 23K-23M, in some example methods creating one or more cuts through the first sheet and the second sheet comprises creating cuts defining a distal portion of the proximal strip that is tapered so that the width of the proximal strip decreases as the proximal strip extends in the distal direction. In some example methods, creating one or more cuts through the first sheet and the second sheet comprises creating cuts defining a proximal portion of the distal strip is tapered so that the width of the distal strip decreases as the distal strip extends in the proximal direction. In some example methods, creating one or more cuts through the first sheet and the second sheet comprises creating cuts defining a distal portion of the distal strip is tapered so that the width of the proximal strip decreases as the proximal strip extends in the distal direction. In some example methods, creating one or more cuts through the first sheet and the second sheet comprises creating cuts defining a distal portion of the distal strip has a truncated triangle shape when viewed as an orthographic projection.

FIG. 23S is a top plan view of a ribbon 210 in accordance with an example embodiment. FIG. 23T is a partial cross-sectional view of the ribbon 210 shown in FIG. 23S. In the embodiment of FIG. 23T, the ribbon 210 has been sectioned along section line T-T shown in FIG. 23S. FIG. 23S and FIG. 23T may be collectively referred to as FIGS. 23S-T. With reference to FIG. 23T, it will be appreciated that ribbon 210 comprises a plurality of layers 10-50. Example methods in accordance this detailed description may include providing a ribbon or sheet having more than one layer, forming an assembly including the ribbon or sheet, and heating the assembly to a process temperature. In some embodiments, upon heating the assembly to the process temperature, the first ribbon reflows to form an encapsulation layer. In some embodiments, a ribbon or sheet having five or more layers is used. In some embodiments, a ribbon or sheet having ten or more layers is used. In some embodiments, a ribbon or sheet having twenty or more layers is used.

FIG. 24A is a perspective view showing an example tubular guiding member 104 in accordance with this detailed description. FIG. 24B is an enlarged perspective view showing a portion of the example tubular guiding member 104 shown in FIG. 24A. FIG. 24A and FIG. 24B may be collectively referred to as FIG. 24. In the embodiment of FIG. 24, tubular guiding member 104 comprises a support structure 166 including a first support member 268 disposed about an inner tubular member and a second support member 270 disposed about the first support member 268. The first support member 268 comprises a wire 138 forming a coil 122 in the embodiment of FIG. 24. The coil may include a plurality of turns with each turn comprising a length of wire extending around the outer surface of the inner tubular member. The second support member 270 comprises a yarn 164 that extends along a spiraling yarn path 272 about the first support member 268. Adjacent revolutions of the yarn path 272 are separated by a yarn pitch distance in the embodiment of FIG. 24. With reference to FIG. 24, it will be appreciated that the yarn pitch distance is greater than the wire pitch distance.

FIG. 25 is a perspective view showing an example support structure 166 including a first support member 268 and a second support member 270. The example support structure 166 shown in FIG. 25 may be included in a tubular guiding member in accordance with this detailed description. In the embodiment of FIG. 25, the first support member 268 comprises a wire 138 forming a coil 122 and the second support member 270 comprises a yarn 164 disposed along a yarn path 272 about the coil 122.

With reference to FIG. 25, it will be appreciated that the yarn path 272 curves in three dimensions. Three axes (X, Y and Z) of a cartesian coordinate system are shown in FIG. 25. A first plane XY is defined by the X-axis and the Y-axis. A second plane XZ is defined by the X-axis and a Z-axis. A third plane YZ is defined by the Y-axis and the Z-axis. With reference to FIG. 25, it will be appreciated that the yarn 164 passes through these three mutually orthogonal planes as it extends along the yarn path 272. Also with reference to FIG. 25, it will be appreciated that the yarn 164 does not lie completely on any one of the three planes (i.e., the first plane xy, the second plane xz, and the third plane yz).

In some embodiments, the yarn 164 has a proximal end, a distal end, and an intermediate portion that extends between the proximal end and the distal end. With reference to FIG. 25, it will be appreciated that the yarn 164 spirals in a clockwise direction CW as it extends distally from the proximal end to distal end of the illustrated yarn portion. In some embodiments, the yarn 164 may spiral in the counterclockwise direction CCW as it extends distally from proximal end to distal end. In the embodiment of FIG. 25, each revolution of the yarn may have an angular span of three hundred and sixty degrees. On half of a revolution (i.e., a one hundred and eighty degree span) can be seen in FIG. 25. In the embodiment of FIG. 25, the yarn 164 forms a helix as it extends along the yarn path 272. It will be appreciated, however, that other paths are possible and that some paths curving in three dimensions do not form helices.

In the example embodiment of FIG. 25, the first support member 268 of the support structure 166 comprises a wire 138 forming a coil 122. The coil 122 includes a number of turns 136 that extend loosely about a Z-axis in the example embodiment of FIG. 25. With reference to FIG. 25, it will be appreciated that the wire 138 also does not lie completely on any one of the three planes shown in FIG. 25 (i.e., first plane xy, second plane xz, and third plane yz). In some example embodiments, each turn 136 comprises a length of wire 138 extending around the outer surface of an inner tubular member. With reference to FIG. 25, it will be appreciated that adjacent turns 136 of the coil 122 are separated by a wire pitch distance WP. The wire pitch WP may be defined as the distance between the centers of adjacent turns 136 of wire 138. In the embodiment of FIG. 25, wire pitch WP is constant along the length of wire 138. Also in the embodiment of FIG. 25, turns 136 have a radius that is substantially constant throughout the rotation of wire 138. In the embodiment of FIG. 25, it will be appreciated that wire 138 forms a helix. It will also be appreciated, however, that other coil shapes are possible and that some of the possible coil shapes are not helices. Additionally, it will be appreciated that coil shapes are possible which have a radius that varies along the length of the coil unlike coil 122 shown in FIG. 25. In the embodiment of FIG. 25, the wire 138 completes about sixteen complete turns 136 with each turn having an angular span of three hundred and sixty degrees. With reference to FIG. 25, it will be appreciated that wire 138 spirals in a clockwise direction CW as it extends along the turns 136 of the coil 122. In other embodiments, the wire 138 may spiral in the counterclockwise direction CCW as it extends through the turns 136 of the coil 122. With reference to FIG. 25, it will be appreciated that wire 138 extends through three mutually orthogonal planes: a first plane xy, a second plane xz, and a third plane yz. First plane xy is defined by an X-axis and a Y-axis. Second plane xz is defined by the X-axis and a Z-axis. Third plane yz is defined by the Y-axis and the Z-axis.

FIG. 26A is a side view showing a device 100 for guiding and supporting catheters such as, for example, stent delivery catheters. FIG. 26B is an enlarged detail view further illustrating a portion of the device 100 shown in FIG. 26A. FIG. 26C is an enlarged side view further illustrating the apparatus shown in FIG. 26B. FIGS. 26A through 16C may be collectively referred to as FIG. 26. In the embodiment of FIG. 26, the device 100 comprises a tubular guiding member 104 and an elongate positioning member 102. As shown in FIG. 26, in some example embodiments, the elongate positioning member 102 extends in a proximal direction beyond the tubular guiding member 104 for advancing and retracting the tubular guiding member 104 in distal and proximal directions. In some example embodiments, a distal portion of the elongate positioning member 102 is coupled to a proximal portion of the tubular guiding member 104. FIG.

26B is an enlarged detail view showing a portion of the device 100 where the distal portion of the elongate positioning member 102 meets the proximal portion of the tubular guiding member 104.

With reference to FIG. 26, it will be appreciated that the tubular guiding member 104 comprises an inner tubular member 120 having a proximal end, a distal end, an outer surface. In the embodiment of FIG. 26, the inner tubular member 120 has an inner surface 116, the inner surface 116 defining a lumen 118 extending between the proximal end and the distal end of the inner tubular member 120. In the embodiment of FIG. 26, the tubular guiding member 104 includes a support structure 166 disposed about the outer surface 140 of the inner tubular member 120. The support structure 166 of FIG. 26 includes a distal collar portion 168, a proximal collar portion 170, and an intermediate part 172 extending between the distal collar portion 168 and the proximal collar portion 170. In embodiments, the portions of the support structure 166 are formed by an elongate support member 180. In embodiments, the elongate support member 180 is disposed along a helical path around the outer surface 140 of the inner tubular member 120. In the example embodiment of FIG. 26, the tubular guiding member 104 includes an encapsulation layer 124 overlaying the inner tubular member 120 and the support structure 166. In some useful embodiments, the encapsulation layer 124 is mechanically interlocked with and adhered to the support structure 166.

Referring to FIG. 26B, a portion of the device 100 (shown in FIG. 18A) where a distal portion of the elongate positioning member 102 meets a proximal portion of the tubular guiding member 104. As shown in FIG. 26B, the proximal collar portion 170 of the support structure 166 may include a proximal closed loop 176. In the embodiment of FIG. 26, the proximal closed loop 176 may comprise a proximal weld 188 and a proximal portion 184 of the elongate support member 180 that extends around the outer surface 140 of the inner tubular member 120. In some example embodiments, the proximal weld 188 comprises a proximal weld body, the proximal weld body comprising jacket material from a first forward part of the elongate support member 180 and jacket material from a second forward part of the elongate support member 180, the materials having melted, mixed and solidified during a welding process.

FIG. 26C is an enlarged side view further illustrating the apparatus shown in FIG. 26B. With reference to FIG. 26C, it will be appreciated that, in some embodiments, the saddle member 152 comprises a saddle interlocking portion 212, the encapsulation layer 124 comprises a complementary interlocking portion 216, and the saddle interlocking portion 212 and the complementary interlocking portion 216 engage each other to form a mechanically interlocking connection 220. In some embodiments, the saddle interlocking portion 212 comprises a plurality of lock features 214 and the complementary interlocking portion 216 of the encapsulation layer 124 comprises a plurality of complementary features 218. In some embodiments, the complementary features 218 are mechanically interlocked with the lock features 214 at the mechanically interlocking connection 220. With reference to FIG. 26B and FIG. 26C, it will be appreciated that the encapsulation layer 124 includes an overhanging lip portion 230.

Figure 26D:
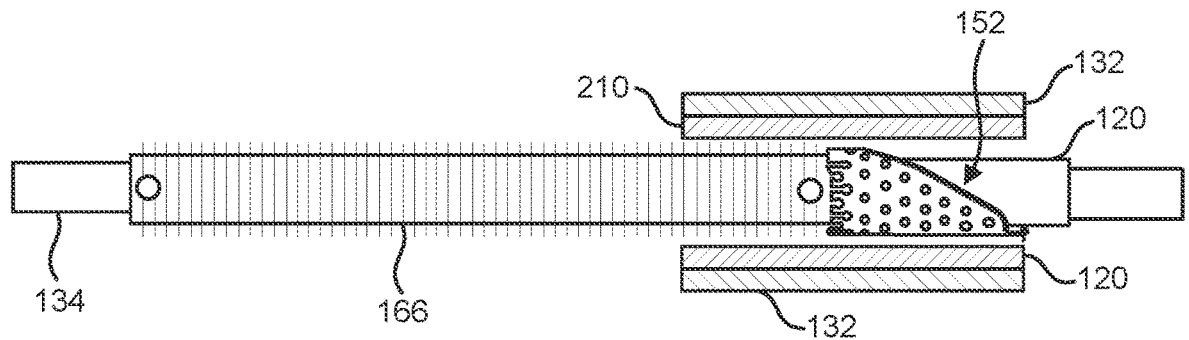

At FIG. 26D, the assembly shown in FIG. 22C is inserted into a lumen defined by a sheet 210 that is part of a sheet assembly 160. In the example embodiment of the FIG. 26D, the sheet assembly 160 comprises the sheet 210 and a piece of shrink tubing 132. In some example embodiments, the shrink tubing 132 comprises a fluoropolymer such as FEP (e.g., Teflon™). In example embodiments, the sheet 210 comprises a thermoplastic material. The thermoplastic material may comprise, by way of example and not limitation, a polyamide material such as nylon (e.g., nylon-12) and/or polyether-block-amide (e.g., Pebax™). In some example methods, the thermoplastic material of the sheet 210 is melted, mixed and solidified to form all or part of an encapsulation layer. In some example embodiments, the sheet 210 is disposed inside a lumen defined by the shrink tubing 132 with the sheet 210 assuming a tubular shape. In some example embodiments, the sheet 210 is urged to assume a tubular shape as the sheet is drawn into the lumen defined by the shrink tubing 132.

Figure 26E:
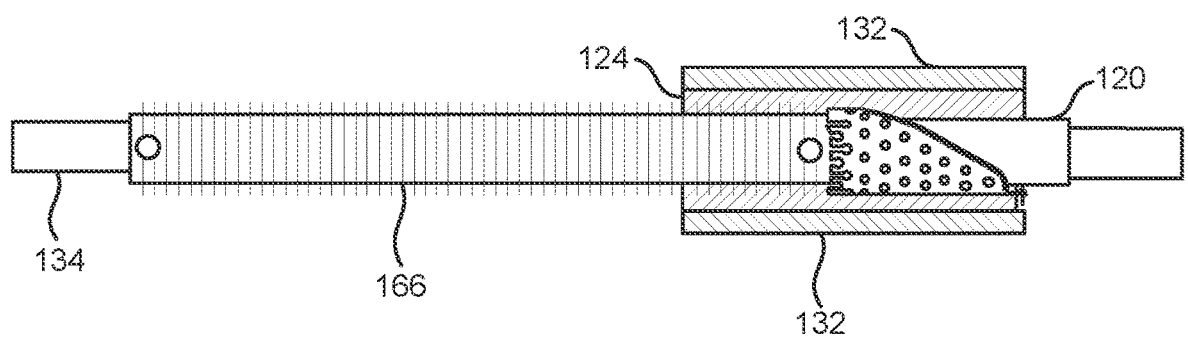

At FIG. 26E, the assembly shown in FIG. 26D is heated. In some example methods, upon heating, the shrink tubing 132 shrinks and the material of the sheet 210 melts and/or reflows to form an encapsulation layer portion 124. In some example embodiments, the encapsulation layer portion 124 comprises thermoplastic material of the sheet 210, the thermoplastic material having melted, mixed and solidified during a reflow process.

Figure 26F:
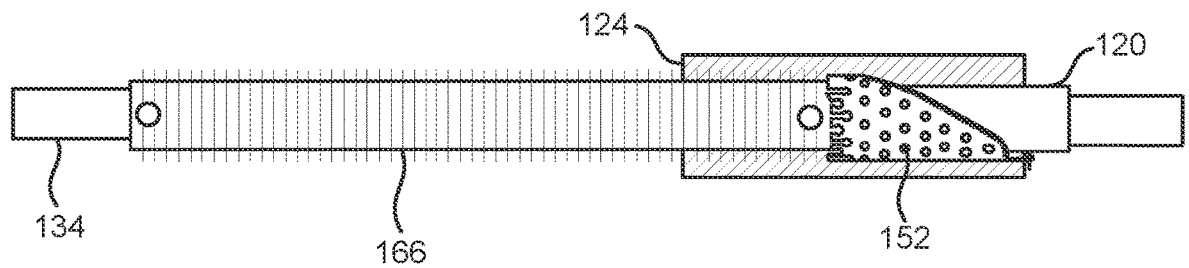

At FIG. 26F, the heat shrink tubing 132 is removed from around the encapsulation layer portion 124.

Figure 26G:
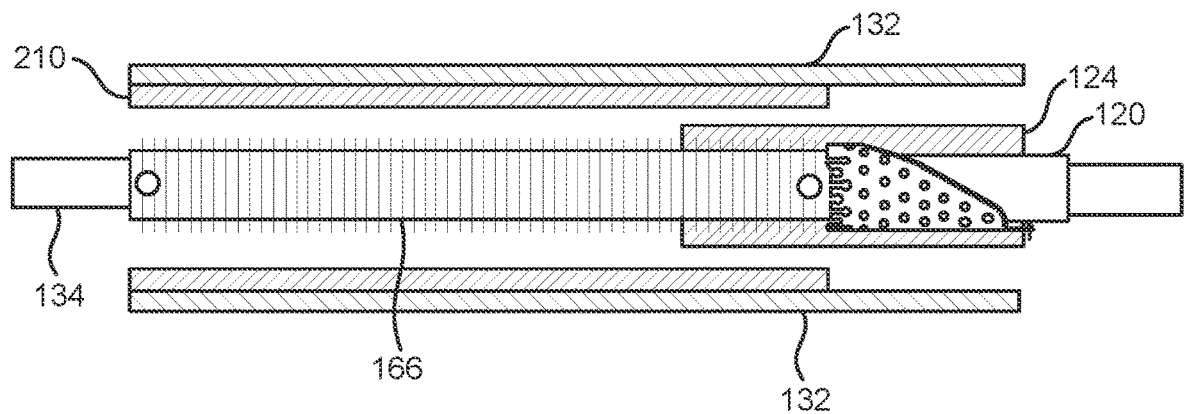

At FIG. 26G, the assembly shown in FIG. 26F is inserted into a lumen defined by a second sheet 210 that is part of a second sheet assembly 160. In the example embodiment of the FIG. 26G, the second sheet assembly 160 comprises the second sheet 210 and a piece of shrink tubing 132. In some example methods, the thermoplastic material of the second sheet 210 is melted, mixed and solidified to form part of the encapsulation layer 120. In some example embodiments, the sheet 210 is disposed inside a lumen defined by the shrink tubing 132 with the sheet 210 assuming a tubular shape. In some example embodiments, the sheet 210 is urged to assume a tubular shape as the sheet is drawn into the lumen defined by the shrink tubing 132.

Figure 26H:
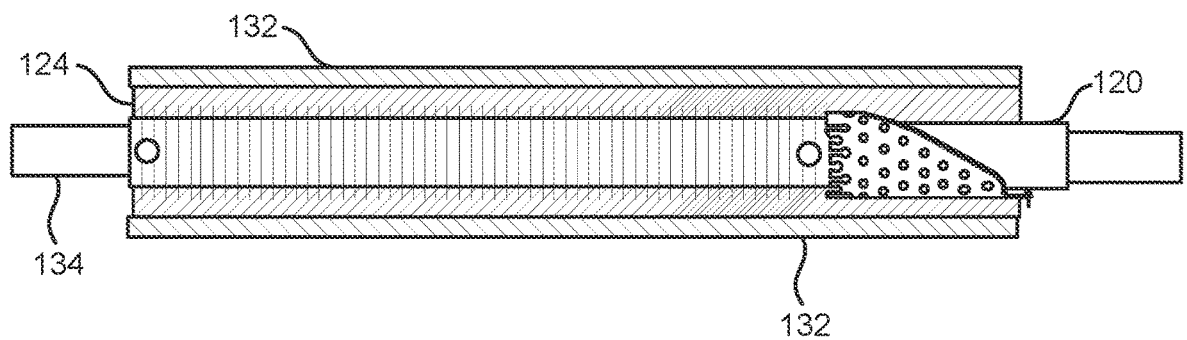

At FIG. 26H, the assembly shown in FIG. 26G is heated. In some example methods, upon heating, the shrink tubing 132 shrinks and the material of the second sheet 210 melts and/or reflows to become part of the encapsulation layer 124. In some example embodiments, the encapsulation layer 124 comprises thermoplastic material from a plurality of sheets 210, the thermoplastic material having melted, mixed and solidified during one or more reflow processes.

Figure 26I:
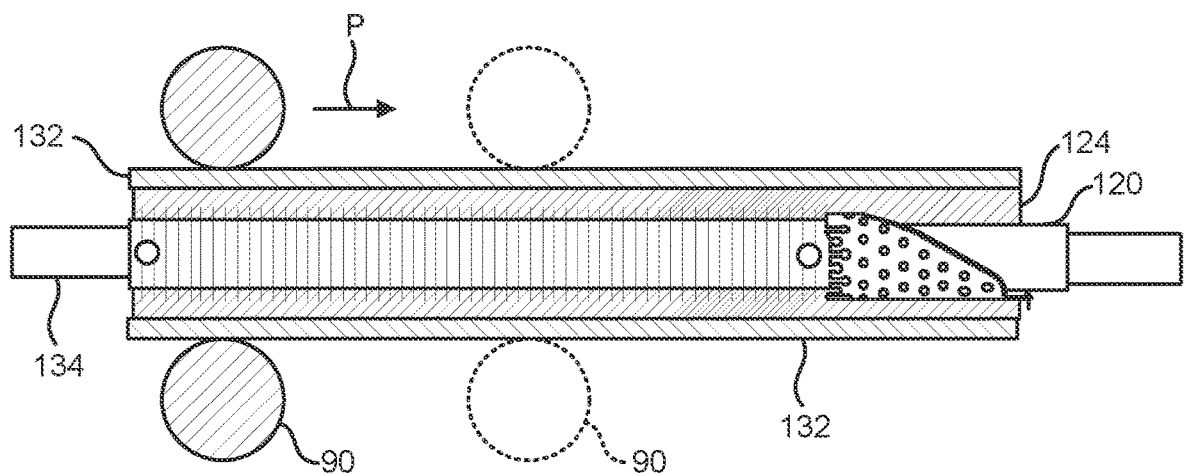
Figure 26J:
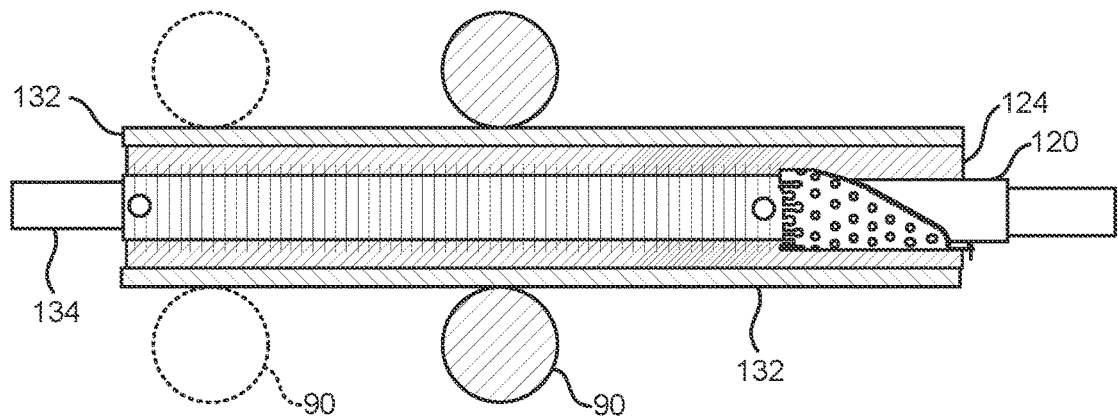

At FIG. 26I, a ring member 90 is positioned about the shrink tubing 132. In some embodiments, the ring member 90 comprises an elastomeric O-ring. Some example methods include sliding the ring member 90 lengthwise along the shrink tubing 132 while the thermoplastic material of the encapsulation layer 124 is molten. In some example methods, sliding the ring member 90 lengthwise along the shrink tubing 132 creates lengthwise flow in the molten thermoplastic material of the encapsulation layer 124. In some example methods, sliding the ring member 90 lengthwise along the shrink tubing 132 redistributes the thermoplastic material of the encapsulation layer 124. In some example methods, sliding the ring member 90 lengthwise along the shrink tubing 132 causes some of the thermoplastic material of the encapsulation layer 124 to be extruded out of the shrink tubing 132. Some example methods include sliding the ring member 90 along the shrink tubing 132 in a proximal direction and/or a distal direction. In the embodiment of FIG. 26I, for example, the ring member 90 is shown in a first position and the ring member 90 may translate in a proximal direction P between the first position and a second, more proximal position. One example of a second position is shown with dashed lines in FIG. 26I. In the embodiment of FIG. 26J, the ring member 90 has been moved from the first position (shown in FIG. 26I) to a second position (shown in FIG. 26J).

Figure 26K:
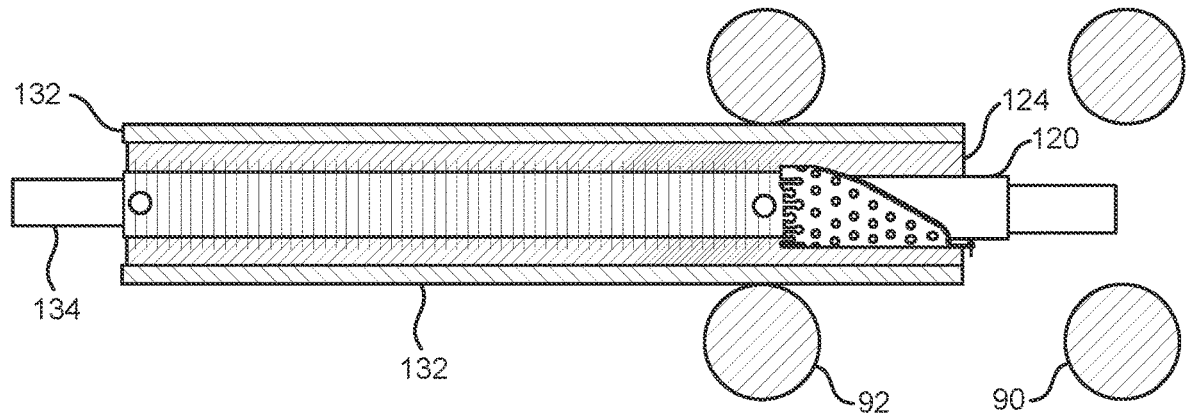

At FIG. 26K, the ring member 90 has been moved proximally beyond a proximal end of the shrink tubing 132. Also at FIG. 26K, a second ring member 92 is positioned about the shrink tubing 132 at a position generally aligned with the saddle member 152. In some example methods, the saddle member 152 is positioned over the inner tubular member 120 and a ring member 92 is positioned about the saddle member 152. In some example methods, elastic clamping forces produced by the ring member 92 are applied to the saddle member 152 so that the saddle member 152 tightly encircles the inner tubular member 120. In some example methods, molten thermoplastic material of the encapsulation layer 124 is allowed to cool while the saddle member 152 is tightly encircling the inner tubular member 120. In some example methods, molten thermoplastic material of the encapsulation layer 124 is allowed to cool while elastic clamping forces produced by the ring member 92 are applied to the saddle member 152.

Figure 26L:
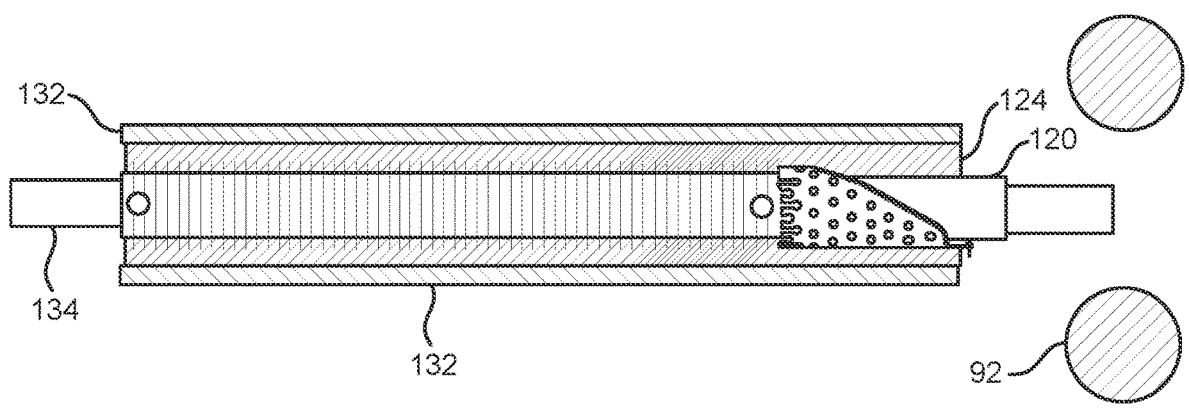

At FIG. 26L, the ring member 92 has been moved proximally beyond a proximal end of the shrink tubing 132.

Figure 26M:
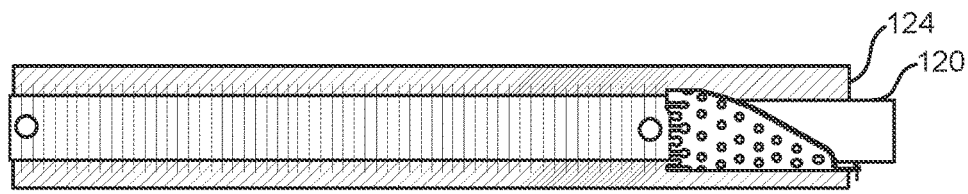

At FIG. 26M, the mandrel 134 is removed from the lumen defined by the inner tubular member 120 and the heat shrink tubing 132 is removed from around the encapsulation layer 124 of the shaft 104.

FIG. 27 is a stylized exploded view further illustrating the saddle interlocking portion 212 of the saddle member 152 and the complementary interlocking portion 216 of the encapsulation layer 124. When the saddle member 152 and the encapsulation layer 124 are in an unexploded state, the saddle interlocking portion 212 and the complementary interlocking portion 216 may engage each other to form a mechanically interlocking connection. In some embodiments, the saddle interlocking portion 212 comprises a plurality of lock features 214 and the complementary interlocking portion 216 of the encapsulation layer 124 comprises a plurality of complementary features 218. In some embodiments, the complementary features 218 are mechanically interlocked with the lock features 214 at the mechanically interlocking connection.

With reference to FIG. 27, it will be appreciated that, in some embodiments, the saddle member 152 has a serrated edge 258 and the encapsulation layer 124 includes an overhanging lip portion 230 having a complementary edge portion 260. In some embodiments, the serrated edge 258 and the complementary edge portion 260 engage each other to form a mechanically interlocking joint 228. In some embodiments, the serrated edge 258 comprises a plurality of edge features 262, the complementary edge portion 260 comprises a plurality of complementary elements 264. In some embodiments, the complementary elements 264 are mechanically interlocked with the edge features 262 of the serrated edge 258.

FIG. 28 is an additional stylized exploded view further illustrating the saddle interlocking portion 212 of the saddle member 152 and the complementary interlocking portion 216 of the encapsulation layer 124. In the stylized view of FIG. 28, the saddle member 152 and the encapsulation layer 124 have shapes that are generally planar. It is noted that various fabrication techniques may be used to fabricate saddle member 152. For example, saddle member 152 can be fabricated by providing a generally flat sheet of material and laser cutting the sheet of material to form saddle member 152 shown in FIG. 28. The saddle member 152 may then be formed into a generally tubular shape as shown in FIG. 28. Any adjoining edges may be, optionally, welded. By way of a second example, the saddle member 152 may be fabricated by providing a length of tubing and laser cutting openings in the tubing material to form the shape shown, for example, in FIG. 26. By way of example, laser cutting may be used to cut patterns in flat stock material and a resulting flat part maybe rolled and/or shaped to define a cylinder shape.

FIG. 29 is an enlarged perspective view showing the encapsulation layer shown in the previous figure. With reference to FIG. 29, it will be appreciated that the encapsulation layer 124 includes an overhanging lip portion 230 having a complementary edge portion 260. In some embodiments, the complementary edge portion 260 comprises a plurality of complementary elements 264. In some embodiments, the complementary elements 264 of the complementary edge portion 260 comprise a plurality of indentations 252 and a plurality of tongues 232. In some embodiments, the indentations 252 and the tongues 232 are arranged in a JKJK pattern in which each J corresponds to an indentation 252 and each K corresponds to a tongue 232. In some embodiments, each of the indentations 252 is disposed between two tongues 232. In some embodiments, each tongue 232 is disposed between two indentations 252.

FIG. 30 is a stylized exploded view further illustrating the saddle interlocking portion 212 of the saddle member 152 and the complementary interlocking portion 216 of the encapsulation layer 124. In the stylized view of FIG. 30, the saddle member 152 and the encapsulation layer 124 have shapes that are generally planar. When the saddle member 152 and the encapsulation layer 124 are in an unexploded state, the saddle interlocking portion 212 and the complementary interlocking portion 216 may engage each other to form a mechanically interlocking connection. In some embodiments, the saddle interlocking portion 212 comprises a plurality of lock features 214 and the complementary interlocking portion 216 of the encapsulation layer 124 comprises a plurality of complementary features 218. In some embodiments, the complementary features 218 are mechanically interlocked with the lock features 214 at the mechanically interlocking connection.

FIG. 31 is a stylized exploded view further illustrating the saddle interlocking portion 212 of the saddle member 152 and the complementary interlocking portion 216 of the encapsulation layer 124. When the saddle member 152 and the encapsulation layer 124 are in an unexploded state, the saddle interlocking portion 212 and the complementary interlocking portion 216 may engage each other to form a mechanically interlocking connection. In some embodiments, the saddle interlocking portion 212 comprises a plurality of lock features 214 and the complementary interlocking portion 216 of the encapsulation layer 124 comprises a plurality of complementary features 218. In some embodiments, the complementary features 218 are mechanically interlocked with the lock features 214 at the mechanically interlocking connection.

FIG. 32 is an additional stylized exploded view further illustrating the serrated edge 258 of the saddle member 152 and the overhanging lip portion of the encapsulation layer 124. With reference to FIG. 32, it will be appreciated that, in some embodiments, the saddle member 152 has a serrated edge 258 and the encapsulation layer 124 includes an overhanging lip portion 230 having a complementary edge portion 260. In some embodiments, the serrated edge 258 and the complementary edge portion 260 engage each other to form a mechanically interlocking joint 228. In some embodiments, the serrated edge 258 comprises a plurality of edge features 262, the complementary edge portion 260 comprises a plurality of complementary elements 264. In some embodiments, the complementary elements 264 are mechanically interlocked with the edge features 262 of the serrated edge 258.

FIG. 33 is an additional stylized exploded view further illustrating the serrated edge 258 of the saddle member 152 and the overhanging lip portion of the encapsulation layer 124. In the stylized view of FIG. 33, the saddle member 152 and the encapsulation layer 124 have shapes that are generally planar. With reference to FIG. 33, it will be appreciated that, in some embodiments, the saddle member 152 has a serrated edge 258 and the encapsulation layer 124 includes an overhanging lip portion 230 having a complementary edge portion 260. In some embodiments, the serrated edge 258 and the complementary edge portion 260 engage each other to form a mechanically interlocking joint 228. In some embodiments, the serrated edge 258 comprises a plurality of edge features 262, the complementary edge portion 260 comprises a plurality of complementary elements 264. In some embodiments, the complementary elements 264 are mechanically interlocked with the edge features 262 of the serrated edge 258.

FIG. 34A through FIG. 34F are elevation and plan views showing six sides of an elongate positioning member 102. Engineer graphics textbooks generally refer to the process used to create views showing six sides of a three dimensional object as multiview projection or orthographic projection. It is customary to refer to multiview projections using terms such as front view, right side view, top view, rear view, left side view, and bottom view. In accordance with this convention, FIG. 34A may be referred to as a left side view of the elongate positioning member 102, FIG. 34B may be referred to as a front side view of the elongate positioning member 102, and FIG. 34C may be referred to as a top view of the elongate positioning member 102. FIG. 34A through FIG. 34F may be referred to collectively as FIG. 34. Terms such as front view and right side view are used herein as a convenient method for differentiating between the views shown in FIG. 34. It will be appreciated that the elements shown in FIG. 34 may assume various orientations without deviating from the spirit and scope of this detailed description. Accordingly, the terms front view, right side view, top view, rear view, left side view, bottom view, and the like should not be interpreted to limit the scope of the invention recited in the attached claims. FIG. 34D may be referred to as a right side view of the elongate positioning member 102, FIG. 34E may be referred to as a rear view of the elongate positioning member 102, and FIG. 34F may be referred to as a bottom view of the elongate positioning member 102.

FIG. 35 is an exploded perspective view showing a distal portion of the elongate positioning member 102 shown in FIG. 34. In the example embodiment of FIGS. 34 and 35, the elongate positioning member 102 comprises a shaft member 150 and a saddle member 152 that is fixed to a distal portion of the shaft member 150. With reference to FIG. 35, it will be appreciated that a distal portion of the shaft member 150 has a generally arcuate shape having a concave inner surface and a convex outer surface. In some embodiments, a distal portion of the shaft member 150 has a truncated C-shape. In some embodiments, the saddle member 152 may be joined to the shaft member 150 using a welding process. In some embodiments, the saddle member 152 and the shaft member 150 both comprise stainless steel and the saddle member 152 is joined to the shaft member 150 using a LASER welding process.

FIG. 36 is an exploded perspective view showing a proximal portion of the elongate positioning member 102 shown in FIG. 34. In the example embodiment of FIGS. 34 and 36, the elongate positioning member 102 comprises a shaft member 150 and a handle 270 that is fixed to a proximal portion of the shaft member 150. With reference to FIG. 36, it will be appreciated that a proximal portion of the shaft member 150 has a generally parallelepiped shape. In some embodiments, a proximal portion of the shaft member 150 has a truncated rectangular shape when viewed in lateral cross-section. In some embodiments, the handle 270 may be formed on the shaft member 150 using an overmolding process. In some embodiments, the handle 270 may be joined to the shaft member 150 using a bonding process. In some embodiments, the handle 270 may be joined to the shaft member 150 using an adhesive.

FIG. 37A is a top view of a shaft member 150 for an elongate positioning member in accordance with this detailed description. FIG. 37B and FIG. 37C are cross-sectional views of the shaft member 150 shown in FIG. 37A. FIGS. 37A-37C may be collectively referred to as FIG. 37. In some useful embodiments, the shaft member 150 includes a proximal portion having a cylindrical shape and a distal portion that tapers to smaller cross-sectional shapes as the shaft member 150 extends distally. In the embodiment of FIG. 37B, the shaft member 150 has been sectioned along section line 37B-37B shown in FIG. 37A. With reference to FIG. 37B, it will be appreciated that the proximal portion of the shaft member 150 has a lateral cross sectional shape that generally corresponds to a circle shape. Also with reference to FIG. 37B, it will be appreciated that the shaft member 150 has a solid lateral cross sectional shape at section line 11B-11B. In some embodiments, the shaft member 150 has a solid lateral cross-sectional shape throughout its length. In the embodiment of FIG. 37C, the shaft member 150 has been sectioned along section line 37C-37C shown in FIG. 37A. With reference to FIG. 37C, it will be appreciated that the distal portion of the shaft member 150 has a lateral cross sectional shape that includes two planar sides. A Thickness TS of the shaft member 150 is illustrated using dimension lines in FIG. 37C. In some useful embodiments, the Thickness TS of the shaft member 150 becomes smaller as the shaft member 150 extends distally.

Figure 38A:
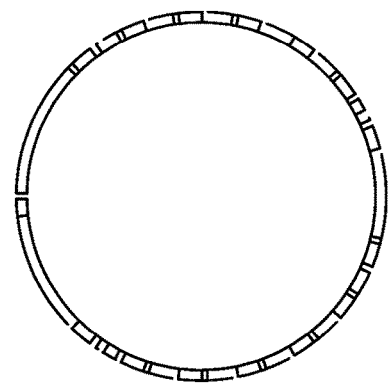
Figure 38C:
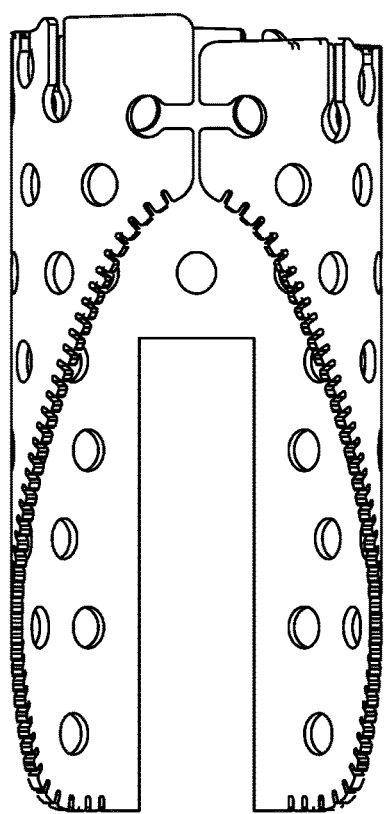
Figure 38B:
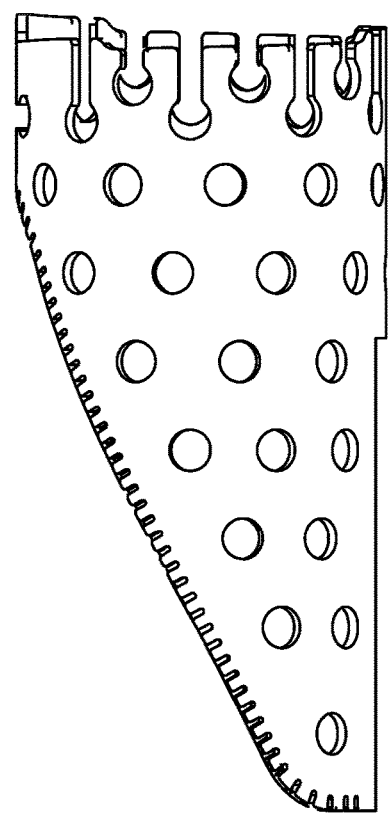
Figure 38E:
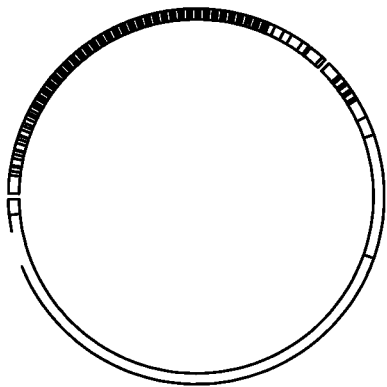
Figure 38D:
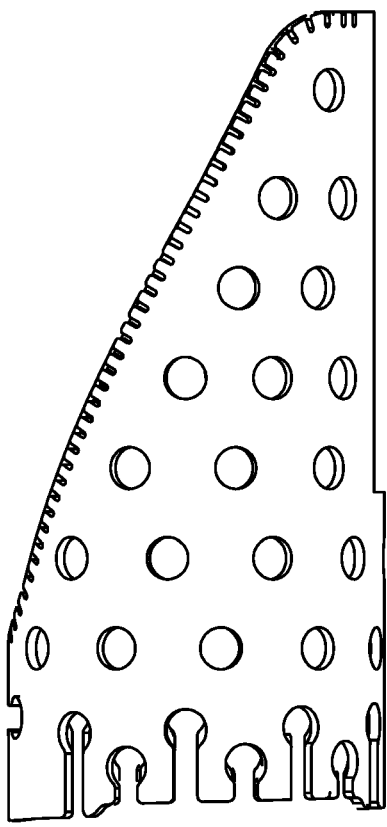
Figure 38F:
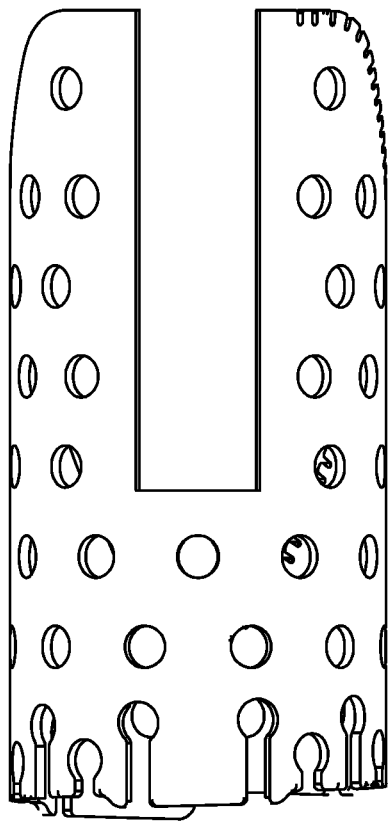

FIG. 38A through FIG. 38F are elevation and plan views showing six sides of a saddle member 152. Engineer graphics textbooks generally refer to the process used to create views showing six sides of a three dimensional object as multiview projection or orthographic projection. It is customary to refer to multiview projections using terms such as front view, right side view, top view, rear view, left side view, and bottom view. In accordance with this convention, FIG. 38A may be referred to as a front view of the saddle member 152, FIG. 38B may be referred to as a left side view of the saddle member 152, and FIG. 38C may be referred to as a top view of the saddle member 152. FIG. 38A through FIG. 38F may be referred to collectively as FIG. 38. Terms such as front view and right side view are used herein as a convenient method for differentiating between the views shown in FIG. 38. It will be appreciated that the elements shown in FIG. 38 may assume various orientations without deviating from the spirit and scope of this detailed description. Accordingly, the terms front view, right side view, top view, rear view, left side view, bottom view, and the like should not be interpreted to limit the scope of the invention recited in the attached claims. FIG. 38D may be referred to as a right side view of the saddle member 152, FIG. 38E may be referred to as a rear view of the saddle member 152, and FIG. 38F may be referred to as a bottom view of the saddle member 152. With reference to FIG. 38, it will be appreciated that the saddle member 152 defines a plurality of holes 154. In some embodiments, a device including the saddle member 152 may also include thermoplastic material extending through the holes 154 in the saddle member 152. For example, a plug of an encapsulating layer of thermoplastic material may extend into each hole 154.

With reference to FIG. 38, it will be appreciated that, in some embodiments, the saddle member 152 has a first end portion, a second end portion and an intermediate part extending along an arcuate path between the first end portion and the second end portion. In the embodiment of FIG. 38, the first end portion of the saddle member defines a first cutout and the second end portion of the saddle member defines a second cutout. Also in the embodiment of FIG. 38, the saddle member has a saddle interlocking portion comprises a plurality of lock features. In the example embodiment of FIG. 38, the lock features of the saddle interlocking portion comprise a plurality of embayments defined by the saddle member and a plurality of peninsular members of the saddle member. In some embodiments, each peninsular member is disposed between two embayments. In some embodiments, each peninsular member of the saddle interlocking portion comprises a neck portion extending distally beyond an edge of the saddle member and a head portion extending distally from the neck portion, the neck portion having a neck width and the head portion having a head width, the head width being greater than the neck width. The saddle member also includes a serrated edge having a plurality of edge features in the embodiment of FIG. 38. In the example embodiment of FIG. 38, the edge features of the serrated edge comprise a plurality of grooves defined by the saddle member and a plurality of serration members of the saddle member. In some embodiments, each serration member is disposed between two grooves.

With reference to FIGS. 19 through 38, a device 100 for guiding and supporting a stent delivery catheter and/or other catheters is disclosed. In some embodiments, the device 100 comprises a tubular guiding member 104 and an elongated positioning member extending in a proximal direction beyond the tubular guiding member 104 for advancing and retracting the tubular guiding member in distal and proximal directions. In some embodiments, the tubular guiding member 104 comprises an inner tubular member 120 having an outer surface 140, an elongate support member 180 disposed along a helical path around the outer surface 140, a saddle member 152 at least partially encircling the inner tubular member 120 at a location rearward of the elongate support member 180, and an encapsulation layer 124 overlaying the support structure 166 and the inner tubular member 120. In some embodiments, the encapsulation layer 124 is mechanically interlocked with and adhered to the elongate support member 180 and the saddle member 152. In some embodiments, the encapsulation layer 124 comprises thermoplastic material from a sheet, the thermoplastic material having melted, mixed and solidified during a reflow process.

With continuing reference to FIGS. 19 through 38, in some embodiments, the inner tubular member 120 has a wall thickness less than 0.0015 inch, the encapsulation layer 124 has a layer thickness less than 0.0020 inch, and the tubular guiding member 104 has a total wall thickness less than 0.0030 inch. In some embodiments, the inner tubular member 120 has a wall thickness less than 0.0010 inch, the encapsulation layer 124 has a layer thickness less than 0.0017 inch, and the tubular guiding member 104 has a total wall thickness less than 0.0027 inch. In some embodiments, the inner tubular member 120 has a wall thickness less than 0.0010 inch, the encapsulation layer 124 has a layer thickness less than 0.0014 inch, and the tubular guiding member 104 has a total wall thickness less than 0.0024 inch. In some embodiments, the tubular guiding member 120 has an inner diameter to wall thickness ratio equal to or greater than 18:1. In some embodiments, the tubular guiding member 120 has an inner diameter to wall thickness ratio equal to or greater than 22:1. In some embodiments, the tubular guiding member 120 has an inner diameter to wall thickness ratio equal to or greater than 24:1.

With continuing reference to FIGS. 19 through 38, in some embodiments, the elongate support member 180 has core portion 190 comprising a core material 192 and a jacket portion 194 disposed about the core portion 190. In some embodiments, the jacket portion 194 comprises a jacket material 196 and the core material 192 is more radiopaque than the jacket material 196. In some embodiments, the core portion 190 of the elongate support member 180 serves as a sole radiographic marker of the device 100, the device 100 having no radiopaque marker separate from the elongate support member 180. In some embodiments, the elongate support member 180 is welded to form a distal closed loop 174. In some embodiments, the distal closed loop 174 comprises a distal weld 186 and a distal portion 182 of the elongate support member 180. In some embodiments, the distal portion 182 extends around the outer surface 140 of the inner tubular member 120. In some embodiments, the distal weld 186 comprises a distal weld body 198 and the distal weld body 198 comprises jacket material 196 from a first forward part 202 of the elongate support member 180 and jacket material 196 from a second forward part 204 of the elongate support member, the materials having melted, mixed and solidified during a welding process. In some embodiments, the elongate support member 180 is welded to form a proximal closed loop 176. In some embodiments, the proximal closed loop 176 comprises a proximal weld 188 and a proximal portion 184 of the elongate support member 180. In some embodiments, the proximal portion 184 extends around the outer surface 140 of the inner tubular member 120. In some embodiments, the proximal weld 188 comprises a proximal weld body 200 and the proximal weld body 200 comprises jacket material 196 from a first rearward part 206 of the elongate support member and jacket material 196 from a second rearward part 208 of the elongate support member 180, the materials having melted, mixed and solidified during a welding process.

With continuing reference to FIGS. 19 through 38, in some embodiments, the saddle member 152 comprises a saddle interlocking portion 212, the encapsulation layer 124 comprises a complementary interlocking portion 216, and the saddle interlocking portion 212 and the complementary interlocking portion 216 engage each other to form a mechanically interlocking connection 220. In some embodiments, the saddle interlocking portion 212 comprises a plurality of lock features 214 and the complementary interlocking portion 216 of the encapsulation layer 124 comprises a plurality of complementary features 218. In some embodiments, the complementary features 218 are mechanically interlocked with the lock features 214 at the mechanically interlocking connection 220. In some embodiments, the lock features 214 of the saddle interlocking portion 212 comprise a plurality of embayments 224 defined by the saddle member 152 and a plurality of peninsular members 222 of the saddle member 152. In some embodiments, the embayments 224 and the peninsular members 222 are disposed along a distal edge of the saddle member 152 in an ABAB pattern in which each A corresponds to a peninsular member 222 and each B corresponds to an embayment 224. In some embodiments, each of the embayments 224 is disposed between two peninsular members 222 and each peninsular member 222 is disposed between two embayments 224. In some embodiments, at least one of the embayments 224 is disposed between two peninsular members 222 and at least one of the peninsular members 222 is disposed between two embayments 224. In some embodiments, each peninsular member 222 of the saddle interlocking portion 212 comprises a neck portion 266 extending distally beyond an edge of the saddle member 152 and a head portion 268 extending distally from the neck portion 266. In some embodiments, each neck portion 266 has a neck width, each head portion 268 has a head width, and the head width being greater than the neck width.

With continuing reference to FIGS. 19 through 38, in some embodiments, the complementary features 218 of the complementary interlocking portion 216 comprise a plurality of recesses 248 and a plurality of protrusions 246. In some embodiments, each peninsular member 222 of the saddle interlocking portion 212 extends into one of the recesses 248 of the complementary interlocking portion 216 of the encapsulation layer 124. In some embodiments, each peninsular member 222 of the saddle interlocking portion 212 is disposed between two of the protrusions 246 of the complementary interlocking portion 216 of the encapsulation layer 124. In some embodiments, at least one peninsular member 222 of the saddle interlocking portion 212 is disposed between two of the protrusions 246 of the complementary interlocking portion 216 of the encapsulation layer 124. In some embodiments, each protrusion 246 of the complementary interlocking portion 216 extends into one of the embayments 224 of the saddle interlocking portion 212. In some embodiments, each protrusion 246 of the complementary interlocking portion 216 is disposed between two of the peninsular members 222 of the saddle interlocking portion 212. In some embodiments, the recesses 248 and the protrusions 246 are arranged in an EFEF pattern in which each E corresponds to a recess 248 and each F corresponds to a protrusion 246. In some embodiments, each of the recesses 248 is disposed between two protrusions 246, and each protrusion 246 is disposed between two recesses 248.

With continuing reference to FIGS. 19 through 38, in some embodiments, the saddle member 152 has a serrated edge 258 and the encapsulation layer 124 includes an overhanging lip portion 230 having a complementary edge portion 260. In some embodiments, the serrated edge 258 and the complementary edge portion 260 engage each other to form a mechanically interlocking joint 228. In some embodiments, the serrated edge 258 comprises a plurality of edge features 262, the complementary edge portion 260 comprises a plurality of complementary elements 264. In some embodiments, the complementary elements 264 are mechanically interlocked with the edge features 262 of the serrated edge 258.

With continuing reference to FIGS. 19 through 38, in some embodiments, the edge features 262 of the serrated edge 258 comprise a plurality of grooves 148 defined by the saddle member 152 and a plurality of serration members 226 of the saddle member 152. In some embodiments, the grooves 148 and the serration members 226 are disposed along a proximal edge of the saddle member 152 in a GHGH pattern in which each G corresponds to a serration member 226 and each H corresponds to a groove 148. In some embodiments, each of the grooves 148 is disposed between two serration members 226 and each serration member 226 is disposed between two grooves 148. In some embodiments, at least one of the grooves 148 is disposed between two serration members 226 and at least one of the serration members 226 is disposed between two grooves 148.

With continuing reference to FIGS. 19 through 38, in some embodiments, the complementary elements 264 of the complementary edge portion 260 comprise a plurality of indentations 252 and a plurality of tongues 232. In some embodiments, the indentations 252 and the tongues 232 are arranged in a JKJK pattern in which each J corresponds to an indentation 252 and each K corresponds to a tongue 232. In some embodiments, each of the indentations 252 is disposed between two tongues 232. In some embodiments, each tongue 232 is disposed between two indentations 252. In some embodiments, each tongue 232 of the complementary edge portion 260 extends into one of the grooves 148 of the serrated edge 258. In some embodiments, each serration member 226 of the serrated edge 258 extends into one of the indentations 252 of the complementary edge portion 260 of the encapsulation layer 124. In some embodiments, each serration member 226 of the serrated edge 258 is disposed between two of the tongues 232 of the complementary edge portion 260 of the encapsulation layer 124. 124. In some embodiments, at least one of the serration members 226 of the serrated edge 258 is disposed between two of the tongues 232 of the complementary edge portion 260 of the encapsulation layer 124. In some embodiments, each tongue 232 of the complementary edge portion 260 is disposed between two of the serration members 226 of the serrated edge 258. In some embodiments, at least one of the tongues 232 of the complementary edge portion 260 is disposed between two of the serration members 226 of the serrated edge 258.

With continuing reference to FIGS. 19 through 38, in some embodiments, the saddle member 152 has a first end portion 240, a second end portion 242 and an intermediate part 250 extending along an arcuate path between the first end portion 240 and the second end portion 242. In some embodiments, the first end portion 240 is coupled to the second end portion 242 by a coupling member 234 of the encapsulation layer 124 so that the coupling member 234 and the saddle member 152 form a ring structure 256 encircling the inner tubular member 120.

With continuing reference to FIGS. 19 through 38, in some embodiments, the coupling member 234 has a first coupling portion 236, a second coupling portion 238, and an intermediate part 250 extending between the first coupling portion 236 and the second coupling portion 238. In some embodiments, the first end portion 240 of the saddle member 152 defines a first cutout 244 and the first coupling portion 236 of the coupling member 234 is received in the first cutout 244. In some embodiments, the second end portion 242 of the saddle member 152 defines a second cutout 254 and the second coupling portion 238 of the coupling member 234 is received in the second cutout 254. In some embodiments, the first cutout 244 and the second cutout 254 are both keyhole shaped. In some embodiments, the coupling member 234 is dogbone shaped. In some embodiments, the first end portion 240 has a first end width, the second end portion 242 has a second end width, and the intermediate portion has an intermediate portion width, the intermediate portion width being less than the first end width and the second end width.

FIG. 39A is a perspective view showing a device 390 in the form a catheter having an elongate catheter shaft 394 defining a lumen 396. In the embodiment of FIG. 39A, the catheter 390 includes a hub 392 that fixed to a proximal portion of the catheter shaft 394. Some methods of making a catheter shaft, such as, for example, catheter shaft 394 shown in FIG. 39A may include providing an inner tubular member and forming or placing a support structure over an outer surface of the inner tubular member. Some methods of making a catheter shaft may also include reflowing one or more thermoplastic materials to form an encapsulation layer overlaying the support structure and the inner tubular member. Some methods of making a medical device, such as catheter 100, may include attaching a hub to a proximal portion of a catheter shaft formed by the inner tubular member, the support structure and the encapsulation layer.

FIG. 39B is a partial cross-sectional view of the catheter shaft 394 shown in FIG. 39A. In the embodiment of FIG. 39B, the catheter shaft 394 has been sectioned along section line B-B shown in FIG. 39A. FIG. 39C is an end view of the catheter shaft 394 shown in FIG. 39B. With reference to FIG. 39B, it will be appreciated that the catheter shaft 394 comprises an inner tubular member 120, a support structure 122 disposed about the inner tubular member 120, and an encapsulation layer 124 overlaying the support structure 122 and the inner tubular member 120. With reference to FIG. 39B, it will be appreciated that the inner tubular member 120 defines a lumen 118/396 extending between a proximal end of the catheter shaft 394 and a distal end of the catheter shaft 394. In some embodiments, the support structure 122 comprises one or more elongate support members 180 disposed about the outer surface of the inner tubular member 120. In some embodiments, the one or more elongate support members 180 are braided about the outer surface of the inner tubular member 120 to form a braid. In some embodiments, each of the one or more elongate support members 180 follows a helical path around the outer surface of the inner tubular member 120. In some embodiments, one or more of the elongate members of the support structure 122 form a coil including a plurality of turns with each turn encircling the inner tubular member 120. In the example embodiment of FIG. 39, the elongate support member 180 comprises a wire 138 that forms a coil 322.

FIG. 40A is a perspective view showing a catheter 400 having an elongate catheter shaft 394 defining a lumen 396. In the embodiment of FIG. 40A, the catheter 400 includes a hub 392 that is fixed to a proximal portion of the catheter shaft 394. FIG. 40B is an enlarged detail view showing a portion of the catheter 400 shown in FIG. 40A. With reference to FIG. 40B, it will be appreciated that catheter 400 includes an occlusion device 402 that is located inside the lumen 396 defined by the catheter shaft 394. Methods in accordance with this detailed description may include forming a tubular structure defining a lumen and placing a therapy device inside the lumen defined by the tubular structure. In some example methods, positioning a therapy device inside the lumen defined by the tubular structure comprises positioning an occlusion device inside the lumen defined by the tubular structure.

FIG. 41A is a perspective view showing a catheter 410 having an elongate catheter shaft 394 defining a lumen 396. In the embodiment of FIG. 41A, the catheter 410 includes a hub 392 that is fixed to a proximal portion of the catheter shaft 394. FIG. 41B is an enlarged detail view showing a portion of the catheter 410 shown in FIG. 41A. With reference to FIG. 41B, it will be appreciated that catheter 410 includes a stent 412 that is located inside the lumen 396 defined by the catheter shaft 394. Methods in accordance with this detailed description may include forming a tubular structure defining a lumen and placing a therapy device inside the lumen defined by the tubular structure. In some example methods, positioning a therapy device inside the lumen defined by the tubular structure comprises positioning a stent inside the lumen defined by the tubular structure.

FIG. 42 is a perspective view showing a balloon catheter 420. In the embodiment of FIG. 42, the catheter 420 includes a hub 392 that is fixed to a proximal portion of the inner catheter shaft catheter 393 and outer shaft 394. With reference to FIG. 42, it will be appreciated that catheter 420 includes a balloon 422 that is fixed proximally to an outside surface of the outer shaft 394 and distally to the inner shaft 393. Methods in accordance with this detailed description may include forming a catheter shaft defining a lumen and attaching a therapy device to the catheter shaft. In some example methods, attaching a therapy device to the catheter shaft comprises attaching a balloon to the outside surface of the catheter shaft.

FIG. 43A is a perspective view showing a catheter 430 having an elongate catheter shaft 394 defining a lumen 396. In the embodiment of FIG. 43A, the catheter 430 includes a hub 392 that is fixed to a proximal portion of the catheter shaft 394. FIG. 43B is an enlarged detail view showing a portion of the catheter shown in FIG. 43A. With reference to FIG. 43B, it will be appreciated that catheter 430 includes an ultrasonic imaging transducer 432 that is located inside the lumen 396 defined by the catheter shaft 394. Methods in accordance with this detailed description may include forming a tubular structure, such as catheter shaft 394, defining a lumen and placing a diagnostic device inside the lumen defined by the tubular structure. In some example methods, positioning a diagnostic device inside the lumen defined by the tubular structure comprises positioning an ultrasonic imaging transducer inside the lumen defined by the tubular structure.

With reference to the figures described above, it will be appreciated that a number of methods for making medical devices and portions of medical devices are provided by this detailed description. The medical devices may include, for example, intravascular catheters, catheter shafts, and tubular guiding members. Example methods may include providing a first ribbon comprising one or more thermoplastic materials and a piece of shrink tubing defining a shrink tube lumen and forming a first assembly by positioning the first ribbon inside the shrink tube lumen and urging the first ribbon to assume a tubular shape in which the first ribbon defines a ribbon lumen. Some example methods may also include forming a second assembly by loading an inner tubular member over a mandrel and forming or placing a support structure over an outer surface of the inner tubular member. A third assembly may be formed by inserting the second assembly into the ribbon lumen defined by the first ribbon of the first assembly in some embodiments. Some methods may include heating the third assembly to a process temperature, the process temperature being selected such that the one or more thermoplastic materials of the first ribbon reflow to form an encapsulation layer overlaying the support structure and the inner tubular member, the encapsulation layer being mechanically interlocked with and adhered to the support structure.

Example methods may further include allowing the third assembly to cool, removing the heat shrink tubing from around the encapsulation layer, and withdrawing the mandrel from the lumen defined by the inner tubular member. In some embodiments, one of the one or more the thermoplastic materials of the first ribbon has a first glass transition temperature, the liner material has a second glass transition temperature, and the second glass transition temperature is greater than the first glass transition temperature. In some embodiments, the process temperature is less than the second glass transition temperature and greater than the first glass transition temperature.

In some example methods, providing the first ribbon comprises providing a first ribbon having more than one layer and, upon heating the third assembly to the process temperature, the first ribbon reflow to form an encapsulation layer. In some embodiments, the first ribbon comprises five or more layers. In some embodiments, the first ribbon comprises ten or more layers. In some embodiments, the first ribbon comprises twenty or more layers.

Example methods may further include providing a second ribbon comprising one or more thermoplastic materials and a second piece of shrink tubing defining a second shrink tube lumen and forming a fourth assembly by positioning the second ribbon inside the second shrink tube lumen and urging the second ribbon to assume a tubular shape in which the second ribbon defines a ribbon lumen. Some methods include forming a fifth assembly by inserting the third assembly into the ribbon lumen defined by the second ribbon of the fifth assembly and heating the fifth assembly to a process temperature, the process temperature being selected such that the one or more thermoplastic materials of the second ribbon reflow and form part of an encapsulation layer overlaying the support structure and the inner tubular member, the encapsulation layer being mechanically interlocked with and adhered to the support structure.

Some example methods may further include positioning a ring member about the shrink tubing and moving the ring member in a proximal direction and/or a distal direction along the shrink tubing. In some embodiments, the ring member comprises an elastomeric O-ring. Some example methods include comprising positioning a ring member about the shrink tubing and moving the ring member in a proximal direction along the shrink tubing while the thermoplastic material of the encapsulation layer is molten and creating proximally directed flow in the molten thermoplastic material. Some example methods include positioning a ring member about the shrink tubing and moving the ring member in a proximal direction along the shrink tubing while the thermoplastic material of the encapsulation layer is molten and extruding a portion of the molten thermoplastic material out of a lumen defined by the shrink tubing. Some example methods may further include positioning a structural member over the inner tubular member and positioning a second ring member around the shrink tubing at a location generally aligned with the structural member while the thermoplastic material of the encapsulation layer is molten, and allowing the thermoplastic material of the encapsulation layer to cool while elastic clamping forces produced by the second ring member are applied to the structural member.

In some example methods, forming or placing the support structure over the inner tubular member comprises winding an elongate support member around the outer surface of the inner tubular member to form a coil. In other example methods, forming or placing the support structure over the inner tubular member comprises braiding one or more elongate support members to form a tubular braid. In other example methods, forming or placing the support structure over the inner tubular member comprises knitting one or more elongate support members to form a tubular knit structure. In some example methods, forming or placing the support structure over the inner tubular member comprises winding an elongate support member around the outer surface of the inner tubular member to form a coil, fixing a distal end of the elongate support member at a distal weld joint, and fixing a proximal end of the elongate support member at a proximal weld joint.

Some example methods further include placing a therapy device inside the lumen defined by the inner tubular member. In some example methods, placing a therapy device inside the lumen defined by the inner tubular member comprises placing a stent inside the lumen defined by the inner tubular member. In some example methods, placing a therapy device inside the lumen defined by the inner tubular member comprises placing an occlusion device inside the lumen defined by the inner tubular member. Some example methods further include attaching a therapy device to a catheter shaft formed by the inner tubular member, the support structure and the encapsulation layer. In some example methods, attaching a therapy device to the catheter shaft comprises attaching a balloon to the outside of the catheter shaft. Some example methods further include attaching a connector to the catheter shaft formed by the inner tubular member, the support structure and the encapsulation layer for delivering fluids to locations inside the body of a patient. Some example methods further include attaching a connector to the catheter shaft formed by the inner tubular member, the support structure and the encapsulation layer for applying vacuum or low pressure to locations inside the body of a patient for removing materials from the body. Some example methods further include attaching a hub to the catheter shaft formed by the inner tubular member, the support structure and the encapsulation layer. In some example methods, the hub is attached using an adhesive bonding process.

Some example methods further include placing a diagnostic device inside the lumen defined by the inner tubular member. In some example methods, placing a diagnostic device inside the lumen defined by the inner tubular member comprises placing an ultrasonic imaging transducer inside the lumen defined by the inner tubular member. Some example methods further include forming a hub on the catheter shaft formed by the inner tubular member, the support structure and the encapsulation layer. In some example methods, the hub formed using a thermoplastic injection molding process.

In some example methods, urging the first ribbon to assume the tubular shape comprises urging the first ribbon to assume the tubular shape having an angular span of less than 360 degrees so that the first ribbon defines a longitudinal gap located between a first longitudinal edge of the first ribbon and a second longitudinal edge of the first ribbon. In some example methods urging the first ribbon to assume the tubular shape comprises urging the first ribbon to assume the tubular shape having an angular span of less than 345 degrees. In some example methods, urging the first ribbon to assume the tubular shape comprises pulling the first ribbon into the shrink tube lumen. In some example methods, pulling the first ribbon into the shrink tube lumen comprises inserting an end of a pulling tool through the lumen of the shrink tube, coupling the end of the pulling tool to a distal portion of the first ribbon, and applying a pulling force to the pull tool to pull the first ribbon into the lumen of the shrink tube. In some embodiments, the pulling tool has a hook shaped distal portion and coupling the end of the pulling tool to a distal portion of the first ribbon comprises inserting a distal end of the hook shaped distal portion through a hole defined by the first ribbon. In some example methods, urging the first ribbon to assume the tubular shape comprises pushing the first ribbon into the shrink tube lumen. In some example methods pushing the first ribbon into the shrink tube lumen comprises coupling the distal portion of a pushing tool to a distal portion of the first ribbon, and applying a pushing force to the pull tool to push the first ribbon into the lumen of the shrink tube. In some embodiments, the pushing tool has a fork shaped distal portion and coupling the end of the pushing tool to a distal portion of the first ribbon comprises inserting a distal end of the hook shaped distal portion through a hole defined by the first ribbon.

The following United States patents are hereby incorporated by reference herein: U.S. Pat. Nos. 10,124,148, 10,124,147, 9,993,613, 9,764,118, 9,486,611, 9,352,123, 8,996,095, U.S. RE45380, U.S. RE45760, U.S. RE45776, and U.S. RE46116.

The above references in all sections of this application are herein incorporated by references in their entirety for all purposes. Components illustrated in such patents may be utilized with embodiments herein. Incorporation by reference is discussed, for example, in MPEP section 2163.07(B).

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any incorporated by reference references, any accompanying claims, abstract and drawings), or to any novel one, or any novel combination, of the steps of any method or process so disclosed The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above-described aspects embodiments of the invention are merely descriptive of its principles and are not to be considered limiting. Further modifications of the invention herein disclosed will occur to those skilled in the respective arts and all such modifications are deemed to be within the scope of the invention.

What is claimed is:

1. A guide catheter extension configured for use with a guide catheter in a blood vessel, the guide catheter extension comprising:
    an elongate member having a proximal portion and a distal portion;
    a saddle member connected to the distal portion of the elongate member;
    a polymeric lip connected to and extending proximally from a proximal-facing leading edge of the saddle;
    a tubular member having a proximal portion connected to the saddle member and a distal portion extending from the saddle member, the tubular member having a lumen extending therethrough from a proximal opening to a distal opening, wherein the elongate member, the saddle member and the tubular member are configured to fit inside the guide catheter with the proximal portion of the elongate member extending proximally out of the guide catheter, the distal portion of the tubular member extending distally out of the guide catheter, and the proximal opening disposed inside the guide catheter to define an open lumen extending through the guide catheter, through the tubular member and into the blood vessel;
    the tubular member comprising:
        an inner tubular liner;
        a reinforcement layer disposed over the liner; and
        a first elongate polymeric encapsulation layer disposed around the reinforcement layer,
        the first elongate polymeric encapsulation layer having two adjacent longitudinal edges extending along a length of the tubular member,
    the guide catheter extension further comprising a second polymeric encapsulation layer disposed around the saddle member, the second polymeric encapsulation layer having two adjacent longitudinal edges extending along a length of the tubular member,
    wherein the first and second polymeric encapsulation layers overlap, and
    wherein the proximal-facing leading edge of the saddle includes a plurality of notches, and wherein the second polymeric encapsulation layer extends through the notches to the inner liner in the saddle.

2. A guide catheter extension as in claim 1, wherein the saddle includes a distal-facing trailing edge having a plurality of notches and wherein the second polymeric encapsulation layer is connected to and extends from the distal-facing trailing edge.

3. A method of making a catheter as in claim 1, comprising:
    providing a mandrel having a longitudinal axis;
    loading the inner tubular liner over the mandrel;
    loading the reinforcement layer onto the inner tubular liner;
    providing the first elongate polymeric encapsulation layer, wherein the first elongate polymeric encapsulation layer has-two longitudinal edges;
    urging the first elongate polymeric encapsulation layer to assume a tubular shape around the reinforcement layer such that the longitudinal edges run parallel with the longitudinal axis of the mandrel; and
    applying heat and compression to the first elongate polymeric encapsulation layer.

4. A method of making a catheter as in claim 3, wherein the step of applying heat and compression causes reflow of the first elongate polymeric encapsulation layer into the reinforcement layer.

5. A method of making a catheter as in claim 4, wherein the step of applying heat and compression causes reflow of the first elongate polymeric encapsulation layer through the reinforcement layer to contact the inner tubular liner.

6. A method of making a catheter as in claim 3, further comprising: loading the first elongate polymeric encapsulation layer into a heat shrink tube.

7. A method of making a catheter as in claim 6, wherein the step of loading the first elongate polymeric encapsulation layer into the heat shrink tube comprises pulling the sheet into the shrink tube causing the sheet to be urged into a tubular shape.

8. A method of making a catheter as in claim 7, wherein the step of applying heat and compression comprises heating the heat shrink tube over the first elongate polymeric encapsulation layer.

9. A method of making a catheter as in claim 3, wherein the step of applying compression comprises rolling a stretched O-ring over the first elongate polymeric encapsulation layer.

10. A method of making a catheter as in claim 3, wherein the step of providing the first elongate polymeric encapsulation layer comprises providing a multilayered polymeric sheet.

11. A method of making a catheter as in claim 3, wherein the step of urging the first elongate polymeric encapsulation layer into a tubular shape defines a gap between the longitudinal edges.

12. A guide catheter extension configured for use with a guide catheter in a blood vessel, the guide catheter extension comprising:
  an elongate member having a proximal portion and a distal portion;
  a saddle member connected to the distal portion of the elongate member;
  a polymeric lip connected to and extending proximally from a proximal-facing leading edge of the saddle;
  a tubular member having a proximal portion connected to the saddle member and a distal portion extending from the saddle member, the tubular member having a lumen extending therethrough from a proximal opening to a distal opening, wherein the elongate member, the saddle member and the tubular member are configured to fit inside the guide catheter with the proximal portion of the elongate member extending proximally out of the guide catheter, the distal portion of the tubular member extending distally out of the guide catheter, and the proximal opening disposed inside the guide catheter to define an open lumen extending through the guide catheter, through the tubular member and into the blood vessel;
  the tubular member comprising:
    an inner tubular liner;
    a reinforcement layer disposed over the liner; and
    an elongate polymeric encapsulation layer disposed around the reinforcement layer, wherein the proximal-facing leading edge of the saddle includes a plurality of notches, and wherein the polymeric encapsulation layer extends through the notches to the inner liner in the saddle.

13. A guide catheter extension as in claim 12, wherein saddle includes a distal-facing trailing edge having a plurality of notches and wherein the second polymeric encapsulation layer is connected to and extends from the distal-facing trailing edge.

* * * * *